US007923221B1

(12) United States Patent
Cabilly et al.

(10) Patent No.: US 7,923,221 B1
(45) Date of Patent: *Apr. 12, 2011

(54) METHODS OF MAKING ANTIBODY HEAVY AND LIGHT CHAINS HAVING SPECIFICITY FOR A DESIRED ANTIGEN

(75) Inventors: Shmuel Cabilly, Monrovia, CA (US); Herbert L. Heyneker, Burlingame, CA (US); William E. Holmes, Pacifica, CA (US); Arthur D. Riggs, La Verne, CA (US); Ronald B. Wetzel, San Francisco, CA (US)

(73) Assignees: Genentech, Inc, South San Francisco, CA (US); City of Hope, Duarte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/422,187

(22) Filed: Apr. 13, 1995

Related U.S. Application Data

(63) Continuation of application No. 07/205,419, filed on Jun. 10, 1988, now Pat. No. 6,331,415, which is a continuation of application No. 06/483,457, filed on Apr. 8, 1983, now Pat. No. 4,816,567.

(51) Int. Cl.
*C12N 15/13* (2006.01)
*C12N 15/00* (2006.01)
*C12N 15/63* (2006.01)

(52) U.S. Cl. ............... 435/69.6; 435/252.1; 435/252.3; 435/252.33; 435/254.11; 435/254.21; 435/69.1; 435/69.7; 435/70.1; 435/70.21; 435/71.1; 435/320.1; 435/455; 435/483; 435/485; 435/440; 435/433; 435/438

(58) Field of Classification Search .............. 435/69.6, 435/69.1, 325, 252.3; 530/387.3
See application file for complete search history.

(56) References Cited

U.S. PATENT DOCUMENTS

| | | | |
|---|---|---|---|
| 4,179,337 A | 12/1979 | Davis | |
| 4,224,404 A | 9/1980 | Viza et al. | |
| 4,237,224 A | 12/1980 | Cohen | |
| 4,338,397 A | 7/1982 | Gilbert | |
| 4,342,832 A | 8/1982 | Goeddel et al. | |
| 4,348,376 A | 9/1982 | Goldenberg | |
| 4,366,246 A | 12/1982 | Riggs | |
| 4,370,417 A | 1/1983 | Hung | |
| 4,399,216 A | 8/1983 | Axel et al. | |
| 4,403,036 A | 9/1983 | Hartley | |
| 4,418,149 A | 11/1983 | Ptashne et al. | |
| 4,419,446 A | 12/1983 | Howley et al. | |
| 4,431,740 A | 2/1984 | Bell et al. | |
| 4,440,859 A | 4/1984 | Rutter et al. | |
| 4,444,878 A | 4/1984 | Paulus et al. | |
| 4,495,280 A | 1/1985 | Bujard et al. | |
| 4,500,637 A | 2/1985 | Neville, Jr. et al. | |
| 4,510,244 A | 4/1985 | Parks et al. | |
| 4,511,502 A | 4/1985 | Builder et al. | |
| 4,512,922 A | 4/1985 | Jones et al. | |
| 4,518,584 A | 5/1985 | Mark | |
| 4,565,785 A | 1/1986 | Gilbert et al. | |
| 4,599,197 A | 7/1986 | Wetzel | |
| 4,634,665 A | 1/1987 | Axel et al. | |
| 4,642,334 A | 2/1987 | Moore et al. | |
| 4,668,629 A | 5/1987 | Kaplan | |
| 4,704,362 A | 11/1987 | Itakura et al. | |
| 4,713,339 A | 12/1987 | Levinson et al. | |
| 4,766,075 A | 8/1988 | Goeddel et al. | |
| 4,792,447 A | 12/1988 | Uhr et al. | |
| 4,816,397 A * | 3/1989 | Boss et al. | ............ 435/68 |
| 4,816,567 A | 3/1989 | Cabilly et al. | |
| 4,965,196 A | 10/1990 | Levinson et al. | |
| 5,081,235 A | 1/1992 | Shively et al. | |
| 5,098,833 A | 3/1992 | Lasky et al. | |
| 5,116,964 A | 5/1992 | Capon et al. | |
| 5,137,721 A | 8/1992 | Dallas | |
| 5,149,636 A | 9/1992 | Axel et al. | |
| 5,179,017 A | 1/1993 | Axel et al. | |
| 5,225,538 A | 7/1993 | Capon et al. | |
| 5,225,539 A | 7/1993 | Winter | |
| 5,336,603 A | 8/1994 | Capon et al. | |
| 5,420,020 A | 5/1995 | Riggs | |
| 5,428,130 A | 6/1995 | Capon et al. | |
| 5,455,165 A | 10/1995 | Capon et al. | |
| 5,500,362 A | 3/1996 | Robinson et al. | |
| 5,514,582 A | 5/1996 | Capon et al. | |
| 5,545,403 A | 8/1996 | Page | |
| 5,545,404 A | 8/1996 | Page | |

(Continued)

FOREIGN PATENT DOCUMENTS

AU 194982 2/1983

(Continued)

OTHER PUBLICATIONS

Gillis, S.D. & J.S. Wesolowski 1990 Hum. Antibod. Hybridomas 1(1): 47-54.*
Owens, R.J. & R.J. Young 1994 Journal of Immunological Methods 168:149-165.*
Skerra et al 1988 Science 240: 1038-1041.*
Better et al. 1989 Methods Enzymol 178: 476-496.*
Taylor et al 1988 Mol Cell Biol 8(10): 4197-4203.*
Letherbarrow 1985 Midec. Immuno (22(4): 407-415.*
Raghunathan et al 1996 Prog. Biophy. &Mol. Biol. 65(5): 143.*
Wright et al 1991 EMBO J. 10(10): 2717-2723.*
Buchner et al 1991 Bio/Technology 9:157-162.*
Morrison et al Adv. Immunol. (1989).*
Horowitz et al. PNAS, (1988).*
Skerrs et al Protein Engineering, (1991).*

(Continued)

*Primary Examiner* — Phillip Gambel
(74) *Attorney, Agent, or Firm* — Sidley Austin LLP

(57) ABSTRACT

The invention relates to processes for producing an immunoglobulin or an immunologically functional immunoglobulin fragment containing at least the variable domains of the immunoglobulin heavy and light chains. The processes can use one or more vectors which produce both the heavy and light chains or fragments thereof in a single cell. The invention also relates to the vectors used to produce the immunoglobulin or fragment, and to cells transformed with the vectors.

47 Claims, 19 Drawing Sheets

U.S. PATENT DOCUMENTS

| | | | |
|---|---|---|---|
| 5,545,405 | A | 8/1996 | Page |
| 5,561,053 | A | 10/1996 | Crowley |
| 5,583,013 | A | 12/1996 | Itakura et al. |
| 5,585,089 | A | 12/1996 | Queen et al. |
| 5,605,689 | A | 2/1997 | Ammann |
| 5,612,185 | A | 3/1997 | Uhr et al. |
| 5,648,237 | A | 7/1997 | Carter |
| 5,686,072 | A | 11/1997 | Uhr et al. |
| 5,721,108 | A | 2/1998 | Robinson et al. |
| 5,736,137 | A | 4/1998 | Anderson et al. |
| 5,807,715 | A | 9/1998 | Morrison et al. |
| 5,840,545 | A | 11/1998 | Moore et al. |
| 5,846,818 | A | 12/1998 | Robinson et al. |
| 5,877,293 | A | 3/1999 | Adair et al. |
| 5,965,405 | A | 10/1999 | Winter et al. |
| 5,997,867 | A | 12/1999 | Waldmann et al. |
| 6,054,297 | A | 4/2000 | Carter et al. |
| 6,054,561 | A | 4/2000 | Ring |
| 6,120,767 | A | 9/2000 | Robinson et al. |
| 6,204,023 | B1 | 3/2001 | Robinson et al. |
| 6,331,415 | B1 * | 12/2001 | Cabilly et al. |
| 6,455,275 | B1 | 9/2002 | Axel et al. |
| 6,548,640 | B1 | 4/2003 | Winter |
| 6,979,556 | B2 | 12/2005 | Simmons et al. |

FOREIGN PATENT DOCUMENTS

| | | | |
|---|---|---|---|
| AU | | 12417/83 | 9/1983 |
| AU | | B-26429/84 | 10/1984 |
| AU | | 46556/85 | 3/1986 |
| AU | | 65981/86 | 5/1987 |
| EP | | 37723 | 10/1981 |
| EP | | 037723 | 10/1981 |
| EP | | 041313 | 12/1981 |
| EP | | 41313 | 12/1981 |
| EP | | 41767 | 12/1981 |
| EP | | 041767 | 12/1981 |
| EP | | 044722 | 1/1982 |
| EP | | 55945 | 7/1982 |
| EP | | 57107 | 8/1982 |
| EP | | 057107 | 8/1982 |
| EP | | 060057 | 9/1982 |
| EP | | 068763 | 1/1983 |
| EP | | 68763 | 1/1983 |
| EP | | 073656 | 3/1983 |
| EP | | 73656 | 3/1983 |
| EP | | 75444 | 3/1983 |
| EP | | 075444 | 3/1983 |
| EP | | A-073656 | 3/1983 |
| EP | | 88994 | 9/1983 |
| EP | | 093619 | 11/1983 |
| EP | | 102634 | 3/1984 |
| EP | | 0 120 694 | 10/1984 |
| EP | | 120694 | 10/1984 |
| EP | | 0 125 023 B1 | 11/1984 |
| EP | | 125023 B1 | 11/1984 |
| EP | | 0171 496 | 2/1986 |
| EP | | 173494 | 3/1986 |
| EP | | 177343 | 4/1986 |
| EP | | 194276 | 9/1986 |
| EP | | 196864 | 10/1986 |
| EP | | 234592 | 9/1987 |
| EP | | 255694 | 2/1988 |
| EP | | 36776 | 5/1988 |
| EP | | 324162 | 7/1989 |
| EP | | 114506 | 11/1989 |
| EP | | 0 365 997 | 5/1990 |
| EP | | 088994 | 6/1991 |
| EP | | 550400 | 7/1993 |
| EP | | 481790 B1 | 2/1999 |
| GB | | 2068969 | 8/1981 |
| GB | | 8308235 | 3/1983 |
| GB | | 8422238 | 9/1984 |
| GB | | 9022543 | 11/1990 |
| GB | | 08235 | 5/2000 |
| JP | | 62 201 581 | 9/1987 |
| WO | | WO 81/02426 | 9/1981 |
| WO | | WO 82/03088 | 9/1982 |
| WO | | WO 83/00164 | 1/1983 |
| WO | | WO 86/01533 | 3/1986 |
| WO | | WO 87/02671 | 5/1987 |
| WO | | WO 89/00999 | 2/1989 |
| WO | | WO 89/01783 | 3/1989 |
| WO | | WO 92/16553 | 10/1992 |
| WO | | WO 93/07899 | 4/1993 |
| WO | | WO 93/10817 | 6/1993 |
| WO | | WO 93/21319 | 10/1993 |
| WO | | 9429351 | * 12/1994 |
| WO | | WO 97/30087 | 8/1997 |
| ZA | | 8809711 | 6/1988 |

OTHER PUBLICATIONS

"Immunoglobulin molecules and genes" *Microbiology Including Immunology and Molecular Genetics*, Third edition, Harper International Edition vol. Chapter 17:338-379.

Accolla et al., "Monoclonal antibodies specific for carcinoembryonic antigen and produced by two hybrid cell lines" *Proc. Natl. Acad. Sci. USA* 77(1):563-566 (1980).

Adams et al., "Molecular cloning of mouse immunoglobulin heavy chain messenger ribonucleic acids coding for μ, α, γ1, γ2a, and γ3 chains" *Biochemistry* 19:2711-2719 (1980).

Amster et al., "Synthesis of part of a mouse immunoglobulin light chain in a bacterial clone" *Nucl. Acids Res.* 8(10):2055-2065 (1980).

Boss and Emtage, "Expression of an immunoglobulin light chain gene in *Escherichia coli*" *Gene Expression—Proc. Cetus-UCLA Symposium* pp. 513-522 (Mar. 26, 1983).

Boss and Wood, "Genetically engineered antibodies" *Immunology Today* 6 (1) : 12-13 (1985).

Colman and Morser, "Export of proteins from oocytes of *Xenopus laevis*" *Cell* 17:517-526 (1979).

Colman et al., "Interactions of mouse immunoglobulin chains within *Xenopus oocytes*" *J. Mol. Biol.* 160:459-474 (1982).

Cowan et al., "Intracellular immunoglobulin chain synthesis in non-secreting variants of a mouse myeloma: detection of inactive light-chain messenger RNA" *J. Mol. Biol.* 90:691-701 (1974).

De Boer et al ., "Construction of a tandem trp-lac promoter and a hybrid trp-lac promoter for efficient and controlled expression of the human growth hormone gene in *Escherichia coli*" *Promoters, Structure and Function* (Praeger Publishers, R. Rodriguez and M. Chamberline, eds.) pp. 462-481 (1982).

Deacon and Ebringer, "Antibody synthesis in *Xenopus oocytes* with messenger ribonucleic acid from immunized rats" *Biochem. Society Transactions* 4(4):818-820 (1976).

Dolby et al., "Cloning and partial nucleotide sequence of human immunoglobulin μ chain cDNA from B cells and mouse-human hybridomas" *Proc. Natl. Acad. Sci. USA* 77(10):6027-6031 (1980).

Eisen, "Antibody Structure: The immunoglobulins" *Immunology, An Introduction to Molecular and Cellular Principles of the Immune Responses*, Second edition, Harper & Row, Publishers, Inc. pp. 415 and 427-436 (1974).

Falkner and Zachau, "Expression of mouse immunoglobulin genes in monkey cells" *Nature* 298:286-288 (1982).

Fujisawa et al., "Direct expression of hepatitis B surface antigen gene in *E. coli*" *Nucl. Acids Res.* 11(11):3581-3591 (1983).

Glennie and Stevenson, "Univalent antibodies kill tumour cells in vitro and in vivo" (1982) *Nature* 295:712-714 (1982).

Gough et al., "Molecular cloning of seven mouse immunoglobulin κ chain messenger ribonucleic acids" *Biochemistry* 19:2702-2710 (1980).

Gough, N., "The rearrangements of immunoglobulin genes" *TIBS* 6(8):203-205 (1981).

Haley et al., "Porcine Relaxin: Molecular Cloning and cDNA Structure" *DNA* 1(2):155-162 (1982).

Hawley et al., "Mutant immunoglobulin genes have repetitive DNA elements inserted into their intervening sequences" *Proc. Natl. Acad. Sci. USA* 79:7425-7429 (1982).

Hitzeman et al., "Secretion of human interferons by yeast" *Science* 219:620-625 (1983).

Hozumi et al., "Characterization of a mouse DNA clone containing an immunoglobulin variable region gene" *Nucl. Acids Res.* (Mammalian Biochem (89:87928t) (1978)) 5(6):1779-1799.

Iserentant and Fiers, "Secondary structure of mRNA and efficiency of translation initiation" *Gene* 9:1-12 (1980).
Kadonaga et al., "The role of the β-lactamase signal sequence in the secretion of proteins by *Escherichia coli*" *Journal of Biological Chemistry* 259(4):2149-2154 (1984).
Kemp and Cowman, "Direct Immunoassay for detecting *Escherichia coli* colonies that contain polypetides encoded by cloned DNA segments" *Proc. Natl. Acad. Sci.* 78(7):4520-4524 (1981).
Kemp et al., "Processing of immunoglobulin heavy chain gene transcripts" *Manipulation and Expression of Genes in Eukaryotes* (Proceedings of an International Conference, held in conjunction with the 12th ) pp. 33-39 (1983).
Keshet et al., "Cloning of Bovine Growth Hormone Gene and Its Expression in Bacteria" *Nucleic Acids Research* 9(1):19-30 (1981).
Klein et al., "Expression of biological effector functions by immunoglobulin G molecules lacking the hinge region" *Proc. Natl. Acad. Sci. USA* 78(1):524-528 (1981).
Kohler et al., "Fusion between immunoglobulin-secreting and nonsecreting myeloma cell lines" *European Journal of Immunology* 6:292-295 (1976).
Kohler, G., "Immunoglobulin chain loss in hybridoma lines" *Proc. Natl. Acad. Sci. USA* 77(4):2197-2199 (1980).
Levy and Dilley, "Rescue of immunoglobin secretion from human neoplastic lymphoid cells by somatic cell hybridization" *Proc. Natl. Acad. Sci. USA* 75(5):2411-2415 (1978).
Lewin, B., "The extraordinary power of DNA technology" *Genes*, Third edition, John Wiley & Sons pp. 359-360 (1987).
Maniatis, T., "Molecular Cloning" *A Laboratory Manual* pp. 433 (Cold Spring Harbor L 1982).
Mercereau-Puijalon et al., "Expression of cloned eukaryotic genes in microorganisms" *Expression of Eukaryotic Viral & Cellular Genes*, Patterson et al. (eds.) pp. 295-303 (1980).
Morrison and Scharff, "Heavy chain-producing variants of a mouse myeloma cell line" *J. Immunol.* 114(2):655-659 (1975).
Morrison, J., "Sequentially derived mutants of the constant region of the heavy chain of murine immunoglobulins" *J. of Immunology* 123(2):793-800 (1979).
Mosmann and Baumal, "Synthesis but not secretion of J chain by variant mouse myeloma cells which lose α-chain-synthesizing ability" *J. Immunol.* 115(4):955-962 (1975).
Mosmann and Williamson, "Structural mutations in a mouse immunoglobulin light chain resulting in failure to be secreted" *Cell* 20:283-292 (1980).
Nisonoff and Rivers; "Recombination of a mixture of univalent antibody fragments of different specificity" *Archives of Biochemistry & Biophysics* 93:460-462 (1961).
Ochi et al., "Transfer of a cloned immunoglobulin light-chain gene to mutant hybridoma cells restores specific antibody production" *Nature* 302:340-342 (1983).
Ohsuye et al., "Expression of chemically synthesized α-neo-endorphin genefused to *E. coli* alkaline phosphatase" *Nucl. Acids Res.* 11(5):1283-1294 (1983).
Oi et al., "Immunoglobulin gene expression in transformed lymphoid cells" *Proc. Natl. Acad. Sci. USA* 80:825-829 (1983).
Picard and Schaffner, "Correct transcription of a cloned mouse immunoglobulin gene in vivo" *Proc. Natl. Acad. Sci. USA* 80:417-421 (1983).
Raso and Griffin, "Hybrid antibodies with dual specificity for the delivery of ricin to immunoglobulin-bearing target cells" *Cancer Research* 41:2073-2078 (1981).
Rice and Baltimore, "Regulated expression of an immunoglobulin κ gene introduced into a mouse lymphoid cell line" *Proc. Natl. Acad. Sci. USA* 79:7862-7865 (1982).
Roberts, TM, "A lac Promoter System for the Overexpression of Prokaryotic and Eukaryotic Genes in *E. coli*" *Promoters: Structure and Function*, Rodriguez & Chamberlin (eds.), Praeger Scientific pp. 452-461 (1982).
Robertson, M., "Chopping and changing in immunoglobulin genes" *Nature* 287:390-392 (1980).
Seidman et al., "Immunoglobulin light-chain structural gene sequences cloned in a bacterial plasmid" *Nature* 271:582-585 (1978).
Skerra and Pluckthun, "Assemby of a functional immunoglobulin $F_v$ fragment in *Escherichia coli*" *Science* 240:1038-1041 (1998).

Stevens and Williamson, "Translational Control of Immunoglobulin Synthesis; II. Cell-free interaction of myeloma immunoglobulin with mRNA" *J. Mol. Biol.* 78:517-525 (1973).
Tagunichi et al., "Expression of the human fibroblast interferon gene in *Escherichia coli*" *Proc. Natl. Acad. Sci. USA* 77 (9) :5230-5233 (1980).
Valle et al., "Anti-ovalbumin monoclonal antibodies interact with their antigen in internal membranes of *Xenopus oocytes*" *Nature* 300:71-74 (1982).
Valle et al., "Synthesis and secretion of mouse immunoglobulin chains from *Xenopus oocytes*" *Nature* 291 :338-340 (1981).
Wetzel et al., "Expression in *Escherichia coli* of a chemically synthesized gene for a "mini-C" analog of human proinsulin" *Gene* 16:63-71 (1981).
Wilde and Milstein, "Analysis of immunoglobulin, chain secretion using hybrid myelomas" *European Journal of Immunology* 10 :462-467 (1980).
Williams et al., "Cytoplasmic inclusion bodies in *Escherichia coli* producing biosynthetic human insulin proteins" *Science* 215:687-689 (1982).
Adelman et al., "In vitro deletional mutagenesis for bacterial production of the 20,000-dalton form of human pituitary growth hormone" *DNA* 2 (3) :183-193 (1983).
Adetugbo, K., "Spontaneous somatic Mutations" *Journal of Biological Chemistry* 253 (17) :6-76-6080 (1978).
Alt et al., "Activity of Multiple Light Chain Genes in Murine Myeloma Cells Producing a Single, Functional Light Chain" *Cell* 21 :1-12 (Aug. 1980)..
Alt et al., "Joining of immunoglobulin heavy chain gene segments: Implications from a chromosome with evidence of three $D-J_H$ fusions" *Proc. Natl. Acad. Sci. USA* 79 :4118-4122 (Jul. 1982).
Alt et al., "Multiple Immounglobulin Heavy-Chain Gene Transcripts in Abelson Murine Leukemia Virus-Transformed Lymphoid Cell Lines" *Molecular & Cellular Biology* 2 (4) :386-400 (Apr. 1982).
Alt et al., "Organization and Reorganization of Immunoglobulin Genes in A-MuLV-Transformed Cells: Rearrangement of Heavy but Not Light Chain Genes" *Cell* 27 :381-390 (Dec. 1981).
Altenburger et al ., "Function and non-functional joining in immunoglobulin light chain genes of a mouse myeloma" *Nature* 287:603-607 (Oct. 16, 1980).
Amzel and Poljak, "Three-dimensional structure of immunoglobulins" *Ann. Rev. Biochem.* 48 :961-967 (1979).
Astaldi et al., "Increase of hybridoma formation by human lymphocytes after stimulation in vitro; effect of antigen, endothelial cells, and PWM" *J. Immunol.* 128(6) :2539-2542 (1982).
August, "Monoclonal Antibodies—I: Discussion" *Cell Fusion: Gene Transfer and Transformation*, Beers et al. pp. 345-351 (1984).
Barnett-Foster and Painter, "The interaction of the Facb fragment with rabbit anti-sheep red cell IgG with guinea pig macrophages, and human monocytes and granulocytes" *Molecular Immunology* 19 (2) :247-252 (1982).
Bernard and Gough, "Nucleotide sequence of immunoglobulin heavy chain joining segments between translocated $V_H$ and μ constant region genes" *Proc. Natl. Acad. Sci. USA* 77(6) :3630-3634 (1980).
Bernard et al., "Plasmacytomas with more than one immunoglobulin κ mRNA: Implications for allelic exclusion" *Proc. Natl. Acad. Sci. USA* 78(9) :5812-5816 (Sep. 1981).
Bernstein et al., "Monoclonal Antibody Therapy of Mouse Leukemia" *Monoclonal Antibodies*, Kennett et al., Plenum Press pp. 275-291 (1980).
Better et al., "*Escherichia coli* secretion of an active chimeric antibody fragment" *Science* 240 :1041-1043 (1988).
Bevan et al., "Biosynthesis of immunoglobulins" *Progress in Biophysics and Molecular Biology*, Butler and Noble, Pergamon Press pp. 133-162 (1972).
Birshtein et al., "Effects of immunoglobulin structure on Fc receptor binding: a mouse myeloma variant immunoglobulin with a γ2b-γ2a hybrid heavy chain having a complete γ2a Fc region fails to bind to γ2a Fc receptors on mouse macrophages" *J. Immunol.* 129(2) :610-614 (1982).

Blythman et al., "Immunotoxins: hybrid molecules of monoclonal antibodies and a toxin subunit specifically kill tumour cells" *Nature* 290 :145-146 (1981).

Bobrzecka et al., "The method of controlled rearrangement of protein disulphides and its us for synthesis of chimeric immunoglobulin G" *Immunology Letters* 2 :151-155 (1980).

Bock et al., "Cloning and expression of the cDNA for human antithrombin III" *Nucleic Acids Research* 10(24) :8113-8125 (1982).

Bock et al., "Hybridization-selected translation of Bombyx mori high-cysteine chorion proteins in Xenopus laevis oocytes" *Proc. Natl. Acad. Sci. USA* 79 :1032-1036 (1982).

Boss et al., "Assembly of functional antibodies from immunoglobulin heavy and light chains synthesised in E. coli" *Nucleic Acids Research* 12(9) :3791-3806 (1984).

Boss et al., "Production of immunoglobulin molecules in *Escherichia coli*" *J. Cell. Biochem.* (Abstract Only) Supplement 7A:140 (0364) (1983).

Bothwell et al., "Dual expression of λ genes in the MOPC-315 plasmacytoma" *Nature* 290:65-67 (1981).

Bothwell et al., "Heavy chain variable region contribution to the $NP^b$ family of antibodies: somatic mutation evident in a γ2a variable region" *Cell* 24 :625-637 (1981).

Bothwell et al., "Somatic variants of murine immunoglobulin α light chains" *Nature* 298 :380-382 (Jul. 22, 1982).

Boulianne et al., "The production of chimeric mouse/human antibodies" *Abstracts of papers presented at the meeting on Cellular and Molecular Biology of Neoplasia* (Abstract only) pp. #25 (1983).

Boulianne et al., "Production of functional chimaeric mouse/human antibody" *Nature* 312 :643-646 (1984).

Boyd et al., "Human monoclonal antibodies—production and potential" *Trends in Biotechnology* 2(3):70-77 (1984).

Boylston et al., "Production of human IgM anti-D in tissue culture by EB-virus-transformed lymphocytes" *Scand. J. Immunol.* 12:355-358 (1980).

Bruggemann et al., "Immunoglobulin V region variants in hybridoma cells. I. Isolation of a variant with altered idiotypic and antigen binding specificity" *EMBO Journal* 1(5):629-634 (1982).

Burrows et al., "Evidence that murine pre-B cells synthesise o heavy chains but no light chains" *Nature* 280:838-841 (Aug. 30, 1979).

Cabilly et al., "Generation of antibody activity from immunoglobulin polypeptide chains produced in *Escherichia coli*" *Proc. Natl. Acad. Sci. USA* 81:3273-3277 (1984).

Chang et al., "Construction and characterization of amplifiable multicopy DNA cloning vehicles derived from the P15A crptic miniplasmid" *J. Bacteriol.* 134(3):1141-1156 (1978).

Choi et al., "RNA splicing generates a variant light chain from an aberrantly rearranged κ gene" *Nature* 286:776-779 (Aug. 21, 1980).

Coffino and Laskov, "Immunoglobulin production: method for quantitatively detecting variant myeloma cells" *Science* 167:186-188 (1970).

Coffino et al., "Suppression of Immunoglobulin Synthesis by Cellular Hybridization" *Nature New Biology* 231:87-90 (May 19, 1971).

Cook and Scharff, "Antigen-binding mutants of mouse myeloma cells" *Proc. Natl. Acad. Sci. USA* 7(12):5687-5691 (1977).

Cook et al., "Somatic mutation in a cultured mouse myeloma cell affects antigen binding" *Proc. Natl. Acad. Sci. USA* 79:1240-1244 (1982).

Cotton and Milstein, "Fusion of two immunoglobulin-producing myeloma cells" *Nature* 244 :42-43 (Jul. 6, 1973).

Croce et al., "Production of human hybridomas secreting antibodies to measles virus" *Nature* 288:488-489 (1980).

Dangl, "Rapid isolation of cloned isotype switch variants using fluorescence activated cell sorting" *Cytometry* , 2(6):395-401 (1982).

Dangl et al., "Segmental flexibility and complement fixation of genetically engineered chimeric human, rabbit and mouse antibodies" *The EMBO Journal* 7(7) :1989-1994 (1988).

De Bernardez-Clark and Georgiou, "Inclusion bodies and recovery of protein from the aggregated state" *Protein Refolding* Chapter 1:1-20 (1991).

Dildrop et al., "Immunoglobulin V region variants in hybridoma cells. II. Recombination between V genes" *EMBO Journal* 1(5) :635-640 (1982).

Duyvesteyn and De Waard, "A new sequence-specific endonuclease from a *Thermophilic cyanobacterium mastigocladus laminosus*" *FEBS Letters* 111(2) :423-426 (1980).

Duyvesteyn et al ., "Sequence-specific endonucleases in strains of anabaena and nostoc" *Arch. Microbiol.* 134 :276-281 (1983).

Early and Hood, "Mouse immunoglobulin genes" *Genetic Engineering, Principles and Methods*, Setlow and Hollaender, N.Y. and London, UK: Plenum Press vol. 3 :157-188 (1981).

Early et al., "Allelic Exclusion and Nonproductive Immunoglobulin Gene Rearrangements" *Cell* 24 :1-3 (Apr. 1981).

Early et al ., "An immunoglobulin heavy chain variable region gene is generated from three segments of DNA: $V_H$ D and $J_H$" *Cell* 19 : 981-992 (1980).

Edelman, G., "Antibody structure and molecular immunology" *Annals of the New York Academy of Sciences* 190 :5-25 (1971).

Edwards et al., "A human-human hybridoma system based on a fast-growing mutant of the ARH-77 plasma cell leukemia-derived line" *European J. Immunol.* 12 :641-648 (1982).

Ellison et al., "The nucleotide sequence of a human immunoglobulin $C_{\gamma 1}$ gene" *Nucleic Acids Research* 10(13) :4071-4079 (1982).

Ellison et al., "Nucleotide sequence of a human immunoglobulin $C_{\gamma 4}$ gene" *DNA* 1(1) :11-18 (1981).

Eshhar et al., "Induction of secretion of IgM from cells of the B cell line 38C-13 by somatic cell hybridization" *J. Immunol.* 122 (6) : 2430-2434 (1979).

Feiss et al., "Separate sites for binding and nicking of bacteriophage λ DNA by terminase" *Proc. Natl. Acad. Sci. USA* 80 :955-959 (1983).

Gillies et al., "A tissue-specific transcription enhancer element is located in the major intron of a rearranged immunoglobulin heavy chain gene" *Cell* 33 :717-728 (1983).

Givol et al., "Diversity of germ-line immunoglobulin $V_H$ genes" *Nature* 292 :426-430 (1981).

Goldsby et al., "Hybrid cell lines with T-cell characteristics" *Nature* 267 :707-708 (Jun. 23, 1977).

Gritz and Davies, "Plasmid-encoded hygromycin B resistance: the sequence of hygromycin B Phosphotransferase gene and its expression in *Escherichia coli* and *Saccharomyces cerevisiae*" *Gene* 25:179-188 (1983).

Herlyn et al., "Inhibition of Growth of Colorectal Carcinoma in Nude Mice by Monoclonal Antibody" *Cancer Research* 40 :717-721 (Mar. 1980).

Herzenberg et al., "Hybridoma Variants Affecting Isotype, Antigen Binding, and Idiotype" *Biotechnology in Diagnostics*, Koprowski et al. vol. 21 :3-16 (1985).

Herzenberg, L. *NIH Grants CA 04681-24, CA 04681-25, and Progress Reports* (1984).

Herzenberg, L., "Genetic studies with mammalian cells (mice)" *Grant ID R01CA04681 as entered into the crisp database* (Abstract only) (Sep. 3, 1992).

Herzenberg, L., "Immunoglobulins: genetics and regulation" *Grant Applications AICA 08917-15, 16, 17, 18, 19* (1978).

Hieter et al., "Cloned human and mouse kappa immunoglobulin constant and J region genes conserve homology in functional segments" *Cell* 22(Part 1) :197-207 (1980).

Honjo et al., "Cloning and complete nucleotide sequence of mouse immunoglobulin γ1 Chain Gene" *Cell* 18 :559-568 (1979).

Honjo et al., "Rearrangements of Immunoglobulin Genes during Differentiation and Evolution" *Immunological Rev*, 59 :33-67 (1981).

Hood et al., "Antibodies" *Immunology*, Forkner and Moore, Philippines:The Benjamin/Cummings Publishing Co., Inc., Chapter 3, pp. 199-221 (1978).

Horwitz et al., "Secretion of functional antibody and Fab fragment from yeast cells" *Proc. Natl. Acad. Sci. USA* 85 :8678-8682 (1988).

Houghton et al., "Detection of cell surface and intracelluar antigens by human monoclonal antibodies" *Journal of Experimental Medicine* 158 :53-65 (1983).

Howard et al., "Long-term culture of normal mouse B lumphocytes" *Proc. Natl. Acad. Sci. USA* 78(9) :5788-5792 (Sep. 1981).

Howard et al., "A Rapid Method for the Detection of Antibodies to Cell Surface Antigens: A Solid Phase Radioimmunoassay Using Cell Membranes" *Journal of Immunological Methods* 38 :75-84 (1980).

Hughes and Murray, "The nucleotide sequences recognized by endonucleases AvaI and AvaII from *Anabaena variabilis*" *Biochemical Journal* 185:65-75 (1980).

Isenman et al., "The structure and fuction of immunoglobulin domains" *J. Immunol.* 114(6):1726-1929 (1975).

Itakura and Riggs, "Chemical DNA synthesis and recombinant DNA studies" *Science* 209:1401-1405 (1980).

Jaton et al., "Conformational changes induced in a homogeneous anti-type III pneumococcal antibody by oligosaccharides of increasing size" *Biochemistry* 14(24):5312-5315 (1975).

Jones et al., "Replacing the complementarity-determining regions in a human antibody with those from a mouse" *Nature* 321:522-525 (May 1986).

Kabat et al., "Sequences of Proteins of Immunological Interest" (National Institute of Health) (1983).

Kabat, E., "Activation of the complement system and its effects on cells" *Structural Concepts in Immunology and Immunochemistry*, Second edition, Holt, Rinehart and Winston vol. Chapter 13:413-435 (1976).

Kaivarainen et al., "Hapten-induced changes in pig anti-Dansyl antibodies revealed by EPR spectra of spin-labelled antibodies" *Immunol. Letters* 3:5-11 (1981)

Kalderon et al., "Deletion loop mutagenesis: a novel method for the construction of point mutations using deletion mutants" *Nucl. Acids Res.* 10:5161-5168 (1982).

Kitai et al., "Extracellular production of human immunoglobulin G FC region" *Microbiol. Biotechnol.* (Abstract only) 28(1):52-56 (1988).

Kohl and Moore, "Human antibody-dependent cellular cytotoxicity and natural killer cytotoxicity to herpes simplex virus-infected autologous and allogeneic cells" *Immunology* 48:187-193 (1983).

Kohler and Milstein, "Continuous cultures of fused cells secreting antibody of predefined specificity" *Nature* 256:495-497 (1975).

Kohler and Milstein, "Derivation of specific antibody-producing tissue culture and tumor lines by cell fusion" *European Journal of Immunology* 6:511-519 (1976).

Konieczny et al., "The combination of IgM subunits and proteolytic IgG fragments by controlled formation of interchain disulphides" *Haematologia* 14(1):95-99 (1981).

Koskimies, S., "Human lymphoblastoid cell line producing specific antibody against Rh-antigen D" *Scand. J. Immunol.* 11:73-77 (1980).

Kuehl, W.M., "Light chain fragments: aberrant expression of immunoglobulin genes" *TIBS* pp. 206-208 (Aug. 1981).

Kwan, "Two Kappa Immunoglobulin Genes Are Expressed in the Myeloma S107" *Cell* 26:57-66 (Oct. 1981).

Larson et al., "*Saccharomyces cerevisiae* actin-*Escherichia coli* lacZ gene fusions: synthetic-oligonucleotide-mediated deletion of the 309 base pair intervening sequence in the actin gene" *Gene* 22:31-39 (1983).

Laskov and Scharff, "Synthesis, assembly, and secretion of gamma globulin by mouse myeloma cells" *Journal of Experimental Medicine* 131(3):515-541 (1970).

Laskov et al., "Induction of amplified synthesis and secretion of IgM by fusion of murine B Lymphoma with myeloma cells" *Proc Natl. Acad. Sci. USA* 76(2):915-919 (Feb. 1979).

Lau and Doolittle, "Aqu I: a more easily purified isoschizomer of AVA I" *FEBS Letters* 121(2):200-202 (1980).

Leder, P., "The genetics of antibody diversity" *Scientific America* 246:72-83 (1982).

Levy and Miller, "Tumor therapy with monoclonal antibodies" *Fed. Proc.* 42:2650-2656 (1983).

Liu et al., "Chimeric mouse-human IgG1 antibody that can mediate lysis of cancer cells" *Proc. Natl. Acad. Sci. USA* 84:3439-3443 (May 1987).

Maniatis, T., "Recombinant DNA procedures in the study of eukaryotic genes" *Cell Biol.* 3:563-608 (1980).

Margulies et al., "Regulation of immunoglobulin expression in mouse myeloma cells" *Immunoglobulin Expression* pp. 781-791.

Margulies et al., "Somatic Cell Hybridization of Mouse Myeloma" *Cell* 8:405-415 (Jul. 1976).

Martinis et al., "Monoclonal antibodies with dual antigen specificity" *Oncology* pp. 311-316.

Mather et al., "Transcriptional regulation of immunoglobulin V genes" *Nucleic Acids Research* 9 (24):6855-6867 (1981).

Matsuuchi and Morrison, "Antigen binding variants of mouse plasmacytoma J558" *Fed. Proc.*(Abstract only) 37:1763 (2703) (1978).

Max et al., "Variation in the Crossover Point of Kappa Immunoglobulin Gene V-J Recombination: Evidence from a Cryptic Gene" *Cell* 21:793-799 (Oct. 1980).

Melchers, F., "Biosynthesis of the carbohydrate portion of immunoglobulin radiochemical and chemical analysis of the carbohydrate moieties of two myeloma proteins purified from different subcellular fractions of plasma cells" *Biochemistry* 10(4):653-659 (1971).

Messing et al., "A System or Shotgun DNA Sequencing" *Nucleic Acids Research* 9 (2):309-321 (1981).

Milstein et al, "Clonal Variants of Myeloma Cells" *Progress in Immunology II* 1:157-168 (1974).

Mohit and Fan, "Hybrid Cell Line from a Cloned Immunoglobulin-Producing Mouse Myeloma and a Nonproducing Mouse Lymphoma" *Science* 171:75-77 (Jan. 8, 1971).

Morrison, "Transfectomas Provide Novel Chimeric Antibodies" *Science* 229:1202-1207 (1985).

Morrison and Oi, "Transfer and expression of immunoglobulin genes" *Annual Review of Immunology* 2:239-256 (1984).

Morrison and Scharff, "Mutational events in mouse myeloma cells" *Critical Reviews in Immunology* 3 (1):1-22 (1981).

Morrison, S. L. et al., "Chimeric human antibody molecules: mouse antigen-binding domains with human constant region domains" *Proc. Natl. Acad. Sci. USA* 81(21):6851-6855 (Nov. 1984).

Nakabayashi et al., "The transforming function of bovine papillomavirus DNA" *Proc. Natl. Acad. Sci. USA* 80:5832-5836 (1983)..

Neuberger, "Switch from hapten-specific immunoglobulin M to immunoglobulin D secretion in a hybrid mouse cell line" *Proc. National. Acad. Sci USA* 78(2):1138-1142 (1981).

Neuberger et al., "Recombinant antibodies possessing novel effector functions" *Nature* 312 (5995):604-608 (Dec. 1984).

Neuberger, M. S. et al., "A hapten-specific chimaeric IgE antibody with human physiological effector function" *Nature* 314:268-270 (Mar. 1985).

Ochi et al., "Functional immunoglobulin M production after transfection of cloned immunoglobulin heavy and light chain genes into lymphoid cells" *Proc Natl Acad. Sci. USA* 80:6351-6355 (1983).

Oi et al., "Correlation between segmental flexibility and effector function of antibodies" *Nature* 307:136-140 (1984).

Oi et al., "Localization of Murine Igh-1$^a$ Allotypic Determinants by Using a Panel of Mouse Myeloma Variant Immunoglobulins" *Journal of Immunology* 130(4):1967-1969 (Apr. 1983).

Oi et al., "Lymphocyte membrane IgG and secreted IgG are structurally and allotypically distinct" *Journal of Experimental Medicine* 151:1260-1274 (1980).

Olsson and Kaplan, "Human-human hybridomas producing monoclonal antibodies of predefined antigenic specificity" *Proc. Natl Acad. Sci. USA* 77(9):5429-5431 (1980).

Orna Zemel-Dreasen et al., "Secretion and processing of an immunoglobulin light chain in *Escherichia coli*" *Gene* 27(3):315-322 (1984).

Parham et al., "Isolation of Heavy Chain Class Switch Variants of a Monoclonal Anti-DC1 Hybridoma Cell Line: Effective Conversion of Noncytotoxic IgG$_1$ Antibodies to Cytotoxic IgG$_2$ Antibodies" *Human Immunology* 8:141-151 (1983).

Peden and Nathans, "Local mutagenesis within deletion loops of DNA heteroduplexes" *Proc. Natl. Acad. Sci. USA* 79:7214-7217 (1982).

Perlman, "IgG Synthesis in Hybrid Cells from an Antibody-producing Mouse Myeloma and an L Cell Substrain" *Nature* 228:1086-1087 (Dec. 12, 1970).

Perry et al., "Transcription of mouse κ chain genes: implications for allelic exclusion" *Proc. Natl. Acad. Sci. USA* 77 (4):1937-1941 (1980).

Plaut et al., "Immunoglobulin M: Fixation of human complement by the Fc Fragment" *Science* 176:55-56 (1972).

Ponte et al., "Transcription of immunoglobulin heavy-chain sequences from the excluded allele" *Nature* 291:594-596 (1981).

Raschke et al., "Assembly and secretion of pentameric IgM in a fusion between a nonsecreting B cell lymphoma and an IgG-secreting plasmacytoma" *Proc. Natl. Acad. Sci. USA* 76(7) :3469-3473 (1979).

Rechavi et al., "Evolutionary aspects of immunoglobulin heavy chain variable region ($V_H$ gene subgroups" *Proc. Natl. Acad. Sci. USA* 80 : 855-859 (1983).

Reth et al., "Analysis of the repertoire of anti-NP antibodies in C57BL/6 mice by cell fusion" *European Journal of Immunology* 8 : 393-400 (1978).

Riley et al., "Induction of light chain expression in a pre-B cell line by fusion to myeloma cells" *Nature* 289:804-806 (1981).

Robins et al., "Regulated Expression of Human Growth Hormone Genes in Mouse Cells" *Cell* 29 :623-631 (1982).

Roizes, "A new specific endonuclease from *Anabaena variabilis*" *FEBS Letters* 104 (1) :39-44 (1979).

Rybarska et al., "The Hemolytic Activity of (Fab-Fc) Recombinant Immunoglobulins with Specificity for the Sheep Red Blood Cells" *Immunology Letters* 4 :279-284 (1982).

Sakano et al., "Domains and the hinge region of an immunoglobulin heavy chain are encoded in separate DNA segments" *Nature* 277 : 627-633 (1979).

Schlom et al., "Generation of human monoclonal antibodies reactive with human mammary carcinoma cells" *Proc. Natl. Acad. Sci. USA* 77 (11) :6841-6845 (1980).

Schroder et al., "Florescence-activated cell sorting of mouse-human hybrid cells aids in locating the gene for the Leu 7 (HNK-1) antigen to human chromosome 11" *Proc. Natl. Acad. Sci. USA* 80 :3421-3424 (Jun. 1983).

Schwaber and Cohen, "Human x mouse somatic cell hybrid clone secreting immunoglobulins of both parental types" *Nature* 244 :444-447 (1973).

Schwaber and Cohen, "Pattern of Immunoglobulin synthesis and assembly in a human-mouse somatic cell hybrid clone" *Proc. Natl. Acad. Sci. USA* 71 (6) :2203-2207 (1974).

Schwaber, J., "Immunoglobulin production by a human-mouse somatic cell hybrid" *Experimental Cell Research* 93 :343-354 (1975).

Schwartz et al., "Multiple expression of Ig λ-chain encoding RNA species in murine plasmacytoma cells" *J. Immunol.* 126 (6) :2104-2108 (1981).

Sears et al., "Phase-I clinical trial of monoclonal antibody in treatment of gastrointestinal tumours" *Lancet* pp. 762-765 (1982).

Secher et al ., "Somatic mutants and antibody diversity" *Immunological Rev.* 36 :51-72 (1977.

Seidman and Leder, "The arrangement and rearrangement of antibody genes" *Nature* 276 :790-795 (1978).

Seidman and Leder, "A mutant immunoglobulin light chain is formed by aberrant DNA- and RNA-splicing events" *Nature* 286 :779-783 (1980).

Seidman et al., "Multiple related immunoglobulin variable-region genes identified by cloning and sequence analysis" *Proc. Natl. Acad. Sci. USA* 75 (8) :3881-3885 (1978).

Seidman et al., "A κ-immunoglobulin gene is formed by site-specific recombination without further somatic mutation" *Nature* 280 :370-375 (1979).

Sharon et al., "Expression of a $V_H-C_{-\kappa}$ chimaeric protein mouse myeloma cells" *Nature* 309 :364-367 (1984).

Shine et al., "Expression of cloned β-endorphin gene sequences by *Escherichia coli*" *Nature* 285 :456-461 (1980).

Shulman *9th Annual Meeting of the Clinical Ligand Assay Society* (Alleged oral presentation Mar. 13-17, 1983, Philadelphia, Pennsylvania) (1983).

Shulman and Kohler, "Fusion of Immunoglobulin Secreting Cells" *Cells of Immunoglobulin Synthesis*, Pernis and Vogel, Academic Press pp. 275-293 (1979).

Siddiqui, M., "Recombinant DNA technology and its application to developmental biology" *J. Craniofacial Genetics and Developmental Biology* 2 :75-92 (1982).

Sninsky et al., "Construction and characterization of a novel two-plasmid system for accomplishing temperature-regulated, amplified expression of cloned adventitious genes in *Escherichia coli*" *Gene* 16 :275-286 (1981).

Sonenshein et al., "Control of immunoglobulin secretion in the murine plasmacytoma line MOPC 315" *Journal of Experimental Medicine* 148 :301-312 (1978).

Stark et al., "Site-directed mutagenesis of ribosomal RNA" *J. Mol. Biol.* 159 :417-439 (1982).

Steinmetz et al., "Cloning of V region fragments from mouse liver DNA and localization of repetitive DNA sequences in the vicinity of immunoglobulin gene segments" *Nucleic Acids Research* 8 :1709-1720 (1980).

Tanaka et al., "Isolation and characterization of polyoma virus mutants which grow in murine embryonal carcinoma and trophoblast cells" *EMBO Journal* 1 (12) :1521-1527 (1982).

Tao et al., "Role of Carbohydrate in the Structure and Effector Functions Mediated by the Human IgG Constant Region" *J. Immunol.* 143 (8) :2595-2601 (1989).

Teng et al., "Construction and testing of mouse-human heteromyelomas for human monoclonal antibody production" *Proc. Natl. Acad. Sci USA* 80 :7308-7312 (1983).

Tonegawa et al., "Cloning of an immunoglobulin variable region gene from mouse embryo" *Proc. Natl. Acad. Sci. USA* 74 (8) :3518-3522 (1977).

Tonegawa et al., "Sequence of a mouse germ-line gene for a variable region of an immunoglobulin light chain" *Proc. Natl. Acad. Sci. USA* 75(3):1485-1489 (1978).

Tucker et al ., "Structure of the constant and 3' untranslated regions of the murine γ2b heavy chain messenger RNA" *Science* 206:1299-1303 (1979).

Underbrink-Lyon et al., "Characterization of a yeast *Mitochondrial locus* necessary for tRNA biosynthesis" *Mol. Gen. Genet.* 191:512-518 (1983).

Uracz et al., "The use of Fab-Fc recombinant antibodies for studying the mechanism of triggering the effector activities of immunoglobulins" *Immunology Letters* 7:215-220 (1984).

Wagener et al., "Monoclonal antibodies for carcinoembryonic antigen and related antigens as a model system: a systematic approach for the determination of epitope specificities of monoclonal antibodies" *J Immunol.* 130(5):2308-2315 (1983).

Wall, R. and Kuehl, M., "Biosynthesis and regulation of immunoglobulins" *Annual Review of Immunology* 1 :393-422 (1983).

Wallace et al., "Directed deletion of a yeast transfer RNA intervening sequence" *Science* 209:1396-1400 (1980).

Wallach et al., "Analysis of immunoglobulin mRNA in murine myeloma cell variants defective in the synthesis of the light or heavy polypeptide chains" *J. Immunol.* 128(2) :684-689 (1982).

Watson et al., "In vitro growth of B lymphocytes infiltrating human melanoma tissue by transformation with EBV: evidence for secretion of anti-melanoma antibodies by some transformed cells" *J. Immunol* 130 (5) :2442-2447 (1983).

Weatherall and Clegg, "Recent developments in the molecular genetics of human hemoglobin" *Cell* 16 :467-479 (1979).

Weck et al., "Antiviral activities of hybrids of two major human leukocyte interferons" *Nucleic Acids Research* 9 (22) :6153-6166 (1981).

Weiss and Green, "Human-mouse hybrid cell lines containing partial complements of human chromosomes and functioning human genes" *Proc. Natl. Assoc. Sci. USA* 58:1104-1111 (1967).

Wetzel, R., "Active immunoglobulin fragments synthesized in *E. coli*—from Fab to Scantibodies" *Protein Engineering* 2 (3) :169-176 (1988).

Whitlock and Witte, "Long-term culture of B lymphocytes and their precursors from murine bone marrow" *Proc. Natl. Acad. Sci. USA* 79 :3608-3612 (1982).

Winberry et al., "Immunoglobulin production and secretion by variant clones of the MOPC 315 mouse myeloma cell line" *J. Immunol .* 124(3) :1174-1182 (1980).

Wood et al., "The synthesis and in vivo assembly of functional antibodies in yeast" *Nature* 314 :446-449 (1985).

Word et al., "Expression of surface and secreted $IgG_{2a}$ by a murine B-lymphoma before and after hybridization to myeloma cells" *Molecular Immunology* 18(4) :311-322 (1981).

Yamawaki-Kataoka, "Complete nucleotide sequence of immunoglobulin γ2b chain gene cloned from newborn mouse DNA" *Nature* 283 :786-789 (1980).

Yamawaki-Kataoka et al., "The complete nucleotide sequence of mouse immunoglobulin γ2a gene and evolution of heavy chain genes: furhter evidence for intervening sequence-mediated domain transfer" *Nucleic Acids Research* 9(6) :1365-1381 (1981).

Yamawaki-Kataoka et al., "Nucleotide sequences of gene segments encoding membrane domains of immunoglobulin γ chains" *Proc. Natl— Acad. Sci. USA* 79 :2623-2627 (1982).

Zakut et al., "Cloning and sequence of the cDNA corresponding to the variable region of immunoglobulin heavy chain MPC11" *Nucleic Acids Research* 8 (16) :3591-3601 (1980).

Zav'yalov et al., "Correspondence between structure and function of immunoglobulin G subclasses" *Haematologia* 14 (1) :85-94 (1981).

"Affidavit of Allan Robert dated Aug. 11, 1994, with enclosures" (1994).

"Declaration of Allan E. Connor dated May 16, 1996, with enclosures" (1996).

"Declaration of Christoph H. Heusser dated May 21, 1996" (1996).

"Declaration of J. Steven Whitaker dated Jun. 23, 1994 with enclosures" (1994).

"Declaration of Lars Abrahmsen dated May 23, 1996" (1996).

"Declaration of Leon R. Lyle dated Aug. 9, 1994, with enclosures" (1994).

"Declaration of March J. Schulman dated May 15, 1996, with enclosures" (1996).

"Declaration of Robert G. Hamilton dated May 16, 1996" (1996).

"Declaration of Theodore T. Herhold dated Jun. 23, 1994, with enclosures" (1994).

"Declaration of Theophil Staehelin dated May 22, 1996" (1996).

"Declaration of Vernon T. Oi of May 1995, with enclosures" (1995).

Uhlen et al., "Gene fusion vectors based on the gene for staphylococcal protein A" *Gene* 23 :369-378 (1983).

Ellison et al., "Linkage and sequence homology of two human immunoglobulin gamma heavy chain constant region genes" *Proc. Natl. Acad. Sci. USA* 79 :1984-1988 (Mar. 1982).

Fiers et al., "Complete Nucleotide Sequence of SV40 DNA" *Nature* 273 :113-120 (May 11, 1978).

Gluzman, Yakov, "SV40-Transformed Simian Cells Support the Replication of Early SV40 Mutants" *Cell* 23 :175-182 (Jan. 1981).

Graham et al., "A New Technique for the Assay of Infectivity of Human Adenovirus 5 DNA" *Virology* 52 :456-467 (1973).

Hedin et al., "Specificities and Binding Properties of Eight Monoclonal Antibodies Against Carcinoembryonic Antigen" *Molecular Immunology* 19 :1641-1648 (1982).

Inouye et al., "Signal Sequence of Alkaline Phosphatase of *Escherichia coli* " *J. Bacteriol.* 149 :434 (1982).

Kipps et al., "Allotype Switch Variants in Cultured Monoclonal Producing Hybridomas" *Journal of Cellular Biochemistry* (abstract only) pp. 163 (—1984).

Kupchik et al., "Monoclonal Antibodies to Carcinoembryonic Antigen Produced by Somatic Cell Fusion" *Cancer Research* 41 :3306-3310 (Sep. 1981).

Lee et al., "Characterization of the Gene Encoding Heat-Stable Toxin II and Preliminary Molecule Epidemiological Studies of Enterotoxigenic *Escherichia coli* Heat-Stable Toxin II Producers" *Infection and Immunity* 42 :264-268 (Oct. 1983).

Liu, Pinghui V., "Pseudomonas Toxins" *J. Infect. Dis.* 130 :S94-S99 (1974).

McCutchan et al., "Enhancement of the Infectivity of Simian Virus 40 Deoxyribonucleic Acid with Diethlaminoethyl-Dextran" *J. Natl. Cancer Institute* 41 :351-356 (1968).

Mertz et al., "Defective Simian Virus 40 Genomes: Isolation and Growth of Individual Clones" *Virology* 62 :112-124 (1974).

Movva et al., "Amino Acid Sequence of the Signal Peptide of ompA Protein, a Major Outer Membrane Protein of *Eschericha coli*" *The Journal of Biological Chemistry* 255 :27-29 (Jan. 10, 1980).

Oi et al., "Hybridoma Antibody-Producing Switch Variant as A Variant Lacking the CH1 Domain" *Cell Fusion: Gene Transfer and Transformation*, R. F. Beers, Jr. and E.G. Bassett, Raven Press, New York pp. 281-287 (1984).

Palva et al., "Secretion of interferon by *Bacillus subtilis*" *Gene* 22 : 229-235 (1983).

Picken et al., "Nucleotide sequence of the gene for heat-stable enterotoxin II of *Escherichia coli*" *Infection and Immunity* 42 (1) : 269-275 (1983) .

Watson, Marion E.E., "Compilation of published signal sequences" *Nucleic Acids Research* 12 :5145-5164 (1984).

Wigler et al., "Transformation of Mammalian Cells with Genes from Procaryotes and Eucaryotes" *Cell* 16 :777-785 (Apr. 1979).

"Fundamental Immunology, 2nd Edition, William E. Paul, M.D., Editor" pp. 209 (1989).

"Fundamental Immunology, 3rd edition, William E. Paul, M.D., Editor" pp. 285-286 (1993).

"Fundamental Immunology, 1st Edition, William E. Paul, M.D. Editor" pp. 137 (1984).

Abbas et al., "Cellular and Molecular Immunology, Second Edition" pp. 38-39 (1994).

Adair et al., "Engineering Antibodies for Therapy" *Immunological Reviews* 130:5-40 (1992).

Boyden, Alan, "Homology and Analogy" *Science* 164:455-456 (Apr. 1969).

Dover, Gabby, "Nonhomologous Views of a Terminology Muddle" *Cell* 51:515-516 (Nov. 20, 1987).

Gupta et al., "General Orientation of Human Lymphocyte Subpopulations" *Clinical Immunobiol.*, Bach and Good, Academic Press vol. 4 :1-18 (1980).

Hunkapiller et al., "The growing immunoglobulin gene superfamily" *Nature* 323:15-16 (1986).

Lewin, Roger, "When Does Homology Mean Something Else?" *Science* 237:1570 (1987).

Reeck et al., "Homology in Proteins and Nucleic Acids: A Terminology Muddle and a Way out of it" *Cell* 50 (Aug. 28, 1987).

Strominger et al., "An Evaluation of the Significance of Amino Acid Sequence Homologies in Human Histocompatibility Antigens (HLA-A and HLA-B) with Immunoglobulins and Other Proteins, Using Relatively Short Sequences" *Scand. J. Immunol* . 11 :573-592 (1980).

Takahashi et al., "Structure of Human Immunoglobulin Gamma Genes: Implications for Evolution of a Gene Family" *Cell* 29 :671-679 (1982).

French deposition transcript (Feb. 27, 2002).

Expert Report of Jay Unkeless, Ph.D., with Exhibit A (Dec. 6, 2001).

Declaration of Jay Unkeless, Ph.D. in Support of Genentech's Claim Construction Brief, with Exhibit A (Jan. 22, 2002).

Unkeless deposition transcript (Feb. 21, 2002).

Expert Report of Gerald H. Bjorge, Esq, with Exhibits A-D (Dec. 7, 2001).

Expert Report of Jeffrey P. Kushan, with Exhibits A and B (Dec. 7, 2001).

Declaration of Jeffrey Kushan in support of Genentech's claim construction brief, with Exhibit A (Jan. 22, 2002).

Kushan deposition transcript (Feb. 21, 2002).

Rebuttal Expert Report of John Robert Adair, Ph.D., with Exhibits A-P (Jan. 25, 2002).

Adair deposition transcript (Feb. 19, 2002).

Rebuttal Expert Report of Lewis L. Lanier Ph.D (Jan. 28, 2002), with Exhibit A.

Rebuttal Expert Report of William J. Harris Ph.D (Jan. 27, 2002), with Exhibit A.

Supplemental Expert Report of William J. Harris, Ph.D (Jun. 28, 2002).

Larrick deposition transcript (Nov. 20, 2001).

Memorandum of Points and Authorities in Support of Genentech's Motion for Summary Judgment re Invalidity for Anticipation and Lack of Priority, with Separate Statement of Undisputed Facts in support thereof (May 6, 2002).

Defendant Genentech, Incs.'s Opposition to Chiron's Motion for Summary Judgment re Priority and Defenses and Counterclaims under 35 USC §§ 112, 101, and Cross Motion for Summary Judgment, with Response to Chiron's Separate Statement of Undisputed Facts (May 20, 2002).

Genentech's Oppositions to Chiron's Motions in Limine (Phase I) (Jul. 26, 2002).

Cetus Internal Memo (May 26, 1982).
Cetus Internal Memo (Mar. 27, 1984).
Cetus Internal Memo (Jul. 17, 1984).
Cetus Internal Memo (Mar. 27, 1984).
Cetus Internal Memo (Aug. 8, 1983).
Cetus Internal Memo (May 26, 1982).
Cetus Internal Memo (Aug. 17, 1983).
Project Proposal—CRAC Meeting (Nov. 10, 1983) (from Cetus).
Genentech's Claim Construction Brief (Jan. 22, 2002), with Genentech's Claim Construction Statement (Dec. 21, 2001).
Decision on Petition, Interference No. 102,572, filed Apr. 4, 2003 (Paper No. 85).
Decision on Petition, Interference No. 102,572, filed Apr. 4, 2003 (Paper No. 86).
Celltech Limited's Notice of Opposition, filed Apr. 19, 1994.
MedImmune, Inc.'s Demand for Jury Trial, Case No. CV-03-2567, dated Apr. 11, 2003.
Grounds of Opposition filed on Behalf of Genentech, Inc. in Respect of Their Opposition to EP-B-0120694 (84301996.9) in the Name of Celltech Limited and entitled 'Processes for the Production of Multichain Polypeptides or Proteins', filed Apr. 19, 1994.
Transcript of Proceedings Before the Honorable Gregory G. Hollows United States Magistrate Judge Hearing *Markman* Hearing (Mar. 6, 2002).
Transcript of Proceedings Before the Honorable Gregory G. Hollows United States Magistrate Judge Hearing *Markman* Hearing (Mar. 7, 2002).
Reporter's Daily Transcript Jury Trial (Aug. 6, 2002).
Reporter's Daily Transcript Jury Trial (Aug. 8, 2002).
Reporter's Daily Transcript Jury Trial (Aug. 9, 2002).
Reporter's Daily Transcript Jury Trial (Aug. 12, 2002).
Reporter's Daily Transcript Jury Trial (Aug. 13, 2002).
Reporter's Daily Transcript Jury Trial (Aug. 14, 2002).
Reporter's Daily Transcript Jury Trial (Aug. 16, 2002).
Reporter's Daily Transcript Jury Trial (Aug. 20, 2002).
Reporter's Daily Transcript Jury Trial (Aug. 21, 2002).
Reporter's Daily Transcript Jury Trial (Aug. 22, 2002).
Reporter's Daily Transcript, Jury Trial (Sep. 3, 2002).
Reporter's Daily Transcript, Jury Trial (Sep. 4, 2002).
Expert Report of Deborah L. French,. Ph.D., with Exhibits A, B, C (Dec. 6, 2001).
Rebuttal Expert Report of Deborah L. French, Ph.D (Jan. 25, 2002).
Supplemental Export Report of Deborah L. French Ph.D. (Jul. 3, 2002).
Declaration of Lewis L. Lanier, Ph.D. with Exhibits A-B (Jan. 8, 2002).
Declaration of Lewis L. Lanier, Ph.D. In Support of Chiron's Oppositions to Genentech's Motions for Summary Judgment (May 20, 2002).
Lanier deposition transcript (Feb. 14, 2002).
Harris deposition transcript (Feb. 27, 2002).
Declaration of William J. Harris, Ph.D. in Support of Chiron's Replies to Summary Judgment Oppositions, with Exhibits A-D (May 27, 2002).
Magistrate's Findings and Recommendations (*Markman* Hearing) (Mar. 20, 2002).
Genentech's Post-Hearing *Markman* Submission (Mar. 12, 2002).
Genentech's Objections to Magistrate's Findings & Recommendations (*Markman* Hearing) (Apr. 1, 2002).
Genentech's Response to Chiron's Objection and Magistrate's Findings & Recommendations [*Markman* Hearing](Apr. 8, 2002), with attached Exhibits.
Memorandum and Order (*Markman*) (Apr. 22, 2002).
Genentech's Reply in Support of its Motion for Summary Judgment re Invalidity for Anticipation and Lack of Priority (May 28, 2002).
Reporter's Transcript, Motion to Preclude Admission of Undisclosed License Agreements and Cross Motions for Summary Judgment (Monday, Jun. 3, 2002).
Memorandum and Order re: Priority, Anticipation, Written Description, Enablement, Best Mode, Utility (Jun. 24, 2002).

Chiron's Motion for Clarification regarding Memorandum and Order re: Priority, Anticipation, Written Description, Enablement, Best Mode, Utility, or, in the alternative, Motion-for Reconsideration (Jul. 3, 2002).
Genentech's Second Supplemental Response to Chiron's Interrogatory No. 25 (May 13, 2002).
Genentech Inc.'s Proposed Jury Instructions (Phase I) (Jul. 26, 2002).
Genentech Inc.'s Responsive Trial Brief (Jul. 26, 2002).
Genentech's Objections to Chiron's Proposed Jury Instructions (Phase I) (Aug. 16, 2002).
Genentech' Inc.'s Memorandum of Points and Authorities in Support of Objections to Chiron's Proposed Limiting Instruction (Aug. 9, 2002).
Genentech Inc.'s Request for a Remedial Jury Instruction, with Exhibits A-C (Aug. 12, 2002).
Memorandum of Points and Authorities Supporting Genentech's Motion for Judgment as a Matter of Law Under Fed. R. Civ. P.50(A) (Sep. 3, 2002).
Genentech's Opposition to Chiron's Motion for Judgment as a Matter of Law Under Fed. R. Civ. P.50(A), with attached testimony cited to therein (Aug. 16, 2002).
Memorandum and Order Re: Rule 50 Motions (Sep. 11, 2002).
Genentech's Opposition to Chiron's Rule 50/59 Motion, with Attached Appendix of transcript and trial transcript pages cited to therein (Oct. 7, 2002).
Memorandum and Order Re: Renewed Motion for JMOL; Motion for New Trial (Oct. 22, 2002).
Brief of Defendant-Cross-Appellant, Genentech, Inc. (May 12, 2003).
Reporter's Transcript, Motion to Dismiss, Monday (May 21, 2001).
Memorandum and Order (May 22, 2001).
Fleischman, J. *BioScience Reports* 5:893-899 (1985).
Kohler, G. *BioScience Reports* 5:533-549 (1985).
Marx, J. *Science* 229:455-456 (1985).
Neuberger, M. *TIBS* 347-349 (1985).
Oi & Morrison *Bio Techniques* 4(3):214-211 (1986).
Takeda et al. *Nature* 314:452-454 (1985).
Morrison, S. *Hospital Practice* 24(10):65-80 (1989).
Morrison et al. *Clin. Chem.* 34/9:1668-1675 (1988).
Tan et al. *J. Immunol.* 135(5):3564-3567 (1985).
Slide entitled "18 Publications Discussing Chimeric Monoclonal Antibodies Before the 1986 Application", presented at Jury trial (2002).
Cheng et al., "Effect of deglycosylation on the binding and immunoreactivity of human thyroxine-binding globulin", Journal of Biological Chemistry, 254(18):8830-8835 (Sep. 25, 1979).
DeBoer et al., "Construction of a Tandem trp-lac Promoter and a Hybrid trp-lac Promoter for Efficient and Controlled Expression of the Human Growth Hormone Gene in *Escherichia coli*", Promoters: Structure and Function, New York, Praeger, pp. 462-481 (1982).
"Decision of the Technical Board of Appeal 3.3.4 of May 14, 2001" (Regarding EP-B 125,023, Sep. 17, 2001) correction to the decision is attached.).
"Decision on preliminary and other motions and final judgment", *Glaxo Wellcome, Inc. v. Shmuel Cabilly, Herbert L. Heyneker, William E. Holmes, and Ronald B. Wetzel* (Patent Interference No. 104,532) (Sep. 4, 2002).
"Final Order After District Court Judgment" *Cabilly et al. v. Boss et al.* (Patent Interference 102,572) (Jul. 25, 2001).
Office Action dated May 27, 1999 from Cabilly's patent application U.S. Appl. No. 08/909,611 (Paper 14).
Declaration of John Ridgway dated Jun. 17, 1999 (with attached Exhibit A) from Cabilly's U.S. Appl. No. 08/909,611 (Paper 15).
Interview Summary dated Jun. 22, 1999 from Cabilly's U.S. Appl. No. 08/909,611 (Paper 16).
Interview Summary dated Jul. 12, 1999 from Cabilly's U.S. Appl. No. 08/909,611 (Paper 17).
Office Action dated Mar. 2, 2000 from Cabilly's U.S. Appl. No. 08/909,611 (Paper 18).
Cabilly U.S. Appl. No. 06/483,457 as originally filed Apr. 8, 1983.
Estabrook, A. and J. A. K. Patterson. 1983. Immunotherapy using monoclonal antibodies. J of Cutaneous Pathology 10:559-66.

Maniatis, T., E.F. Fritsch, and J. Sambrook. 1982. Table of Contents; "Extraction, Purification, and Analysis of MRNA from Eukaryotic Cells", 187-209; "Synthesis and Cloning of CDNA", 211-246; and "Construction of Genomic Libraries", 269-307. In Molecular Cloning A Laboratory Manual, New York: Cold Spring Harbor Laboratory.

Maniatis, T., E.F. Fritsch, and J. Sambrook. 1989. Table of Contents; "Expression of Cloned Genes in Cultured Mammalian Cells", 16.1-16.8 1; "Expression of Cloned Genes in *Escherichia coli*", 17.1-17.44. In Molecular Cloning A Laboratory Manual. 2 ed. New York: Cold Spring Harbor Laboratory.

Headings in the Cabilly Application.

Curriculum Vitae of Dr. Richard Youle.

Declaration 1 of Dr. Richard Youle.

Hale et al. 1988. Remission induction in nonHodgkin lymphoma with reshaped human monoclonal antibody CAMPATH-I H. Lancet 2 (8625):1394-1399.

Kipriyanov et al. 1999. Generation of recombinant antibodies. Molecular Biotechnology 12:173-201.

CD Molecules printout ("Human cell surface molecule recognized by the International Workshops on Human Leukocyte Differentiation Antigens").

Renner et al. 1997. Monoclonal antibodies in the treatment of non-Hodgkin's lymphoma: recent results and future prospects. Leukemia 11(2):S55-S59.

Greipp, P. 1992. Advances in the diagnosis and management of myeloma. Seminars in Hematology 29(3: Suppi. 2):24-45.

Leatherbarrow et al. 1985. Effector functions of a monoclonal aglycosylated mouse IgG2a: binding and activation of complement component C I and interaction with human monocyte Fc receptor. Molecular Immunology 22(4):407-415.

Nose, M. and H. Wigzell. 1983. Biological significance of carbohydrate chains on monoclonal antibodies. Proc. Natl. Acad. ScL USA 80:6632-6636.

Geochee, C. F., and T. Monica. 1990. Environmental effects on protein glycosylation. BiolTechnology 8:421-427.

Van Brunt, J. 1986. There's nothing (quite) like the real thing. BiolTechnology 4:835-839.

Geisse et al. 1996. Eukaryotic expression systems: a comparison. Protein Expression and Purification 8:271-282.

Dean, C.J. 1994. Preparation and characterization of monoclonal antibodies to proteins and other cellular components. Methods in Molecular Biology 32:361-379.

Raju et al. 2000. Species-specific variation in glycosylation of IgG: evidence for the species-specific sialylation and branch-specific galactosylation and importance for engineering recombinant glycoprotein therapeutics. Glycobiology 10(51:477-486.

Vitetta Declaration 1 (Dr. Ellen Vitetta).

Alberts et al. Molecular Biology of the Cell, pp. 285 and 375. Garland Publishing, Inc., (1983).

Urlaub, G. and L. A. Chasin. 1980. Isolation of Chinese hamster cell mutants deficient in dihydrofolate reductase activity. Proc. NatL Acad Sci. USA 77:4216-4220.

Hodge, J.W. 1996. carcinoembryonic antigen as a target for cancer vaccines. Cancer Immunol and Immunother 43:127-134.

Lifely Declaration Apr. 6, 1994.

Wickens et al. 1978. Synthesis of double-stranded DNA complementary to lysozyme, ovomucoid, and ovalbumin mRNAs. Optimization for full length second strand synthesis by *Escherichia coli* DNA polymerase 1. Journal of biological Chemistry 253(7):2483-95.

Goeddel et al. 1979. Direct expression in *Escherichia coli* of a DNA sequence coding for human growth hormone. Nature 281(5732):544-8.

Andrews, D.W. and J.D. Capra. 1980. Clinical Immunobiology. pp. 1-18, W.B. Sanders.

Takei et al. 1980. Monoclonal antibody H9/25 reacts with functional subsets of T and B cells: killer, killer precursor and plaque-forming cells. European Journal of Immunology 10(7):503-9.

van Nagell et al. 1980. Radioimmunodetection of primary and metastatic ovarian cancer using radiolabeled antibodies to carcinoembryonic antigen. Cancer Research 40(3):502-6.

Minutes of the public oral proceedings before the Technical Board of Appeal 3.3.4 of May 22, May 26, 2000, in the European Patent Office concerning Cabilly's corresponding European Patent.

Riechmann et al. 1988. Reshaping human antibodies for therapy. Nature 322:323-327.

Hale et al., 1990. The Campath- I antigen (cDw52). Tissue Antigens 35:118-127.

Huynh et al, 1984. Constructing and screening CDNA libraries in kgt IO and kgtl 1. DNA Cloning, vol. I- A practical Approach 49-78. Glover, D(Editor), IRL Press, Oxford.

Medline Abstracts regarding rat anti-CDw52 therapeutic antibodies.

File Wrapper of Page U.S. Appl. No. 07/777,730, filed Oct. 16, 1991.

Curriculum vitae of Dr. Ellen Vitetta.

Matsuuchi et al. 1981. An analysis of heavy chain glycopeptides of hybridoma antibodies: correlation between antibody specificity and sialic acid content. Journal of immunology 127(5):2188-90.

Medline Abstracts regarding murine anti-CD4 therapeutic antibodies.

Cobbold, S.P. and H. Waldmann. 1984. Therapeutic potential of monovalent monoclonal antibodies. Nature 308(5958):460-62.

Neuberger et al. 1984. Recombinant antibodies possessing novel effector functions. Nature 312(5995):604-8.

Bindon et al. 1985. Therapeutic potential of monoclonal antibodies to the leukocyte-common antigen. Synergy and interference in complement-mediated lysis. Transplantation 40(5):538-44.

Cabilly, S. and A.D. Riggs. 1985. Immunoglobulin transcripts and molecular history of a hybridoma that produces antibody to carcinoembryonic antigen. Gene 40(I):157-61.

Hale et al. 1985. Reactivity of rat monoclonal antibody CAMPATH-I with human leukemia cells and its possible application for autologous bone marrow transplantation. British Journal of Haematology 60(I):41-8.

Kaufman et al. 1987. Coamplification and coexpression of human tissue-type plasminogen activator and murine dihydrofolate reductase sequences in Chinese hamster ovary cells. Molecular and Cellular Biology 5:1750-1759..

Neuberger et al. 1985. A hapten-specific chimaeric IgE antibody with human physiological effector function. Nature 314(60081:268-70.

Tan et al. 1985. A human-mouse chimeric inimunoglobulin gene with a human variable region is expressed in mouse myeloma cells. Journal of immunology 135(5):3564-7.

Bruggemann et al. 1987. Comparison of the effector ftmctions of human immunoglobulins using a matched set of chimeric antibodies. Journal of Experimental Medicine 166(5):1351-61.

Sun et al. 1987. Chimeric antibody with human constant regions and mouse variable regions directed against carcinoma-associated antigen 17IA. Proc. NatL Acad. Sci. 84(I):214-8.

Weidle et al. 1987. Reconstitution of fimctionally active antibody directed against creatine kinase from separately expressed heavy and light chains in non-lymphoid cells. Gene 51(I):21-9.

Weidle et al. 1987. Expression of antibody CDNA in murine myeloma cells: possible involvement of additional regulatory elements in transcription of inununoglobulin genes. Gene 60 (2-3):205-216.

Zettlmeissl et al. 1987. Expression of biologically active human antithrombin III in chinese hamster ovary cells. BiolTechnology 5:720-5.

Dangl et al. 1988. Segmental flexibility and complement fixation of genetically engineered chimeric human, rabbit and mouse antibodies. EMBO Journal 7(7):1989-94.

Morrison et al. 1988. Genetically engineered antibody molecules: new tools for cancer therapy. Cancer Investigation 6(2):185-92.

Morrison et al. 1988. Production and characterization of genetically engineered antibody molecules. Clinical Chemistry 34(91):1668-75.

Riechmann et al. 1988. Expression of an antibody Fv fragment in myeloma cells. Journal of Molecular Biology 203(3):825-8.

James Scott Crowe Declaration dated Nov. 2, 1994.

Verhoeyen et al. 1988. Reshaping human antibodies: grafting an antilysozyme activity. Science 239(4847):1534-6.

Wallick et al. 1988. Glycosylation of a VH residue of a monoclonal antibody against alpha (1→6) dextran increases its affinity for antigen. Journal of Experimental Medicine 168(3):1099-109.

Tsuchiya et al. 1989. Effects of galactose depletion from oligosaccharide chains on immunological activities of human IgG. Journal of rheumatology 16:285-90.
Baldwin, R.W. et al. 1990. Monoclonal Antibodies and Immunoconjugates. The Parthenon Publishing Group.
Grossbard, M.L. 1998. Monoclonal AntibodyBased Therapy of Cancer. Marcel Dekker.
Jefferis et al. 1998. IgG-Fc-mediated effector functions: molecular definition of interaction sites for effector ligands and the role of glycosylation. immunological Reviews 163:59-76.
Cabilly Claims Corresponding to the Count.
Availability of CEA.66-E3.
Declaration 2 of Dr. Richard Youle.
Sidman, C. 1981. Differing requirements for glycosylation in the secretion of related glycoproteins is determined neither by the producing cell nor by the relative number of oligosaccharide units. Journal of biochemistry 256(18):9374-9376.
Blatt, C. and J. Haimovich. 1981. The selective effect of tunicamycin on the secretion of IgM and IgG produced by the same cells. European Journal of Immunology 11:65-66.
Cabilly U.S. Appl. No. 07/205,419, filed Jun. 10, 1988.
Cabilly U.S. Appl No. 08/909,611, filed Aug. 12, 1997.
Trill et al. 1995. Production of monoclonal antibodies in COS and CHO cells. Current Opinion in Biotechnology 6: 553-560.
De Waele et al. 1988. Expression in non-tymphoid cells of mouse recombinant immunoglobulin directed against the tumor marker human placental alkaline phosphatase. European Journal of Biochemistry 176:287-295.
Jun. 2, 1987 Communication from EPO Examiner during prosecution of Cabilly et al. European appl. No. 84302368.0-2105.
Jan. 29, 1987 response of Cabilly et al. filed before EPO during prosecution of Cabilly et al. European appl. No. 84302368.0-2105.
Feb. 9, 1988 response of Cabilly et al. filed before EPO during prosecution of Cabilly et al. European appl. No. 84302368.0-2105.
Search results of ATCC product listing of deposited cell lines.
Tarentino et al. 1974. The release of intact oligosaccharides from specific glycoproteins by Endo-o-N-acetylglucosaminidase H. Journal of Biological Chemistry 249:818-824.
Morell et al. 1971. The role of sialic acid in determining the survival of glycoproteins in the circulation. J BioL Chem. 246:1461-1467.
Achord et al. 1978. Human O-glucuronidase: in vivo clearance and in vitro uptake by a glycoprotein recognition system on reticuloendothelial cells. Cell 15:269-278.
Oldham, R. 1983. Monoclonal antibodies in cancer therapy. Journal of Clinical Oncology 1:582-590.
Rosen et al. 1983. Application of monoclonal antibodies to tumor diagnosis and therapy. Annals of Clinical and Laboratory Science 13:173-184.
Levy, R. and R.A. Miller. 1983. Biological and clinical implications of lymphocyte hybridomas: tumor therapy with monoclonal antibodies. Ann. Rev. Med-34:107-116.
Krolick et al. 1982. In vivo therapy of a Murine B cell tumor (BCL I) using antibody-ricin a chain irrimunotoxins. J Exp. Med. 155:1797-1809.
Frenkel et al. 1980. Analysis and detection of B cell neoplasms. Blood Cells 6:783-793.
Amendment filed in Cabilly U.S. Appl. No. 08/909,611 on Aug. 12, 1997.
Amendment filed in Cabilly U.S. Appl. No. 08/909,611 on Feb. 22, 1999.
Legal Analysis Concerning Written Description.
Declaration 4 of Dr. Richard Youle.
Preliminary Amendment of Mar. 30, 1994 submitted in the '403 patent.
Examiner's Interview Summary Record issued on Jun. 6, 1995 in the '403 patent.
Amendment of May 8, 1995 submitted in the '404 patent.
Amendment of May 11, 1995 submitted in the '405 patent.
Gold et al. 1978. Carcinoembryonic antigen (CEA) in clinical medicine. Cancer 42:1399-1405.
Interference Initial Memorandum.
Genentech, Inc. released product sales for Rituxan.
Genentech, Inc. Press release of Oct. 11, 2000.
Genentech, Inc. Press release of 1999 year end results issued Jan. 20, 2000.
Cancer data sheet from the National Cancer Institute "CancerNet" internet site.
FDA Product Description Sheet.
Grillo-Lopez et al. Overview of the clinical development of rituximab: first monoclonal antibody treatment approved for the treatment of lymphoma. Seminars in Oncology 26:66-73.
Ma, S. and W. Nashabeh. 1999. Carbohydrate analysis of a chimeric recombinant monoclonal by capillary electrophoresis with laser-induced fluorescence detection. Analytical Chemistry 71:5185-5192.
Datasheet on CD52 from Workshop on Leukocyte Antigens.
Lingappa et al. 1980. Signal sequences for early events in protein secretion and membrane Ann. NYAcad. Sci. 343:356-61.
Declaration 3 of Dr. Richard Youle.
File Wrapper of Page U.S. Appl. No. 07/943,146, filed Sep. 10, 1992.
File Wrapper of Page U.S. Appl. No. 08/046,893, filed Apr. 15, 1993.
Datasheet on CD4 from Workshop on Leukocyte Antigens.
Kaetzel et al. 1985. Expression of biologically active bovine luteinizing hormone in Chinese hamster ovary cells. Proc. Natl. Acad Sci. USA 82:7280-7283.
Robinson U.S. Appl. No. 07/016,202, filed Preliminary Jan. 8, 1987.
Robinson U.S. Appl. No. 08/471,984, filed Jun. 6, Preliminary 1995.
Request for Admissions 1-11—Rituxan.
Herceptin—description sheets (4 pages).
Vitetta Declaration 2.
Youle Declaration 5.
Mark Sydenham Declaration.
Declaration 2 of J. Scott Crowe.
Robinson U.S. Appl. No. 09/021,934, filed Feb. 12, 1998 and selected papers from the file wrapper.
File Wrapper of USP 5,545,404.
File Wrapper of USP 5,545,405.
Rademacher et al. (1988) Ann. Rev. Biochem. 57:785-838.
Hale Declaration.
Youle Declaration 6.
Deposition Transcript of Ellen Vitetta, Jan. 8, 2001.
Deposition Transcript of James S. Crowe Dec. 14, 2000.
VS Form 16-6A—U.S Veterinary Permit for Importation and Transportation of Controlled Materials and Organisms and Vectors—Permit No. 27899—Date Issued: Nov. 8, 1991—Re: Campath 1H Monoclonal Antibody.
Internal Notice of Shipment of Campath 1H May 10, 1990.
Deposition Transcript of Stephen Desiderio Dec. 28, 2000.
Deposition Transcript of Richard Youle Jan. 3, 2001.
Deposition Transcript of Sharon Krag Jan. 5, 2001.
Deposition Transcript of Mark Robert Lifely Jan. 9, 2001.
Deposition Transcript of John Shively Jan. 12, 2001.
Stevenson et al., 1989, A Chimeric Antibody With Dual Fc Regions (b!sFabFc) Prepared by Manipulations at the IgG Hinge, Anti-Cancer Drug Design 3, 219-230.
Cobbold et al., Bone Marrow Purging and Processing, Jan. 1, 1990.
Cabilly Claims 53-67.
Potamianos et al. 2000, Radioimmunoscintigraphy and Radioimmunotherapy in Cancer: Principles and Application, Anticancer Research 20, 925-948.
Wright and Morrison, 1994 Effect of Altered CH2-associated Carbohydrate Structure on the Functional Properties and In Vivo Fate of Chimeric Mouse-Human Immunoglobulin GI, J Exp. Med 180,1087-1096.
Goochee et al. 1991, "The Oligosaccharides of Glycoproteins: BioProcess Factors Affecting Oligosaccharide Structure and Their Effect on Glycoprotein Properties", BiolTechnology 9, 1347-1355.
Ashford et al. 1993 "Site-specific Glycosylation of Recombinant Rat and Human Soluble CD4 Variants Expressed in Chinese Hamster Ovary Cells", J BioL Chem., 268, 3260-3267.
Davis et al. 1990, "High Level Expression in Chinese Hamster Ovary Cells of Soluble Forms of CD4 T Lymphocyte Glycoprotein Including Glycosylation Variants." J BioL Chem. 265, 10410-10418.
Mar. 28, 1989—Lab Meeting—handwritten notes—First Mention of Campath-1H, 3 pages.
Mar. 6, 1989 Memorandum from Jeffrey M. Johnston, M.D. Re: CAMPATH and Rheumatoid Arthritis Overview Medical Position.

Jul. 13, 1989—handwritten notes—4 pages.
Jun. 11, 1990—Laboratory Notebook 90/0522, Iodination of C- I H.
CV of Linda Thurmond.
CV of Mark Sydenham.
131 Declaration of Rapson.
Laboratory Notebook (Glaxo Exh. 2212).
Laboratory Notebook (Glaxo Exh. 2213).
Laboratory Notebook (Glaxo Exh. 2214).
Laboratory Notebook (Glaxo Exh. 2215).
Laboratory Notebook—Feb. 25-Sep. 3, 1992.
Laboratory Notebook (Glaxo Exh. 2217).
CV of James S. Crowe.
Page et al., Biotech, 9:64-68 (1991).
Vitetta Declaration 3.
Jul. 13, 1989 Memorandum from Jeffrey M. Johnston to Research Committee RE: Campath—1H: A Humanized Anti-lymphocyte monoclonal antibody.
Joziasse, et al., 2000 "a3-Galactosylated glycoproteins can bind to the hepatic asialoglycoprotein receptor" Eur. J Biochem. 267:6501-6508.
Clynes et al., 2000 "Inhibitory Fc receptors modulate in vivo cytoxicity against tumor antigens" Nature Med 6: 443-446.
Thurmond Personal Notebook Entry for Oct. 17, 1994.
Whittle et al. Expression in COS cells of a mouse—human chimaeric B72.3 antibody, 1987, pp. 499-505, vol. 1, No. 6.
Thurmond 131 Declaration.
Crowe Declaration with Exhibits.
Lifely Declaration with Exhibits dated Apr. 6, 1994.
Youle Declaration 7.
Herceptin description sheets from Genentech web site (16 pages).
Rituxan description sheets from Genentech web site (11 pages).
Historical Product Sales (from Genentech web site 3 pages).
Genentech Reports 1999 Year-End Results (from Genentech web site).
Genentech Reports 25 Percent Increase in Product Sales for Third Quarter (from Genentech web site).
Hale, "Effects of Monoclonal Anti-lymphocyte Antibodies in Vivo in Monkeys and Humans", Mol Biol Med (1983) 1, 321-334.
Reuters news article and San Francisco Chronicle News article.
Results of Medline search of "therapeutic antibodies" years 1966-1990.
Vitetta Declaration 4 position.
Certificate of Correct Inventorship USP 5,545,404, Jun. 17, 1997.
Certificate of Correct Inventorship USP 5,545,405, Jun. 17, 1997.
J. Baselga et al., "Recombinant Humanized Anti-HER2 Antibody (Herceptin™) Enhances the Antitumor Activity of Paclitaxel and Doxorubicin against HER2/neu Overexpressing Human Breast Cancer Xenografts", Cancer Res. (1988) 58: 2825-2831.
T.E. Hotaling et al., "The humanized anti-HER2 antibody rhuMAb HER2 mediates antibody dependent cell-mediated cytotoxicity via FcyR III", Proc. Am. Assoc. Cancer Res., 1996, 37:471 (#3215).
M.D. Pegram et al., "Antibody dependent cell-mediated cytotoxicity in breast cancer patients in Phase III clinical trials of a humanized anti-HER2 antibody", Proc Am. Assoc. Cancer Res., 1997, 38:602 (#4044).
Declaration of Mary Anne Armstrong.
Declaration of Jeffrey J. Berns.
Library of Congress Online Catalog record for Cabilly Exhibit 1074.
Deposition of Vitetta Mar. 19, 2001.
Glaxo Wellcome Inc. Objection to Admissibility of Evidence, Dec. 20, 2000.
Glaxo Wellcome Inc. Objection to Admissibility of Evidence, Jan. 23, 2001.
Glaxo Wellcome Inc. Objection to Admissibility of Evidence, Feb. 9, 2001.
Glaxo Wellcome Inc. Objection to Admissibility of Evidence, Apr. 3, 2001.
Transcript of teleconference with APJ on Apr. 5, 2001.
Order authorizing Glaxo Supplemental Oppositions.
Code of Medical Ethics and Current Opinions, excerpts from pp. 339-379.
Excerpts from 21 C.F.R.
Vitetta Declaration 5.
Supplemental 131 Declaration of Thurmond.
*Horne* v. *Potton*.
Office Action in U.S. Appl. No. 08/046,893 to Page dated Jun. 23, 1993.
Amendment in Page U.S. Appl. No. 08/155,864 dated Feb. 28, 1995.
Cabilly Objection to Evidence, Nov. 13, 2000.
Letter dated Apr. 20, 2001 from Jean Harney to Jerry Murphy.
Excerpts from Lifely Lab notebook ZEIA/90/17.
National Library of Medicine PubMed MEDLINE record for Cabilly Exhibit 1074.
Oct. 17, 1994 Teleconference on Campath Long Term Follow Up (handwritten sheet and translation page).
Declaration 3 of Crowe.
Declaration 2 of Jeffrey J. Berns.
Library of Congress Online Catalog record for Cabilly Exhibit 1073.
Keshet et al, "Cloning of bovine growth hormone gene and its expression in bacteria" Nucleic Acids Research, 9:19-30 (1981).
Rice et al., "Measurement of transient cDNA expression in mammalian cells using flow cytometric cell analysis and sorting", Cytometry, 12:221-233 (1991).
Taniguchi et al., "Expression of the Human Fibroblast Interferon Gene in *Escherichia coli*", Proc. Natl. Acad. Sci. USA, 77(9):5230-5233 (Sep. 1980).
Winkelhake et al., "Effects of pH treatments and deglycosylation of rabbit immunoglobulin G on the binding of Clq" Journal of Biological Chemistry, 255(7):2822-2828 (Apr. 10, 1980).
Notice of Allowability, Paper No. 21 dated Jun. 13, 1995 in the '864 application.
Notice of Allowability, Paper No. 9 dated Jun. 7, 1995 in the '400 application.
Notice of Allowability, Paper No. 9 dated Jun. 8, 1995 in the '401 application.
Beatty et al., Cancer Research 49:1587-1594 (Mar. 15, 1989).
Beatty et al., Cancer Research (Suppl.) 50:922s-926s (Feb. 1, 1990).
Williams et al., Cancer Research (Suppl.) 50:1029s-1030s (Feb. 1, 1990).
Neumaier et al., Cancer Research 50:2128-2134 (Apr. 1, 1990).
Duda et al., J. Surgical Oncology 44:73-77 (Jun. 1990).
Riechmann et al, Nature 332:323 (Mar. 1988).
Friend et al., Transplantation 48:248-253 (Aug. 1, 1989).
Hale et al., The Lancet, Dec. 17, 1988, pp. 1394-1399.
Dyer et al., Blood 73:1431-1439 (May 1, 1989).
Stevenson et al., Blood 77:1071-1079 (Mar. 1, 1991).
Cobbold et al., Bone Marrow Purging and Processing, pp. 139-154 (Jan. 1, 1990).
Declaration of Stephen V. Desiderio, M.D., Ph.D.
Declaration of Sharon S. Krag, Ph.D.
Declaration of John E. Shively, Ph.D.
Kaufman et al., Molecular and Cellular Biology 5:1750-1759 (Jul. 1985).
Neuhaus et al., JACC 14:1566-1569 (Nov. 15, 1989).
Activase® (Alteplase) package insert dated Jun. 1988.
Declaration of James Scott Crowe, submitted in the '864 application, dated Nov. 17, 1994.
Declaration of Robert Lifely, submitted in the '864 application, dated Jun. 4, 1994.
Declaration of Geoffrey Hale, submitted in the '864 application, dated Nov. 16, 1994.
Joziasse et al., Subcell Biochem. 32:25-48 (1999).
Peakman et al., Hum. Antibod. Hybridomas 5:65-74 (1994).
Curriculum vitae of John E. Shively, Ph.D.
Curriculum vitae of Stephen V. Desiderio, M.D., Ph.D.
Curriculum vitae of Sharon S. Krag, Ph.D.
Krag, J. Biol. Chem. 254:9167-9177 (1979).
Rhodes, Adv. Anim. Cell. Biol. Technol. Bioprocess., 472-74 (1988).
Rhodes and Birch Biotechnology 6:518, 521, 523 (1988).
Colcher et al., Cancer Res. 49:1738-1745 (1989).
Citation of Information, dated Sep. 6, 1995 in the '400 application.
Citation of Information, Paper No. 14 dated Sep. 6, 1995 in the '401 application.
Examiner Communication, Paper No. 30 dated May 16, 1996 in '864 application.

Examiner Communication, Paper No. 17 dated Dec. 29, 1995 in the '400 application.
Examiner Communication, Paper No. 15 dated Jan. 5, 1996 in the '401 application.
Byrn, et al., Nature 344:667-670 (Apr. 12, 1990).
Sekigawa et al., J. Virology 64:5194-5198 (Oct. 1990).
Office Action dated Mar. 10, 1992, Paper No. 5 in U.S. Appl. No. 07/770,730, filed Oct. 16, 1991.
Preliminary Amendment, Paper No. 9 in U.S. Appl. No. 08/155,864, filed Nov. 23, 1993 in U.S. Appl. No. 08/155,864, filed Nov. 23, 1993.
Declaration of Robert Lifely, Paper No. 10, received in executed form in Group 1800 on Apr. 12, 1994 in the '864 application.
Preliminary Communication, Paper No. 15, received in Group 1800 on Nov. 17, 1994 in the '864 application.
Declaration of James Scott Crowe, Paper No. 16, received in executed form in Group 1800 on Nov. 17, 1994 in the '864 application.
Declaration of Geoffrey Hale, Paper No. 16, received in executed form in Group 1800 on Nov. 17, 1994 in the '864 application.
Amendment, Paper No. 18, received in Group 1800 on Feb. 28, 1995 in the '864 application.
Office Action dated Jan. 6, 1995, Paper No. 4 in U.S. Appl. No. 08/335,400, filed Nov. 3, 1994.
Amendment dated May 8, 1995, Paper No. 7 in the '400.
Office Action dated Jan. 11, 1995, Paper No. 4 in U.S. Appl. No. 08/335,401, filed Nov. 3, 1994.
Amendment dated May 11, 1995, Paper No. 7 in the '400.
Routledge et al., Eur. J. Immunol. 1991, 21:2717-2725.
Finnegan et al., J. Rheumatology 1997, 24:7, 1448-1449.
Crowe, et al., "Clinical Experimental Immunology", 1992, 87, pp. 105-110.
Second Declaration of Sharon S. Krag, Ph.D.
Hale, Progress Report (May 1990-Dec. 31, 1990), MRC Wellcome Therapeutic Antibody Center.
Harris, et al., Proceedings of the 34$^{th}$ Oholo Conference, Eilat, Israel (1990).
Khazaeli, et al., Cancer Research, 51, 5461-5466 (1991).
Third Declaration of Sharon S. Krag, Ph.D.
Zettlmeissl, et al., Bio/Technology, 5:720-725 (1987).
Goeddel, Methods in Enzymology, vol. 185, "Gene Expression Technology" (1990).
U.S. Appl. No. 08/909,611 application.
205,419 application.
483,457 application.
Amendment filed concurrently herewith in the '611 application.
Interference Initial Memorandum (Form 850), dated signed by the Examiner on Apr. 12, 2000.
Meredith, et al., Hum. Antibod. Hybridomas, 1993, 4:190-197.
Declaration of Steven B. Kelber.
Emery & Adair, Exp. Opin. Invest. Drugs (1994) 3(3):241-251.
Begent et al., Br. J. Cancer, 62:487 (1990).
Wood et al., J. Immunol., vol. 145:3011-3016, No. 9, Nov. 1, 1990.
Protocol UAC 180 of the University of Alabama's Comprehensive Cancer Center, describing Clinical Phase I trials conducted over the period Nov. 1989 through Oct. 1990. (See in particular, §5.1, p. 9.).
Data Report for Protocol UAC 180 dated Aug. 24, 1990: Patient data collected after administration of cB72.3 monoclonal antibody.
Status Report: Phase I Contract Cancer Therapy Evaluation Program No. 1-CM-97611 dated Feb. 4, 1992 (pp. 1-12).
Meredith et al, J. Nucl. Med, Jan. 1992, 33:23-29 (pp. 13-19).
Khazaeli et al., Manuscript—Frequent Anti-V Region Immune Response to Mouse B72.3 Monoclonal Antibody (pp. 25-63).
Meredith et al., J. Nucl. Med., vol. 33, No. 9: 1648-1653, Sep. 1992.
Sheeley et al., Analytical Biochemistry 247, 102-110 (1997).
Amendment filed Feb. 25, 1999 in '611 application.
File History U.S. Appl. No. 08/909,611.
James Scott Crowe Deposition Transcript.
Methods in Enzymology, vol. 101, Part C, Table of Contents, p. v-viii.
Chang et al., Proc. Natl. Acad. Sci. USA, vol. 84, pp. 5640-5644 (1987).
Haynes and Weissmann, Nucl. Acid. Res., vol. 11 No. 3 (1983).
Hutchins et al., Proc. Natl. Acad. Sci. USA, vol. 92, (1995).
Reff et al., Blood, vol. 83, No. 2, pp. 435-445 (1994).
Yarrington Deposition Transcript and Supporting Exhibits.
Second Declaration of Stephen V. Desiderio, M.D., Ph.D.
LoBuglio Deposition Transcript.
Krag et al., J. Biological Chemistry, vol. 257, No. 14, p. 8424 (1983).
Berman et al, Science, Nov. 4, 1983; 222(4623): 524-7.
Fourth Declaration of Sharon S. Krag, Ph.D.
Deposition Transcript of Ellen Vitetta, Ph.D.
Deposition Transcript of Richard Youle, Ph.D.
Third Declaration of Stephen V. Desiderio, M.D., Ph.D.
Deposition Transcript of Sharon S. Krag, Ph.D.
Deposition Transcript of Robert Lifely, Ph.D., Jan. 9, 2001.
Deposition Transcript of Stephen V. Desiderio, M.D., Ph.D.
ATCC deposit verification for CEA.66-E3 .
Chart Entitled "Human Leucocyte Surface Markers" by Immunotech.
Ettinger, et al. Cancer Treatment Reports vol. 83, No. 1, pp. 131-134, Jan. 1979.
Spellman et al, 1989, J. Bio. Chem. 264:14100-14111.
Takeuchi et al., J. Biol. Chem., 263:3657-3663.
Kagawa Y; J Biol Chem Nov 25, 1988;263(33):17508-15.
Excerpts from '403 Prosecution File History ('864 application) (not entire file history).
Excerpts from '404 Prosecution File History ('400 application) (not entire file history).
Arthritis & Rheumatism, Abstract Suppl. vol. 39, No. 9, Sep. 1996, p. S244.
Science, vol. 232, Jun. 1986—Arathoon, et al.—Large-Scale Cell Culture in Biotechnology pp. 1390-1395.
LoBuglio and Saleh, Am. J. Medical Sciences, Sep. 1992 vol. 304, No. 3, pp. 214-224.
Primus et al., Cancer Immunol. Immunotherapy (1990) 31:349-357.
Transcript from Second Deposition of Robert Lifely, Ph.D.
Transcript from Deposition of Nicholas Rapson, Ph.D.
Transcript from Second Deposition of James Scott Crowe, Ph.D.
Transcript from Second Deposition of Richard Youle, Ph.D.
Transcript from Second Deposition of Ellen Vitetta, Ph.D.
Lifely et al., Glycobiology, vol. 5 No. 8;813-822, 1995.
Transcript from Second Deposition of Sharon Krag, Ph.D.
Deposition Transcript of Mark Sydenham.
Excerpts from the '405 Prosecution File History ('401 application).
Declaration of Vladimir Drozdoff, Ph.D.
Verdict—United States District Court, District of Delaware.
Ellen Vitetta Deposition Transcript , May 21, 2001.
Abstract, Journal of Nuclear Medicine, May 1990, No. 613.
Abstract, World Federation of Nuclear Medicine & Biology, Abstract submitted Jan. 15, 1990.
Linda Thurmond Deposition Transcript, May 18, 2001.
1990 Abstract Form for Scientific Papers by M. B. Khazaeli, Ph.D.
Cancer Principles & Practice of Oncology, 5$^{th}$ Edition, vol. 1, Chapter 18, pp. 360-372.
Abstract 76, Antibody Immunoconjugates and Radiopharmaceuticals, 1990.
Notice Declaring Interference, May 15, 2000.
Notice of Real Party-in-Interest, May 25, 2000.
Glaxo Wellcome Inc. Notice of Real Party in Interest, May 26, 2000.
Glaxo Wellcome Notice of Intent to File Preliminary Motions, Jul. 10, 2000.
Cabilly List of Preliminary Motions, Jul. 11, 2000.
Cabilly Notice, 37 C.F.R. §1.660(d), Jul. 11, 2000.
Glaxo Wellcome Inc.'s List of Preliminary Motions It Intends to File, Jul. 11, 2000.
Glaxo Wellcome Inc. Notice of Related Litigation, Jul. 11, 2000.
Glaxo Wellcome Inc.'s Miscellaneous Motion 1 (with attachments), Sep. 28, 2000.
Cabilly Opposition to Miscellaneous Motion 1, Oct. 5, 2000.
Glaxo Wellcome Reply to Opposition to Miscellaneous Motion 1, Oct. 10, 2000.
Order Denying Glaxo Wellcome Inc. Miscellaneous Motion 1, Oct. 18, 2000.
Order Regarding Discovery, Oct. 26, 2000.
Cabilly Preliminary Statement, Nov. 1, 2000.
Cabilly Preliminary Motion 1, Nov. 1, 2000.
Cabilly Preliminary Motion 2, Nov. 1, 2000.

Cabilly Preliminary Motion 3, Nov. 1, 2000.
Cabilly Preliminary Motion 4, Nov. 1, 2000.
Cabilly Preliminary Motion 5, Nov. 1, 2000.
Cabilly Preliminary Motion 6, Nov. 1, 2000.
Glaxo Wellcome, Inc.'s Preliminary Motion 1, Nov. 1, 2000.
Glaxo Wellcome, Inc.'s Preliminary Motion 2, Nov. 1, 2000.
Glaxo Wellcome, Inc.'s Preliminary Motion 3, Nov. 1, 2000.
Glaxo Wellcome, Inc.'s Preliminary Motion 4, Nov. 1, 2000.
Glaxo Wellcome, Inc.'s Preliminary Motion 5, Nov. 1, 2000.
Glaxo Wellcome, Inc.'s Preliminary Motion 6, Nov. 1, 2000 .
Glaxo Wellcome, Inc.'s Preliminary Motion 7, Nov. 1, 2000.
Glaxo Wellcome, Inc.'s Preliminary Motion 8, Nov. 1, 2000.
Glaxo Wellcome, Inc.'s Preliminary Motion 9, Nov. 1, 2000.
Glaxo Wellcome, Inc.'s Preliminary Motion 10, Nov. 1, 2000.
Glaxo Wellcome, Inc.'s Preliminary Motion 11, Nov. 1, 2000.
Glaxo Wellcome, Inc.'s Preliminary Motion 12, Nov. 1, 2000.
Glaxo Wellcome, Inc.'s Preliminary Motion 13, Nov. 1, 2000.
Glaxo Wellcome, Inc.'s Preliminary Motion 14, Nov. 1, 2000.
Letter Regarding Error in Notice Declaring Interference, Nov. 1, 2000.
Glaxo Wellcome Inc. Preliminary Statement, Nov. 8, 2000.
Glaxo Wellcome Objection to Admissibility of Evidence, Nov. 8, 2000.
Cabilly Preliminary Motion 7, Nov. 13, 2000.
Cabilly Preliminary Motion 8, Nov. 13, 2000.
Cabilly Preliminary Motion 9, Nov. 13, 2000.
Cabilly Miscellaneous Motion 1 (Motion for Permission to Issue a Subpoena, 35 U.S.C. §24), Dec. 8, 2000.
Opposition to Cabilly Miscellaneous Motion 1, Dec. 15, 2000.
Cabilly Reply to Opposition to Cabilly Miscellaneous Motion 1, Dec. 20, 2000.
Decision Granting Cabilly Miscellaneous Motion 1, Dec. 20, 2000.
Cabilly Response to Objections to Admissiblity of Evidence. Jan. 16, 2001.
Glaxo Response to Cabilly's Objection to Evidence, Jan. 16, 2001.
Glaxo Wellcome Miscellaneous Motion 2, Jan. 16, 2001.
Glaxo Wellcome Miscellaneous Motion 3, Jan. 16, 2001.
Order Denying Glaxo Motions Miscellaneous Motions 1 and 2, Jan. 29, 2001.
Cabilly Opposition 1, Feb. 2, 2001.
Cabilly Opposition 2, Feb. 2, 2001.
Cabilly Opposition 3, Feb. 2, 2001.
Cabilly Opposition 4, Feb. 2, 2001.
Cabilly Opposition 5, Feb. 2, 2001.
Cabilly Opposition 6, Feb. 2, 2001.
Cabilly Opposition 7, Feb. 2, 2001.
Cabilly Opposition 8, Feb. 2, 2001.
Cabilly Opposition 9, Feb. 2, 2001.
Cabilly Opposition 10, Feb. 2, 2001.
Cabilly Opposition 11, Feb. 2, 2001.
Cabilly Opposition 12, Feb. 2, 2001.
Cabilly Opposition 13, Feb. 2, 2001.
Cabilly Opposition 14, Feb. 2, 2001.
Glaxo Opposition to Motion 1, Feb. 2, 2001.
Glaxo Opposition to Motion 2, Feb. 2, 2001.
Glaxo Opposition to Motion 3, Feb. 2, 2001.
Glaxo Opposition to Motion 4, Feb. 2, 2001.
Glaxo Opposition to Motion 5, Feb. 2, 2001.
Glaxo Opposition to Motion 6, Feb. 2, 2001.
Glaxo Opposition to Motion 7, Feb. 2, 2001.
Glaxo Opposition to Motion 8, Feb. 2, 2001.
Glaxo Opposition to Motion 9, Feb. 2, 2001.
Glaxo Miscellaneous Motion 4, Feb. 2, 2001.
Glaxo Miscellaneous Motion 5, Feb. 2, 2001.
Cabilly Response to Glaxo Miscellaneous Motion 4, Feb. 8, 2001.
Order Granting Glaxo Miscellaneous Motion 4, Feb. 13, 2001.
Cabilly Response to Objection to Admissibility of Evidence, Feb. 22, 2001.
Glaxo Wellcome Miscellaneous Motion 6 (Correct Opp. No. 3), Mar. 9, 2001.
Glaxo Wellcome Miscellaneous Motion 7 (Correct Opp. No. 5), Mar. 9, 2001.
Glaxo Wellcome Miscellaneous Motion 8 (Correct Opp. No. 6), Mar. 9, 2001.
Glaxo Wellcome Inc.'s Miscellaneous Motion No. 9, Mar. 16, 2001.
Cabilly Reply 1, Mar. 27, 2001.
Cabilly Reply 2, Mar. 27, 2001.
Cabilly Reply 3, Mar. 27, 2001.
Cabilly Reply 4, Mar. 27, 2001.
Cabilly Reply 5, Mar. 27, 2001.
Cabilly Reply 6, Mar. 27, 2001.
Cabilly Reply 7, Mar. 27, 2001.
Cabilly Reply 8, Mar. 27, 2001.
Cabilly Reply 9, Mar. 27, 2001.
Glaxo Reply 1, Mar. 27, 2001.
Glaxo Reply 2, Mar. 27, 2001.
Glaxo Reply 3, Mar. 27, 2001.
Glaxo Reply 4, Mar. 27, 2001.
Glaxo Reply 5, Mar. 27, 2001.
Glaxo Reply 6, Mar. 27, 2001.
Glaxo Reply 7, Mar. 27, 2001.
Glaxo Reply 8, Mar. 27, 2001.
Glaxo Reply 9, Mar. 27, 2001.
Glaxo Reply 11, Mar. 27, 2001.
Glaxo Reply 14, Mar. 27, 2001.
Order Granting Glaxo Wellcome Inc. Miscellaneous Motions, Apr. 2, 2001.
Order Authorizing Glaxo Supplemental Opposition 6, Apr. 6, 2001.
Cabilly Motion to Suppress, 37 C.F.R. §1.656(h), Apr. 18, 2001.
Glaxo Wellcome Inc.'s Request for Defer Decision on Motions Until Final Hearing or to Permit the Filing of Briefs, Apr. 18, 2001.
Glaxo Wellcome Inc.'s Observations, Apr. 18, 2001.
Glaxo Wellcome Inc.'s Miscellaneous Motion 10*(Suppress New Evidence Supporting Cabilly Reply 6), Apr. 18, 2001.
Glaxo Wellcome Inc.'s Miscellaneous Motion 11(Suppression of Certain Deposition Exhibits and Deposition Testimony), Apr. 18, 2001.
Glaxo Wellcome Inc.'s Miscellaneous Motion 12 (Suppression of Deposition Testimony), Apr. 18, 2001.
Glaxo Wellcome Inc.'s Notice of Change of Real Party in Interest, Apr. 19, 2001.
Petition from the Apr. 6, 2001 Order of the APJ Under 37 C.F.R. 1.644(a)(1), Apr. 20, 2001.
Memorandum Opinion and Order, Apr. 30, 2001.
Order Regarding Glaxo Wellcome Inc. Motions, May 2, 2001.
Cabilly's Opposition to Glaxo Wellcome Misc. Motion 10, May 2, 2001.
Cabilly's Opposition to Glaxo Wellcome Misc. Motion 11, May 2, 2001.
Cabilly's Opposition to Glaxo Wellcome Misc. Motion 12, May 2, 2001.
Glaxo Wellcome Inc.'s Opposition to Cabilly Motion to Suppress (With exhibits attached), May 2, 2001.
Glaxo Wellcome's Supplemental Opposition to Cabilly's Preliminary Motion 6, May 4, 2001.
Cabilly's Reply to Glaxo's Supplemental Opposition to Preliminary Motion 6, Jun. 1, 2001.
Glaxo Wellcome Objection to Admissibilty of Evidence, Jun. 8, 2001.
Cabilly Reply to the Opposition to It's Motion to Suppress Evidence, Jul. 2, 2001.
Glaxo Wellcome's Reply to Cabilly's Opposition to Misc. Motion 10, Jul. 2, 2001.
Glaxo Wellcome's Reply to Cabilly's Oppositions to Misc. Motion 11, Jul. 2, 2001.
Glaxo Wellcome's Reply to Cabilly's Oppositions to Misc. Motion 12, Jul. 2, 2001.
Order Regarding Filing of Glaxo Supplemental Evidence, Nov. 13, 2001.
Glaxo Wellcome Inc's Submission of Late Evidence, Nov. 15, 2001.
Cabilly Motion to Suppress, Nov. 20, 2001.
Glaxo Wellcome Inc's Opposition to Cabilly Motion to Suppress, Nov. 21, 2001.
Curriculum Vitae of Art Riggs.
Proposal to Genentech re: funding for IgG (Bates Nos. 0921-0926).

Curriculum Vitae of Jack Shively.
Wagener, Shively publication (Bates Nos. 0927-0934).
Curriculum Vitae of Ron Wetzel.
Wetzel Nbk #1432 (Bates Nos. 0034-0044, 0047, 0049-0050, 0053, 0061-0064, 0077-0081, 0087-0088).
Curriculum Vitae of Jeanne Perry.
Perry Nbk #1290 (Bates Nos. 0136a-0136b, 0142-0147, 0149-0154, 0156-0158, 0160-0161, 0164-0173, 0181, 0187-0188, 0190-0192, 0197-0218, 0223, 0237, 0244-0261, 0304-0307).
Holmes Nbk #1446 (Bates Nos. 0941-0943, 0946-0947, 0950, 0954-0957).
Holmes Spiral #4 (Bates Nos. 0825, 0830, 0837-0838, 0840-0843, 0845-0846, 0848-0849, 0852-0853, 0855, 0858).
Holmes Spiral #5 (Bates Nos. 0876, 0881-0882, 0885-0887, 0889).
Curriculum Vitae of Michael Rey.
Rey Nbk #1173 (Bates Nos. 0502, 0504, 0509-0516, 0521-0522, 0525-0528, 0530-0531, 0533-0537, 0541, 0543-0544).
Curriculum Vitae of Michael Mumford.
Mumford Nbk #1247 (Bates Nos. 0615, 0617, 0626-0627, 0645).
Curriculum Vitae of Schmuel Cabilly.
Cabilly Nbk (Bates Nos. 0970-0976, 0982-0987, 0989, 0991-0992, 0994-01001, 01013-01014).
Declaration of Interference, Feb. 28, 1991.
Summary of Times Running, Feb. 28, 1991.
Designation of Lead Attorney (Cabilly), Mar. 14, 1991.
Appointment of Associate Attorney, Mar. 25, 1991.
Submission of Associate Attorneys, Apr. 8, 1991.
Revocation and Power of Attorney, Apr. 15, 1991.
Boss et al. Substitution of Lead Attorney, Apr. 19, 1991.
Associate Power of Attorney, Apr. 19, 1991.
Cabilly et al. Motion for Extension of Time, May 28, 1991.
Cabilly et al. Extension of Time-Approved, Jun. 3, 1991.
Certificate of Service and List of Documents Filed, Jun. 4, 1991.
Cabilly et al. Request for the Exercise of Discretion Pursuant to 37 CFR §1.642, Jun. 4, 1991.
The Preliminary Statement of the Party Cabilly et al., Jun. 4, 1991.
Cabilly et al. Notice of Filing of Preliminary Statement, Jun. 4, 1991.
Transmittal of Preliminary Statement of Boss et al. and Notice to Opposing Party, Jun. 4, 1991.
Boss et al. Motion for Benefit of its PCT Application (Boss Motion 1), Jun. 4, 1991.
Boss et al. Motion for Benefit of its British Application (Boss Motion 2), Jun. 4, 1991.
Declaration of Timothy John Roy Harris in Support of Boss Motion for Benefit of its British Application (Boss Motion 2), Jun. 4, 1991.
Boss et al. Motion for Judgment of Unpatentability of Cabilly Claims (Boss Motion 3), Jun. 4, 1991.
Boss et al. Opposition to Cabilly et al. Request Pursuant to 37 CFR §1.642, Jun. 24, 1991.
Opposition to Boss et al. Motion for Judgment of Unpatentability of Cabilly et al. Claims (Boss Motion 3), Jun. 24, 1991.
Declaration of Paul Carter in Support of Cabilly et al Opposition to Boss et al Motion For Judgment of Unpatentability of Cabilly et al Claims 101-120 (Boss Motion 3), Jun. 24, 1991.
Boss et al Reply to Opposition to Boss et al Motion for Judgment of Unpatentability of Cabilly Claims, Jul. 9, 1991.
Decision on Motions, Jul. 26, 1991.
Order Regarding Testimony, Jul. 26, 1991.
Service of Boss et al. Preliminary Statement; Boss et al. Preliminary Statement, Jul. 31, 1991.
Service of Cabilly et al. Preliminary Statement, Aug. 13, 1991.
"Communication" to PTO from Cabilly et al. (Paper #28); Information Disclosure Statement, Sep. 20, 1991.
Cabilly et al. Motion for Extension of Time, Sep. 25, 1991.
Decision—dismissal of "Communication" paper, Sep. 26, 1991.
Transmittal Letter re: Declarations of Riggs, Shively, Wetzel, Perry, Holmes, Rey, Mumford, Cabilly and Exhibits 1-20, Notice Pursuant to 37 CFR 1.671(e), Oct. 28, 1991.
Proposed Revision to Schedule for Records and Briefs, Dec. 3, 1991.
Cabilly et al. Notice of Filing Record, Jan. 8, 1992.
Cabilly et al. Record, Jan. 8, 1992.

Motion be the Party Cabilly et al Pursuant to 37 CFR §1.635 to Replace Exhibits 1-20 Filed on Jan. 8, 1992 With a Corrected Set of Exhibits and for the Return of Exhibits 1-20 Filed 1-20 on Jan. 8, 1992, Jan. 22, 1992.
Corrected Submission of Stipulation Concerning Testimony, Feb. 5, 1992.
Cabilly et al. Motion for Extension of Time, Feb. 10, 1992.
Main Brief at Final Hearing of Junior Party Cabilly et al., Feb. 18, 1992.
Transmittal of Brief for the Party Boss et al., Mar. 18, 1992.
Brief at Final Hearing for Senior Party Boss et al., Mar. 18, 1992.
Cabilly et al. Supplemental Brief at Final Hearing, Apr. 5, 1992.
Reply Brief at Final Hearing of Junior Party Cabilly et al., Apr. 7, 1992.
Cabilly et al Motion Pursuant to 37 C.F. R. §1.635 to Enter Additional Pages Into the Cabilly et al Record, Apr. 14, 1992.
Opposition to Cabilly et al Motion Pursuant to 37 C.F. R. §1.635 to Enter Additional Pages Into the Cabilly et al Record, Apr. 22, 1992.
Cabilly et al Reply to Boss et al Opposition to Cabilly et al Motion Pursuant to 37 C.F. R. §1.635 to Enter Additional Pages Into the Cabilly et al Record, May 7, 1992.
Cabilly et al. Notice of Submission of Replacement Set of Exhibits 1-20, May 7, 1992.
Notice of Filing Substitute Exhibits 8 and 20 for the Cabilly et al. Record, May 7, 1992.
Notice of Final Hearing for Mar. 29, 1994 (paper #54), Feb. 4, 1992.
Final Decision (Priority awarded to Boss et al.) (paper #57), Aug. 13, 1998.
Transmittal and Filing of Agreements Under 35 USC §135(c); Agreements, Aug. 25, 1998.
Communication form BPAI re: Filing of agreements and request to keep separate from Interference file acknowledged (paper #59), Oct. 10, 1998.
Notice From PTO Requesting Communication Regarding Appeal, Nov. 9, 1998.
Belated Response to Communication Regarding Appeal, Dec. 1, 1998.
Boss et al. Power to Inspect and Make Copies, Dec. 9, 1998.
Decision Granting Petition to Correct the Assignee on the Cover Page of U.S. Appl. No. 07/205,419, May 7, 2002.
Petition Pursuant to 37 C.F.R. §1.666(b) for Access to Settlement Agreement (filed by MedImmune), May 8, 2002.
Order on Petition for Access Pursuant to 35 U.S.C. §165(c) and 37 C.F.R. §1.666(b), Jun. 19, 2002.
Cabilly et al. Objection to Petition for Access to Settlement Agreement, Jul. 22, 2002.
Celltech's Objection to Petition for Access to Settlement Agreement, Jul. 22, 2002.
Reply to Objections of Celltech R&D Ltd. and Cabilly et al. to MedImmune's Petition for Access to Settlement Agreement, Aug. 1, 2002.
Alberts, B. *Molekularbiologie der Zelle*, Weinheim:VCH pp. 1075 (1987).
"Appeal No. T400/97-334, Appellant: Genentech, Inc., European Patent No. 120694 (Celltech), European Patent Application No. 84301996.9, Grounds of Appeal" (Apr. 1, 1997 Notice of Appeal attached) (Jun 13, 1997).
"Appeal T1212/97-334 in Re Genentech EP-B-125023 Substantiation of the Proprietor's Appeal" (Feb 26, 1998).
Bagdasarian et al., "Activity of the hybrid trp-lac (tac) promoter of *Escherichia coli* in Pseudomonas putida. Construction of broad-host-range, controlled-expression vectors" *Gene* 26(2-3):273-282 (Dec 1983).
Cabilly, S. (Letter from Shmuel Cabilly to Arthur D. Riggs) (Aug 5, 1980).
Cabilly, Shmuel, "Growth at sub-optimal temperatures allows the production of functional, antigen-binding Fab fragments in *Escherichia coli*" *Gene* 85:553-557 (1989).
Carter et al., "High Level *Escherichia coli* Expression and Production of a Bivalent Humanized Antibody Fragment." *Bio/Technology*. 10(2):163-167 (Feb 1992).
DeBoer, "The tac promoter: A functional hybrid derived from the trp and lac Promoters" *Proc. Natl. Acad. Sci. USA* 80:21-25 (1983).

Decision of PCR EP 0200362 and decision of PCR EP 0201184. Sections 5 only. Submitted by PDL on Mar. 27, 1997. (Dec 14, 1995).
"Decision of the Technical Board of Appeal 3.3.4 of May 14, 2001" (Regarding EP-B-125,023. Sep. 27, 2001 correction to the decision attached.).
"Decision Revoking the European Patent (Article 102(1) EPC)" (EP 125,023 with Minutes attached) (Oct 16, 1997).
"Decision to Maintain the European Patent in Amended Form (Article 102(3) EPC)" (Regarding EP 120694) (Mar 14, 2002).
"Declaration of Atsuo Ochi" (CV attached. Regarding EP 120694 and EP 125023 oppositions.) (May 17, 1996).
"Declaration of Gabrielle L. Boulianne" (Exhibits A-C attached. Regarding EP 120694 and EP 125023 oppositions.) (May 15, 1996).
"Declaration of Paul J. Carter dated Apr. 20, 2000 with Exhibit A and ATCC letter".
Documents from EP 120694 file. Namely Aug. 30, 1988 Celltech's request to amend the application and Jun. 15, 1990 Minutes of the Oral Proceedings.
EP 120,694, Declaration of Michael Francis Tuite with CV attached (May 26, 1995).
EP 125,023, Documents submitted by Genentech prior to oral proceedings (Mar. 27, 1997).
EP 125,023, Genentech's opposition to PDL's request to admit the entire Boss file as documentation at the oral proceedings (Mar. 18, 1997).
EP 125,023, Genentech's request for Opponent IV to provide the subject matter to be presented by Dr. Shulman at the oral proceedings (Mar. 3, 1997).
"European Patent EP-B-125023 (Genentech, Inc.) Declaration of Dr. Richard Axel dated Apr. 18, 2000 with Exhibit A".
European Patent Office communication with copy of EP 120694 maintained patent in amended form (Oct. 17, 2001).
"FOI Advisory 76-7, Procedure for Requests for Grant Applications and Progress Reports" (May 19, 1976 Memo from the NIH Freedom of Information Coordinator at the US Department of Health, Education, and Welfare, and May 10, 1976 letter accompanying the memo) (May 1997).
Genentech's submissions in response to Board of Appeals' Feb. 2, 2000 communication. Richard Axel's Apr. 18, 2000 Declaration with Exhibit A, Paul J. Carter's Apr. 20, 2000 Declaration with Exhibit A, ATCC letter, Walter Moore's Apr. 21, 2000 Statement and claim requests.
Glaser et al., "Functional interrelationship between two tandem *E. coli* ribosomal RNA promoters" *Nature* 302(5903):74-76 (Mar. 3, 1983).
Goeddel et al., "Synthesis of Human Fibroblast Interferon by *E. coli*" *Nucleic Acids Research* 8(18):4057-4074 (1980).
Goodman and MacDonald, "Cloning of hormone genes from a mixture of cDNA molecules" *Methods in Enzymology* 68 :75-90 (1979).
Hamilton, R., "Application of engineered chimeric antibodies to the calibration of human antibody standards" *Annales de Biologie Clinique* 49 (4) :242-248 (1991).
Harris, "Expression of Eukaryotic Genes in *E.coli*" *Genetic Engineering*, R. Williamson, 4th edition pp 127-185 (1983).
"Interlocutory Decision in Opposition Proceedings (Article 106(3)EPC)" (EP 120694) (Feb. 14, 1997).
Kabat et al. *Sequences of Proteins of Immunological Interest*, Bethesda, MD:National Institute of Health pp. i, xxi, xxii (1983).
Klausner, A., "Genentech makes monoclonal precursors from *E.coli*" *Bio/Technology* 1(5):396-397 (1983).
Liu et al., "Expression of mouse::human immunoglobulin heavy-chain cDNA in lymphoid cells" *Gene* 54(1):33-40 (1987).
Minutes from the EP 120694 oral proceedings (Aug. 13, 1996).
"Minutes of the public oral proceedings before the Technical Board of Appeal 3.3.4 of May 14, 2001" (EP 0125023).
"Minutes of the public oral proceedings before the Technical Board of Appeal 3.3.4 of May 22, 2000" (Regarding EP 120694).
Morrison, S., "In vitro antibodies: strategies for production and application" *Annual Review of Immunology* 10 :239-265 (1992).
Munro, "Uses of chimaeric antibodies" *Nature* 312:597 (1984).
"Opposition to EP 125023 B of Genentech, Patentee's Response to the Opponents' Arguments" (Feb. 22, 1993).

"Opposition to European Patent No. EP-B-0125023 (84302368.0-2106)" (Genentech's submission prior to the oral proceedings with affidavit from Christopher Denison dated Apr. 19, 2000 and exhibits attached) (Apr. 20, 2000).
Papers relevant to the interpretation of Ellison et al. PNAS 79:1984-1988 (1982), Fig. 2 from Ellison paper and pp. 203 & 211 from New England Biolabs Catalog with Ellison paper attached.
"Plaintiff MedImmune, Inc.'s First Amended Complaint, Demand for Jury Trial" (U.S. District Court, Case No. 03- 2567 MRP (CTX) *MedImmune, Inc.* vs. *Genentech, Inc., City of Hope, and Celltech R&D Ltd.*) (Aug. 13, 2003).
*Public Information Regulation* (Paragraphs 5.71(c) and 5.72(e) only), U.S. Department of Health, Education, and Welfare (Aug. 1974).
Queen and Baltimore, "Immunoglobulin gene transcription is activated by downstream sequence elements" *Cell* 33 (3) :741-748 (Jul. 1983).
Queen, C., "Comparison of human and mouse VH domains" (Submitted by PDL on Mar. 27, 1997).
Queen, C., "Comparison of mouse and human V-kappa domains" (Submitted by PDL Mar. 27, 1997).
Reasons for the Decision of T612/92 and T694/92. Submitted by PDL on Mar. 27, 1997.
Regarding EP 125023. Genentech's suggestions on the time frame of the oral proceedings (Nov. 18, 1999).
"Response on behalf of the Patentees to the Further Submissions filed on behalf of Opponents I and IV in connection with Opposition Proceedings to EP-B-0126023 (84302368.0)" (Aug. 9, 1994 Declaration of Leon R. Lyle with Exhibits A-B and Aug. 11, 1994 Affidavit of Allan Robert Adler with Exhibits A-E) (Oct. 31, 1995).
Schein et al., "Formation of Soluble Recombinant Proteins in *Escherichia coli* is Favored by Lower Growth Temperature" *Bio/Technology* 6:291-294 (1988).
Schein, Catherine H., "Production of soluble recombinant proteins in bacteria" *Bio/Technology* 7:1141-1149 (1989).
Stafford and Queen, "Cell-type specific expression of a transfected immunoglobulin gene" *Nature* 306(5938) :77-79 (Nov. 3, 1983).
"Statement by Walter Moore" (Regarding the non-availability of the Herzenberg grant application) (Apr. 21, 2000).
Taniguchi et al., "Expression of the Human Fibroblast Interferon Gene in *Escherichia coli*" *Proc. Natl. Acad. Sci. USA* 77(9) :6230-5233 (Sep. 1980).
Plaintiffs' Joint Contentions on Invalidity Due to Non-Statutory Double Patenting with Exhibits 1-2, U.S. District Court for the District of Massachusetts, MDL No. 1592 (MLW).
Expert Report of Dr. Rodney E. Kellems, U.S. District Court for the District of Massachusetts, MDL No. 1592 (MLW).
Rebuttal Expert Report of Dr. Rodney E. Kellems, U.S. District Court for the District of Massachusetts, MDL No. 1592 (MLW).
Deposition Transcript of Rodney E. Kellems, Oct. 2, 2004, U.S. District Court for the District of Massachusetts, MDL No. 1592 (MLW).
Decision—Priority—Bd. R. 125(a), *Hudziak* v. *Ring*, Paper No. 32, Sep. 30, 2005 (Interference No. 105,267).
Decision—Priority—Bd. R. 125(a), *Hudziak* v. *Ring*, Paper No. 39, Sep. 30, 2005 (Interference No. 105,266).
Decision on Motions, *Genentech* v. *Chiron*, Paper No. 258, Nov. 30, 2004 (Interference No. 105,048).
Decision dated Mar. 30, 2004, *Chiron* v. *Genentech*, CAFC Case Nos. 03-1158 and 03-1159.
Final Decision (Priority awarded to Boss et al.), Paper No. 57, Aug. 13, 1998 (Interference No. 102,572).
Decision on Preliminary and Other Motions and Final Judgment, Sep. 4, 2002 (Interference No. 104,532).
Decision, U.S. Court of Appeals for the Federal Circuit, Case Nos. 04-1300 & 04-1384, Oct. 18, 2005.
Alt et al. "Immunoglobulin heavy-chain expression and class switching in a murine leukaemia cell line," *Nature*, vol. 296, p. 325-31, (Mar. 25, 1982).
Banerji et al., "A Lymphocyte-Specific Cellular Enhancer Is Located Downstream of the Joining Region in Immunoglobulin Heavy Chain Genes," *Cell*, vol. 33, 729-740 (Jul. 1983).

Benoist, C., et al., "In vivo sequence requirements of the SV40 early promoter region," *Nature*, 290: 304-310 (1981).

Bergman, Y., et al., "Two regulatory elements for immunoglobulin κ light chain gene expression," *Proc. Natl. Acad. Sci.*, 81 :7041-45 (1984).

Bernier, "Proliferative Disorders of the Immune System," Chapter 21 (pp. 622-643) in Bellanti, *Immunology II* (1978).

Blair, DG, et al., "Activation of the transforming potential of a normal cell sequence: a molecular model for oncogenesis," *Science*, 212: 941-43 (1981).

Breathnach, R., et al. "Correct splicing of a chicken ovalbumin gene transcript in mouse L cells," *Proc. Natl. Acad Sci.*, 77: 740-44 (1980).

Chang, E., et al., "Transformation by cloned Harvey murine sarcoma virus DNA: efficiency increased by long terminal repeat DNA," *Science*, 210: 1249-51 (1980).

Davies, J., et al., "A new selective agent for eukaryotic cloning vectors," *Am J. Trop. Med. Hyg.*, 29 (5 Suppl): 1089-92 (1980).

Fittler et al., "Localization in Mouse-L-Cell Chromosomal Sites of Transferred Immunoglobulin Genes," *Chromosome* (Berl.) 84, 717-727 (1982).

Fundenberg and Koistinen, "Human Allotype Detection by Passive Hemagglutination, with Special Reference to Immunoglobulin A Allotypes" Chapter 103 (pp. 767-774) in Rose and Friedman, *Manual of Clinical Immunology*, Second Edition (1980).

Gillies et al., "Expression of cloned immunoglobulin genes introduced into mouse L cells," *Nucl. Acids Res.*, vol. 11, No. 22, pp. 7982-7997 (1983).

Gruss, P., et al., "Simian virus 40 tandem repeated sequences as an element of the early promoter," *Proc. Natl. Acad. Sci.*, 78:943-47 (1981).

Habara et al. "Rauscher Murine Leukemia Virus: Molecular Cloning of Infectious Integrated Proviral DNA,"*J. of Virology*, vol. 44, No. 2, pp. 731-735 (Nov. 1982).

Jackson and Davis, "Quantitation of Immunoglobulins," Chapter 14 (pp. 109-120) in Rose and Friedman, *Manual of Clinical Immunology*, Second Edition (1980).

Köhler, G., et al., "Immunoglobulin chain loss in hybridoma lines," *Proc. Natl Acad. Sci.*, 77:2197-99 (1980).

Kyle, "Classification and Diagnosis of Monoclonal Gammopathies," Chapter 16 (pp. 135-150) in Rose and Friedman, *Manual of Clinical Immunology*, Second Edition (1980).

Linscott's Directory (formerly Catalog) of Immunological and Biological Reagents, second edition 1982-83, pp. 1-57.

Mercola et al., "Transcriptional Enhancer Elements in the Mouse Immunoglobulin Heavy Chain Locus," *Science*, vol. 221, No. 4611, p. 663-65 (Aug. 12, 1983).

Miles Biochemicals 1979-80, p. 140-142.

Miller et al, "Transfection of human lymphoblastoid cells with herpes simplex viral DNA," *Proc. Natl. Acad. Sci.*, vol. 76, No. 2, pp. 949-953 (Feb. 1979).

Morrison SL, et al., "A mouse myeloma variant with a defect in light chain synthesis," *Eur. J. Immunol.*, 9:461-65 (1979).

Mulligan, RC, et al., "Selection for animal cells that express the *Escherichia coli* gene coding for xanthine-guanine phosphoribosyltransferase," *Proc. Natl. Acad. Sci.*, 78 :2072-76 (1981).

Orfila et al., "Immunofluorescence study of "non-idiopathic" renal amyloidosis," *Hum. Pathol*14(4):362-7 (1983).

Tomino et al., "Specificity of eluted antibody from renal tissues of patients with IgA nephropathy," *Am. J. Kidney Dis.* I(5):276-80 (1982).

Solomon, "Bence Jones Proteins and Light Chains of Immunoglobulins," *Scand. J. Immunol.*, vol. 5, 685-695 (1976).

Southern, PJ et al. "Transformation of mammalian cells to antibiotic resistance with a bacterial gene under control of the SV40 early region promoter," *J. Molec. Appl. Genet.*, 1:327-41 (1982).

Summers et al., "Stable expression in mouse cells of nuclear neoantigen after transfer of a 3.4-megadalton cloned fragment of Epstein-Barr virus DNA," *Proc.. Natl. Acad. Sci.*, vol. 79, pp. 5688-5692 (Sep. 1982).

Villiers, J., et al., "Transcriptional 'enhancers' from SV40 and polyoma virus show a cell type preference," *Nucleic Acids Research*, 10:7965-76 (1982).

Wold et al., "Introduction and expression of a rabbit β-globin gene in mouse fibroblasts," *Proc. Natl. Acad. Sci.*, vol. 76, No. 11 pp. 5694-5788 (Nov. 1979).

Abreau S.L. et al. *Biochem. Biophys. Res. Comm.* 82(4): 1300-1305, Jun. 1978. Intracellular location of human fibroblast interferon messenger RNA.

Adams J.M. et al. *Biochem.* 55: 147-155, 1966. N-formylmethionyl-tRNA as the initiator of protein synthesis.

Alberts B. et al. Molecular Biology of the Cell. 107-108, 921, 1983.

Alt F. et al. *Cell* 27: 381-390, Dec. 1981. Organization and reorganization of immunoglobulin genes in A-MuLv-transformed cells: rearrangement of heavy but not light chain genes.

Applebaum S.W. et al. *Biochem. J.* 193: 209-216, 1981. The preparation and characterization of locust vitellogenin messenger RNA and the synthesis of its complementary DNA.

Atherton K.T. et al. *J. Gen. Virol.* 29: 297-304, 1975. Interferon induction by viruses and polynucleotides: a differential effect of camptothecin.

Aviv H. et al. *Proc. Nat. Acad. Sci. USA* 68(9): 2303-2307, Sep. 1971. Protein synthesis directed by encephalomyocarditis virus RNA: properties of a transfer RNA-dependent system.

Aviv H. et al. *Proc. Nat. Acad. Sci. USA* 69(6): 1408-1412, Jun. 1972. Purification of biologically active globin messenger RNA by chromatography on oligothymidylic acid-cellulose.

Ballantine J.E.M. et al. *J. Embryol. Exp. Morph.* 51: 137-153, 1979. Changes in protein synthesis during the development of *Xenopus laevis*.

Banerji J. et al. *Cell* 33: 729-740, 1983. A lymphocyte-specific cellular enhancer is located downstream of the joining region in immunoglobulin heavy chain genes.

Bantle J.A. et al. *Analytical Biochem*. 72: 413-427, 1976. Specificity of oligo (dT)-cellulose chromatography in the isolation of polyadenylated RNA.

Beato M. et al. *FEBS Lett.* 59(2): 305-309, Nov. 1975. Translation of the messenger RNA for rabbit uterglobulin in *Xenopus oocytes*.

Bergman W. et al. *J. Biol. Chem*. 254(13): 5690-5694, 1979. Formation of intermolecular disulfide bonds on nascent immunoglobulin polypeptides.

Berridge M.V. et al. *Cell* 8: 283-297, Jun. 1976. Translation of *Xenopus* liver messenger RNA in *Xenopus* oocytes: vitellogenin synthesis and conversion to platelet proteins.

Bevan M.J. *Biochem. J.* 122: 5-11, 1971. The vectoral release of nascent immunoglobulin peptides.

Blobel G. *FEBS Gene Expression*, 1977. Mechanisms for the intracellular compartmentaion an of newly synthesized proteins.

Blobel G. et al. *J. Cell Biol*. 67: 835-851, 1975. Transfer of proteins across membranes.

Bole D.G. et al. *J Cell. Biol*. 102: 1558-1566, 1986. Posttranslational association of Immunoglobulin heavy chain binding protein with nascent heavy chains in nonsecreting and secreting hybridomas.

Boss M. et al. *Nucl Acids. Res*. 12(9): 3791-3806, 1984. Assembly of functional antibodies from immunoglobulin heavy and light chains synthesised in *E. coli*.

Brack C. et al. *Cell* 15: 1-14, Sep. 1978. A complete immunoglobulin gene is created by somatic recombination.

Brinster R.L. et al. *Nature* 306: 332-336, 1983. Expression of a microinjected immunoglobulin gene in the spleen of transgenic mice.

Britten R.J. *Science* 142: 963-965, Nov. 1963. Complementary strand association between nucleic acids and nucleic acid gels.

Browne C.L. *Science* 203: 182-183, Jan. 1979. Oocyte-follicle cell gap junctions in *Xenopus laevis* and the effects of gonadotropin on their permeability.

Burke D. et al. *Nature* 271: 10-11, Jan. 1978. Translation of interferon messenger RNA in vivo and in vitro.

Calos M.P. et al. *Proc. Natl. Acad. Sci. USA* 80: 3015-3019, 1983. High mutation frequency in DNA transfected into mammalian cells.

Campbell P.N. et al. *FEBS Lett*. 72(2): 215-226, Dec. 1976. The role of organelles in the chemical modification of the primary translation products of secretory proteins.

Cattaneo A. et al. *EMBO J.* 6(9): 2753-2758, 1987. Polymeric immunoglobulin M is secreted by transfectants of non-lymphoid cells in the absence of immunoglobulin J chain.

Cavalieri R.L. et al. *Proc. Natl. Acad. Sci. USA* 74(10): 4415-4419. Oct. 1977. Induction and decay of human fibroblast interferon mRNA.
Chan L. et al. *J. Clin. Invest.* 57: 576-585, Mar. 1976. Translation of ovalbumin mRNA in *Xenopus laevis* oocytes.
Chen T.T. et al. *J. Biol. Chem.* 253(15): 5325-5331, 1978. Vittellin and vitellogenin from locusts (*Locusta migratoria*).
Coffin P. et al. *Proc. Natl. Acad. Sci. USA* 68(1): 219-223, Jan. 1971. Rate of somatic mutation in immunoglobulin production by mouse myeloma cells.
Cohn M. *Nucleic Acids in Immunology*, 671-715, 1968. The molecular biology of expectation.
Colman A. *Transcript. Translat.* 2: 49-69, 1984. Expression of exogenous DNA in *Xenopus* oocytes.
Colman A. Transcription and Translation, a practical approach, edited by B.D. James and S. J. Higgins, 271-302, 1984. Translation of eukaryotic messenger RNA in *Xenopus* oocytes.
Colman A. et al. *Ciba Found. Symp.* 98: 249-67, 1983. The oocyte as a secretory cell.
Colman A. et al. *Cell* 17: 517-526, 1979. Export of proteins from oocytes of *Xenopus laevis*.
Colman A. et al. *Eur. J. Biochem.* 113:339-348, 1981. The influence of topology and glycosylation on the fate of heterologous secretory proteins made in *Xenopus* oocytes.
Colman A. et al. *J. Cell Biol.* 91: 770-780, Dec. 1981. Fate of secretory proteins trapped in oocytes of *Xenopus laevis* by disruption of the cytoskeleton or by imbalanced subunit synthesis.
Colman A. et al. *J. Mol. Biol.* 160: 459-474, 1982. Interaction of Mouse immunoglobulin chains within *Xenopus* oocytes.
Craig R.K. et al. *Biochem. J.* 160: 57-74, 1976. Guinea-pig milk-protein synthesis.
Craig R.K. et al. *Biochem. J.* 173: 633-641, 1978. Separation and partial characterization of guinea-pig caseins.
Darnell J.E. et al. *Proc. Nat. Acad. Sci. USA* 68(6): 1321-1325, Jun. 1971. An adenylic acid-rich sequence in messenger RNA of HeLa cells and its possible relationship to reiterated sites in DNA.
Darnell J.E. et al. *Science* 174: 507-510, Oct. 1971. Polyadenylic acid sequences: role in conversion of nuclear RNA into messenger RNA.
De Robertis E.M. et al. *Sci. Amer.* 75-82, Oct. 1979. Gene transplantation and the analysis of development.
Deacon N. J. et al. *FEBS Lett.* 79(1): 191-194, Jul. 1977. Fucose incorporation into oocyte-synthesized rat immunoglobulins.
Deacon N. J. et al. *Immunol.* 38(1): 137-144, Sep. 1979. Post-translational modification of rat immunoglobulins synthesized in the *Xenopus* oocyte translation system.
Deshpande A. K. et al. *J. Biol. Chem.* 254(18): 8937-8942, Sep. 1979. Translation and stability of rat liver messenger RNA for $\alpha_{2a}$-globulin in *Xenopus* oocyte.
Dicou E. et al. FEBS Lett. 104(2): 275-278, Aug. 1979. Synthesis of *Dyctyosleium discoideum* secretory proteins in *Xenopus laevis* oocytes.
Doel M.T. *Cell* 8: 51-58, May 1976. The translational capacity of deadenylated ovalbumin messenger RNA.
Dryer W.J. et al. *Proc. Natl. Acad. Sci. USA* 54: 864-869, 1965. The molecular basis for antibody formation: a paradox.
Dulis B. *J. Biol. Chem.* 258(4): 2181-2187, 1983. Regulation of protein expression in differentiation by subunit assembly.
Dumont J.N. et al. *J. Morph.* 155(1): 73-98, 1978. Oogenesis in *Xenopus laevis* (Daudin).
Edmonds M. et al. *Proc. Natl. Acad. Sci USA* 68(6): 1336-1340, Jun. 1971. Polyadenylic acid sequences in the heterogeneous nuclear RNA and rapidly-labeled polyribosomal RNA of HeLa Cells: possible evidence for a precursor relationship.
Eppig J.J. et al. *Dev. Biol.* 28: 531-536, 1972. Amino acid pools in developing oocytes of *Xenopus laevis*.
European Patent Office, Case No. T 0400/97 (Celltech Therapeutics Ltd.), Decision of the Technical Board of Appeal, May 24, 2000.
Falcoff E. et al. *Virol.* 75: 384-393, 1976. Intracellular location of newly synthesized interferon in human FS-4 cells.
Falkner G.F. et al. *Nature* 298(5871): 286-288, 1982. Expression of mouse immunoglobulin genes in monkey cells.
Feit H. et al. *J. Neurochem.* 28(4): 697-706, 1977. Comparison of the isoelectric and molecular weight properties of tubulin subunits.

Ford C.C. et al. *J Embryol. Exp. Morph.* 37: 203-209, 1977. A method for enucleating oocytes of *Xenopus laevis*.
Fraser T. H. et al. *Proc. Nat. Acad. Sci. USA* 75(12): 5936-5940, Dec. 1978. Chicken ovalbumin is synthesized and secreted by ovalbumin is synthesized and secreted by *Escherichia coli*.
Futuichi Y. et al. *Nature* 266: 235-239, Mar. 1977. 5'-terminal structure and mRNA stability.
Gally J.A. et al. *Nature* 227: 341-348, Jul. 1970. Somatic translocation of antibody genes.
Gillies S.D. et al. *Cell* 33: 717-728, Jul. 1983. A tissue-specific transcription enhancer element is locate in the major intron of a rearranged immunoglobulin heavy chain gene.
Gillies S.D. et al. *Nucl. Acids Res.* 11(22): 7981-7997, 1983. Expression of cloned immunoglobulin genes introduced into mouse L cells.
Goldman B.M. *Proc. Nat. Acad. Sci. USA* 75(10): 5066-5070, Oct. 1978. Biogenesis of peroxisomes: intracellular site of synthesis f catalase and uricase.
Goodridge A. et al. *Eur. J. Biochem.* 98(1): 1-8, 1979. Synthesis of albumin and malic enzyme in wheat-germ lysates and *Xenopus laevis* oocytes programmed with chicken-liver messenger RNA.
Grässman A. et al. *Hoppe-Seyler's Z Physiol. Chem.* 352: 527-532, Apr. 1971. Über die bildung von melanin in muskelzellen nach der direkten übertragung von RNA aus Harding-Passey-melamnomzellen.
Gray W.R. et al. *Science* 465-467, Jan. 1967. Mechanism of antibody synthesis: size differences between mouse kappa chains.
Gurdon J.B. *J. Embryol. exp. Morph.* 20(3): 401-414, Nov. 1968. Changes in somatic cell nuclei inserted into growing and maturing amphibian oocytes.
Gurdon J.B. et al. *Ann. Rev. Genet.* 15: 189-218, 1981. Gene transfer in amphibian eggs and oocytes.
Gurdon J.B. et al. *J. Mol. Biol.* 80: 539-551, 1973. Message stability in injected frog oocytes: long life of mammalian $\alpha$ and $\beta$ globin messages.
Gurdon J.B. et al. *Nature* 233: 177-182, Sep. 1971. Use of frog eggs and oocytes for the study of messenger RNA and its translation in living cells.
Gurdon J.B. et al. *Transcript Translat.*, xvii-xviii, 1984. A practical approach.
Haas I.G. et al. *Nature* 306(24): 387-389, 1983. Immunoglobulin heavy chain binding protein.
Hanks J.H. et al. *Proc. Soc. Exp. Biol. Med.* 71: 196-200, 1949. Relation of oxygen and temperature in the preservation of tissues by refrigeration.
Harry P. et al. *Comp. Biochem. Physiol.* 63B(2): 287-293, 1979. Changes in the pattern of secretion of locust female diglyceride-carrying lipoprotein and vitellogenin by the fat body in vitro during oocyte development.
Hendershot L. et al. *J. Cell Biochem.* 104: 761-767, 1987. Assembly and secretion of heavy chains that do not associate posttranslationally with immunoglobulin heavy chain-binding protein.
Hendershot L. et al. *Mol. Cell. Biol.* 8(10): 4250-4256, 1988. Identity of the immunoglobulin heavy-chain protein with the 78,000-dalton glucose-regulated protein and the role of posttranslational modifications in its binding function.
Hew C.L. et al. *Biochem. Biophys. Res. Comm.* 71(3), 845-850, 1976. The synthesis of freezing-point-depressing protein of the winter founder *Pseudopleuronectus americanus* in *Xenopus laevis* oocytes.
Higgins S.J. et al. *Biochem. J.* 158: 271-282, 1976. Androgen-dependent synthesis of basic secretory proteins by the rat seminal vesicle.
Higgins S.J. et al. *Biochem. J.* 174: 543-551, 1978. Effects of testosterone on messenger ribonucleic acid and protein synthesis in rat seminal vesicle.
Hood L. et al. *Science* 168: 325-343 1979. Mechanism of antibody diversity: germ line basis for variability.
Hood L.E. *Fed. Proc.* 31(1): 177-187, 1972. Two genes, one polypeptide chain—fact or fiction?.
Housman D. et al. *Nature* 227: 913-918, 1970. Initiation of Haemoglobin synthesis by methionyl-tRNA.
Huez G. et al. *Nature* 271: 572-573, Feb. 1978. Functional stabilisation of HeLa cell histone messenger RNAs injected into *Xenopus* oocytes by 3'-OH polyadenylation.

Huez G. et al. *Proc. Nat. Acad. Sci. USA* 71(8): 3143-3246, Aug. 1974. Role of the polyadneylate segment in the translation of globin messenger RNA in *Xenopus* oocytes.

Jackson R. C. et al. *Proc. Natl. Acad. Sci.* 74(12): 5598-5602, Dec. 1977. Post-translational cleavage of presecretory proteins with an extract of rough microsomes from dog pancreas containing signal peptidase activity.

Jackson R. et al. *Nature* 227: 672-676, Aug. 1970. Role of methionine in the initiation of haemoglobin synthesis.

Jilka R. L. et al. *Arch. Biochem Biophys.* 192(1): 290-295, 1979. Synthesis and processing of the mouse MOPC-321 κ Chain in *Xenopus laevis* oocytes.

Jilka R.L. et al. *Biochem. Biophys. Res. Comm.* 79(3): 625-630, 1977. Synthesis and glycosylation of the MOPC-46V immunoglobulin in kappa chain in *Xenopus laevis* oocytes.

Kacian D.L. et al. *Nature* 23(58)5: 167-169, 1972. In vitro synthesis of DNA components of human genes for globins.

Katz F.N. et al. *Proc. Natl. Acad. Sci. USA* 74(8): 3278-3282, Aug. 1977. Membrane in vitro synthesis, glycosylation, and asymmetric insertion of a transmembrane protein.

Kindas-Miügge I. et al. *J. Mol. Biol.* 87: 451-462, 1974. Insect protein synthesis in frog cells: the translation of honey bee promelittin messenger RNA in *Xenopus* oocytes.

Kitajewski J. et al. *Mol. Cell. Biol.* 12(2): 784-790, 1992. Interaction of *Wnt*-1 proteins with the binding protein BiP.

Koch G. *J. Biol. Chem.* 251(19): 6097-6107, 1976. Synthesis of the mitochondrial inner membrane in cultured *Xenopus laevis* oocytes.

Köhler G. *Proc. Natl. Acad. Sci. USA* 77(4): 2197-99, 1980. Immunoglobulin chain loss in hybridoma lines.

Kortbeek-Jacobs N. et al. *J. Immunol. Meth.* 24(1/2):195-199, 1978. Detection of specific antibody producing cells in porcine colostrum by in ovo translation of their mRNA.

Kourides I.A. et al. *Proc. Natl. Acad. Sci. USA* 76(1): 298-302, Jan. 1979. mRNA-directed biosynthesis of α subunit of thyrotopin: translation in cell-free and whole-cell systems.

Kreil G. *Ann. Rev. Biochem.* 50:317-348, 1981. Transfer of proteins across membranes.

Kvist S. et al. *Cell* 29: 61-69, May 1982. Membrane insertion and oligomeric assembly of HLA-DR histocompatibility antigens.

Labarca C. et al. *Proc. Natl. Acad. Sci. USA* 74(10): 4462-4465, Oct. 1977. mRNA-directed synthesis of catalytically active mouse β-glucuronidase in *Xenopus* oocytes.

Labrie F. *Nature* 221: 1217-1222, Mar. 1969. Isolation of an RNA with the properties of haemoglobin messenger.

Laemmli U.K. *Nature* 227, 680-685, Aug. 1970. Cleavage of structural proteins during the assembly of the head of bacteriophage T4.

Lanclos K.D. *Cell Diff.* 7: 259-270, 1978. Effects of estradiol on early messenger RNA in male *Xenopus laevis* liver.

Lane C. et al. *Eur. J. Biochem.* 101(2): 485-495, 1979. Sequestration and turnover of guinea-pig milk proteins and chicken ovalbumin in *Xenopus* oocytes.

Lane C. et al. *J. Mol. Biol.* 61: 73-91, 1971. Rabbit haemoglobin synthesis in frog cells: the translation of reticulocyte 9 s RNA in frog oocytes.

Lane C.D. *Curr. Top. Dev. Biol.* 18: 89-116, 1983. The fate of genes, messengers, and proteins introduced into *Xenopus* oocytes.

Lane C.D. et al. *Biochem. Animal Dev.* 145-181, 1975. The injection of RNA into living cells: the use of frog oocytes for the assay of mRNA and the study of the control of gene expression.

Lane C.D. et al. *Eur. J. Biochem.* 111: 225-235, 1980. The *Xenopus* oocyte as a surrogate secretory system.

Larkins B.A. et al. *Proc. Natl. Acad. Sci. USA* 76(12): 6448-6452, Dec. 1979. Synthesis and processing of maize storage proteins in *Xenopus laevis* oocytes.

Laskov R. et al. *J. Exp. Med.* 515-541, 1970: Synthesis, assembly, and secretion of gamma globulin by mouse myeloma cells.

Lebreleu B. et al. *Biochem. Biophys. Res. Comm.* 82(2): 665-673, 1978. Translation of mouse interferon mRNA *Xenopus laevis* oocytes.

Lederberg J. *Science* 1649-1653, Jun. 1959. Genes and antibodies.

Lee S.Y. et al. *Proc. Nat. Acad. Sci. USA* 68(6): 1331-1335, Jun. 1971. A polynucleotide segment rich in adenylic acid in the rapidly-labeled polyribosomal RNA component of mouse sarcoma 180 ascites cells.

Lennox E.S. et al. *Cold Spring Harbor Symposia on Quantitative Biology* 32: 249-254, 1967. A search for biosynthetic subunits of light and heavy chains of immunoglobulins.

Lim L. et al. *Biochim. Biophys. Acta* 361: 241-247, 1974. Isolation of microsomal poly(a)-RNA from rat brain directing the synthesis of the myelin encephalitogenic protein in *Xenopus* oocytes.

Lim L. et al. *Nature* 227: 710-712, 1970. Adenine-rice polymer associated with rabbit reticulocyte messenger RNA.

Lingappa V.R. et al. *J. Cell Biol.* 79: 567-572, Nov. 1978. Nascent chicken ovalbumin contains the functional equivalent of a signal sequence.

Lingappa V.R. et al. *Nature* 281: 117-121, Sep. 1979. Chicken ovalbumin contains an internal signal sequence.

Lingappa V.R. et al. *Proc. Natl. Acad. Sci. USA* 74(7): 2432-2436, Jun. 1977. Nascent prehormones are intermediates in the biosynthesis of authentic bovine pituitary growth hormone and prolactin.

Lisowska-Bernstein B. et al. *Proc. Natl. Acad. Sci. USA* 66(2): 425-532, Jun. 1970. Synthesis of immunoglobulin heavy and light chains by the free ribosomes of a mouse plasma cell tumor.

Liu C.P. et al. *Proc. Natl. Acad. Sci. USA* 76(9): 4503-4506, Sep. 1979. Biological detection of specific mRNA molecules by microinjection.

Lockard R.E. et al. *Nucl. Acids Res.* 5(9): 3237-3247, Sep. 1978. Requirement for 7-methylguanosine in translation of globin mRNA in vivo.

Mach B. et al. *Mol. Biol. Rep.* 1: 3-6, 1973. Different size of the product of the 14s light chain mRNA translated in vitro and in amphibian oocytes.

Mains P.E. et al. *J. Biol. Chem.* 258(8): 5027-5033, 1983. The requirement of light chain for the surface deposition of the heavy chain of immunoglobulin M.

Maizel J.V. *Methods in Virology*, 5: 179-246, 1971. Polyacrylamide gel electrophoresis of viral proteins.

Masui Y. *J. Exp. Zool.* 166(3): 365-376, 1967. Relative roles of the pituitary, follicle cells, and progesterone in the induction of oocyte maturation in *Rana pipiens*.

Mechler B. et al. *J. Cell Biol.* 67: 1-15, 1975. Membrane-bound ribosomes of myeloma cells.

*MedImmune, Inc.* v. *Genentech, Inc.*, No. 05-608 (U.S.), Brief for Petitioner.

*MedImmune, Inc.* v. *Genentech, Inc.*, No. 05-608 (U.S.), Brief for Respondent City of Hope.

*MedImmune, Inc.* v. *Genentech, Inc.*, No. 05-608 (U.S.), Brief of Respondent Genentech, Inc.

*MedImmune, Inc.* v. *Genentech, Inc.*, No. 05-608 (U.S.), Reply Brief for Petitioner.

*MedImmune, Inc.* v. *Genentech, Inc.*, No. 05-608 (U.S.), transcript of oral argument.

Miflin B.J. et al. *Seed Prot. Improv.* 1: 137-159, 1979. The biology and biochemistry of cereal seed prolamins.

Mills F.C. et al. *Nature* 306: 809-812, Dec. 1983. DNase I hypersensitive sites in the chromatin of human μ immunoglobulin heavy-chain genes.

Moar V.A. et al. *J. Mol. Biol.* 61: 93-103, 1971. Translational capacity of living frog eggs and oocytes, as judged by messenger RNA injection.

Morrison S. *Ann. Rev. Immunol.* 2: 239-56, 1984. Transfer and expression of immunoglobulin genes.

Morrison S. et al. *Adv. Immunol.* 44: 65-92, 1989. Genetically engineered antibody molecules.

Morrison S. et al. *Proc. Natl. Acad. Sci. USA* 81: 6851-6855, 1984. Chimeric human antibody molecules: mouse antigen-binding domains with human constant region domains.

Morrison S.L. *Science* 229(4719): 1202-1207, 1985. Transfectomas provide novel chimeric antibodies.

Morser J. et al. *J. Gen. Virol.* 44(1): 231-234. Characterization of interferon messenger RNA from human lymphoblastoid cells.

Mous J. et al. *Biochem. Biophys. Res. Comm.* 79(4): 1111-1116, 1979. Synthesis of rat prostatic binding protein in *Xenopus* oocytes and in wheat germ.

Mous J. et al. *Eur. J. Biochem.* 94: 393-400, 1979. Translation of biologically active messenger RNA from human placenta in *Xenopus* oocytes.

Mous J.M. et al. *J. Biol. Chem.* 257(19): 11822-11828, Oct. 1982. Assembly, glycosylation, and secretion of the oligomeric rat prostatic binding protein in *Xenopus* oocytes.

Neuberger M. *Embo J.* 2(8): 1373-1378, 1983. Expression and regulation of immunoglobulin heavy chain gene transfected into lymphoid cells.

O'Farrell P. *J. Biol. Chem.* 250(10): 4007-4021, 1975. High resolution two-dimensional electrophoresis of proteins.

Ochi A. et al. *Proc. Natl. Acad. Sci. USA* 80: 6351-6355, 1983. Functional immunoglobulin M production after transfection of cloned immunoglobulin heavy and light chain genes into lymphoid cells.

Olsson L. *Proc. Natl. Acad. Sci. USA* 77(9): 5429-5431, 1980. Human-human hybridomas producing monoclonal antibodies of predefined antigenic specificity.

Olsson L. et al. *J. Immunol. Meth.* 61: 17-32, 1983. Antibody producing human-human hybridomas.

Palade G. *Science* 189: 347-358, 1975. Intracellular aspects of the process of protein synthesis.

Palmiter R. et al. *J. Biol. Chem.* 246(3): 724-737, 1971. Modulation of ovalbumin synthesis by estradiol-17β and actinomycin D as studied in explants of chick oviduct in culture.

Papkoff J. et al. *Mol. Cell. Biol.* 10(6): 2723-2730, 1990. Secreted *int*-1 Protein Is Associated with the Cell Surface.

Penman S. et al. *J. Mol. Biol.* 34: 49-69, 1968. Localization and kinetics of formation of nuclear heterodisperse RNA, cytoplasmic heterodisperse RNA and polyribosome-associated messenger RNA in HeLa cells.

Pilz I. et al. *Proc. Natl. Acad. Sci. USA* 77(1): 117-121, 1980. Effect of cleaving interchain disulfide bridges on the radius of gyration and maximum length of anti-poly(D-alanyl) antibodies before and after reaction with tetraalanine hapten.

Potter M. *Methods in Cancer Research II*: 105-157, 1967. The plasma cell tumors and myeloma proteins of mice.

Potter M. et al. *J. Gen. Virol.* 24(5): 1153-1163, 1960. Studies on eight transplantable plasma-cell neoplasms of mice.

Queen C. et al. *Cell* 33: 741-748, 1983. Immunoglobulin gene transcription is activated by downstream sequence elements.

Raftery M.A. et al. *Biochem. Biophys. Res. Comm.* 10(6): 467-72, 1963. Tryptic cleavage at cysteinyl peptide bonds.

Rapoport T.A. et al. *Eur. J. Biochem.* 87: 229-233, 1978. Synthesis of carp proinsulin in *Xenopus* oocytes.

Raschke W. C. et al. *Proc. Natl. Acad. Sci. USA* 76(7): 3469-3473, Jul. 1979. Assembly and secretion of pentameric IgM in a fusion between a nonsecreting B cell lymphoma and an IgG-secreting plasmacytoma.

Reynolds, Jr. F.H., et al. *Proc. Natl. Acad. Sci. USA* 72(12): 4881-4885, 1975. Interferon activity produced by translation of human interferon messenger RNA in cell-free ribosomal systems and in *Xenopus* oöcytes.

Robertson M. *Nature* 301(13): 114, 1983. Control of antibody production.

Rollins J.W. et al. *Science* 178: 1204-1205, 1972. Collagen synthesis in *Xenopus* oocytes after injection of nuclear RNA of frog embryos.

Ross J. et al. *Proc. Nat. Acad. Sci. USA* 69 (1): 264-268, 1972. In vitro synthesis of DNA complementary to purified rabbit globin mRNA.

Roth R.A. et al. *Biochem.* 20: 6594-6599, 1981. Role of disulfide interchange enzyme in immunoglobulin synthesis.

Rothman J.F. et al. *Nature* 269: 775-780, 1977. Synchronised transmembrane insertion and glycosylation of a nascent membrane protein.

Rubinstein M. et al. *Science* 202: 1289-1290, 1978. Human leukocyte interferon purified to homogeneity.

Scherrer, K. *Proc. Nat. Acad. Sci. USA* 56: 1571-1578, 1966. Patterns of RNA metabolism in a differentiated cell: a rapidly labeled, unstable 60S RNA with messenger properties in duck erythroblasts.

Schubert D. et al. *J. Mol. Biol.* 53: 305-320, 1970. Immunoglobulin biosynthesis.

Sehgal P.B. et al *Proc. Natl. Acad. Sci. USA* 74(8): 3409-3413, 1977. Interferon messenger RNA content of human fibroblasts during induction, shutoff, and superinduction of interferon production.

Sehgal P.B. et al. *Proc. Natl. Acad. Sci. USA* 75(10): 5000-5033, 1978. Does 3'-terminal poly(A) stabilize human fibroblast interferon mRNA in oocytes of *Xenopus laevis*?.

Seidman J.G. et al. *Nature* 276(21): 790-795, 1978. The arrangement and rearrangement of antibody genes.

Sherr C.J. et al. *Proc. Natl. Acad. Sci. USA* 66(4): 1183-1189, 1970. Immunoglobulin synthesis and secretion, V. Incorporation of leucine and glucosamine into immunoglobulin on free and bound polyribosomes.

Shore G.C. et al. *J. Cell Biol.* 72: 726-743, 1977. Two fractions of rough endoplasmic reticulum from rat liver.

Siden E. et al. *Proc. Natl. Acad. Sci. USA* 78(3): 1823-1827, Mar. 1981. Synthesis of immunoglobulin μ chain gene products precedes synthesis of light chains during B-lymphocyte development.

Siden E.J. et al. *Cell* 16: 389-396, 1979. Immunoglobulin Synthesis by Lymphoid Cells transformed in vitro by abelson murine leukemia virus.

Smith A.E. et al. *J. Virol.* 28(1): 140-153, 1978. Extraction and fingerprint analysis of simian virus 40 large and small T-antigens.

Smith M. et al. *J. Mol. Biol.* 80: 553-557, 1973. Translation of Messenger RNA for mouse immunoglobulin light chains in living frog oocytes.

Smithies O. *Science* 157: 267-273, 1967. Antibody variability.

Snel P. et al. *Neth. J. Med.* 21: 138-143, 1978. Removal of bile acids by plasma exchange or plasma cell separation followed by perfusion through a charcoal adsorber.

Soeiro R. et al. *J. Cell Biol.* 39: 112-118, 1968. The turnover of nuclear DNA-like RNA in HeLa cells.

Soreq, H. *Critical Reviews in Biochemistry* 18(3): 199-238, 1985. The biosynthesis of Biologically Active Proteins in mRNA-Microinjected *Xenopus* Oocytes.

Stavnezer J. et al. *Nature New Biology* 230(14): 172-176, 1971. Synthesis of a mouse immunoglobulin light chain in a rabbit reticulocyte cell-free system.

Stevens R.H. et al. *J. Cell Biol.* 50: 818-829, 1971. RNA metabolism in HeLa cells at reduced temperature.

Stevens R.H. et al. *Nature* 239: 143-146, 1972. Specific IgG mRNA molecules from myeloma cells in heterogeneous nuclear and cytoplasmic RNA containing poly-A.

Stevens R.H. et al. *Proc. Natl. Acad. Sci. USA* 70(4): 1127-1131, 1973. Isolation of messenger RNA coding for mouse heavy-chain immunoglobulin.

Stevens R.H. et al. *Proc. Natl. Acad. Sci. USA* 72: 4679, 1975. Authors' statement on the isolation of mRNA coding for immunoglobulin heavy chain.

Strauss A.W. et al. *Critical Reviews in Biochemistry*, ed. Fasman G.D. 205-235, Mar. 1982. Compartmentaion of newly synthesized proteins.

Summers D.F. et al. *Proc. Natl. Acad. Sci. USA* 54: 505-513, 1965. Evidence for virus-specific noncapsid proteins in poliovirus-infected HeLa cells.

Swan D. et al. *Proc. Natl. Acad. Sci. USA* 69(7): 1967-1971, 1972. Purification and properties of biologically active messenger RNA for a myeloma light chain.

Szilard L. *Proc. Natl. Acad. Sci. USA* 46: 293-302, 1960. The molecular basis of antibody formation.

Valle G. et al. *Eur. J Biochem.* 132: 131-138, 1983. Post-translational fate of variant MOPC 315 λ chains in *Xenopus* oocytes and mouse myeloma cells.

vanderDonk J.A. et al. *Nature* 271: 479-481, 1978. The use of *Xenopus* egg cells to assay the mRNA of single cells.

Vassalli P. et al. *J. Mol. Biol.* 56: 1-19, 1971. Cell-free synthesis of rat immunoglobulin.

Vassalli P. et al. *Proc. Natl. Acad. Sci. USA* 58: 2422-2429, 1967. Studies on cell-free synthesis of rat immunoglobulins, II. Synthesis of immunoglobulin and of antibody to the dinitrophenyl hapten.

Vassart G. et al. *Eur. J. Biochem.* 55: 15-22, 1975. Thyroglobulin messenger RNA: Translation of a 33-S mRNA into a peptide immunologically related to thyroglobulin.

Vassart G. et al. *Proc. Nat. Acad. Sci. USA* 72(10): 3839-3843, 1975. Translation of thyroglobulin 33S messenger RNA as a means of determining thyroglobulin quaternary structure.

Verma I.M. et al. *Nature New Biology* 235(58): 163-167, 1972. In vitro synthesis of DNA complementary to rabbit reticulocyte 10S RNA.

Vernon T.O. *Proc. Natl. Acad. Sci. USA* 80: 825-829, 1983. Immunoglobulin gene expression in transformed lymphoid cells.

Wabl M. et al. *Proc. Natl. Acad. Sci. USA* 79: 6976-6978, 1982. A theory of allelic and isotypic exclusion for immunoglobulin genes.

Wallace R.A. et al. *Developmental Biology* 19: 498-526, 1969. Studies on amphibian yolk.

Wallace R.A. et al. *J. Cell. Physiol.* 72(2): 73-89, 1968. The induced synthesis and transport of yolk proteins and their accumulation by the oocyte in *Xenopus laevis*.

Wallace R.A. et al. *J. Exp. Zool.* 175(3): 259-270, 1970. Protein incorporation by isolated amphibian oocytes.

Wheeler T. et al. *J. Virol.* 21(1): 215-224, 1977. Cell-free synthesis of polyoma virus capsid proteins VP1 and VP2.

White J.O. et al. *Biochem. Soc. Trans.* 3: 94-95, 1975. Properties of rat brain microsomal ribonucleeic acid containing polyadenylate.

Wilde C.D. et al. *Eur. J. Immunol.* 10: 462-267, 1980. Analysis of immunoglobulin chain secretion using hybrid myelomas.

Williamson A.R. *Biochem. Soc. Trans.* 5: 139-175, 1969. The Biosynthesis of multichain proteins.

Williamson R. et al. *Ser. Haemat.* IV(3): 23-36, 1971. The isolation and DNA/RNA hybridization of messenger RNA for globin.

Winberry L. et al. *J. Immunol.* 124(3): 1174-1182, 1980. Immunoglobulin production and secretion by variant clones of the MOPC315 mouse myeloma cell line.

Woodland H.R. et al. *Developmental Biology* 39(1): 134-140, 1974. The translation of mammalian globin mRNA injected into fertilised eggs of *Xenopus laevis*.

Yip C.C. et al. *Proc, Natl. Acad. Sci. USA* 72(12): 4777-4779, 1975. Translation of messenger ribonucleic acid from isolated pancreatic islets and human insulinomas.

Zehavi-Willner T. et al. *Cell* 11: 683-693, 1977. Subcellular compartmentation of albumin and globin made in oocytes under the direction of injected messenger RNA.

Herzenberg, L., "Genetic studies with mammalian cells (mice)" Grant ID R01CA04681 as entered into the CRISP database, Sep. 3, 1992 (Abstract only).

Kabat et al., "Sequences of immunoglobulin chains: tabulation and analysis of amino acid sequences of precursors, V-regions, C-regions, J-chain and [beta]2-microglobulins . . . ," The Kabat Database of Sequences of Proteins of Immunological Interest, 1979, Publication No. 80-2008, p. 185, National Institute of Health, Bethesda, MD.

Kuehl, W.M., "Light chain fragments: aberrant expression of immunoglobulin genes," Trends Biochem. Sci., Aug. 1981, pp. 206-208, vol. 6, No. 8, Elsevier, Cambridge, England.

Martinis et al., "Monoclonal antibodies with dual antigen specificity," Protides of the Biological Fluids Proceedings Colloquium, vol. 30, Neuroproteins, Monoclonal Antibodies Separation Methods, 1983, pp. 311-316, vol. 30, Peeters, H. (Ed.), Pergamon Press, Oxford, England.

Margulies et al., "Regulation of immunoglobulin expression in mouse myeloma cells" Cold Spring Harbor Symposia on quantitative biology, 1979, pp. 781-791.

Sears et al., "Phase-I clinical trial of monoclonal antibody in treatment of gastrointestinal tumours," Lancet, Apr. 3, 1982, pp. 762-765, Lancet Publishing Group, London, England.

Reeck et al., "Homology" in Proteins and Nucleic Acids: A Terminology Muddle and a Way Out of it, Cell, Aug. 28, 1987, p. 667, vol. 50, No. 5, Cell Press, Cambridge, MA.

Davis, "Immunoglobulin molecules and genes" Microbiology Including Immunology and molecular Genetics, Third edition, 1980, Chapter 17, pp. 338-379, Harper & Row, Hagerstown, MD.

U.S. Appl. No. 07/233,430, Boss et al. (File History), filed Aug. 18, 1988.

U.S. Appl. No. 07/930,821, Boss et al. (File History), filed Aug. 14, 1992.

U.S. Appl. No. 08/165,530, Winter et al. (File History) filed Dec. 13, 1993.

U.S. Appl. No. 08/320,381, Boss et al. (File History) filed Oct. 11, 1994.

U.S. Appl. No. 08/450,727, Boss et al. (File History) filed May 26, 1995.

U.S. Appl. No. 08/452,420, Boss et al. (File History) filed May 26, 1995.

U.S. Appl. No. 08/453,449, Boss et al. (File History) filed May 30, 1995.

U.S. Appl. No. 08/461,071, Moore et al. (File History) filed Jun. 5, 1995.

"14th Annual Report—Top 100 Biotechnology Companies" *Med Ad News* 24 (7) : cover page 22-28, 30, 32, 34, 35 (Jul. 2005).

"Columbia, Co-transformation, Commercialization & Controversy, The Axel Patent Litigation" *Harvard Journal of Law & Technology* 17 (2) :583-618 (Spring 2004).

"Recommendations on Bacterial Production of Antibodies" (Memo from RRG to Herbert Heyneker, Cabilly Ex 2134, *Cabilly v. Boss*, Interference 105, 531) (Feb. 2, 1983).

"ReoPro" (package insert, Boss Ex. 1031, *Cabilly v. Boss*, Interference 105,531) pp. 1-4 (Nov. 16, 2005).

48 Federal Register 2696 (LEXSEE 48 FR 2708), effective Feb. 27, 1983 (Boss Exhibit 1040, *Cabilly v. Boss*, Interference 105, 531) pp. 1-35 (Jan. 20, 1983).

A collection of pictures, graphs and drawings (Cabilly Ex. 2138, *Cabilly v. Boss*, Interference 105,531).

A description of experiments and drawings (Cabilly Ex. 2137, *Cabilly v. Boss*, Interference 105,531).

A document containing single chain expression, double chain expression and list of references (Cabilly Ex. 2136, *Cabilly v. Boss*, Interference 105,531).

Affidavit of Herbert L. Heyneker; EP 0125023 Opposition (Cabilly Exhibit 2151; *Cabilly v. Boss*, Interference No. 105,531) (Mar. 20, 1997).

Affidavit of Ronald Wetzel in U.S. Appl. No. 06/483,457 (Cabilly Exhibit 2170, *Cabilly v. Boss*, Interference No. 105,531) (Jul. 22, 1986).

Alberta et al. *Molecular Biology of the Cell*, New York:Garland Publishing, Inc. (1983).

Alexander et al., "γ heavy chain disease in man: cDNA sequence supports partial gene deletion model" *Proc. Natl. Acad. Sci. USA* 79(10) :3260-3264 (May 1982).

Allore and Barber, "A recommendation for visualizing disulfide bonding by one-dimensional sodium dodecyl sulfate—polyacrylamide gel electrophoresis" *Analytical Biochemistry* 137(2):523-527 (Mar. 1984).

Amzel et al., "The Three Dimensional Structure of a Combining Region-Ligand Complex of Immunoglobulin NEW at 3.5-A Resolution" *Proc. Natl. Acad. Sci. USA* 71(4):1427-1430 (Apr. 1974).

Andersen et al., "Production technologies for monoclonal antibodies and their fragments" *Curr. Op. Biotechnol.* 15:456-462 (2004).

Answer and Counterclaim to the Complaint for Declaratory Judgment of Invalidity, Unenforceability, and Noninfringement with Exhibits (*GlaxoSmithKline v. Genentech and City of Hope*, Case No. 3:10-cv-00675-JSW) (Mar 10, 2010).

Arthur Riggs Proposal to Genentech (Cabilly Exhibit 2149; *Cabilly v. Boss*, Interference No. 105,531) (Oct. 5, 1981).

Associated Press, "RI scientists find way to mass-produce possible cancer fighters" pp. 1-2 (Jul. 11, 1982).

Auffray and Rougeon, "Nucleotide sequence of a cloned cDNA corresponding to secreted μ chain of mouse immunoglobulin" *Gene* 12(1-2):77-86 (Dec. 1980).

Baker et al., "Expression of an immunoglobulin kappa light-chain gene in lymphoid cells using a bovine papillomavirus-1 (BPV-1) vector" *Gene* 69(2):349-355 (Sep. 30, 1988).

Banerji et al., "A Lymphocyte-specific Cellular Enhancer Is Located Downstream of the Joining Region in Immunoglobulin Heavy Chain Genes" *Cell* 33:729-740 (Jul. 1983).

Banerji et al., "Expression of a β-globin gene is enhanced by remote SV40 DNA sequences" *Cell* 27(2 Pt 1):299-308 (Dec. 1981).

Barrett et al., "Enzyme-linked immunosorbent assay for detection of human antibodies to Salmonella typhi Vi antigen" *Journal of Clinical Microbiology* 17(4) :625-627 (Apr. 1983).

*Basic & Clinical Immunology* (pp. 28-29, 34-37, 83-95, 254-257, 266-267, 342-381, 742, 745-746), H. Hugh Fudenberg, 3rd edition, Los Altos:Lange Medical Publications (1980).
Bergman and Kuehl, "Co-translational modification of nascent immunoglobulin heavy and light chains" *Journal of Supramolecular Structure* 11(1) :9-24 (1979).
*Black's Law Dictionary*, Garner, Brian A., 7th edition, St. Paul:West Group pp. 129 (1999).
Bolivar et al., "Construction and Characterization of New Cloning Vehicles. II. A Multipurpose Cloning System" *Gene* 2 :95-113 (1977).
Bollen et al., "Expression in *Escherichia coli* of urokinase antigenic determinants" *Biochemical & Biophysical Research Communications* 103(2) :391-401 (1981).
Boss List of Exhibits (as updated Oct. 17, 2008) (*Cabilly* v. *Boss*, Interference 105,531).
Boss List of Exhibits (as updated Sep. 28, 2007) (*Cabilly* v. *Boss*, Interference 105,531).
Boss List of Proposed Motions (*Cabilly* v. *Boss*, Interference 105,531) (Mar. 2, 2007).
Boss Miscellaneous Motion 2 (Motion to Exclude Evidence) (*Cabilly* v. *Boss*, Interference 105,531) (Oct. 31, 2007).
Boss Miscellaneous Motion 3 (Motion to Strike Cabilly Reply 5) (*Cabilly* v. *Boss*, Interference 105,531) (Oct. 21, 2008).
Boss Notification of Notice of Appeal (*Cabilly* v. *Boss*, Interference 105,531) (Feb. 11, 2009).
Boss Objection to Served Evidence Served with Cabilly Reply 1 (*Cabilly* v. *Boss*, Interference 105,531) (Oct. 5, 2007).
Boss Opposition 1 (*Cabilly* v. *Boss*, Interference 105,531) (Aug. 24, 2007).
Boss Opposition 2 (*Cabilly* v. *Boss*, Interference 105,531) (Aug. 24, 2007).
Boss Opposition 4 (*Cabilly* v. *Boss*, Interference 105,531) (Aug. 29, 2008).
Boss Opposition 5 (*Cabilly* v. *Boss*, Interference 105,531) (Aug. 29, 2008).
Boss Reply 1 (*Cabilly* v. *Boss*, Interference 105,531) (Sep. 28, 2007).
Boss Reply 2 (Motion to Exclude Evidence) (*Cabilly* v. *Boss*, Interference 105,531) (Dec. 5, 2007).
Boss Reply 3 (*Cabilly* v. *Boss*, Interference 105,531) (Nov. 4, 2008).
Boss Response to Cabilly Reply 4—Additional Material Facts (*Cabilly* v. *Boss*, Interference 105,531) (Oct. 17, 2008).
Boss Response to Cabilly Response to Paper No. 80 (*Cabilly* v. *Boss*, Interference 105,531) (Apr. 4, 2008).
Boss Response to Memorandum Opinion and Order (*Cabilly* v. *Boss*, Interference 105,531) (Mar. 2, 2007).
Boss Substantive Motion 1 (for judgment based on obviousness-type double patenting) (*Cabilly* v. *Boss*, Interference 105,531) (May 25, 2007).
Boss UK application GB 8308235 (Cabilly Ex. 2186, *Cabilly* v. *Boss*, Interference 105,531) (Mar. 25, 1983).
Boss' Response to Cabilly Reply 5—Additional Material Facts (*Cabilly* v. *Boss*, Interference 105,531) (Oct. 17, 2008).
Boven and Pinedo, "Monoclonal antibodies in cancer treatment: where do we stand after 10 years?" *Radiotherapy & Oncology* 5 (2) :109-117 (Feb. 1986).
Bowden et al., "Cloning of eukaryotic genes in single-strand phage vectors: the human interferon genes" *Gene* 27(1) :87-99 (Jan. 1984).
Braun et al., "The second century of the antibody. Molecular perspectives in regulation, pathophysiology, and therapeutic applications" *Western Journal of Medicine* 157(2) :158-168 (Aug. 1992).
Brekke and Sandlie, "Therapeutic antibodies for human diseases at the dawn of the twenty-first century" *Nature Reviews. Drug Discovery* 2(1) :52-62 (Jan. 2003).
Brousseau et al., "Synthesis of a human insulin gene V. Enzymatic assembly, cloning and characterization of the human proinsulin DNA" *Gene* 17 :279-289 (1982).
Burton, D., "Human Monoclonal Antibodies: Achievement and Potential" *Hospital Practice* 27(8) :67-74 (Aug. 15, 1992).
Cabilly Exhibit List (Interference 104,532).
Cabilly List of Exhibits (as filed on Sep. 17, 2007) (*Cabilly* v. *Boss*Interference 105,531).
Cabilly List of Exhibits (as filed on Sep. 28, 2007) (*Cabilly* v. *Boss*, Interference 105,531).
Cabilly Motions List (*Cabilly* v. *Boss*, Interference 105,531) (Mar. 2, 2007).
Cabilly Notice of Related Proceedings (*Cabilly* v. *Boss*, Interference 105,531) (Jan. 30, 2007).
Cabilly Notice of Service of Supplemental Evidence (Responding to Boss's Objection to Cabilly Exhibit 2089) (*Cabilly* v. *Boss*, Interference 105,531) (Sep. 17, 2007).
Cabilly Opposition 1 (*Cabilly* v. *Boss*, Interference 105,531) (Aug. 24, 2007).
Cabilly Opposition 2 (Opposing Boss Motion to Exclude Evidence) (*Cabilly* v. *Boss*, Interference 105,531) (Nov. 20, 2007).
Cabilly Opposition 3 (*Cabilly* v. *Boss*, Interference 105,531) (Oct. 28, 2008).
Cabilly Reply (Regarding Boss "Response" to Paper No. 80) (*Cabilly* v. *Boss*, Interference 105,531) (Apr. 8, 2008).
Cabilly Reply 1 (Reply to Boss Opposition 1 to Cabilly Substantive Motion 1) (*Cabilly* v. *Boss*, Interference 105,531) (Sep. 28, 2007).
Cabilly Reply 2 (Reply to Boss Opposition 2 to Cabilly Substantive Motion 2) (*Cabilly* v. *Boss*, Interference 105,531) (Sep. 28, 2007).
Cabilly Reply 4 (Reply to Boss Opposition 4) (*Cabilly* v. *Boss*, Interference 105,531) (Oct. 10, 2008).
Cabilly Reply 5 (Reply to Boss Opposition 5) (*Cabilly* v. *Boss*, Interference 105,531) (Oct. 10, 2008).
Cabilly Response to Paper No. 80 (*Cabilly* v. *Boss*, Interference 105,531) (Mar. 17, 2008).
Cabilly Substantive Motion 1 (For Judgment Based on Estoppel) (*Cabilly* v. *Boss*, Interference 105,531) (May 25, 2007).
Cabilly Substantive Motion 2 (For Judgment under 35 U.S.C. 102(g)) (*Cabilly* v. *Boss*, Interference 105,531) (May 25, 2007).
Cabilly Substantive Motion 4 (To Change Benefit Accorded Boss) (*Cabilly* v. *Boss*, Interference 105,531) (Jun. 27, 2008).
Cabilly Substantive Motion 5 (For Judgement on Priority) (*Cabilly* v. *Boss*, Interference 105,531) (Jun. 27, 2008).
Cabilly Supplemental Notice of Related Proceedings (*Cabilly* v. *Boss*, Interference 105,531) (Sep. 17, 2007).
Cabilly Tutorial (*Cabilly* v. *Boss*, Interference 105,531) (May 25, 2007).
Cabilly's Response to Request for Prior Art (in responding to the memorandum opinion and order (paper No. 3) dated Jan. 16, 2007 (*Cabilly* v. *Boss*, Interference 105,531) (Mar. 2, 2007).
Cabilly's Responsive Paper Discussing Moore Patent (in responding to the memorandum opinion and order (paper No. 3) dated Jan. 16, 2007 (*Cabilly* v. *Boss*, Interference 105,531) (Mar. 2, 2007).
Cabilly's Updated List of Exhibits (as of Nov. 12, 2008) (*Cabilly* v. *Boss*, Interference 105,531) (Nov. 12, 2008).
Calendar for year 1983 (Cabilly Exhibit 2153, *Cabilly* v. *Boss*, Interference No. 105,531) (1983).
Celltech R&D Ltd.'s Reply Brief in Support of Its Motion for Judgment on the Pleadings (Redacted, Non-Confidential Version), *Medimmune* v. *Genentech, City of Hope, and Celltech*, Case No. CV 03-02567 MRP (CTx) (Cabilly Ex. 2127, *Cabilly* v. *Boss*, Interference 105,531) (Dec. 5, 2003).
Centocor's Reply to Defendants' First Amended Counterclaims (*Centocor* v. *Genentech and City of Hope*, Case No. CV 08-03573 MRP (CTx)) (Nov. 26, 2008).
Centocor, Inc.'s Opening Brief on Claim Construction with Exhibits (*Centocor* v. *Genentech and City of Hope*, Case No. CV 08-03573 MRP (CTx)) (Apr. 14, 2009).
Chang et al., "Phenotypic Expression in *E. coli* of a DNA Sequence Coding for Mouse Dihydrofolate Reductase" *Nature* 275 :617-624 (Oct. 19, 1978).
City of Hope's Answer to First Amended Complaint and Affirmative Defenses, Jury Trial Demanded (*Centocor* v. *Genentech and City of Hope*, Case No. CV 08-03573 MRP (CTx)) (Sep. 19, 2008).
City of Hope's Answer to Second Amended Complaint and Affirmative Defenses, Jury Trial Demanded (*Centocor* v. *Genentech and City of Hope*, Case No. CV 08-03573 MRP (CTx)) (Jul. 14, 2009).
Civil MInutes—General, Scheduling Conference (*Centocor* v. *Genentech and City of Hope*, Case No. CV 08-03573 MRP (CTx)) (Feb. 9, 2009).

Claim Construction Order (*Centocor* v. *Genentech and City of Hope*, Case No. CV 08-03573 MRP (CTx))' (Jun. 8, 2009).
Claim Construction Order (*MedImmune* v. *Genentech*, Case No. CV 03-2567 MRP (CTx)) (Aug. 16, 2007).
Clarification (Decision on Cabilly request for clarification) (*Cabilly* v. *Boss*, Interference 105,531) (Dec. 30, 2008).
Cohen et al., "Nonchromosomal Antibiotic Resistance in Bacteria: Genetic Transformation of *Escherichia coli* by R-Factor DNA" *Proc. Natl. Acad. Sci. USA* 69(8) :2110-2114 (Aug. 1972).
Comparison of Draft U.S. Appl. No. 06/483,457 dated Mar. 25, 1983 with U.S. Appl. No. 06/483,457, filed Apr. 8, 1983 (Cabilly Ex. 2124, *Cabilly* v. *Boss*, Interference 105,531).
Comparison of Draft U.S. Appl. No. 06/483,457 dated Mar. 31, 1983 with U.S. Appl. No. 06/483,457, filed Apr. 8, 1983 (Cabilly Ex. 2125, *Cabilly* v. *Boss*, Interference 105,531).
Comparison of Draft Application of U.S. Appl. No. 06/483,457 dated Feb. 25, 1983 and U.S. Appl. No. 06/483;457, filed Apr. 8, 1983 (Cabilly Ex. 2123, *Cabilly* v. *Boss*, Interference 105,531).
Complaint for Declaratory Judgment (*Centocor* v. *Genentech & City of Hope*, case No. CV08-03573PA (AGRx), C.D. Cal.) (May 30, 2008).
Complaint for Declaratory Judgment of Invalidity, Unenforceability, and Noninfringement with Exhibits (*GlaxoSmithKline* v. *Genentech and City of Hope*, Case No. 3:10-cv-00675-JSW) (Feb. 17, 2010).
Complaint wth Exhibits (*GlaxoSmithKline* v. *Genentech and City of Hope*, Civil Action 09-61608) (Oct. 8, 2009).
Cordingley and Preston, "Transcription and translation of the herpes simplex virus type 1 thymidine kinase gene after microinjection into *Xenopus laevis* oocytes" *Journal of General Virology* 54 (Pt 2) :409-414 (Jun. 1981).
Correspondence between counsel for Cabilly and counsel for Boss regarding joint response to Paper No. 80 in Interference 105,531 (Cabilly Ex. 2126, *Cabilly* v. *Boss*, Interference 105,531) (Mar. 2008).
Cosimi et al., "Use of monoclonal antibodies to T-cell subsets for immunologic monitoring and treatment in recipients of renal allografts" *New England J. of Medicine* 305(6) :308-314 (Aug. 6, 1981).
Cover letter, Extension of Time, Reply, and Terminal Disclaimer in U.S. Appl. No. 08/422,187 (Cabilly Exhibit 2201, *Cabilly* v. *Boss*, Interference No. 105,531) (Mar. 3, 2003).
Crea et al., "Chemical Synthesis of Genes for Human Insulin" *Proc Natl Acad Sci U S A* 75(12) :5765-5769 (Dec. 1978).
Croce et al., "Chromosomal location of the genes for human immunoglobulin heavy chains" *Proc. Natl. Acad. Sci. USA* 76 (7) :3416-3419 (Jul. 1979).
Croce et al., "Preferential retention of human chromosome 14 in mouse X human B cell hybrids" *European Journal of Immunology* 10 :486-488 (1980).
Cross-Examination of Michael Botchan, Ph.D. (Boss Exhibit 1043, *Cabilly* v. *Boss*, Interference 105,531) (Jul. 31, 2008).
Cross-Examination of Ronald B. Wetzel, Ph.D. (Boss Exhibit 1039 *Cabilly* v. *Boss*, Interference 105,531) (Aug. 5, 2008).
Cross-Examination of Shmuel Cabilly (Boss Exhibit 1042, *Cabilly* v. *Boss*, Interference 105,531) (Aug. 12, 2008).
Curriculum Vitae of Ian Andrew Wilson, D. Phil., D.Sc., F.R.S. (Cabilly Exhibit 2067, *Cabilly* v. *Boss*, Interference 105,531).
Curriculum Vitae of Steven Lanier McKnight (Cabilly Exhibit 2107, *Cabilly* v. *Boss*, Interference 105,531).
Dalla-Favera et al., "Human c-myc onc gene is located on the region of chromosome 8 that is translocated in Burkitt lymphoma cells" *Proc. Natl. Acad. Sci. USA* 79(24) :7824-7827 (Dec. 1982).
Date stamped postcard from PTO (Cabilly Exhibit 2158, *Cabilly* v. *Boss*, Interference No. 105,531) (Apr. 8, 1983).
Date stamped receipt from PTO dated Apr. 8, 1983; cover letter dated Apr. 22, 1983 from De Gastyne to Johnston; and debit note dated Apr. 22, 1983 (Cabilly Exhibit 2143, *Cabilly* v. *Boss*, Interference 105,531) (Apr. 1983).
de Saint Vincent et al., "The Cloning and Reintroduction into Animal Cells of a Functional CAD Gene, a Dominant Amplifiable Genetic Marker" *Cell* 27(Part 1) :267-277 (Dec. 1981).

Declaration for Patent Application dated Apr. 4, 1983 and Apr. 5, 1983 (Cabilly Exhibit 2140, *Cabilly* v. *Boss*, Interference 105,531) (1983).
Declaration of Arthur D. Riggs, Ph.D., filed on Jun. 27, 2008 (Cabilly Exhibit 2200, *Cabilly* v. *Boss*, Interference No. 105,531) (Jun. 20, 2008).
Declaration of Arthur Riggs in Patent Interference 102,572 (Cabilly Exhibit 2144, *Cabilly* v. *Boss*, Interference 105,531) (Oct. 28, 1991).
Declaration of Daralyn J. Durie in Support of Defendants Genentech, Inc. and City of Hope's Motion to Transfer with Exhibits (*GlaxoSmithKline* v. *Genentech and City of Hope*, Case No. 3:10-cv-00675-JSW) (Mar. 10, 2010).
Declaration of Dennis R. Burton, Ph.D. with Exhibit (Boss Exhibit 1004, *Cabilly* v. *Boss*, Interference 105,531) (May 25, 2007).
Declaration of Dr. Kate H. Murashige, Esq., filed Jun. 27, 2008 (Cabilly Exhibit 2195, *Cabilly* v. *Boss*, Interference No. 105,531) (Jun. 23, 2008).
Declaration of Dr. Mary-Jane Gething with Exhibit (*Centocor* v. *Genentech and City of Hope*, Case No. CV 08-03573 MRP (CTx)) (Mar. 24, 2009).
Declaration of Dr. Richard Axel, filed Oct. 5, 1999 in US Appl. No. 08/422,187 with Exhibits.
Declaration of Geoffrey Thomas Yarranton (Received at PTO on Jul. 17, 1995 for U.S. Appl. No. 08/450,727, Cabilly Ex. 2078A, *Cabilly* v. *Boss*, Interference 105,531) (Jun. 1, 1995).
Declaration of Geoffrey Thomas Yarranton, filed Apr. 3, 1996 in U.S. Appl. No. 08/165,530 (Cabilly Ex. 2094, *Cabilly* v. *Boss*, Interference 105,531) (Mar. 13, 1996).
Declaration of Geoffrey Thomas Yarranton, filed in U.S. Appl. No. 08/233,430 (Cabilly Ex. 2070, *Cabilly* v. *Boss*, Interference 105,531) (Mar. 24, 1992).
Declaration of Geoffrey Thomas Yarranton, filed in U.S. Appl. No. 08/450,727 (Cabilly Ex. 2078, *Cabilly* v. *Boss*, Interference 105,531) (Jun. 1, 1995).
Declaration of Herbert L. Heyneker, Ph.D., filed Jun. 27, 2008 (Cabilly Exhibit 2198, *Cabilly* v. *Boss*, Interference No. 105,531) (Jun. 24, 2008).
Declaration of Ian A. Wilson, D. Phil., D.SC., F.R.S. (Cabilly Ex. 2066, *Cabilly* v. *Boss*, Interference 105,531) (May 22, 2007).
Declaration of Jeanne Perry in Patent Interference No. 102,572 (Cabilly Exhibit 2179, *Cabilly* v. *Boss*, Interference No. 105,531) (Oct. 27, 1991).
Declaration of L. Jeanne Perry, Ph.D., filed Jun. 27, 2008 (Cabilly Exhibit 2203, *Cabilly* v. *Boss*, Interference No. 105,531) (Jun. 23, 2008).
Declaration of Marcus E. Sernel in Support of Genentech, Inc.'s and City of Hope's Opening Brief on Claim Construction with Exhibits (*Centocor* v. *Genentech and City of Hope*, Case No. CV 08-03573 MRP (CTx)) (Mar. 24, 2009).
Declaration of Mark Lemley in Support of Defendants Genentech, Inc. and City of Hope's Motion to Transfer (*GlaxoSmithKline* v. *Genentech and City of Hope*, Case No. 3:10-cv-00675-JSW) (Mar. 10, 2010).
Declaration of Martin P. Hoffman, Esquire, filed Jun. 27, 2008 (Cabilly Exhibit 2190, *Cabilly* v. *Boss*, Interference No. 105,531) (Jun. 24, 2008).
Declaration of Michael Botchan under 37 CFR 1.132 with Exhibit, filed in Reexamination Control Nos. 90/007,542 and 90/007,859 (Cabilly Exhibit 2193, *Cabilly* v. *Boss*, Interference No. 105,531) (May 20, 2007).
Declaration of Michael Botchan, Ph.D., filed Jun 27, 2008 (Cabilly Exhibit 2187, *Cabilly* v. *Boss*, Interference No. 105,531) (Jun. 23, 2008).
Declaration of Ronald B. Wetzel, Ph.D., filed Jun. 27, 2008 (Cabilly Exhibit 2199, *Cabilly* v. *Boss*, Interference No. 105,531) (Jun. 24, 2008).
Declaration of Ronald Wetzel in Patent Interference No. 102,572 (Cabilly Exhibit 2169, *Cabilly* v. *Boss*, Interference No. 105,531) (Oct. 28, 1991).
Declaration of Shmuel Cabilly in Patent Interference No. 102,572 (Cabilly Exhibit 2162, *Cabilly* v. *Boss*, Interference No. 105,531) (Oct. 28, 1991).

Declaration of Shmuel Cabilly, Ph.D. (In Support of Priority of Invention), filed Jun. 27, 2008 (Cabilly Exhibit 2204, *Cabilly* v. *Boss*, Interference No. 105,531) (Jun. 25, 2008).
Declaration of Steven Lanier McKnight, filed Aug. 24, 2007 (Cabilly Ex. 2093, *Cabilly* v. *Boss*, Interference 105,531) (Aug. 23, 2007).
Declaration of William E. Holmes, Ph. D., filed Jun. 27, 2008 (Cabilly Exhibit 2188, *Cabilly* v. *Boss*, Interference No. 105,531) (Jun. 20, 2008).
Declaration of William Holmes in Patent Interference No. 102,572 (Cabilly Exhibit 2159, *Cabilly* v. *Boss*, Interference No. 105,531) (Oct. 28, 1991).
Declaration of Yvonne Bobadilla, filed Jun. 27, 2008 (Cabilly Exhibit 2202, *Cabilly* v. *Boss*, Interference No. 105,531) (Jun. 24, 2008).
Defendant Genentech, Inc.'s and City of Hope's Counterclaims, Jury Trial Demanded with Exhibits (*Centocor* v. *Genentech and City of Hope*, Case No. CV 08-03573 MRP (CTx)) (Sep. 19, 2008).
Defendant Genentech, Inc.'s and City of Hope's First Amended Counterclaims, Jury Trial Demanded with Exhibits (*Centocor* v. *Gerientech and City of Hope*, Case No. CV 08-03573 MRP (CTx)) (Oct. 10, 2008).
Defendant Genentech, Inc.'s Answer to First Amended Complaint and Affirmative Defenses, Jury Trial Demanded (*Centocor* v. *Genentech and City of Hope*, Case No. CV 08-03573 MRP (CTx)) (Sep. 19, 2008).
Defendant Genentech, Inc.'s Answer to Second Amended Complaint and Affirmative Defenses, Jury Trial Demanded (*Centocor* v. *Genentech and City of Hope*, Case No. CV 08-03573 MRP (CTx)) (Jul. 14, 2009).
Defendants Genentech Inc.'s and City of Hope's Second Amended Counterclaims, Jury Trial Demand (*Centocor* v. *Genentech and City of Hope*, Case No. CV 08-03573 MRP (CTx)) (Jul. 1, 2009).
Defendants Genentech, Inc. and City of Hope's Motion to Transfer; Memorandum of Points and Authorities (*GlaxoSmithKline* v. *Genentech and City of Hope*, Case No. 3:10-cv-00675-JSW) (Mar. 10, 2010).
Defendants' Motion to Dismiss or in the Alternative Transfer Action to the United States District Court for the Central District of California and Supporting Memorandum of Law (GlaxoSmithKline v. Genentech and City of Hope, Civil Action 09-61608) (Dec 16, 2009).
Deposition of Arthur D. Riggs, Ph.D. with Exhibits (*Centocor* v. *Genentech and City of Hope*, Case No. CV 08-03573 MRP (CTx)) (Mar. 26, 2010).
Deposition of Dennis Burton, Ph.D. (Boss Exhibit 1035, *Cabilly* v. *Boss*, Interference 105,531) (Aug. 2, 2007).
Deposition of Dennis Burton, Ph.D. (Boss Exhibit 1051, *Cabilly* v. *Boss*, Interference 105,531) (Sep. 24, 2008).
Deposition of Dennis R. Burton, Ph.D. (Cabilly Ex. 2092, *Cabilly* v. *Boss*, Interference 105,531) (Aug. 2, 2007).
Deposition of Herbert Heyneker, Ph.D. with Exhibits (*Centocor* v. *Genentech and City of Hope*, Case No. CV 08-03573 MRP (CTx)) (Apr. 2, 2010).
Deposition of John E. Shively with Exhibits (*Centocor* v. *Genentech and City of Hope*, Case No. CV 08-03573 MRP (CTx)) (Mar. 2, 2010).
Deposition of John McLaughlin (*Centocor* v. *Genentech and City of Hope*, Case No. CV 08-03573 MRP (CTx)) (Jul. 31, 2009).
Deposition of Kate H. Murashige with Exhibits (*Centocor* v. *Genentech and City of Hope*, Case No. CV 08-03573 MRP (CTx)) (Mar. 9, 2010).
Deposition of Kate H. Murashige, Ph.D. (Boss Exhibit 1041, *Cabilly* v. *Boss*, Interference 105,531) (Aug. 7, 2008).
Deposition of L. Jeanne Perry with Exhibits (*Centocor* v. *Genentech and City of Hope*, Case No. CV 08-03573 MRP (CTx)) (Apr. 30, 2010).
Deposition of Ronald Wetzel with Exhibits (*Centocor* v. *Genentech and City of Hope*, Case No. CV 08-03573 MRP (CTx)) (Jan. 28, 2010).
Deposition of Shmuel Cabilly, Ph.D. with Exhibits (*Centocor* v. *Genentech and City of Hope*, Case No. CV 08-03573 MRP (CTx)) (Apr. 9, 2010).
Deposition of Wendy M. Lee (*Centocor* v. *Genentech and City of Hope*, Case No. CV 08-03573 MRP (CTx)) (Apr. 27, 2010).

Deposition of William E. Holmes, Ph.D. (*Centocor* v. *Genentech and City of Hope*, Case No. CV 08-03573 MRP (CTx)) (Apr. 30, 2010).
Deposition Transcript of Arthur D. Riggs, M.D. with Exhibits (*Medimmune*, Inc. v. *Genentech, Inc. and City of Hope*, Case No. CV03-2567 MRP (CTx)) (Nov. 16, 2007).
Deposition Transcript of Danny Huntington, Esq. (*Medimmune, Inc.* v. *Genentech, Inc and City of Hope*Case No. CV03-2567 MRP (CTx)), (Dec. 18, 2007).
Deposition Transcript of E. Fintan Walton, Ph.D. (*Medimmune* v. *Genentech and City of Hope*, Case No. 03-2567 MRP (CTx) ) (Apr. 23, 2008).
Deposition Transcript of Ginger Dreger with Exhibits (*Medimmune, Inc.* v. *Genentech, Inc. and City of Hope*, Case No. CV03-2567 MRP (CTx)) (Oct. 17, 2007).
Deposition Transcript of Henry Lowman, Ph.D. (*Medimmune, Inc.* v. *Genentech, Inc. and City of Hope*, Case No. CV03-2567 MRP (CTx)) (Feb. 6, 2008).
Deposition Transcript of Herbert Heyneker with Exhibits (*Medimmune, Inc.* v. *Genentech, Inc. and City of Hope*, Case No. CV03-2567 MRP (CTx)) (Oct. 28, 2007).
Deposition Transcript of Ian M. Armitage with Exhibits (*Medimmune, Inc.* v. *Genentech, Inc. and City of Hope*, Case No. CV03-2567 MRP (CTx)) (Oct. 16, 2007).
Deposition Transcript of Jeanne Perry, Ph.D. (*Medimmune, Inc.* v. *Genentech, Inc. and City of Hope*, Case No. CV03-2567 MRP (CTx)) (Jan. 18, 2008).
Deposition Transcript of Laurie H. Glimcher, M.D. (*Medimmune, Inc.* v. *Genentech, Inc. and City of Hope*, Case No. CV03-2567 MRP (CTx)) (Apr. 22, 2008).
Deposition Transcript of Matthew P. Scott, Ph.D. (*Medimmune, Inc.* v. *Genentech, Inc. and City of Hope*, Case No. CV03-2567 MRP (CTx)) (Apr. 16, 2008).
Deposition Transcript of Max D. Hensley with Exhibits (*Medimmune, Inc.* v. *Genentech, Inc. and City of Hope*, Case No. CV03-2567 MRP (CTx)) (Oct. 24, 2007).
Deposition Transcript of Ronald Burnell Wetzel with Exhibits (*Medimmune, Inc.* v. *Genentech, Inc. and City of Hope*, Case No. CV03-2567 MRP (CTx)) (Nov. 29, 2007).
Deposition Transcript of Scott Chambers, Ph.D. (*Medimmune, Inc.* v. *Genentech, Inc. and City of Hope*, Case No. CV03-2567 MRP (CTx)) (Apr. 24, 2008).
Deposition Transcript of Sean Johnston (*Medimmune, Inc,* v. *Genentech, Inc. and City of Hope*, Case No. CV03-2567 MRP (CTx)) (Nov. 9, 2007).
Deposition Transcript of Sharon E. Crane, Ph.D. (*Medimmune, Inc.* v. *Genentech, Inc. and City of Hope*, Case No. CV03-2567 MRP (CTx)) (Dec. 18, 2007).
Deposition Transcript of Shmuel Cabilly (with exhibits, *Medimmune, Inc.* v. *Genentech, Inc. and City of Hope*, Case No. CV03-2567 MRP (CTx)) (Nov. 1, 2007).
Deposition Transcript of Timothy R. Schwartz (*Medimmune, Inc.* v. *Genentech, Inc. and City of Hope*, Case No. CV03-2567 MRP (CTx)) (Dec. 4, 2007).
Deposition Transcript of William E. Holmes with Exhibit (*Medimmune, Inc.* v. *Genentech, Inc. and City of Hope*, Case No. CV03-2567 MRP (CTx)) (Oct. 19, 2007).
Diagram (Plaintiff Exhibit 76, *Centocor* v. *Genentech and City of Hope*, Case No. CV 08-03573 MRP (CTx)).
Diagram (Plaintiff Exhibit 77, *Centocor* v. *Genentech and City of Hope*, Case No. CV 08-03573 MRP (CTx)).
Dillman et al., "Therapy of chronic lymphocytic leukemia and cutaneous T-cell lymphoma with T101 monoclonal antibody" *Journal of Clinical Oncology* 2(8) :881-891 (Aug. 1984).
Dillman, R., "Monoclonal antibodies in the treatment of cancer" *Critical Reviews in Oncology-Hematology* 1 (4) :357-385 (1984).
Docket report as of Sep. 17, 2007, *Medimmune Inc.* v. *Genentech, Inc.*, U.S. District Court, Central District Court of California, Case No. 2:03-cv-02567-MRP-CT (Cabilly Ex. 2112, *Cabilly* v. *Boss*, Interference 105,531).
Document entitled "Legend to Figures" (Cabilly Exhibit 2165, *Cabilly* v. *Boss*, Interference No. 105,531).

Draft Application of U.S. Appl. No. 06/483,457 (Annotated with handwritten line numbers, Cabilly Ex. 2120A, *Cabilly v. Boss*, Interference 105,531) (Feb. 25, 1983).

Draft Application of U.S. Appl. No. 06/483,457 (Cabilly Ex. 2120, *Cabilly v. Boss*, Interference 105,531) (Feb. 25, 1983).

Draft Application of U.S. Appl. No. 06/483,457 (Cabilly Ex. 2121, *Cabilly v. Boss*, Interference 105,531) (Mar. 25, 1983).

Draft Application of U.S. Appl. No. 06/483,457 (Cabilly Ex. 2122, *Cabilly v. Boss*, Interference 105,531) (Mar. 31, 1983).

Dunnick et al., "A mouse immunoglobulin heavy chain deletion mutant: isolation of a cDNA clone and sequence analysis of the mRNA" *Nucleic Acids Research* 8(7) :1475-1484 (Apr. 11, 1980).

Ebersman, D., "Investment Community Meeting: Financial Overview" (Slides presented on Genentech, Inc. webcast) pp. 1-23 (Mar. 14, 2008).

Echols and Murialdo, "Genetic map of bacteriophage lambda" *Microbiological Reviews* 42(3) :577-591 (Sep. 1978).

Edelman et al., "Reconstitution of Immunologic Activity by Interaction of Polypepitde Chains of Antibodies" *Proc. Natl. Acad. Sci. USA* 50 :753-761 (1963).

Edelman et al., "The covalent structure of an entire γG immunoglobulin molecule" *Proc. Natl. Acad. Sci. USA* 63 :78-85 (1969).

Edelman, "Antibody Structure and Molecular Immunology" (Nobel Lecture: Physiology or Medicine) pp. 31-54 (Dec. 12, 1972).

Edge et al., "Total Synthesis of a Human Leukocyte Interferon Gene" *Nature* 292:756-762 (1981).

Engvall and Perlmann, "Enzyme-linked immunosorbent assay (ELISA) Quantitative assay of immunoglobulin G" *Immunochemistry* 8(9) :871-874 (Sep. 1971).

Erikson et al., "Assignment of the genes for human λ immunoglobulin chains to chromosome 22" *Nature* 294(5837) :173-175 (Nov. 12, 1981).

Errata Correcting Declaration (Paper No. 1.5) (*Cabilly v. Boss*, Interference 105,531) (Mar. 9, 2007).

Etkin and Maxson Jr., "The synthesis of authentic sea urchin transcriptional and translational products by sea urchin histone genes injected into *Xenopus laevis* oocytes" *Developmental Biology* 75(1) :13-25 (Mar. 1980).

Excerpts from Prosecution File History (Exhibit 1173, *Glaxo v. Cabilly*, Interference No. 104,532, dated 1994-1995).

Excerpts from the prosecution history of U.S. Appl. No. 08/165,530 (Winter et al.) filed Dec. 13, 1993 (dated 1996-1997).

Expense Reimbursement Document (Cabilly Exhibit 2150; *Cabilly v. Boss*, Interference No. 105,531).

Expert Rebuttal Report of John E. Shively, Ph.D. (Plaintiff Exhibit 134, *Centocor v. Genentech and City of Hope*, Case No. CV 08-03573 MRP (CTx)) (May 5, 2000).

Expert Report of Arne Skerra, Ph.D. (*Centocor v. Genentech and City of Hope*, Case No. CV 08-03573 MRP (CTx)) (May 14, 2010).

Expert Report of Carlo M. Croce, M.D. with Exhibits (*MedImmune, Inc. v. Genentech, Inc. and City of Hope*, Case No. CV03-2567 MRP (CTx), C.D.Cal.) (Mar. 1, 2008).

Expert Report of E. Fintan Walton (*Medimmune v. Genentech and City of Hope*, Case No. CV03-2567 (CTx)) (Feb. 29, 2008).

Expert Report of Esther M. Kepplinger with Exhibits (*MedImmune, Inc. v. Genentech, Inc. and City of Hope* (Case No. CV03-2567 MRP (CTx), C.D.Cal.)) (Mar. 1, 2008).

Expert Report of Eugene Rzucidlo (*Centocor v. Genentech and City of Hope*, Case No. CV 08-03573 MRP (CTx)) (May 14, 2010).

Expert Report of James A. Forstner with Exhibits (*MedImmune, Inc. v. Genentech, Inc. and City of Hope* (Case No. CV03-2567 MRP (CTx), C.D.Cal.)) (Jan. 24, 2008).

Expert Report of Kathryn L. Calame, Ph.D. with Exhibits (*MedImmune, Inc. v. Genentech, Inc. and City of Hope* (Case No. CV03-2567 MRP (CTx), C.D.Cal.)) (Jan. 25, 2008).

Expert Report of Laurie H. Glimcher, M.D. with Exhibits (*MedImmune, Inc. v. Genentech, Inc. and City of Hope* (Case No. CV03-2567 MRP (CTx), C.D.Cal.)) (Jan. 25, 2008).

Expert Report of Mary-Jane H. Gething, Ph.D. with Exhibits (*MedImmune, Inc. v. Genentech, Inc. and City of Hope* (Case No. CV03-2567 MRP (CTx), C.D.Cal.)) (Mar. 1, 2008).

Expert Report of Matthew P. Scott, Ph.D. with Exhibits (*MedImmune, Inc. v. Genentech, Inc. and City of Hope* (Case No. CV03-2567 MRP (CTx), C.D.Cal.)) (Mar. 1, 2008).

Expert Report of Michel C. Nussenzweig, M.D., Ph.D. with Exhibits (*MedImmune, Inc. v. Genentech, Inc. and City of Hope* (Case No. CV03-2567 MRP (CTx), C.D.Cal.)) (Jan. 25, 2008).

Expert Report of Randolph Wall, Ph.D. (*Centocor v. Genentech and City of Hope*, Case No. CV 08-03573 MRP (CTx)) (May 14, 2010).

Expert Report of Robert B. Freedman with Exhibits (*MedImmune, Inc. v. Genentech, Inc. and City of Hope* (Case No. CV03-2567 MRP (CTx), C.D.Cal.)) (Feb. 29, 2008).

Expert Reports of Dennis R. Burton, Ph.D. And Jonathan S. Weissman, Ph.D., *Genentech, Inc. v. Celltech Therapeutics, Ltd.*, Case No. C98-3926 MMC ENE (Cabilly Ex. 2089A, *Cabilly v. Boss*, Interference 105,531) (Apr. 14, 2000).

Expert Witness Report of Scott A.M. Chambers, Ph.D. with Exhibits (*MedImmune, Inc. v. Genentech, Inc. and City of Hope* (Case No. CV03-2567 MRP (CTx), C.D.Cal.)) (Jan. 24, 2008).

Express Mail Post Office Receipt dated Mar. 22, 1983 and City of Hope Request for Petty Cash (Cabilly Exhibit 2166, *Cabilly v. Boss*, Interference No. 105,531) Mar. 22, 1983).

Express mail receipt dated Mar. 29, 1983 and City of Hope Request for Petty Cash (Cabilly Ex. 2139, *Cabilly v. Boss*, Interference 105,531) (1983).

First Amended Complaint for Declaratory Judgment (*Centocor v. Genentech and City of Hope*, Case No. CV 08-03573 MRP (CTx)) (Sep. 3, 2008).

First Reclaration (Paper No. 19) (*Cabilly v. Boss*, Interference 105,531) (Feb. 14, 2007).

Fjermedal, G. *Magic Bullets* (dust jacket and table of contents), New York:Macmillian Publishing Company (1984).

Flight itinerary for Dr. Cabilly (Cabilly Exhibit 2168, *Cabilly v. Boss*, Interference No. 105,531) (Jan. 1983).

Folger et al., "Patterns of integration of DNA microinjected into cultured mammalian cells: evidence for homologous recombination between injected plasmid DNA molecules" *Molecular & Cellular Biology* 2(11) :1372-1387 (Nov. 1982).

Foon et al., "Effects of monoclonal antibody therapy in patients with chronic lymphocytic leukemia" *Blood* 64(5) :1085-1093 (Nov. 1984).

Freedman and Sela, "Recovery of specific activity upon reoxidation of completely reduced polyalanyl rabbit antibody" *Journal of Biological Chemistry* 241(22) :5225-5232 (Nov. 25, 1966).

Genentech, Inc.'s and City of Hope's Corrected Opening Brief on Claim Construction (*Centocor v. Genentech and City of Hope*, Case No. CV 08-03573 MRP (CTx)) (Apr. 2, 2009).

Genentech, Inc.'s and City of Hope's Opening Brief on Claim Construction (*Centocor v. Genentech and City of Hope*, Case No. CV 08-03573 MRP (CTx)) (Mar. 24, 2009).

Genentech, Inc.'s and City of Hope's Reply Brief on Claim Construction (*Centocor v. Genentech and City of Hope*, Case No. CV 08-03573 MRP (CTx)) (Apr. 28, 2009).

Genentech, Inc., "Genentech and Lilly Reach Settlement" (Press release: Boss Exhibit 1030, *Cabilly v. Boss*, Interference 105,531) pp. 1 (Jan. 5, 1995).

Gerhard et al., "Repertoire of antiviral antibodies expressed by somatic cell hybrids" *Proc. Natl. Acad. Sci. USA* 75(3) :1510-1514 (Mar. 1978).

Gheysen and Fiers, "Expression and excretion of human fibroblast $\beta_1$ interferon in monkey cells after transfection with a recombinant SV40 plasmid vector" *Journal of Molecular & Applied Genetics* 1 (5) :385-394 (1982).

Glaxo Group Limited and GlaxoSmithKline's Notice of Dismissal Without Prejudice (*GlaxoSmithKline v. Genentech and City of Hope*, Civil Action 09-61608) (Feb. 17, 2010).

Glaxo Wellcome Inc. Exhibit List (*Glaxo v. Cabilly*, Interference 104,532).

Goeddel et al:, "Expression in *Escherichia coli* of chemically synthesized genes for human insulin" *Proc. Natl. Acad. Sci. USA* 76 (1) :106-110 (1979).

Goto and Hamaguchi, "Unfolding and refolding of the constant fragment of the immunoglobulin light chain" *Journal of Molecular Biology* 156 (4) :891-910 (Apr. 25, 1982).

Goto and Hamaguchi, "Unfolding and refolding of the reduced constant fragment of the immunoglobulin light chain. Kinetic role of the intrachain disulfide bond" *Journal of Molecular Biology* 156 (4) : 911-926 (Apr. 25, 1982).
Graham and van der Eb, "Transformation of rat cells by DNA of human adenovirus 5" *Virology* 54 (2) :536-539 (Aug. 1973).
Graves et al., "Sequence-specific DNA uptake in transformation of *Neisseria gonorrhoeae*" *Journal of Bacteriology* 152 (3) :1071-1077 (Dec. 1982).
Grosschedl and Baltimore, "Cell-type specificity of immunoglobulin gene expression is regulated by at least three DNA sequence elements" *Cell* 41 (3) :885-897 (Jul. 1985).
Grosschedl et al., "Introduction of a μ immunoglobulin gene into the mouse germ line: specific expression in lymphoid cells and synthesis of functional antibody" *Cell* 38 (3) :647-658 (Oct. 1984).
Grunstein and Hogness, "Colony hybridization: a method for the isolation of cloned DNAs that contain a specific gene" *Proc. Natl. Acad. Sci. USA* 72 (10) :3961-3965 (Oct. 1975).
Gunge, N., "Yeast DNA plasmids" *Annual Review of Microbiology* 37 :253-276 (1983).
Haber, E., "Antibodies as models for rational drug design" *Biochemical Pharmacology* 32 (13) :1967-1977 (Jul. 1, 1983).
Haber, E., "Antibodies in vivo" *Pharmacological Reviews* 34 (1) : 77-84 (Mar. 1982).
Haber, E., "Monoclonal antibodies to drugs: new diagnostic and therapeutic tools" *Monoclonal Antibodies in Clinical Medicine*, A.J. McMichael et al., New York:Academic Press pp. 477-500 (1982).
Haber, E., "Recovery of Antigenic Specificity After Denaturation and Complete Reduction of Disulfides in a Papain Fragment of Antibody" *Proc. Natl. Acad. Sci. USA* 52:1099-1106 (Oct. 1964).
Hamer and Leder, "Expression of the chromosomal mouse βmaj - globin gene cloned in SV40" *Nature* 281(5726) :35-40 (Sep. 6, 1979).
Hamer et al., "SV40 recombinants carrying rabbit β-globin gene coding sequences" *Cell* 17(3) :725-735 (Jul. 1979).
Hanahan et al., "Characteristics of an SV40-plasmid recombinant and its movement into and out of the genome of a murine cell" *Cell* 21 :127-139 (Aug. 1980).
Handwritten Yield Calculation (Plaintiff Exhibit 82, *Centocor v. Genentech and City of Hope*, Case No. CV 08-03573 MRP (CTx)) (2010).
Hardy et al., "Production in *B. subtilis* of hepatitis B core antigen and a major antigen of foot and mouth disease virus" *Nature* 293 (5832) :481-483 (Oct. 8, 1981).
Hawley et al., "Immunoglobulin synthesis in non-B cell lines" *Immunology Letters* 12 (5-6) :257-262 (Jun. 1986).
Hellman et al., "Characterization and molecular cloning of the mRNA for the heavy (ε) chain of rat immunoglobulin E" *Proc. Natl. Acad. Sci. USA* 79 (4) :1264-1268 (Feb. 1982).
Hess et al., "Cooperation of Glycolytic Enzymes" *Advances in Enzyme Regulation*, George Weber, New York:Pergamon Press vol. 7 :149-167 (1968).
Hiatt et al., "Production of antibodies in transgenic plants" *Nature* 342 (6245) :76-78 (Nov. 2, 1989).
Hitzeman et al., "Expression of a Human Gene for Interferon in Yeast" *Nature* 293 :717-722 (1981).
Hitzeman et al., "Expression of Hepatitis B Virus Surface Antigen in Yeast" *Nucleic Acids Research* 11 (9) :2745-2763 (1983).
Hitzeman et al., "Isolation and Characterization of the Yeast 3-Phosphoglycerokinase Gene (PGK) by an Immunological Screening Technique" *Journal of Biological Chemistry* 255 (24) :12073-12080 (Dec. 25, 1980).
Hodgson, J., "Making monoclonals in microbes" *Bio/Technology* 9 (5) :421-425 (May 1991).
Holland and Holland, "Isolation and Identification of Yeast Messenger Ribonucleic Acids Coding for Enolase, Glyceraldehyde-3-phosphate Dehydrogenase, and Phosphoglycerate Kinase" *Biochemistry* 17 (23) :4900-4907 (1978).
Hood et al., "The organization, expression, and evolution of antibody genes and other multigene families" *Ann. Rev. Genet.* 9 :305-353 (1975).
Howard, M.C., "Antigen-induced B lymphocyte differentiation" *CRC Crit. Rev. Immunol.* 3 (3) :181-208 (1982).

Huber, R., "Spatial structure of immunoglobulin molecules" *Klinische Wochenschrift* 58 (22) :1217-1231 (Nov. 17, 1980).
Hung, P., "The cloning, isolation and characterization of a biologically active human enzyme, urokinase, in *E. coli*" *Advances in Experimental Medicine & Biology* 172 :281-293 (1984).
Index of Documents Entered in Interference No. 105,531 (as of Sep. 13, 2007).
Itakura et al., "Expression in *Escherichia coli* of a Chemically Synthesized Gene for the Hormone Somatostatin" *Science* 198 :1056-1063 (1977).
Jirgensons et al., "Structure studies on human serum γ-globulins and myeloma proteins. III. Oxidative sulfitolysis of myeloma globulins and reconstitution of the macromolecules" *Archives of Biochemistry & Biophysics* 111 (2) :283-295 (Aug. 1965).
Joint Declaration of Shmuel Cabilly, Herbert Heyneker, William Holmes, Arthur Riggs and Ronald Wetzel filed Nov. 3, 2003 in U.S. Appl. No. 08/422,187 (Cabilly Ex. 2145, *Cabilly v. Boss*, Interference 105,531).
Joint Rule 26(f) Report (*Centocor v. Genentech and City of Hope*, Case No. CV 08-03573 MRP (CTx)) (Feb. 2, 2009).
Jones, E., "Proteinase Mutants of *Saccharomyces cerevisiae*" *Genetics* 85 (1) :23-33 (Jan. 1977).
Judgment (Paper No. 141) (*Cabilly v. Boss*, Interference 105,531) (Dec. 8, 2008).
Judgment (U.S. Court of Appeals for the Federal Circuit, *Boss v. Cabilly*, Interference 105,531) (Dec. 11, 2009).
Judgment, *Genentech v. Celltech*, Case No. C98-3926 MMC (WDB) U.S. District Court, Northern District of California, San Francisco Division (Cabilly Ex. 2027, *Cabilly v. Boss*, Interference No. 105,531) (Mar. 16, 2001).
Kabat et al. *Sequences of Immunoglobulin Chains* (NIH Pub. No. 80-2008), Bethesda, MD:National Institutes of Health pp. 133-154 (1979).
Kabat et al. *Sequences of Immunoglobulin Chains* (NIH Pub. No. 80-2008), Bethesda, MD:National Institutes of Health pp. 185 (1979).
Kearney JF et al, "A new mouse myeloma cell line that has lost immunoglobulin expression but permits the construction of antibody-secreting hybrid cell lines" *J. Immunol* 123 (4) :1548-1550 (Oct. 1979).
Kenten et al., "Cloning and sequence determination of the gene for the human immunoglobulin ε chain expressed in a myeloma cell line" *Proc. Natl. Acad. Sci. USA* 79 (21) :6661-6665 (Nov. 1982).
Kenten et al., "Properties of a human immunoglobulin ε-chain fragment synthesized in *Escherichia coli*" *Proc. Natl. Acad. Sci. USA* 81 (10) :2955-2959 (May 1984).
Kingsman et al., "Replication in *Saccharomyces cerevisiae* of Plasmid pBR313 Carrying DNA from the yeast trpl Region" *Gene* 7 :141-152 (1979).
Kipps et al., "Allotype Switch Variants in Cultured Monoclonal Producing Hybridomas" *Journal of Cellular Biochemistry* (Abstract 0443) 26 (S8A) :163 (1984).
Koide et al., "Recognition of IgG by Fc receptor and complement: effects of glycosidase digestion" *Biochemical & Biophysical Research Communications* 75 (4) :838-844 (Apr. 25, 1977)
Koprowski et al., "Production of antibodies against influenza virus by somatic cell hybrids between mouse myeloma and primed spleen cells" *Proc. Natl. Acad. Sci. USA* 74 (7) :2985-2988 (Jul. 1977).
Kurokawa et al., "Expression of human immunoglobulin E ε chain cDNA in *E. coli*" *Nucleic Acids Research* 11 (10) :3077-3085 (1983).
Larson et al., "Imaging of melanoma with I-131-labeled monoclonal antibodies" *Journal of Nuclear Medicine* 24 (2) :123-129 (Feb. 1983).
Laub et al, "Expression of the Human Insulin Gene in an Alternate Mammalian Cell and in Cell Extracts" *Journal of Biological Chemistry* 258 (10) :6037-6042 (1983).
Laub et al., "Expression of the Human Insulin Gene and cDNA in a Heterologous Mammalian System" *Journal of Biological Chemistry* 258 (10) :6043-6050 (1983).
Law Department Status Report (Cabilly Ex. 2131, *Cabilly v. Boss*, Interference 105,531) (Nov. 3, 1982).

Lennox, E., "Monoclonal antibodies and tumor antigens—a perspective" *Hybridomas in Cancer Diagnosis and Treatment* (Progress in Cancer Research and Therapy vol. 21), Mitchell et al., New York: Raven Press pp. 5-13 (1982).

Letter from Ronald Wetzel to George Rose regarding IgG (Plaintiff Exhibit 78, *Centocor v. Genentech and City of Hope*, Case No. CV 08-03573 MRP (CTx)) (Apr. 14, 1983).

Letter to Martin P. Hoffman from Linda K. Johnston (Cabilly Ex. 2141, *Cabilly v. Boss*, Interference 105,531) (Apr. 6, 1983).

Liu et al., "Cloning and nucleotide sequence of mouse immunoglobulin ε chain cDNA" *Proc. Natl. Acad. Sci. USA* 79 (24) :7852-7856 (Dec. 1982).

Marked-up copy of Mar. 25, 1983 Draft Application (Cabilly Ex. 2142, *Cabilly v. Boss*, Interference 105,531) (Mar. 25, 1983).

Marked-up copy of proposed Ex. 2122, forwarded to Boss by Cabilly with Draft Joint Submission Responding to Paper 80, showing comparison bet. Cabilly Mar. 25, 1983 draft appln. and Cabilly Mar. 31, 1983 draft appln. (Boss Exhibit 1036, *Cabilly v. Boss*, Int. 105,531) (Mar. 31, 1983).

Marston, "The purification of eukaryotic polypeptides synthesized in *Escherichia coli*" *Biochemical Journal* 240 :1-12 (1986).

Martens et al., "Heavy chain genes of rabbit IgG: isolation of a cDNA encoding γ heavy chain and identification of two genomic $C_\gamma$ genes" *Proc. Natl. Acad. Sci. USA* 79 (19) :6018-6022 (Oct. 1982).

McCarty, M., "Chemical Nature and Biological Specificity of The Substance Inducing Transformation of Pneumococcal Types" *Bacteriological Reviews* 10 (1-2) :63-71 (Mar. 1946).

McCormick et al., "Inducible expression of amplified human beta interferon genes in CHO cells" *Molecular & Cellular Biology* 4 (1) :166-172 (Jan. 1984).

*Med Ad News* (Top 50 pharmaceutical companies charts and lists included) 13 (9) :10, 12, 14 (Sep. 2007).

*Medimmune, Inc. v. Genentech, Inc., City of Hope and Celltech*, Order remanding to district court (Fed. Cir. Nos. 04-1300,-1364 (Mar. 7, 2007).

*Medimmune, Inc. v. Genentech, Inc., City of Hope and Celltech*, Stipulation and Order Rescheduling Apr. 17, 2007 Status Conference (C.D. Cal. No. CV 03-2567 MRP (CTx)) (Apr. 12, 2007).

*MedImmune, Inc. v. Genentech, Inc.*, No. 05-608 (U.S.), slip opinion (Jan. 9, 2007).

MedImmune, Inc.'s Responses and Objections to Genentech, Inc.'s Second Set of Interrogatories (*Medimmune v. Genentech, City of Hope and Celltech*, Case No. CV03-2567 MRP (CTx)) (Feb. 24, 2004).

Meeting notes prepared by Kate Murashige (Cabilly Ex. 2135, *Cabilly v. Boss*, Interference 105,531) (Mar. 14, 1983).

Mellon et al., "Identification of DNA sequences required for transcription of the human α1 - globin gene in a new SV40 host-vector system" *Cell* 27(2 part 1):279-288 (1981).

Mellor et al., "Efficient synthesis of enzymatically active calf chymosin in *Saccharomyces cerevisiae*" *Gene* 24 (1) :1-14 (Sep. 1983).

Memorandum Opinion and Order (Decision on Cabilly Motion 1—estoppel) (Paper No. 95) (*Cabilly v. Boss*, Interference 105,531) (Jun. 4, 2008).

Memorandum Opinion and Order (Decision on Cabilly Motion 2—patentability) (Paper No. 139) (*Cabilly v. Boss*, Interference 105,531) (Dec. 8, 2008).

Memorandum Opinion and Order (Decision on Cabilly Motion 5—priority) (Paper No. 140) (*Cabilly v. Boss*, Interference 105,531) (Dec. 8, 2008).

Memorandum Opinion and Order (Paper No. 3) (*Cabilly v. Boss*, Interference 105,531) (Jan. 16, 2007).

Memorandum Opinion and Order (Paper No. 80) (*Cabilly v. Boss*, Interference 105,531) (Feb. 12, 2008).

Mertz and Gurdon, "Purified DNAs are transcribed after microinjection into *Xenopus* oocytes" *Proc. Natl. Acad. Sci. USA* 74 (4) :1502-1506 (Apr. 1977).

Miller and Levy, "Response of cutaneous T cell lymphoma to therapy with hybridoma monoclonal antibody" *Lancet* 2 (8240) :226-230 (Aug. 1, 1981).

Miller et al., "Considerations for treatment with hybridoma antibodies" *Hybridomas in cancer diagnosis and treatment* (Progress in Cancer Research and Therapy, vol. 21), Mitchell et al., New York: Raven Press pp. 133-145 (1982).

Miller et al., "Treatment of B-cell lymphoma with monoclonal anti-idiotype antibody" *New England J. of Medicine* 306 (9) :517-522 (Mar. 4, 1982).

Milstein et al., "Interchain Disulphide Bridges of Mouse Immunoglobulin M" *Biochemical Journal* 151 :615-624 (1975).

Minutes from Markman Hearing, *Centocor v. Genentech and City of Hope*, Case No. CV 08-03573 MRP (CTx) (May 12, 2009).

Minutes of Order, *Centocor v. Genentech and City of Hope*, Case No. CV 08-03573 MRP (CTx) (Jun. 9, 2009).

Minutes of Telephonic Status Conference, *Centocor v. Genentech and City of Hope*, Case No. CV 08-03573 MRP (CTx) (Jun. 10, 2009).

Miozzari and Yanofsky, "Translation of the leader region of *Escherichia coli* tryptophan operon" *Journal of Bacteriology* 133 (3) :1457-1466 (1978).

*Monoclonal Antibodies*, Roger H. Kennett et al., New York:Plenum Press pp. 8-11, 75-99, 171-182, 275-289 (1980).

Morrison and Schlom, "Recombinant chimeric monoclonal antibodies" *Important Advances in Oncology 1990*, Philadelphia:J.B. Lippincott Company pp. 3-18 (1990).

Morrison et al., "Production of novel immunoglobulin molecules by gene transfection" *Mount Sinai Journal of Medicine* 53 (3) :175-180 (Mar. 1986).

Mushinski et al., "Mouse immunoglobulin D: construction and characterization of a cloned δ chain cDNA" *Proc. Natl. Acad. Sci. USA* 77 (12) :7405-7409 (Dec. 1980).

Myers and Spiegelman, "Sodium pyrophosphate inhibition of RNA. DNA hybrid degradation by reverse transcriptase" *Proc. Natl. Acad. Sci. USA* 75 (11) :5329-5333 (Nov. 1978).

Nakamura, R., "Monoclonal antibodies: methods and clinical laboratory applications" *Clinical Physiology & Biochemistry* 1 (2-5) : 160-172 (1983).

Neumaier et al., "Cloning of the genes for T84.66, an antibody that has a high specificity and affinity for carcinoembryonic antigen, and expression of chimeric human/mouse T84.66 genes in myeloma and Chinese hamster ovary cells" *Cancer Research* 50 (7) :2128-2134 (Apr. 1, 1990).

Newman et al., "Selection and properties of a mouse L-cell transformant expressing human transferrin receptor" *Nature* 304 (5927) :643-645 (Aug. 1983).

Ng et al., "Monoclonal antibodies and immunologic approaches to malignant tumors" *Advances in Internal Medicine* 28 :253-276 (1983).

Norman, P., "Immunotherapy" *Progress in Allergy* 32 :318-346 (1982).

Nose et al., "Biological Significance of Carbohydrate Chains on Monoclonal Antibodies" *Proc. Natl. Acad. Sci. USA* 80 :6632-6636 (Nov. 1983).

Notes on Cabilly Patent (Plaintiff Exhibit 135, *Centocor v. Genentech and City of Hope*, Case No. CV 08-03573 MRP CTx)) (2000).

Notice of Declaration (Paper No. 1) (*Cabilly v. Boss*, Interference 105,531) (Jan. 16, 2007).

Notice of Ex Parte Reexamination Certificate Issuance, *Centocor v. Genentech and City of Hope*, Case No. CV 08-03573 MRP (CTx) (May 21, 2009).

Notice of Manual Filing, *Centocor v. Genentech and City of Hope*, Case No. CV 08-03573 MRP (CTx) (Jun. 15, 2009).

Obata et al., "Immunoglobulin γ1 heavy chain gene: structural gene sequences cloned in a bacterial plasmid" *Gene* 9 (1-2) :87-97 (Apr. 1980).

Ohno and Taniguchi, "Inducer-responsive expression of the cloned human interferon $β_1$ gene introduced into cultured mouse cells" *Nucleic Acids Research* 10 (3) :967-977 (Feb. 11, 1982).

Oldham and Smalley, "Immunotherapy: the old and the new" *Journal of Biological Response Modifiers* 2 (1) :1-37 (1983).

Olsson and Kaplan, "Human—human monoclonal antibody-producing hybridomas: technical aspects" *Methods in Enzymology* 92 :3-16 (1983).

Olsson, L., "Monoclonal antibodies in clinical immunobiology. Derivation, potential, and limitations" *Allergy* 38 (3) :145-154 (Apr. 1983).

Order—Motion Times—Bd.R. 104(c) (*Cabilly* v. *Boss*, Interference 105,531) (Mar. 9, 2007).

Order—Oral Argument and Other Matters (*Cabilly* v. *Boss*, Interference 105,531) (Oct. 3, 2008).

Order—Priority Motion Times—Bd.R. 104(c) (Paper No. 90) (*Cabilly* v. *Boss*, Interference 105,531) (Apr. 16, 2008).

Order Dismissing Case (*GlaxoSmithKline* v. *Genentech and City of Hope*, Civil Action 09-61608) (Feb. 17, 2010).

Order Regarding Resolution of Interference, *Genentech, Inc.* v. *Celltech Therapeutics, Ltd.*, Case No. C98-3926 MMC (Cabilly Ex. 2083, *Cabilly* v. *Boss*, Interference 105,531) (Mar. 16, 2001).

Overhead slides presented by Dr. Heyneker (Cabilly Ex. 2133, *Cabilly* v. *Boss*, Interference 105,531) (Feb. 1, 1983).

Overhead slides presented by Dr. Heyneker with Kate Murashige's notes (Cabilly Exhibit 2183, *Cabilly* v. *Boss*, Interference No. 105,531) (Feb. 1, 1983).

Paabo et al., "Association between transplantation antigens and a viral membrane protein synthesized from a mammalian expression vector" *Cell* 35 (2) :445-453 (Jun. 1983).

Page 57 from Notebook of Dr. Ronald Wetzel, provided to Cabilly during deposition of Dr. Wetzel on Aug. 5, 2008 (Boss Exhibit 1037, *Cabilly* v. *Boss*, Interference 105,531) (Feb. 24, 1983).

Pages from Dr. Ronald Wetzel's Lab Notebook compiled during deposition of Dr. Wetzel on Aug. 5, 2008, provided to Cabilly during deposition of Dr. Wetzel on Aug. 5, 2008 (Boss Exhibit 1038, *Cabilly* v. *Boss*, Interference 105,531) (1983).

Pavlakis and Hamer, "Regulation of a metallothionein-growth hormone hybrid gene in bovine papilloma virus" *Proc. Natl. Acad. Sci. USA* 80 (2) :397-401 (Jan. 1983).

PCT application No. PCT/GB84/00094 (WO84/03712 published Sep. 27, 1984), filed by Boss et al. (Cabilly Exhibit 2194, *Cabilly* v. *Boss*, Interference No. 105,531) (Mar. 23, 1984).

Pennica et al., "Cloning and Expression of Human Tissue-type Plasminogen Activator cDNA in *E. coli*" *Nature* 301 :214-221 (1983).

Perry and Wetzel, "Disulfide bond engineered into T4 lysozyme: stabilization of the protein toward thermal inactivation" *Science* 226 (4674) :555-557 (Nov. 2, 1984).

Perry et al., "Purification of monoclonal antibodies using high performance liquid chromatography (HPLC)" *Preparative Biochemistry* 14 (5) :431-447 (1984).

Perry laboratory notebook 1683 (Cabilly Exhibit 2185, *Cabilly* v. *Boss*, Interference No. 105,531) pp. 19-21 and 25-27.

Perry laboratory notebook No. 1290 (Cabilly Exhibit 2152, *Cabilly* v. *Boss*, Interference No. 105,531) pp. 48-51.

Perry laboratory notebook No. 1290 (Cabilly Exhibit 2182, *Cabilly* v. *Boss*, Interference No. 105,531) pp. 9 (1983).

Petersen and Dorrington, "An in vitro system for studying the kinetics of interchain disulfide bond formation in immunoglobulin G" *Journal of Biological Chemistry* 249 (17) :5633-5641 (Sep. 10, 1974).

Piggee, C., "Therapeutic antibodies coming through the pipeline" *Analytical Chemistry* 80 (7) :2305-2310 (Apr. 1, 2008).

Plaintiff Centocor Ortho Biotech Inc. and Third Party Defendants Global Pharmaceutical Supply Group, LLC, Centocor Biologics, LLC and Jom Pharmaceutical Services, Inc.'s First Amended Reply to Defendants' Second Amended Counterclaims (*Centocor* v. *Genentech & City of Hope*, Case CV 08-03573 MRP) (Jul. 20, 2009).

Plaintiff Centocor Ortho Biotech Inc. and Third Party Defendants Global Pharmaceutical Supply Group, LLC, Centocor Biologics, LLC and Jom Pharmaceutical Services, Inc.'s Reply to Defendants' Second Amended Counterclaims, *Centocor* v. *Genentech and City of Hope*, Case No. CV 08-03573 MRP (CTx) (Jul. 14, 2009).

Plaintiff Exhibit 74, Drawing page from US Patent 6,331,415 (*Centocor* v. *Genentech and City of Hope* Case No. CV 08-03573 MRP (CTx)) (Dec. 18, 2001).

Plaintiffs Glaxo Group Limited and GlaxoSmithKline LLC's Opposition to Defendants' Motion to Transfer with Exhibits (*GlaxoSmithKline* v. *Genentech and City of Hope*, Case No. 3:10-cv-675-JSW) (Mar. 26, 2010).

Pluckthun and Skerra, "Expression of functional antibody Fv and Fab fragments in *Escherichia coli*" *Methods in Enzymology* 178 :497-515 (1989).

Pluckthun, A., "*Escherichia coli* Producing Recombinant Antibodies" *Recombinant Microbes for Industrial and Agricultural Applications* (Part of Bioprocess Technology Series v. 19), Murooka and Imanaka, New York:Marcel Dekkeer, Inc., Chapter 13, pp. 233-252 (1994).

Polisky, B., "ColE1 replication control circuitry: sense from antisense" *Cell* 55 (6) :929-932 (1988).

Poljak et al., "Structure of Fab' New at 6 A resolution" *Nature New Biology* 235 :137-140 (Feb. 2, 1972).

Poynton and Reading, "Monoclonal antibodies: the possibilities for cancer therapy" *Experimental Biology* 43 (1) :13-33 (1984).

Preliminary Amendment in the Moore U.S. Appl. No. 08/461,071 pp. 1-4 (Jun. 5, 1995).

Preliminary Statement of the Party Cabilly et al., *Boss et al.* v. *Cabilly et al.*, Interference 102,572 (Boss Exhibit 1049, *Cabilly* v. *Boss*, Interference 105,531) (Jun. 4, 1991).

Prentice et al., "Use of anti-T-cell monoclonal antibody OKT3 to prevent acute graft-versus-host disease in allogeneic bone-marrow transplantation for acute leukaemia" *Lancet* 1 (8274) :700-703 (Mar. 27, 1982).

Proposed Order Granting Glaxo Group Limited and SmithKline Beecham Corporation d/b/a GlaxoSmithKline's Unopposed Motion for Enlargement of Time to Respond to Motion to Dismiss or in the Alternative Transfer Action (*GlaxoSmithKline* v. *Genentech and City of Hope*, Civil Action 09-61608) (Dec. 23, 2009).

Putnam, F., "Immunoglobulin structure: variability and homology" *Science* 163 (868) :633-643 (Feb. 14, 1969).

Ratzkin et al., "Expression in *Escherichia coli* of biologically active enzyme by a DNA sequence coding for the human plasminogen activator urokinase" *Proc. Natl. Acad. Sci. USA* 78 (6) :3313-3317 (Jun. 1981).

Record of Oral Hearing (Oral Hearing Held: Jan. 23, 2008) (Paper No. 79) (*Cabilly* v. *Boss*, Interference 105,531) (Feb. 11, 2008).

Report on the Filing or Determination of an Action Regarding a Patent or Trademark (*GlaxoSmithKline* v. *Genentech and City of Hope*, Case No. 3:10-cv-00675-JSW) (Feb. 18, 2010).

Report to PTO on the Filing of Action Regarding Patent (*GlaxoSmithKline* v. *Genentech and City of Hope*, Civil Action 09-61608) (Oct. 8, 2009).

Reporter's Transcript of Proceedings, Markman Hearing, *Centocor* v. *Genentech and City of Hope*, Case No. CV 08-03573 MRP (CTx) (May 12, 2009).

Request for Clarification (regarding disposition of Cabilly Motion 4) (*Cabilly* v. *Boss*, Interference 105,531) (Dec. 18, 2008).

Response Expert Report of Mark E. Nusbaum with Exhibits (*MedImmune, Inc.* v. *Genentech, Inc. and City of Hope* (Case No. CV03-2567 MRP (CTx), C.D.Cal.)) (Mar. 1, 2008).

Response to Genentech's Second Set of Interrogatories to Centocor, Inc. (Nos. 11-21) (*Centocor* v. *Genentech and City of Hope*, Case No. CV 08-03573 MRP (CTx)) (Apr. 15, 2009).

Ringold et al., "Co-expression and Amplification of Dihydrofolate Reductase cDNA and the *Escherichia coli* XGPRT Gene in Chinese Hamster Ovary Cells" *Journal of Molecular & Applied Genetics* 1 (3) :165-175 (1981).

Rituxan(R) Prescribing Information (Provided to Boss during the Second Deposition of Dennis Burton, Ph.D., Sep. 24, 2008) (Cabilly Exhibit 2211, *Cabilly* v. *Boss*, Interference No. 105,531) (Sep. 2008).

Ritz and Schlossman, "Utilization of monoclonal antibodies in the treatment of leukemia and lymphoma" *Blood* 59 (1) :1-11 (Jan. 1982).

Rogers et al., "Binding studies on two different monoclonal antibodies raised against CEA" *European Journal of Cancer & Clinical Oncology* 19 (5) :629-639 (May 1983).

Rogers et al., "Two mRNAs with different 3' ends encode membrane-bound and secreted forms of immunoglobulin μ chain" *Cell* 20 (2) : 303-312 (Jun. 1980).

Ross, J., "mRNA stability in mammalian cells" *Microbiol. Rev.* 59 (3) :423-450 (1995).

RRG Presentation by Herb Heyneker (Cabilly Ex. 2132, *Cabilly* v. *Boss*, Interference 105,531) (Feb. 1, 1983).

Russell et al., "Monoclonal antibodies for the diagnosis and treatment of transplant rejection" *Annual Review of Medicine* 35 :63-81 (1984).

Russell, P., "New approaches to the use of antibodies for immunosuppression" *Transplantation Proceedings* 14 (3) :506-508 (Sep. 1982).

Sann et al., "Rapid fractionation of serum immunoglobulins by high pressure liquid gel permeation chromatography. Application to routine serologic procedures" *Journal of Immunological Methods* 59 (1) :121-127 (Apr. 15, 1983).

Sarma et al., "The Three-Dimensional Structure at 6 A Resolution of a Human γG1 Immunoglobulin Molecule" *J. Biological Chem*. 246 : 3753-3759 (1971).

Satz and Singer, "Differential expression of porcine major histocompatibility DNA sequences introduced into mouse L cells" *Molecular & Cellular Biology* 3 (11) :2006-2016 (Nov. 1983).

Schlom et al., "Generation of human monoclonal antibodies reactive with human mammary carcinoma cells" *Proc. Natl. Acad. Sci. USA* 77 (11) :6841-6845 (1980).

Schreier et al., "Multiple differences between the nucleic acid sequences of the IgG2a$^a$ and IgG2a$^b$ alleles of the mouse" *Proc. Natl. Acad. Sci. USA* 78 (7) :4495-4499 (Jul. 1981).

Schrohenloher and Hester, "Reassembly of immunoglobulin M heavy and light chains in vitro" *Scandinavian Journal of Immunology* 5 (6-7) :637-646 (1976).

Second Amended Complaint for Declaratory Judgment, *Centocor v. Genentech and City of Hope*, Case No. CV 08-03573 MRP (CTx) (Jul. 2, 2009).

Second Supplemental Notice of Related Proceedings (*Cabilly v. Boss*, Interference 105,531) (Jun. 13, 2008).

Segal et al., "The three-dimensional structure of a phosphorylcholine-binding mouse immunoglobulin Fab and the nature of the antigen binding site" *Proc. Natl. Acad. Sci. USA* 71 (11) :4298-4302 (Nov. 1974).

Seto et al., "Monoclonal anti-MM46 antibody:ricin A chain conjugate: in vitro and in vivo antitumor activity" *Cancer Research* 42 (12) :5209-5215 (Dec. 1982).

Shulman et al., "A better cell line for making hybridomas secreting specific antibodies" *Nature* 276 (5685) :269-270 (Nov. 16, 1978).

Silverton et al., "Three-dimensional structure of an intact human immunoglobulin" *Proc. Natl. Acad. Sci. USA* 74 :5140-5144 (1977).

Simmons, L. et al., "Expression of full-length immunoglobulins in *Escherichia coli*: Rapid and efficient production of aglycosylated antibodies" *Journal of Immunological Methods* 263 :133-147 (2002).

Sire et al., "Rat immunoglobulin delta heavy chain gene: nucleotide sequence derived from cloned cDNA" *Gene* 20 (3) :377-386 (Dec. 1982).

Skerra, Arne, "Bacterial Expression of Immunoglobulin Fragments" *Current Opinion in Immunology* 5 :256-262 (1993).

Statement of Material Facts and Responses Thereto (In Motion 4, Opposition 4, and Reply 4) (*Cabilly v. Boss*, Interference 105,531) (Oct .24, 2008).

Statement of Material Facts and Responses Thereto (In Motion 5, Opposition 5, and Reply 5) (*Cabilly v. Boss*, Interference 105,531) (Oct. 24, 2008).

Status Report Regarding Notice of Intent to Issue Ex Parte Reexamination Certificate, *Centocor v. Genentech and City of Hope*, Case No. CV 08-03573 MRP (CTx) (Feb. 24, 2009).

Stepien et al., "Synthesis of a Human Insulin Gene VI. Expression of the synthetic proinsulin gene in yeast" *Gene* 24 (2-3) :289-297 (Oct. 1983).

Stinchcomb et al., "Isolation and characterisation of a yeast chromosomal replicator" *Nature* 282 (5734) :39-43 (Nov. 1, 1979).

Stipulation Re Filing of Amended Complaint to Identify Correct City of Hope Entity as Defendant, *Centocor v. Genentech and City of Hope*, Case No. CV 08-03573 MRP (CTx) (May 13, 2009).

Sun et al., "Antigen recognition by an antibody light chain" *Journal of Biological Chemistry* 269 (1) :734-738 (Jan. 7, 1994).

Supplemental and Amended Responses to Genentech Interrogatories (Nos. 13-15 & 18) (*Centocor v. Genentech and City of Hope*, Case No. CV 08-03573 MRP (CTx)) (Mar. 5, 2010).

Supplemental Declaration of Marcus E. Sernel in Support of Genentech, Inc.'s and City of Hope's Reply Brief on Claim Construction with Exhibits, *Centocor v. Genentech and City of Hope*, Case No. CV 08-03573 MRP (CTx) (Apr. 28, 2009).

Supplemental Report of Dr. Kathryn Calame (*MedImmune, Inc. v. Genentech, Inc. and City of Hope* (Case No. CV03-2567 MRP (CTx), C.D.Cal.)) (Apr. 8, 2008).

Supplemental Report of Dr. Laurie H. Glimcher (*MedImmune, Inc. v. Genentech, Inc. and City of Hope* (Case No. CV03-2567 MRP (CTx), C.D.Cal.)) (Apr. 8, 2008).

Supplemental Report of Dr. Michel C. Nussenzweig (*MedImmune, Inc. v. Genentech, Inc. and City of Hope* (Case No. CV03-2567 MRP (CTx), C.D.Cal.)) (2008).

Supplemental Report'of James A. Forstner, Ph.D. (*MedImmune, Inc. v. Genentech, Inc. and City of Hope* (Case No. CV03-2567 MRP (CTx), C.D.Cal.)) (Apr. 7, 2008).

Supplemental Report of Scott A.M. Chambers, Ph.D. (*MedImmune, Inc. v. Genentech, Inc. and City of Hope* (Case No. CV03-2567 MRP (CTx), C.D.Cal.)) (Apr. 7, 2008).

Supplemental Responses to Genentech's Interrogatories Nos. 16 & 17 (*Centocor v. Genentech and City of Hope*, Case No. CV 08-03573 MRP (CTx)) (Apr. 21, 2010).

Supplemental Submission in Response to Paper No. 3 (*Cabilly v. Boss*, Interference 105,531) (Apr. 25, 2008).

Thaler et al. *Medical Immunology*, Philadelphia:J.B. Lippincott Company pp. 3-8 (1977).

Third Declaration of Dennis Burton, Ph.D. (Boss Exhibit 1045, *Cabilly v. Boss*, Interference 105,531) (Aug. 28, 2008).

Timeline of Events Preceding Submission of Boss Claim 49 (Cabilly Ex. 2068, *Cabilly v. Boss*, Interference 105,531).

*Tissue Culture: Methods and Applications*, Kruse, Jr. and Patterson, Jr., New York:Academic Press pp. 72-122 (1973).

Transcript of Deposition of Jeanne Perry (Cabilly Exhibit 2184, *Cabilly v. Boss*, Interference No. 105,531) (Jan. 18, 2008).

Transcript of Deposition of *Michael Botchan in City of Hope National Medical Center v. Genentech, Inc.*, Case No. BC215152 (Los Angeles Co. (Cal.) Super. Ct. (Cabilly Exhibit 2192, *Cabilly v. Boss*, Interference No. 105,531) (May 23, 2001).

Transcript of Deposition of Shmuel Cabilly (Cabilly Exhibit 2163, *Cabilly v. Boss*, Interference No. 105,531) (Dec. 1, 1999).

Transcript of Oral Hearing on Nov. 13, 2008 (Part 1) (Paper No. 144) (*Cabilly v. Boss*, Interference 105,531) (Jan. 7, 2009).

Transcript of Oral Hearing on Nov. 13, 2008 (Part 2) (Paper No. 145) (*Cabilly v. Boss*, Interference 105,531) (Jan. 7, 2009).

Transcript of Proceedings before Honorable Mariana Pfaelzer, United States District Judge, Markman Hearing, *MedImmune; Inc. v. Genentech, Inc*. (C.D. Cal. No. CV 03,2567 MRP (CTx)) (Jul. 11, 2007).

Transcript of Second Deposition of Dennis Burton, Ph.D. (Cabilly Exhibit 2212, *Cabilly v. Boss*, Interference No. 105,531) (Sep. 24, 2008).

Travel request (Cabilly Exhibit 2167, *Cabilly v. Boss*, Interference No. 105,531) (Mar. 10, 1983).

Tsukada et al., "Effect of a conjugate of daunomycin and antibodies to rat α-fetoprotein on the growth of α-fetoprotein-producing tumor cells" *Proc. Natl. Acad. Sci. USA* 79 (2) :621-625 (Jan. 1982).

Tuite et al., "Regulated high efficiency expression of human interferon-α in *Saccharomyces cerevisiae*" *EMBO Journal* 1 (5) :603-608 (1982).

Turner and Rowe, "Antibodies of IgA and IgG class in normal human urine" *Immunology* 12 (6) :689-699 (Jun. 1967).

Tutorial Declaration of Dennis R. Burton, Ph.D. with Exhibit (Boss Exhibit 1016, *Cabilly v. Boss*, Interference 105,531) (May 25, 2007).

Tyler et al., "mRNA for surface immunoglobulin γ chains encodes a highly conserved transmembrane sequence and a 28-residue intracellular domain" *Proc. Natl. Acad. Sci. USA* 79 (6) :2008-2012 (Mar. 1982).

U.S. Department of Commerce Patent and Trademark Office, "Chapter 500: Receipt and Handling of Mail and Papers" *Manual of Patent Examining Procedure* (Boss Ex. 1044, *Cabilly v. Boss*, Interference 105,531), Fourth edition pps. table of contents and 55-70 (Sep. 1982).

U.S. Appl. No. 06/358,414 (Moore et al.) (patent application) (Mar. 15, 1982).

U.S. Appl. No. 07/385,102 File History (Plaintiff Exhibit 139, *Centocor v. Genentech and City of Hope*, Case No. CV 08-03573 MRP (CTx)).

Valenzuela at al., "Synthesis and Assembly of Hepatitis B Virus Surface Antigen Particles in Yeast" *Nature* 298 :347-350 (Jul. 22, 1982).

Verma et al., "Antibody engineering: comparison of bacterial, yeast, insect and mammalian expression systems" *Journal of Immunological Methods* 216 (1-2) :165-181 (Jul. 1, 1998).

Voller et al., "Enzyme immunoassays with special reference to ELISA techniques" *Journal of Clinical Pathology* 31 (6) :507-520 (Jun. 1978).

Ward et al., "Binding Activities of a Repertoire of Single Immunoglobulin Variable Domains Secreted from *Escherichia coli*" *Nature* 341 :544-546 (Oct. 12, 1989).

Watson, J. *Molecular Biology of the Gene*, Menlo Park, CA:W.A. Benjamin (1976).

Weidle et al., "Reconstitution of functionally active antibody directed against creatine kinase from separately expressed heavy and light chains in non-lymphoid cells" *Gene* 51 (1) :21-29 (1987).

Weissman et al. *Essential Concepts in Immunology*, Menlo Park:The Benjamin/Cummings Publishing Company, Inc. pp. 2, 12-19, 23-26, 49-54 (1978).

Weitzman et al., "Mutations in mouse myeloma cells: implications for human multiple myeloma and the production of immunoglobulins" *Annals of Internal Medicine* 85 (1) :110-116 (Jul. 1976).

Wellborn et al., "Spawning New Forms of Life; Now the Payoff Starts" *U.S. News & World Report* (Found on p. 48 of Special Report section.) pp. 1-5 (Mar. 28, 1983).

Wetzel et al., "Production of Biologically Active Nα-Desacetylthymosin α1 in *Escherichia coli* through Expression of a Chemically Synthesized Gene" *Biochemistry* 19 :6096-6104 (1980).

Wetzel laboratory notebook 1432 (Cabilly Exhibit 2173, *Cabilly v. Boss*, Interference No. 105,531) pp. 26, 59, 70,72, 74, 80 and 81 (1983).

Wetzel laboratory notebook No. 1432 (Cabilly Ex. 2156, *Cabilly v. Boss*, Interference No. 105,531) pp. 78 (1983).

Wetzel, R., "Applications of Recombinant DNA Technology" *American Scientist* 68 (6) :664-675 (1980).

Whitney and Tanford, "Recovery of specific activity after complete unfolding and reduction of an antibody fragment" *Proc. Natl. Acad. Sci. USA* 53 :524-532 (Mar. 1965).

Wigler et al., "Biochemical transfer of single-copy eucaryotic genes using total cellular DNA as donor" *Cell* 14 :725-731 (1978).

Wigler et al., "Transfer of purified herpes virus thymidine kinase gene to cultured mouse cells" *Cell* 11 (1) :223-232 (May 1977).

Williams, Jr. et al., "Studies of biologic and serologic activities of rabbit-IgG antibody depleted of carbohydrate residues" *Journal of Immunology* 111 (6) :1690-1698 (Dec. 1973).

Yarmush et al., "Identification and characterization of rabbit-mouse hybridomas secreting rabbit immunoglobulin chains" *Proc. Natl. Acad. Sci. USA* 77 (5) :2899-2903 (1980).

Zalcberg and McKenzie, "Hybridomas and monoclonal antibodies: applications in oncology" *Australian & New Zealand Journal of Surgery* 52 (4) :431-438 (Aug. 1982).

Zevalin(R) Prescribing Information (Provided to Boss during the Second Deposition of Dennis Burton, Ph.D., Sep. 24, 2008) (Cabilly Exhibit 2210, *Cabilly v. Boss*, Interference No. 105,531) (2008).

Amended Memorandum of Decision Re: Defendant Celltech's Motion for Judgment on the Pleadings and Defendant Genentech's Motion for Summary Judgment (*MedImmune, Inc. v. Genentech, Inc., City of Hope, and Celltech R&D Ltd.*) pps 1-26 (Jan. 12, 2004).

Celltech R&D Ltd.'s Amended Answer to First Amended Complaint (*MedImmune, Inc. v. Genentech, Inc., City of Hope, and Celltech R&D Ltd.*) pp. 1-38 (Sep. 22, 2003).

Celltech R&D Ltd.'s Answer (*MedImmune, Inc. v Genentech, Inc., City of Hope, and Celltech R&D Ltd.*) pp. 1-25 (Jun. 4, 2003).

Celltech R&D Ltd.'s Answer to First Amended Complaint (*MedImmune, Inc. v. Genentech, Inc., City of Hope, and Celltech R&D Ltd.*) pp. 1-38 (Sep. 2, 2003).

Cheng et al ., "Effect of deglycosylation on the binding and immunoreactivity of human thyroxine-binding globulin" *Journal of Biological Chemistry* 254 (18) :8830-8835 (Sep. 25, 1979).

Civil Minute Order—General (*MedImmune, Inc. v. Genentech , Inc., City of Hope, and Celltech R&D Ltd.*. pp. 1-4 (Aug. 4, 2003).

Declaration of Dean G. Dunlavey in Support of Defendant Genentech, Inc.'s Opening Brief Regarding Claim Construction (*MedImmune, Inc. v. Genentech, Inc., City of Hope, and Celltech R & D Ltd.*) pp. 1-3 with Exhibits A-P (Dec. 19, 2003).

Declaration of Jeffrey R. Witham in Support of MedImmune, Inc.'s Opposition Brief in Support of Claim Construction (*MedImmune, Inc. v. Genentech, Inc., City of Hope, and Celltech R&D Ltd.*) pp. 1-3 with Exhibits A-M (Jan. 16, 2004).

Declaration of Susan L. Friedman in Support of Genentech, Inc.'s Request for Judicial Notice in Support of Reply memorandum for Motion to Dismiss the Third and Eleventh Causes of Action (*MedImmune, Inc. v. Genentech, Inc., City of Hope, and Celltech R&D Ltd.*) pp. 1 (Jul. 28, 2003).

Defendant City of Hope National Medical Center's Answer (*MedImmune, Inc. v. Genentech , Inc., City of Hope, and Celltech R&D Ltd.*) pp. 1-37 (Sep. 2, 2003).

Defendant City of Hope's Joinder in Defendant Genentech, Inc.'s Opening Brief Re Claim Construction (*MedImmune, Inc. v. Genentech, Inc., City of Hope, and Celltech R&D Ltd.*) pp. 1-2 (Dec. 22, 2003).

Defendant Genentech, Inc.'s Answer and Affirmative Defenses (*MedImmune, Inc. v. Genentech, Inc., City of Hope, and Celltech R&D Ltd.*) pp. 1-32 (Sep. 2, 2003).

Defendant Genentech, Inc.'s Opening Brief Regarding Claim Construction (*MedImmune, Inc. v. Genentech, Inc., City of Hope, and Celltech R&D Ltd.*) pp. 1-39 (Dec. 22, 2003).

Genentech Inc.'s Notice of Motion and Motion to Dismiss the Third and Eleventh Causes of Action; Memorandum of Points and Authorities in Support (*MedImmune, Inc. v. Genentech, Inc., City of Hope, and Celltech R&D Ltd.*) pp. 1-14 (Jun. 4, 2003).

Genentech, Inc.'s Reply Memorandum of Points and Authorities in Support of Motion to Dismiss the Third and Eleventh Causes of Action (*MedImmune, Inc. v. Genentech, Inc., City of Hope, and Celltech R&D Ltd.*) pp.-i-v and 1-14 (Jul. 28, 2003).

Genentec , Inc.'s Request or Judicial Notice in Support of Reply Memorandum for Motion to Dismiss the Third and Eleventh Causes of Action (*MedImmune, Inc. v. Genentech, Inc., City of Hope, and Celltech R&D Ltd.*) pp. 1-22 (Jul. 28, 2003).

Gillies and Tonegawa, "Expression of cloned immunoglobulin genes introduced into mouse L cells" *Nucleic Acids Research* 11 (22) : 7981-7997 (Nov. 25, 1983).

Intitial Disclosures of Plaintiff MedImmune, Inc. (*MedImmune, Inc. v. Genentech, Inc., City of Hope, and Celltech R&D Ltd.*) pp. 1-10 (Aug. 21, 2003).

Joint Claim Construction Statement (*MedImmune, Inc. v. Genentech, Inc., City of Hope, and Celltech R&D Ltd.*) pp. 1-8 (Nov. 7, 2003).

MedImmune, Inc.'s Opposition Brief Regarding Claim Construction (*MedImmune, Inc. v. Genentech , Inc., City of Hope, and Celltech R&D Ltd.*) pp. i-ii and 1-38 (Jan. 16, 2004).

MedImmune, Inc.'s Responses and Objections to Genentech, Inc.'s First Set of Interrogatories pp. 1-14 (Sep. 3, 2003).

MedImmune, Inc.'s Responses and Objections to Genentech, Inc.'s First Set of Requests for Admission (*MedImmune, Inc. v. Genentech, Inc., City of Hope, and Celltech R&D Ltd.*) pp. 1-18 (Sep. 3, 2003).

MedImmune, Inc.'s Responses and Objections to Genentech, Inc.'s First Set of Requests for the Production of Documents (*MedImmune, Inc. v. Genentech, Inc., City of Hope, and Celltech R&D Ltd.*) pp. 1-28 (Sep. 3, 2003).

Memorandum of Decision Re: Defendant Celltech's Motion for Judgment on the Pleadings and Defendant Genentech's Motion for Summary Judgment (*MedImmune, Inc. v. Genentech, Inc., City of Hope, and Celltech R&D Ltd.*) pp. 1-26 (Dec. 22, 2003).

Neuberger, M., "Expression and regulation of immunoglobulin heavy chain gene transfected into lymphoid cells" *EMBO Journal* 2 (8) :1373-1378 (1983).

Order Granting Genentec Inc.'s Motion to Dismiss the Third and Eleventh Causes of Action (*MedImmune, Inc. v. Genentech, Inc., City of Hope, and Celltech R&D Ltd.*) pp. 1-2 (Aug. 11, 2003).

Plaintiff MedImmune, Inc.'s Opposition to Motion by Defendant Genentech, Inc to Dismiss the Third and Eleventh Causes of Action (*MedImmune, Inc. v. Genentech, Inc., City of Hope, and Celltech R&D Ltd.*) pp. 1-19 (Jul. 14, 2003).
Winkelhake et al., "Effects of pH treatments and deglycosylation of rabbit immunoglobulin G on the binding of Clq" *Journal of Biological Chemistry* 255 (7) :2822-2828 (Apr. 10, 1980).
Request for Reexamination under 35 U.S.C. § 302 and 37 C.F.R. 1.510 with Appendices A-D.
Centocor Ortho Biotech, Inc.'s and Its Counter-Defendant Affiliates' Opposition to Defendants' Motion to Preclude or Strike Testimony of Dr. Wall (*Centocor v. Genentech and City of Hope*, Case No. CV 08-03573 MRP (CTx)) (Jul. 27, 2010).
Centocor Ortho Biotech, Inc.'s and Its Counter-Defendant Affiliates' Reply in Support of Their Motion for Construction of Claim Term "Immunoglobulin" (Motion No. 2) (*Centocor v. Genentech and City of Hope*, Case No. CV 08-03573 MRP (CTx)) (Aug. 3, 2010).
Centocor Ortho Biotech, Inc.'s and Its Counter-Defendant Affiliates' Reply in Support of Their Motion for Summary Judgment of Anticipation (Motion No. 5) (*Centocor v. Genentech and City of Hope*, Case No. CV 08-03573 MRP (CTx)) (Aug. 3, 2010).
Centocor Ortho Biotech, Inc.'s and Its Counter-Defendant Affiliates' Reply in Support of Their Motion for Summary Judgment of Invalidity of Claim 33 for Failure to Comply with 35 USC 112 (Motion No. 4) (*Centocor v. Genentech and City of Hope*, Case No. CV 08-03573 MRP (CTx)) (Aug. 3, 2010).
Centocor Ortho Biotech, Inc.'s and Its Counter-Defendant Affiliates' Reply in Support of Their Motion for Summary Judgment That Claim 33 is Invalid for Failure to Disclose the Best Mode (Motion No. 6) (*Centocor v. Genentech and City of Hope*, Case No. CV 08-03573 MRP (CTx)) (Aug. 3, 2010).
Genentech, Inc. and City of Hope's Opposition to Centocor Inc.'s Motion for Summary Judgment That Claim 33 is Invalid for Failure to Disclose the Best Mode (Motion No. 6) (*Centocor v. Genentech and City of Hope*, Case No. CV 08-03573 MRP (CTX)) (Jul. 27, 2010).
Genentech, Inc. and City of Hope's Opposition to Centocor's Motion for Summary Judgment of Invalidity of Claim 33 for Failure to Comply with 35 USC 112 (Motion No. 4) (*Centocor v. Genentech and City of Hope*, Case No. CV 08-03573 MRP (CTx)) (Jul. 27, 2010).
Memorandum in Support of Centocor Ortho Biotech, Inc.'s and Its Counter-Defendant Affiliates' Motion for Construction of Claim Term "Immunoglobulin" (Motion No. 2) (*Centocor v. Genentech and City of Hope*, Case No. CV 08-03573 MRP (CTx) (Jul. 12, 2010).
Memorandum in Support of Centocor Ortho Biotech, Inc.'s and Its Counter-Defendant Affiliates' Motion for Summary Judgment of Anticipation (Motion No. 5) (*Centocor v. Genentech and City of Hope*, Case No. CV 08-03573 MRP (CTx)) (Jul. 12, 2010).
Memorandum in Support of Centocor Ortho Biotech, Inc.'s and Its Counter-Defendant Affiliates' Motion for Summary Judgment of Invalidity of Claim 33 for Failure to Comply with 35 USC 112 (Motion No. 4) (*Centocor v. Genentech and City of Hope*, Case No. CV 08-03573 MRP (CTx) (Jul. 12, 2010).
Memorandum in Support of Centocor Ortho Biotech, Inc.'s and Its Counter-Defendant Affiliates' Motion for Summary Judgment That Claim 33 is Invalid for Failure to Disclose the Best Mode (Motion No. 6) (*Centocor v. Genentech and City of Hope*, Case No. CV 08-03573 MRP (CTx) (Jul. 12, 2010).
Memorandum of Points and Authorities in Support of Defendants Genentech, Inc. and City of Hope's Motion to Preclude or Strike Testimony of Dr. Wall (*Centocor v. Genentech and City of Hope*, Case No. CV 08-03573 MRP (CTx)) (Jul. 12, 2010).
Opposition by Genentech, Inc. and City of Hope to Centocor Ortho Biotech, Inc.'s and Its Counter-Defendant Affiliates' Motion for Summary Judgment of Anticipation (Motion No. 5) (*Centocor v. Genentech and City of Hope*, Case No. CV 08-03573 MRP (CTx)) (Jul. 27, 2010).
Opposition of Genentech, Inc. & City of Hope to Centocor Ortho Biotech, Inc.'s Motion for Construction of Claim Term "Immunoglobulin" (Motion No. 2) (*Centocor v. Genentech and City of Hope*, Case No. CV 08-03573 MRP (CTx)) (Jul. 27, 2010).

Order of Dismissal of Entire Action with Prejudice (*Centocor v. Genentech and City of Hope*, Case No. CV 08-03573 MRP (CTx)) (Sep. 1, 2010).
Reply Memorandum of Points and Authorities in Support of Defendants Genentech, Inc. and City of Hope's Motion to Preclude or Strike Testimony of Dr. Wall (*Centocor v. Genentech and City of Hope*, Case No. CV 08-03573 MRP (CTx)) (Aug. 3, 2010).
Report on the Determination of the Action, Order of Dismissal of Entire Action with Prejudice (*Centocor v. Genentech and City of Hope*, Case No. CV 08-03573 MRP (CTx)) (Sep. 1, 2010).
Reporter's Transcript of Proceedings (Status Conference) (*Glaxo, et al. v. Genentech, et al.*, Case No. CV 10-2764-MRP (FMOx)) (Oct 13, 2010).
Stipulation of Dismissal of Entire Action with Prejudice (*Centocor v. Genentech and City of Hope*, Case No. CV 08-03573 MRP (CTx) ) (Aug. 30, 2010).
Transcript of Proceedings, Motions Hearing (*Centocor v. Genentech and City of Hope*, Case No. CV 08-03573 MRP (CTx) (Aug. 17, 2010).
MedImmune, Inc.'s Responses and Objections to Genentech, Inc.'s Second Set of Interrogatories (Feb. 24, 2004).
Joint Claim Construction Statement (Nov. 7, 2003).
Declaration of Dean G. Dunlavey in Support of Defendant Genentech, Inc.'s Opening Brief Regarding Claim Construction with Exhibits A-P (Dec. 22, 2003).
Supplemental Declaration of Dean G. Dunlavey in Support of Defendant Genentech, Inc.'s Reply Brief Regarding Claim Construction with Exhibit Q (Feb. 13, 2004).
Defendant Genentech, Inc.'s Reply Brief Regarding Claim Construction (Feb. 13, 2004).
Deposition Transcript of Genentech through witness, Janet Hasak (Feb. 25, 2004).
Deposition Transcript Exhibits 1-29 of Janet Hasak (Feb. 25, 2004).
Deposition Transcript and Exhibits 30-33 of Genentech through witness, Janet Hasak (Feb. 25, 2004).
Deposition Transcript of Wendy M. Lee and Exhibits 34-47 (Mar. 4, 2004).
Deposition Transcript of Wendy M. Lee and Exhibits 48-60 (Mar. 5, 2004).
Joint Statement Responsive to Court's Jan. 28, 2004 Order re: Terms to be Construed at Markman Hearing (Feb. 9, 2004).
Expert Report of Carlo M. Croce (*Centocor v. Genentech and City of Hope*, Case No, CV 08-03573 MRP (CTx)) (Jun. 4, 2010).
Expert Report of Matthew P. Scott (*Centocor v. Genentech and City of Hope*, Case No. CV 08-03573 MRP (CTx)) (Jun. 4, 2010).
Expert Report of Robert B. Freedman (*Centocor v. Genentech and City of Hope*, Case No. CV 08-03573 MRP (CTx)) (Jun. 4, 2010).
Oral deposition of Eugene C. Rzuoidlo (*Centocor v. Genentech and City of Hope*, Case No. CV 08-03573 MRP (CTX)) (Jun. 25, 2010).
Response Expert Report of Mark E. Nusbaum (*Centocor v. Genentech and City of Hope*, Case No. CV 08-03573 MRP (CTx)) (Jun. 4, 2010).
Videotaped Deposition of Arne Skerra (*Centocor v. Genentech and City of Hope*, Case No. CV 08-03573 MRP (CTX)) (Jun. 24, 2010).
Videotaped Deposition of Carlo M. Croce (*Centocor v. Genentech and City of Hope*, Case No. CV 08-03573 MRP (CTX)) (Jul. 8, 2010).
Videotaped Deposition of Daniel G. Yansura (*Centocor v. Genentech and City of Hope*, Case No. CV 08-03573 MRP (CTx)) (Apr. 20, 2010).
Videotaped Deposition of Jeffrey Kushan (*Centocor v. Genentech and City of Hope*, Case No. CV 08-03573 MRP (Ctx)) (Jun. 1, 2010).
Videotaped Deposition of Mark E. Nusbaum (*Centocor v. Genentech and City of Hope*, Case. No. CV 08-03573 MRP (CTx)) (Jun. 22, 2010).
Videotaped Deposition of Mark X. Sliwkowski (*Centocor v. Genentech and City of Hope*, Case No. CV 08-03573 MRP (CTx)) (Apr. 30, 2010).
Videotaped Deposition of Matthew Peter Scott (*Centocor v. Genentech and City of Hope*, Case No. CV 08-03573 MRP (CTx)) (Jun. 15, 2010).
Videotaped Deposition of Robert B. Freedman (*Centocorv. Genentech and City of Hope*, Case No. CV 08-03573 MRP (CTx)) (Jun. 22, 2010).

Videotaped Deposition of Sharon Elizabeth Crane (*Centocor* v. *Genentech and City of Hope*, Case No. CV 08-03573 MRP (CTX)) (Jun. 10, 2010).
Request for Reexamination filed on May 13, 2005 for U.S. Patent No. 6,331,415 with Appendices 1-21.
Restriction Requirement (Paper No. 4) dated Mar. 8, 1990 in U.S. Appl. No. 07/205,419.
Restriction Requirement (Paper No. 11) dated Sep. 7, 1990 in U.S Appl. No. 07/205,419.
Interview Summary (Paper No. 22) in U.S. Appl. No. 07/205,419.
Amendment After Interference (Paper No. 24) filed Oct. 4, 2001 in U.S. Appl. No. 07/205,419.
File History of U.S. Patent No. 4,816,397 (Boss et al.).
Aiba et al., "New approach to tryptophan production by *Escherichia coli*: genetic manipulation of composite plasmids in vitro" *Appl. Environ. Microbiol.* 43 (2) :289-297 (Feb. 1982).
Brandsma et al., "Effect of lexA and ssb genes, present on a uvrA recombinant plasmid, on the UV survival of *Escherichia coli* K-12" *Gene* 18(1) :77-85 (Apr. 1982).
Enger-Valk et al., "Construction of new cloning vehicles with genes of the tryptophan operon of *Escherichia coli* as genetic markers" *Gene* 9 (1-2) : 69-85 (Apr. 1980).
Enger-Valk et al., "The construction of new vehicles for the cloning of transcription termination signals" *Nucleic Acids Research* 9 (8) : 1973-1989 (Apr. 1981).
Fiandt et al., "Physical mapping of the trp endpoint in the n-tL segment of phage lambda trpE-A" *Virology* 61 (1) :312-314 (Sep. 1974).
Friesen and An, "Expression vehicles used in recombinant DNA technology" *Biotechnol. Adv.* 1 (2) :205-227 (1983).
Gough and Murray, "Expression of the hepatitis B virus surface, core and E antigen genes by stable rat and mouse cell lines" *J. Mol. Biol.* 162 (1) :43-67 (Nov. 25, 1982).
Hallewell and Emtage, "Plasmid vectors containing the tryptophan operon promoter suitable for efficient regulated expression of foreign genes" *Gene* 9 (1-2) :27-47 (Apr. 1980).
Hershfield et al., "Plasmid ColEl as a molecular vehicle for cloning and amplification of DNA" *Proc. Natl. Acad. Sci. USA* 71 (9) :3455-3459 (Sep. 1974).
Horowitz and Platt, "Identification of trp-p2, and internal promoter in the tryptophan operon of *Escherichia coli*" *J. Mol. Biol.* 156 (2) : 257-267 (Apr. 5, 1982).
Imamoto and Tani, "Diversity of regulation of genetic transcription" *Nat. New. Biol.* 240 (101) :172-175 (Dec. 6, 1972).
Kaufman and Sharp, "Amplification and Expression of Sequences Cotransfected with a Modular Dihydrofolate Reductase Complementary DNA Gene" *J. Mol. Biol.* 159 (4) :601-621 (Aug. 25, 1982).
Legrain et al., "Structural and regulatory mutations allowing utilization of citrulline or carbamoylaspartate as a source of carbamoylphosphate in *Escherichia coli* K-12" *J. Bacteriol.* 128 (1) :39-48 (Oct. 1976).

Maniatis et al. *Molecular Cloning—A Laboratory Manual*, New York: Cold Spring Harbor Laboratory pp. 1-545 (1982).
Nagahari at al., "Control of tryptophan synthetase amplified by varying the numbers of composite plasmids in *Escherichia coli* cells" *Gene* 1 (2) :141-152 (Mar. 1977).
Nagahari et al., "Derepression of *E. coli* trp operon on interfamilial transfer" *Nature* 266 (5604) :745-746 (Apr. 21, 1977).
Nagahari et al., "Expression of *Escherichia coli* tryptophan operon in *Rhizobium leguminosarum*" *Mol. Gen. Genet.* 171 (2) :115-119 (Mar. 20, 1979).
Pauza et al., "Genes encoding *Escherichia coli* aspartate transcarbamoylase: the pyrB-pyrI operon" *Proc. Natl. Acad. Sci. USA* 79 (13) :4020-4024 (Jul. 1982).
Plaintiffs and counterclaim defendants' preliminary contentions regarding the invalidity of U.S. Patent No. 6,331,415 (*Glaxo et al.* v. *Genentech and City of Hope*, Case No. CV-10-02764 MRP (FMOx), Exhibits A & B attached.) (Dec 13, 2010).
Rapoport et al., "Construction of a colony bank of *E. coli* containing hybrid plasmids representative of the *Bacillus subtilis* 168 genome. Expression of functions harbored by the recombinant plasmids in *B. subtilis*" *Mol. Gen. Genet.* 176 (2) :239-245 (Oct. 3, 1979).
Roof et al., "The organization and regulation of the pyrBI operon in *E. coli* includes a rho-independent attenuator sequence" *Mol. Gen. Genet.* 187 (3) :391-400 (1982).
Turnbough Jr., C., "Regulation of *Escherichia coli* aspartate transcarbamylase synthesis by guanosine tetraphosphate and pyrimidine ribonucleoside triphosphates" *J. Bacteriol.* 153 (2) :998-1007 (Feb. 1983).
Turnbough, Jr. et al., "Attenuation control of pyrBI operon expression in *Escherichia coli* K-12" *Proc. Natl. Acad. Sci. USA* 80 (2) :368-372 (Jan. 1983).
van Leerdam et al., "Cloning of both ends and the thermo-inducible genes A and B of bacteriophage Mu on a multicopy plasmid" *Gene* 13 (1) :111-114 (Jan.-Feb. 1981).
Wagner et al., "Transport of hemolysin across the outer membrane of *Escherichia coli* requires two functions" *J. Bacteriol.* 154 (1) :200-210 (Apr. 1983).
Watson et al. *Recombinant DNA—A Short Course*, New York:Scientific American Books (W.H. Freeman & Company) pp. 1-260 (1983).
Wild at al., "A mutation in the catalytic cistron of aspartate carbamoyltransferase affecting catalysis, regulatory response and holoenzyme assembly" *Nature* 292 (5821) :373-375 (Jul. 23, 1981).
Williams et al., "Expression of *Escherichia coli* trp genes and the mouse dihydrofolate reductase gene cloned in *Bacillus subtilis*" *Gene* 16 (1-3) :199-206 (Dec. 1981).
Yamamoto and Imamoto, "Differential stability of trp messenger RNA synthesized originating at the trp promoter and pL promoter of lambda trp phage" *J. Mol. Biol.*92 (2) :289-304 (Feb. 25, 1975).

* cited by examiner

```
                                                                                 tthlII              hphI    haeIII
                                                                                                             haeI
  1  GTTGCTGTGG TTGTCTGGTG TTGAAGGAGA CATTGTGATG ACCCAGTCTC ACAAATTCAT GTCCACATCA GTAGGAGACA GGGTCAGCAT CACCTGCAAG
     CAACGACACC AACAGACCAC AACTTCCTCT GTAACACTAC TGGGTCAGAG TGTTTAAGTA CAGGTGTAGT CATCCTCTGT CCCAGTCGTA GTGGACGTTC
                                                                                                  sfaNI
                                                                                                           scrFI
                                                                                                           ncII
                 fnu4HI      scrFI                                                                hpaII    hpaII    hinfI
          fokI   bbv         ecoRII                                                               fokI     sfaNI
101  GCCAGTCAGG ATGTGGGTGC TGCTATAGCC TGGTATCAAC AGAAACCAGG ACAATCTCCT AAACTACTGA TTTACTGGGC ATCCACCCGG CACACTGGAG
     CGGTCAGTCC TACACCCACG ACGATATCGG ACCATAGTTG TCTTTGGTCC TGTTAGAGGA TTTGATGACT AAATGACCCG TAGGTGGGCC GTGTGACCTC
                                                                                                           scrFI
                                                                                                           ncII
                                                                                                           hpaII
                                                                    hpaI    hincII                         sfaNI
       xhoII                                               hphI
       sau3A                                                                                                       hincII
       dpnI
201  TCCCTGATCG CTTCACAGGC AGTGTCCGTG GGACAGATTT CACTCTCACC ATTAGCAATG TGACTTGGCA GATTATTTCT GTCAACAATA
     AGGGACTAGC GAAGTGTCCG TCACAGGCAC CCTGTCTAAA GTGAGAGTGG TAATCGTTAC ACGTGAACCT CTAATAAAGA CAGTTGTTAT
                                                                                          hpaI
                                                                                          hincII
              mnII              sau96                                             mboII
                                avaII    aluI   sfaNI                      fnu4HI
                                         aluI                              bbv
301  TAGCGGGTAT CCTCTCAAGT TCGGTGCTGG GACCAAGCTG GAGCTGAAAC GGGCTGATGC TGCACCAACT GTATCCATCT TCCCACCATC CAGTGAGCAG
     ATCGCCCATA GGAGAGTTCA AGCCACGACC CTGGTTCGAC CTCGACTTTG CCCGACTACG ACGTGGTTGA CATAGGTAGA AGGGTGGTAG GTCACTCGTC
                                                                                                  fokI
         mnII                            xmnI                                    mboII                             acyI
              mnII    ddeI
401  TTAACATCTG GAGGTGCCTC AGTGTGTGTGC TTCTTGAACA ACTTCTACCC CAAAGACATC AATGTCAAGT GGAAGATTGA CGACAAAATG
     AATTGTAGAC CTCCACGGAG TCACACACG AAGAACTTGT TGAAGATGGG GTTTCTGTAG TTACAGTTCA CCTTCTAACT GCTGTTTAC
```

```
                                                              sau3A                                                    fnu4HI
              hgaI                                            dpnI                                                     bbv         mnlI hincII              sau96 hgaI
              hgaI                                            bclI                                                                                           avaII  ddeI     acyI
     GCGTCCTGAA CAGTTGGACT GATCAGGACA GCAAGACACAG CACCTACAGC ATGAGCAGCA CCCTCACGTT GACCAAGGAC GAGTATGAAC GACATAACAG
501  CGCAGGACTT GTCAACCTGA CTAGTCCTGT CGTTTCTGTC GTGGATGTCG TACTCGTCGT GGGAGTGCAA CTGGTTCCTG CTCATACTTG CTGTATTGTC mnlI                                              hphI                      aluI
                 haeIII                                                                                                                                  avaII  ddeI     acyI
                 haeI                                                                                                                                   GGTCCTGAGA CGCCACCACC
601  CTATACCTGT GAGGCCACTC ACAAGACATC AACTTCACCC ATTGTCAAGA GCTTCAACAG GAATGAGTGT TAGAGACAAA CGCCACCACC
     GATATGGACA CTCCGGTGAG TGTTCTGTAG TTGAAGTGGG TAACAGTTCT CGAAGTTGTC CTTACTCACA ATCTCTGTTT CCAGGACTCT GCGGTGGTGG aluI   aluI                            mboII    ddeI               mnlI                                                  hgiA                         mnlI
     AGCTCCCCAG CTCCATCCTA TCTTCCCTTC TAAGGTCTTG GAGGCTTCCC CACAAGCGAC CTACCACTGT TGCGGTGCTC CAAACCTCCT CCCCACCTCC
701  TCGAGGGGTC GAGGTAGGAT AGAAGGGAAG ATTCCAGAAC CTCCGAAGGG GTGTTCGCTG GATGGTGACA ACGCCACGAG GTTTGGAGGA GGGGTGGAGG
                  fokI
                                     mnlI
          mnlI mnlI                                                                                     xmnI                                    hinfI
     TTCTCCTCCT CCTCCCTTTC CTTGGCTTTT ATCATGCTAA TATTTGCAGA AAATATTCAA TAAAGTGAGT CTTTGCACTT GA
801  AAGAGGAGGA GGAGGGAAAG GAACCGAAAA TAGTACGATT ATAAACGTCT TTTATAAGTT ATTTCACTCA GAAACGTGAA CT nucleotides: 882
```

Fig. 3

```
      -9
      leu trp leu ser gly val glu gly asp ile
      UUG UGG CUG UCU GGU GUU GAA GGA GAC AUU
G
                              1                               10                              20
      val met thr gln ser his lys phe met ser thr ser val gly asp arg val ser
      GUG AUG ACC CAG UCU CAC AAA UUC AUG UCC ACA UCA GUA GGA GAC AGG GUC AGC 30                                                              50
      ile thr cys lys ala ser gln asp val gly thr ala ile ala trp tyr gln gln lys pro gly gln ser pro lys leu leu ile tyr trp
      AUC ACC UGC AAG GCC AGU CAG GAU GUG GGU ACU GCU AUA GCC UGG UAU CAG CAG AAA CCA GGA CAA UCA CCU AAA CUA CUG AUU UAC UGG 60                                                              80
      ala ser thr arg his thr gly val pro asp arg phe thr gly ser gly ser gly thr asp phe thr leu thr ile ser asn val gln ser
      GCA UCC ACC CGG CAC ACU GGA GUC CCU GAU CGC UUC ACA GGC AGU GGA UCU GGG ACA GAU UUC ACU CUC ACC AUU AGC AAU GUG CAG UCU 90                                                              110
      glu asp leu ala asp tyr phe cys gln gln tyr ser ser tyr pro leu thr phe gly gly gly thr lys leu glu leu lys arg ala asp
      GAA GAU UUG GCA GAU UAU UUC UGU CAA CAA UAU AGC AGC UAU CCU CUC ACG UUC GGU GGG GGG ACC AAG CUG GAG CUG AAA CGG GCU GAU 120                                                             140
      ala ala pro thr val ser ile phe pro pro ser ser glu gln leu thr ser gly gly ala ser val val cys phe leu asn asn phe tyr
      GCU GCA CCA ACU GUA UCC AUC UUC CCA CCA UCC AGU GAG CAG UUA ACA UCU GGA GGU GCC UCA GUC GUG UGC UUC UUG AAC AAC UUC UAC 150                                                             170
      pro lys asp ile asn val lys trp lys ile asp gly ser glu arg gln asn gly val leu asn ser trp thr asp gln asp ser lys asp
      CCC AAA GAC AUC AAU GUC AAG UGG AAG AUU GAU GGC AGU GAG CGA CAA AAU GGC GUC CUG AAC AGU UGG ACU GAU CAG GAC AGC AAA GAC 180                                                             200
      ser thr tyr ser met ser ser thr leu thr leu thr lys asp glu tyr glu arg his asn ser tyr thr cys glu ala thr his lys thr
      AGC ACC UAC AGC AUG AGC AGC ACC CUC ACG UUG ACC AAG GAC GAG UAU GAA CGA CAU AAC AGC UAU ACC UGU GAG GCC ACU CAC AAG ACA 210      214
      ser thr ser pro ile val lys ser phe asn arg asn glu cys AM
      UCA ACU UCA CCC AUU GUC AAG AGC UUC AAC AGG AAU GAG UGU UAG AGACAAGGUCCUGAUGACGCCACCACCAGCUCCCAGCUCCUCCUCCAUCCUUACUUCCCUUCUAA GGUCUUGGAGGCUUCCCACAAGGCUGACUACCACACUGUUGGGGUGCCAAACCUCCCCACCUCCUCCUCCUUGGCUUUUAUCAUGCUAAUAUUUGCAGAAAA

UAUUCAAUAAAGUGAGUCUUUGCACUUGA
```

```
        hinfI   sau96
                avaII mnlI                          ddeI                        ahaIII          sfaNI
        hinfI   avaII mnlI    CCCCTCACGA TGAACTTCGG GCTCAGCTTG ATTTACCTTG TCCTTGTTTT AAAAGTTGTC CAGTGTGAAG TGATGCTGGT
  1     GAGTCAGCAC TGAACACGGA CCCCTCACGA TGAACTTCGG GCTCAGCTTG ATTTACCTTG TCCTTGTTTT AAAAGTTGTC CAGTGTGAAG TGATGCTGGT
        CTCAGTCGTG ACTTGTGCCT GGGGAGTGCT ACTTGAAGCC CGAGTCGAAC TAAATGGAAC AGGAACAAAA TTTTCAACAG GTCACACTTC ACTACGACCA scrFI   sau96                          fnu4HI
                     mnlI    ecoRII avaII                   bbv mnlI      hinfI
        hinfI   hinfI        AGGGTCCCTG AGGGTCCCTC TGGAGCCTTC GTGCAGCCCTC TGGATTCACT TTCAGTAGAT ATGCCATGTC TTGGGTTCGC
 101    GGAGTCTGGG CCTCAGAATT ACCTCGGACC TCCCAGGGAC TTTGAGAGGA CACGTCGGAG ACCTAAGTGA AAGTCATCTA TACGGTACAG AACCCAAGCG hpaII       mnlI                                                                           hphI
        hinfI mboII     mnlI                                              hinfI
        CAGACTCCGG AGAAGAGGCT GGAGTGGGTC GCAACCATTA GTAGTTCACAC CTTCCATCCA GACAGTGTGA AGGGCGATTC ACCATCTCCA
 201    CAGACTCCGG AGAAGAGGCT GGAGTGGGTC GCAACCATTA GTAGTTCACAC CTTCCATCCA GACAGTGTGA AGGGCGATTC ACCATCTCCA
        GTCTGAGGCC TCTTCTCCGA CCTCACCCAG CGTTGGTAAT CATCAAGTGTG GAAGGTAGGT CTGTCACACT TCCCGCTAAG TGGTAGAGGT
                                                       fokI mnlI
                              rsaI                              mnlI ddeI   haeIII                    mnlI
        GAGACAATGC CAAGAACACC CTGTACCTGC AAATGAGCAG TCTGAGGTCT GAGGACACGG CCATGTATTA CTGTGCAAGA CCCCCTCTTA TTTCGTTAGT
 301    GAGACAATGC CAAGAACACC CTGTACCTGC AAATGAGCAG TCTGAGGTCT GAGGACACGG CCATGTATTA CTGTGCAAGA CCCCCTCTTA TTTCGTTAGT
        CTCTGTTACG GTTCTTGTGG GACATGGACG TTTACTCGTC AGACTCCAGA CTCCTGTGCC GGTACATAAT GACACGTTCT GGGGAGAAT AAAGCAATCA xhoII
                                                                                                      scrFI   sau3A
                                                                                              sau96           ecoRII
                                                                  mnlI                                haeIII dpnI
                                               mnlI   hphI        ddeI
        AGCGGACTAT GCTATGGACT ACTGGGGTCA AGGAACCTCA GTCACCGTCT CCTCAGCCAA AACGACACCC CCATCTGTCT ATCCACTGGC CCCTGGATCT
 401    AGCGGACTAT GCTATGGACT ACTGGGGTCA AGGAACCTCA GTCACCGTCT CCTCAGCCAA AACGACACCC CCATCTGTCT ATCCACTGGC CCCTGGATCT
        TCGCCTGATA CGATACCTGA TGACCCCAGT TCCTTGGAGT CAGTGGCAGA GGAGTCGGTT TTGCTGTGGG GGTAGACAGA TAGGTGACCG GGGACCTAGA
```

Fig. 4A.

```
                         ncoI         scrFI
                         hphI  sfaNI  fokI
       fnu4HI            bstEII ecoRI      ddeI                                                      xhoII
       bbv                                                                                           sau3A
                                                                                                     dpnI
                                                                       scrFI                         bamHI
                                                                       ecoRII
501    GCTGCCCAAA CTAACTCCAT GGTGACCCTG GGATGCCTGG TCAAGGGCTA TTTCCCTGAG CCAGTGACAG CTCTGGATCC CTGTCCAGCG
       CGACGGGTTT GATTGAGGTA CCACTGGGAC CCTACGGACC AGTTCCCGAT AAAGGGACTC GGTCACTGTC GAGACCTAGG GACAGGTCGC fnu4HI
                   pvuII                                   bbv  ddeI                         sau96
             hgiA  aluI          pstI          mnlI             aluI                                hphI
601    GTGTGCACAC CTTCCCAGCT GTCCTGCAGT CTGACCTCTA CACTCTGAGC AGCTCAGTGA CTGTCCCCTC CAGCCCTCGG CCGTCACCTG
       CACACGTGTG GAAGGGTCGA CAGGACGTCA GACTGGAGAT GTGAGACTCG TCGAGTCACT GACAGGGGAG GTCGGGAGCC GGCAGTGGAC scrFI                                                                            mnlI  haeIII
                   ncil fnu4HI                                                                      scrFI
             bglI  hpaII bbv                                              scrFI
701    CAACGTTGCC CACCCGGCCA GCAGCACCAA GGTGGACAAG AAAATTGTGC CCAGGGATTG TGGTTGTAAG CCTTGCATAT GTACAGTCCC AGAAGTATCA
       GTTGCAACGG GTGGGCCGGT CGTCGTGGTT CCACCTGTTC TTTTAACACG GGTCCCTAAC ACCAACATTC GGAACGTATA CATGTCAGGG TCTTCATAGT mstII                                  sau3A
                                                             hinfI                        accI      dpnI mnlI
             mboII                                  hpaI                         fokI hgiA          fokI aval
       mboII                                        foki hgiA
801    TCTGTCTTCA TCTTCCCCCC AAAGCCCAAG GATGTGCTCA CCATTACTCT GACTCCTAAG GTCACGTGTG TTGTGGTAGA CATCAGCAAG GATGATCCCG
       AGACAGAAGT AGAAGGGGGG TTTCGGGTTC CTACACGAGT GGTAATGAGA CTGAGGATTC CAGTGCACAC AACACCATCT GTAGTCGTTC CTACTAGGGC smaI
                                                   scrFI
                                                   scrFI
                                                   ncil
                                         ddeI      ncil
             sau96 pvuII                 aluI hgaI hpaII        mnlI
             avaII aluI                  ddeI     aval
901    AGGTCCAGTT CAGCTGGTTT GTAGATGATG TGGAGGTGCA CACAGCTCAG ACGCAACCCC GGGAGGAGCA GTTCAACAGC ACTTTCCGCT CAGTCAGTGA
       TCCAGGTCAA GTCGACCAAA CATCTACTAC ACCTCCACGT GTGTCGAGTC TGCGTTGGGG CCCTCCTCGT CAAGTTGTCG TGAAAGGCGA GTCAGTCACT
```

Fig. 4B.

```
                         scrFI                            hincII                         fnu4HI
                         ecoRII                                                          bbv                    taqI
                                                                               fnu4HI    alul                   
1001  ACTTCCCATC ATGCACCAGG ACTGGCTCAA TGGCAAGGAG TTCAAATGCA GGGTCAACAG TGCAGCTTTC CCTGCCCCCA TCGAGAAAAC CATCTCCAAA
      TGAAGGGTAG TACGTGGTCC TGACCGAGTT ACCGTTCCTC AAGTTTACGT CCCAGTTGTC ACGTCGAAAG GGACGGGGGT AGCTCTTTTG GTAGAGGTTT rsaI                           haeIII
                                                             haeI
                                              mnlI           balI
1101  ACCAAAGGCA GACCGAAGGC TCCACAGGTG TACACCATTC CACCTCCCAA GGAGCAGATG GCCAAGGATA AAGTCAGTCT GACCTGCATG ATAACAGACT
      TGGTTTCCGT CTGGCTTCCG AGGTGTCCAC ATGTGGTAAG GTGGAGGGTT CCTCGTCTAC CGGTTCCTAT TTCAGTCAGA CTGGACGTAC TATTGTCTGA fnu4HI
      mboII                   bbv                                        ddeI
      mboII                                                                                                    
1201  TCTTCCCTGA AGATCATTACT GTGGAGTGGC AGTGGAATGG GCAGCCAGCG GAGAACTACA AGAACACTCA GCCCATCATG AACACGAATG GCTCTTACTT
      AGAAGGGACT TCTGTAATGA CACCTCACCG TCACCTTACC CGTCGGTCGC CTCTTGATGT TCTTGTGAGT CGGGTAGTAC TTGTGCTTAC CGAGAATGAA sau96
                                          mboII             hphI                             mnlI             mboII
      accI     aluI                                                                                   haeIII          ddeI
1301  CGTCTACAGC AAGCTCAATG TGCAGAAGAG CAACTGGGAG GCAGGAAATA CTTTCACCTG CTCTGTGTTA CATGAGGGCC TGCACAACCA CCATACTGAG
      GCAGATGTCG TTCGAGTTAC ACGTCTTCTC GTTGACCCTC CGTCCTTTAT GAAAGTGGAC GAGACACAAT GTACTCCCGG ACGTGTTGGT GGTATGACTC scrFI    sau3A           sau96                                        mnlI
             mnlI      ecoRII   dpnI            avaII                hinfI                   mnlI
1401  AAGAGCCTCT CCCACTCTCC TGGTAAATGA TCCCAGTGTC CTTGGAGCCC TCTGGTCCTA CAGGACTCTG ACACCTACCT CCACCCCTCC CTGTATAAAT
      TTCTCGGAGA GGGTGAGAGG ACCATTTACT AGGGTCACAG GAACCTCGGG AGACCAGGAT GTCCTGAGAC TGTGGATGGA GGTGGGGAGG GACATATTTA

1501  AAAGCACCCA GCACTGCCTT GGGAAAAA
      TTTCGTGGGT CGTGACGGAA CCCTTTTT
```

```
ile phe pro pro lys pro lys asp val leu thr ile thr pro lys val thr cys val val asp ile ser lys asp pro
AUC UUC CCC CCA AAG CCC AAG GAU GUG CUC ACC AUU ACU CCU AAG GUC ACG GUU GUA GAC AUC AGC AAG GAU CCC
                              250                         260                         270 glu val gln phe ser trp phe val asp val glu val his thr ala gln thr pro arg glu glu gln phe asn ser thr phe arg
GAG GUC CAG UUC AGC UGG UUU GUA GAU GUG GAG GUG CAC ACA GCU CAG ACG CCC CGG GAG GAG CAG UUC AAC AGC ACU UUC CGC
                              280                         290                         300 ser val ser glu leu pro ile met his gln asp trp leu asn gly lys glu phe lys cys arg val asn ser ala ala phe pro ala pro
UCA GUC AGU GAA CUU CCC AUC AUG CAC CAG GAC UGG CUC AAU GGC AAG GAG UUC AAA UGC AGG GUC AAC AGU GCA GCU UUC CCU GCC CCC
                              310                         320                         330 ile glu lys thr ile ser lys thr lys gly arg pro lys ala pro gln val tyr thr ile pro pro pro lys glu gln met ala lys asp lys
AUC GAG AAA ACC AUC UCC AAA ACC AAA GGC AGA CCG AAG GCU CCA CAG GCU GUG UAC ACC AUU CCA CCU CCC AAG GAG CAG AUG GCC AAG GAU
                              340                         350                         360 lys val ser leu thr cys met ile thr asp phe phe pro glu asp ile thr val glu trp gln trp asn gly gln pro ala glu asn tyr
AAA GUC AGU CUG ACC UGC AUG AUA ACA GAC UUC UUC CCU GAA GAC AUU ACU GUG GAG UGG CAG UGG AAU GGG CAG CCA GCG GAG AAC UAC
                              370                         380                         390 lys asn thr gln pro ile met asn thr asn gly ser tyr phe val tyr ser lys leu asn val gln lys ser asn trp glu ala gly asn
AAG AAC ACU CAG CCC AUC AUG AAC ACG AAU GGC UCU UAC UUC GUC UAC AGC AAG CUC AAU GUG CAG AAG AGC AAC UGG GAG GCA GGA AAU
                              400                         410                         420 thr phe thr cys ser val leu his glu gly leu his asn his his thr glu lys ser leu ser his ser pro gly lys OP
ACU UUC ACC UGC UCU GUU UUA CAU GAG GGC CUG CAC AAC CAU CAC ACU GAG AAG AGC CUC UCC CAC UCU CCU GGU AAA UGA UCCCAGUGUCCU
                              430                         440                         447

UGGAGCCCUCUGGUCCUUACAGGACUCUGACACCUUCACCCCUCCCCUGUAAAUAAAGCACCCAGCACUGCCUUGGGAAAAA
```

*Fig. 5B.*

ND LIGHT CHAINS HAVING SPECIFICITY
METHODS OF MAKING ANTIBODY HEAVY AND LIGHT CHAINS HAVING SPECIFICITY FOR A DESIRED ANTIGEN

This is a continuation of application(s) Ser. No. 07/205,419 filed on 10 Jun. 1988, now U.S. Pat. No. 6,331,415, issued on 18 Dec. 2001, which is a continuation of Ser. No. 06/483,457 filed on 8 Apr. 1983, now U.S. Pat. No. 4,816,567, issued on 28 Mar. 1989, which applications are incorporated herein by reference and to which application(s) priority is claimed under 35 USC §120.

BACKGROUND OF THE INVENTION

This invention relates to the field of immunoglobulin production and to modification of naturally occurring immunoglobulin amino acid sequences. Specifically, the invention relates to using recombinant techniques to produce both immunoglobulins which are analogous to those normally found in vertebrate systems and to take advantage of these gene modification techniques to construct chimeric or other modified forms.

A. Immunoglobulins and Antibodies

Antibodies are specific immunoglobulin polypeptides produced by the vertebrate immune system in response to challenge by foreign proteins, glycoproteins, cells, or other antigenic foreign substances. The sequence of events which permits the organism to overcome invasion by foreign cells or to rid the system of foreign substances is at least partially understood. An important part of this process is the manufacture of antibodies which bind specifically to a particular foreign substance. The binding specificity of such polypeptides to a particular antigen is highly refined, and the multitude of specificities capable of being generated by the individual vertebrate is remarkable in its complexity and variability. Thousands of antigens are capable of eliciting responses, each almost exclusively directed to the particular antigen which elicited it.

Immunoglobulins include both antibodies, as above described, and analogous protein substances which lack antigen specificity. The latter are produced at low levels by the lymph system and in increased levels by myelomas.

A.1 Source and Utility

Two major sources of vertebrate antibodies are presently utilized—generation in situ by the mammalian B lymphocytes and in cell culture by B-cell hybrids. Antibodies are made in situ as a result of the differentiation of immature B lymphocytes into plasma cells, which occurs in response to stimulation by specific antigens. In the undifferentiated B cell, the portions of DNA coding for the various regions on the immunoglobulin chains are separated in the genomic DNA. The sequences are reassembled sequentially prior to transcription. A review of this process has been given by Gough, *Trends in Biochem Sci,* 6: 203 (1981). The resulting rearranged genome is capable of expression in the mature B lymphocyte to produce the desired antibody. Even when only a single antigen is introduced into the sphere of the immune system for a particular mammal, however, a uniform population of antibodies does not result. The in situ immune response to any particular antigen is defined by the mosaic of responses to the various determinants which are present on the antigen. Each subset of homologous antibody is contributed by a single population of B cells—hence in situ generation of antibodies is "polyclonal".

This limited but inherent heterogeneity has been overcome in numerous particular cases by use of hybridoma technology to create "monoclonal" antibodies (Kohler, et al., *Eur. J. Immunol.,* 6: 511 (1976)). In this process, splenocytes or lymphocytes from a mammal which has been injected with antigen are fused with a tumor cell line, thus producing hybrid cells or "hybridomas" which are both immortal and capable of producing the genetically coded antibody of the B cell. The hybrids thus formed are segregated into single genetic strains by selection, dilution, and regrowth, and each strain thus represents a single genetic line. They therefore produce immunoreactive antibodies against a desired antigen which are assured to be homogenous, and which antibodies, referencing their pure genetic parentage, are called "monoclonal". Hybridoma technology has to this time been focused largely on the fusion of murine lines, but human-human hybridomas (Olsson, L. et al., *Proc. Natl. Acad. Sci. (USA),* 77: 5429 (1980)); human-murine hybridomas (Schlom, J., et al. (ibid) 77: 6841 (1980)) and several other xenogenic hybrid combinations have been prepared as well. Alternatively, primary, antibody producing, B cells have been immortalized in vitro by transformation with viral DNA.

Polyclonal, or, much more preferably, monoclonal, antibodies have a variety of useful properties similar to those of the present invention. For example, they can be used as specific immunoprecipitating reagents to detect the presence of the antigen which elicited the initial processing of the B cell genome by coupling this antigen-antibody reaction with suitable detection techniques such as labeling with radioisotopes or with enzymes capable of assay (RIA, EMIT, and ELISA). Antibodies are thus the foundation of immuno diagnostic tests for many antigenic substances. In another important use, antibodies can be directly injected into subjects suffering from an attack by a substance or organism containing the antigen in question to combat this attack. This process is currently in its experimental stages, but its potential is clearly seen. Third, whole body diagnosis and treatment is made possible because injected antibodies are directed to specific target disease tissues, and thus can be used either to determine the presence of the disease by carrying with them a suitable label, or to attack the diseased tissue by carrying a suitable drug.

Monoclonal antibodies produced by hybridomas, while theoretically effective as suggested above and clearly preferable to polyclonal antibodies because of their specificity, suffer from certain disadvantages. First, they tend to be contaminated with other proteins and cellular materials of hybridoma, (and, therefore, mammalian) origin. These cells contain additional materials, notably nucleic acid fragments, but protein fragments as well, which are capable of enhancing, causing, or mediating carcinogic responses. Second, hybridoma lines producing monoclonal antibodies tend to be unstable and may alter the structure of antibody produced or stop producing antibody altogether (Kohler, G., et al., *Proc. Natl. Acad. Sci (USA)* 77: 2197 (1980); Morrison, S. L., *J. Immunol.* 123: 793 (1979)). The cell line genome appears to alter itself in response to stimuli whose nature is not currently known, and this alteration may result in production of incorrect sequences. Third, both hybridoma and B cells inevitably produce certain antibodies in glycosylated form (Melchers, F., *Biochemistry,* 10: 653 (1971)) which, under some circumstances, may be undesirable. Fourth, production of both monoclonal and polyclonal antibodies is relatively expensive. Fifth, and perhaps most important, production by current techniques (either by hybridoma or by B cell response) does not permit manipulation of the genome so as to produce antibodies with more effective design components than those normally elicited in response to antigens from the mature B cell in situ. The antibodies of the present invention do not suffer from the foregoing drawbacks, and, furthermore, offer the opportunity to provide molecules of superior design.

Even those immunoglobulins which lack the specificity of antibodies are useful, although over a smaller spectrum of potential uses than the antibodies themselves. In presently understood applications, such immunoglobulins are helpful in protein replacement therapy for globulin related anemia. In this context, an inability to bind to antigen is in fact helpful, as the therapeutic value of these proteins would be impaired by such functionality. At present, such non-specific antibodies are derivable in quantity only from myeloma cell cultures suitably induced. The present invention offers an alternative, more economical source. It also offers the opportunity of cancelling out specificity by manipulating the four chains of the tetramer separately.

A.2 General Structure Characteristics

The basic immunoglobin structural unit in vertebrate systems is now well understood (Edelman, G. M., *Ann. N.Y. Acad. Sci.*, 190: 5 (1971)). The units are composed of two identical light polypeptide chains of molecular weight approximately 23,000 daltons, and two identical heavy chains of molecular weight 53,000-70,000. The four chains are joined by disulfide bonds in a "Y" configuration wherein the light chains bracket the heavy chains starting at the mouth of the Y and continuing through the divergent region as shown in FIG. 1. The "branch" portion, as there indicated, is designated the Fab region. Heavy chains are classified as gamma, mu, alpha, delta, or epsilon, with some subclasses among them, and the nature of this chain, as it has a long constant region, determines the "class" of the antibody as IgG, IgM, IgA, IgD, or IgE. Light chains are classified as either kappa or lambda. Each heavy chain class can be prepared with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells. However, if non-covalent association of the chains can be effected in the correct geometry, the aggregate will still be capable of reaction with antigen, or of utility as a protein supplement as a non-specific immunoglobulin.

The amino acid sequence runs from the N-terminal end at the top of the Y to the C-terminal end at the bottom of each chain. At the N-terminal end is a variable region which is specific for the antigen which elicited it, and is approximately 100 amino acids in length, there being slight variations between light and heavy chain and from antibody to antibody. The variable region is linked in each chain to a constant region which extends the remaining length of the chain. Linkage is seen, at the genomic level, as occurring through a linking sequence known currently as the "J" region in the light chain gene, which encodes about 12 amino acids, and as a combination of "D" region and "J" region in the heavy chain gene, which together encode approximately 25 amino acids.

The remaining portions of the chain are referred to as constant regions and within a particular class do not to vary with the specificity of the antibody (i.e., the antigen eliciting it).

As stated above, there are five known Major classes of constant regions which determine the class of the immunoglobulin molecule (IgG, IgM, IgA, IgD, and IgE corresponding to $\gamma$, $\mu$, $\alpha$, $\delta$, and $\epsilon$ heavy chain constant regions). The constant region or class determines subsequent effector function of the antibody, including activation of complement (Kabat, E. A., *Structural Concepts in Immunology and Immunochemistry*, 2nd Ed., p. 413-436, Holt, Rinehart, Winston (1976)), and other cellular responses (Andrews, D. W., et al., *Clinical Immunobiology* pp 1-18, W. B. Sanders (1980); Kohl, S., et al., *Immunology*, 48: 187 (1983)); while the variable region determines the antigen with which it will react.

B. Recombinant DNA Technology

Recombinant DNA technology has reached sufficient sophistication that it includes a repertoire of techniques for cloning and expression of gene sequences. Various DNA sequences can be recombined with some facility, creating new DNA entities capable of producing heterologous protein product in transformed microbes and cell cultures. The general means and methods for the in vitro ligation of various blunt ended or "sticky" ended fragments of DNA, for producing expression vectors, and for transforming organisms are now in hand.

DNA recombination of the essential elements (i.e., an origin of replication, one or more phenotypic selection characteristics, expression control sequence, heterologous gene insert and remainder vector) generally is performed outside the host cell. The resulting recombinant replicable expression vector, or plasmid, is introduced into cells by transformation and large quantities of the recombinant vehicle is obtained by growing the transformant. Where the gene is properly inserted with reference to portions which govern the transcription and translation of the encoded DNA message, the resulting expression vector is useful to produce the polypeptide sequence for which the inserted gene codes, a process referred to as "expression." The resulting product may be obtained by lysis, if necessary, of the host cell and recovery of the product by appropriate purifications from other proteins.

In practice, the use of recombinant DNA technology can express entirely heterologous polypeptides—so-called direct expression—or alternatively may express a heterologous polypeptide fused to a portion of the amino acid sequence of a homologous polypeptide. In the latter cases, the intended bioactive product is sometimes rendered bioinactive within the fused, homologous/heterologous polypeptide until it is cleaved in an extracellular environment.

The art of maintaining cell or tissue cultures as well as microbial systems for studying genetics and cell physiology is well established. Means and methods are available for maintaining permanent cell lines, prepared by successive serial transfers from isolated cells. For use in research, such cell lines are maintained on a solid support in liquid medium, or by growth in suspension containing support nutriments. Scale-up for large preparations seems to pose only mechanical problems.

SUMMARY OF THE INVENTION

The invention relates to antibodies and to non-specific immunoglobulins (NSIs) formed by recombinant techniques using suitable host cell cultures. These antibodies and NSIs can be readily prepared in pure "monoclonal" form. They can be manipulated at the genomic level to produce chimeras of variants which draw their homology from species which differ from each other. They can also be manipulated at the protein level, since all four chains do not need to be produced by the same cell. Thus, there are a number of "types" of immunoglobulins encompassed by the invention.

First, immunoglobulins, particularly antibodies, are produced using recombinant techniques which mimic the amino acid sequence of naturally occurring antibodies produced by either mammalian B cells in situ, or by B cells fused with suitable immortalizing tumor lines, i.e., hybridomas. Second, the methods of this invention produce, and the invention is directed to, immunoglobulins which comprise polypeptides not hitherto found associated with each other in nature. Such reassembly is particularly useful in producing "hybrid" antibodies capable of binding more than one antigen; and in producing "composite" immunoglobuins wherein heavy and light chains of different origins essentially damp out specificity. Third, by genetic manipulation, "chimeric" antibodies can be formed wherein, for example, the variable regions correspond to the amino acid sequence from one mammalian model system, whereas the constant region mimics the amino acid sequence of another. Again, the derivation of these two mimicked sequences may be from different species. Fourth, also by genetic manipulation, "altered" antibodies with improved specificity and other characteristics can be formed.

Two other types of immunoglobulin-like moieties may be produced: "univalent" antibodies, which are useful as homing carriers to target tissues, and "Fab proteins" which include only the "Fab" region of an immunoglobulin molecule i.e, the branches of the "Y". These univalent antibodies and Fab fragments may also be "mammalian" i.e., mimic mammalian amino acid sequences; novel assemblies of mammalian chains, or chimeric, where for example, the constant and variable sequence patterns may be of different origin. Finally, either the light chain or heavy chain alone, or portions thereof, produced by recombinant techniques are included in the invention and may be mammalian or chimeric.

In other aspects, the invention is directed to DNA which encodes the aforementioned NSIs, antibodies, and portions thereof, as well as expression vectors or plasmids capable of effecting the production of such immunoglobulins in suitable host cells. It includes the host cells and cell cultures which result from transformation with these vectors. Finally, the invention is directed to methods of producing these NSIs and antibodies, and the DNA sequences, plasmids, and transformed cells intermediate to them.

BRIEF DESCRIPTION OF THE DRAWINGS

FIGS. 2A-B show the detailed sequence of the cDNA insert of pK17G4 which encodes kappa anti CEA chain.

FIG. 3 shows the coding sequence of the fragment shown in FIG. 2, along with the corresponding amino acid sequence.

FIGS. 4A-C show the combined detailed sequence of the cDNA inserts of pγ298 and pγ11 which encode gamma anti CEA chain.

FIGS. 5A-B show the corresponding amino acid sequence encoded by the fragment in FIG. 4.

DETAILED DESCRIPTION

A. Definitions

Figure 1:
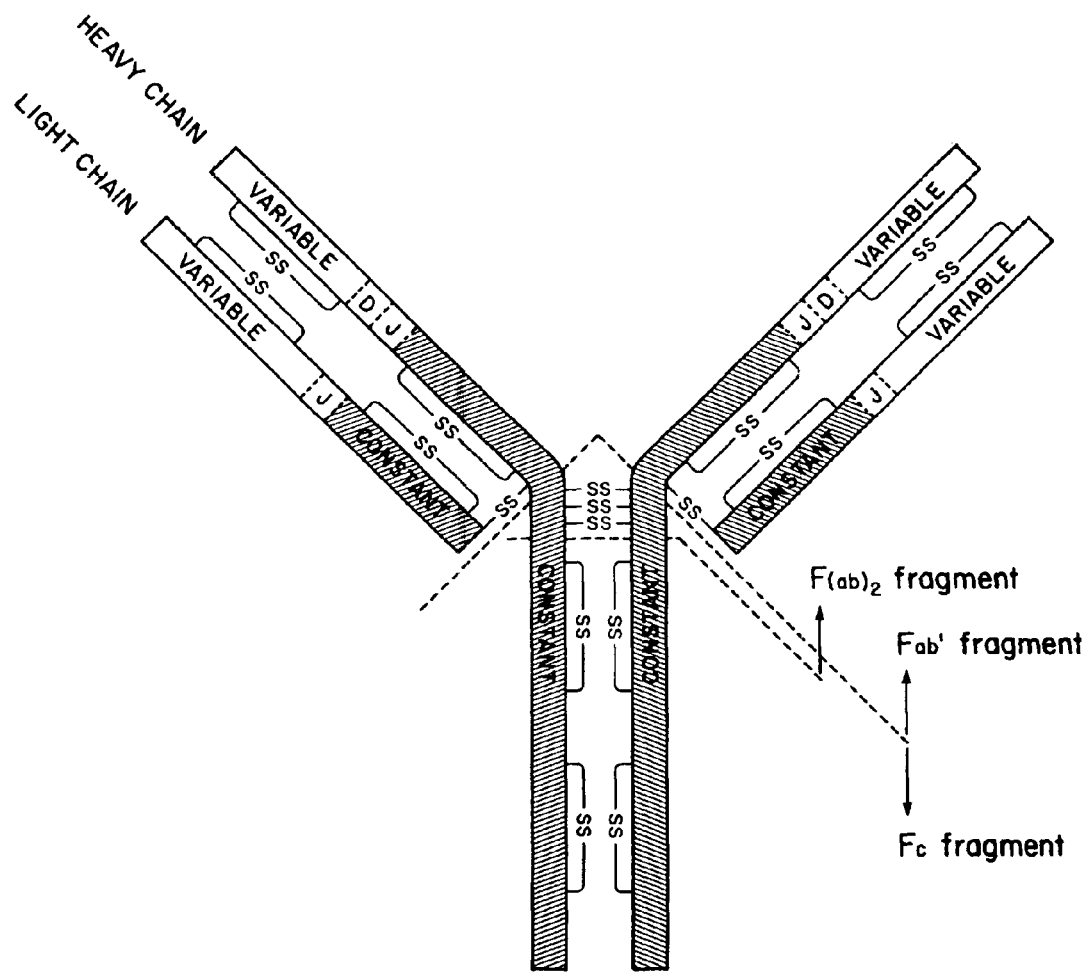
FIG. 1 is a representation of the general structure of immunoglobulins.

As used herein, "antibodies" refers to tetramers or aggregates thereof which have specific immunoreactive activity, comprising light and heavy chains usually aggregated in the "Y" configuration of FIG. 1, with or without covalent linkage between them; "immunoglobulins" refers to such assemblies whether or not specific immunoreactive activity is a property. "Non-specific immunoglobulin" ("NSI") means those immunoglobulins which do not possess specificity—i.e., those which are not antibodies.

"Mammalian antibodies" refers to antibodies wherein the amino acid sequences of the chains are homologous with those sequences found in antibodies produced by mammalian systems, either in situ, or in hybridomas. These antibodies mimic antibodies which are otherwise capable of being generated, although in impure form, in these traditional systems.

"Hybrid antibodies" refers to antibodies wherein chains are separately homologous with referenced mammalian antibody chains and represent novel assemblies of them, so that two different antigens are precipitable by the tetramer. In hybrid antibodies, one pair of heavy and light chain is homologous to antibodies raised against one antigen, while the other pair of heavy and light chain is homologous to those raised against another antigen. This results in the property of "divalence" i.e., ability to bind two antigens simultaneously. Such hybrids may, of course, also be formed using chimeric chains, as set forth below.

"Composite" immunoglobulins means those wherein the heavy and light chains mimic those of different species origins or specificities, and the resultant is thus likely to be a non-specific immunoglobulin (NSI), i.e. —lacking in antibody character.

"Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source.

However, the definition is not limited to this particular example. It includes any antibody in which either or both of the heavy or light chains are composed of combinations of sequences mimicking the sequences in antibodies of different sources, whether these sources be differing classes, differing antigen responses, or differing species of origin and whether or not the fusion point is at the variable/constant boundary. Thus, it is possible to produce antibodies in which neither the constant nor the variable region mimic known antibody sequences. It then becomes possible, for example, to construct antibodies whose variable region has a higher specific affinity for a particular antigen, or whose constant region can elicit enhanced complement fixation or to make other improvements in properties possessed by a particular constant region.

"Altered antibodies" means antibodies wherein the amino acid sequence has been varied from that of a mammalian or other vertebrate antibody. Because of the relevance of recombinant DNA techniques to this invention, one need not be confined to the sequences of amino acids found in natural antibodies; antibodies can be redesigned to obtain desired characteristics. The possible variations are many and range from the changing of just one or a few amino acids to the complete redesign of, for example, the constant region. Changes in the constant region will, in general, be made in order to improve the cellular process characteristics, such as complement fixation, interaction with membranes, and other effector functions. Changes in the variable region will be made in order to improve the antigen binding characteristics. The antibody can also be engineered so as to aid the specific delivery of a toxic agent according to the "magic bullet" concept. Alterations, can be made by standard recombinant techniques and also by oligonucleotide-directed mutagenesis techniques (Dalbadie-McFarland, et al *Proc. Natl. Acad. Sci. (USA)*, 79:6409 (1982)).

"Univalent antibodies" refers to aggregations which comprise a heavy chain/light chain dimer bound to the Fc (or stem) region of a second heavy chain. Such antibodies are specific for antigen, but have the additional desirable property of targeting tissues with specific antigenic surfaces, without causing its antigenic effectiveness to be impaired—i.e., there is no antigenic modulation. This phenomenon and the property of univalent antibodies in this regard is set forth in Glennie, M. J., et al., *Nature*, 295: 712 (1982). Univalent antibodies have heretofore been formed by proteolysis.

"Fab" region refers to those portions of the chains which are roughly equivalent, or analogous, to the sequences which comprise the Y branch portions of the heavy chain and to the light chain in its entirety, and which collectively (in aggregates) have been shown to exhibit antibody activity. "Fab protein", which protein is one of the aspects of the invention, includes aggregates of one heavy and one light chain (commonly known as Fab'), as well as tetramers which correspond to the two branch segments of the antibody Y, (commonly known as $F(ab)_2$), whether any of the above are covalently or non-covalently aggregated, so long as the aggregation is capable of selectively reacting with a particular antigen or antigen family. Fab antibodies have, as have univalent ones, been formed heretofore by proteolysis, and share the property of not eliciting antigen modulation on target tissues. However, as they lack the "effector" Fc portion they cannot effect, for example, lysis of the target cell by macrophages.

"Fab protein" has similar subsets according to the definition of the present invention as does the general term "antibodies" or "immunoglobulins". Thus, "mammalian" Fab protein, "hybrid" Fab protein "chimeric" Fab and "altered" Fab protein are defined analogously to the corresponding definitions set forth in the previous paragraphs for the various types of antibodies.

Individual heavy or light chains may of course be "mammalian", "chimeric" or "altered" in accordance with the above. As will become apparent from the detailed description of the invention, it is possible, using the techniques disclosed to prepare other combinations of the four-peptide chain aggregates, besides those specifically defined, such as hybrid antibodies containing chimeric light and mammalian heavy chains, hybrid Fab proteins containing chimeric Fab proteins of heavy chains associated with mammalian light chains, and so forth.

"Expression vector" includes vectors which are capable of expressing DNA sequences contained therein, i.e., the coding sequences are operably linked to other sequences capable of effecting their expression. It is implied, although not always explicitly stated, that these expression vectors must be replicable in the host organisms either as episomes or as an integral part of the chromosomal DNA. Clearly a lack of replicability would render them effectively inoperable. A useful, but not a necessary, element of an effective expression vector is a marker encoding sequence—i.e. a sequence encoding a protein which results in a phenotypic property (e.g. tetracycline resistance) of the cells containing the protein which permits those cells to be readily identified. In sum, "expression vector" is given a functional definition, and any DNA sequence which is capable of effecting expression of a specified contained DNA code is included in this term, as it is applied to the specified sequence. As at present, such vectors are frequently in the form of plasmids, thus "plasmid" and "expression vector" are often used interchangeably. However, the invention is intended to include such other forms of expression vectors which serve equivalent functions and which may, from time to time become known in the art.

"Recombinant host cells" refers to cells which have been transformed with vectors constructed using recombinant DNA techniques. As defined herein, the antibody or modification thereof produced by a recombinant host cell is by virtue of this transformation, rather than in such lesser amounts, or more commonly, in such less than detectable amounts, as would be produced by the untransformed host.

In descriptions of processes for isolation of antibodies from recombinant hosts, the terms "cell" and "cell culture" are used interchangeably to denote the source of antibody unless it is clearly specified otherwise. In other words, recovery of antibody from the "cells" may mean either from spun down whole cells, or from the cell culture containing both the medium and the suspended cells.

B. Host Cell Cultures and Vectors

The vectors and methods disclosed herein are suitable for use in host cells over a wide range of prokaryotic and eukaryotic organisms.

In general, of course, prokaryotes are preferred for cloning of DNA sequences in constructing the vectors useful in the invention. For example, *E. coli* K12 strain 294 (ATCC No. 31446) is particularly useful. Other microbial strains which may be used include *E. coli* strains such as *E. coli* B, and *E. coli* X1776 (ATTC No. 31537).

These examples are, of course, intended to be illustrative rather than limiting.

Prokaryotes may also be used for expression. The aforementioned strains, as well as *E. coli* W3110 (F⁻, λ⁻, prototrophic, ATTC No. 27325), bacilli such as *Bacillus subtilus*, and other enterobacteriaceae such as *Salmonella typhimurium* or *Serratia marcesans*, and various *Pseudomonas* species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species (Bolivar, et al., *Gene* 2: 95 (1977)). pBR322 contains genes for ampicillin and tetracycline resistance and thus provides easy means for identifying transformed cells. The pBR322 plasmid, or other microbial plasmid must also contain, or be modified to contain, promoters which can be used by the microbial organism for expression of its own proteins. Those promoters most commonly used in recombinant DNA construction include the β-lactamase (penicillinase) and lactose promoter systems (Chang et al, *Nature*, 275: 615 (1978);

Itakura, et al, *Science,* 198: 1056 (1977); (Goeddel, et al *Nature* 281: 544 (1979)) and a tryptophan (trp) promoter system (Goeddel, et al, *Nucleic Acids Res.,* 8: 4057 (1980); EPO Appl Publ No. 0036776). While these are the most commonly used, other microbial promoters have been discovered and utilized, and details concerning their nucleotide sequences have been published, enabling a skilled worker to ligate them functionally with plasmid vectors (Siebenlist, et al, *Cell* 20: 269 (1980)).

In addition to prokaryates, eukaryotic microbes, such as yeast cultures may also be used. *Saccharomyces cerevisiae,* or common baker's yeast is the most commonly used among eukaryotic microorganisms, although a number of other strains are commonly available. For expression in *Saccharomyces,* the plasmid YRp7, for example, (Stinchcomb, et al, *Nature,* 282: 39 (1979); Kingsman et al, *Gene,* 7: 141 (1979); Tschemper, et al, *Gene,* 10: 157 (1980)) is commonly used. This plasmid already contains the trp1 gene which provides a selection marker for a mutant strain of yeast lacking the ability to grow in tryptophan, for example ATCC No. 44076 or PEP4-1 (Jones, *Genetics,* 85: 12 (1977)). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman, et al., *J. Biol. Chem.,* 255: 2073 (1980)) or other glycolytic enzymes (Hess, et al, *J. Adv. Enzyme Reg.,* 7: 149 (1968); Holland, et al, *Biochemistry,* 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter regions for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization (Holland, ibid.). Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However interest has been greatest in vertebrate cells, and propogation of vertebrate cells in culture (tissue culture) has become a routine procedure in recent years (*Tissue Culture,* Academic Press, Kruse and Patterson, editors (1973)). Examples of such useful host cell lines are VERO and HeLa cells, Chinese hamster ovary (CHO) cell lines, and W138, BHK, COS-7 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers, et al, *Nature,* 273: 113 (1978)) incorporated herein by reference. Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g. Polyoma, Adeno, VSV, BPV, etc.) source, or may be provided by the host cell chromosomal replication mechanism. If the vector is integrated into the host cell chromosome, the latter is often sufficient.

It will be understood that this invention, although described herein in terms of a preferred embodiment, should not be construed as limited to those host cells, vectors and expression systems exemplified.

C. Methods Employed

C.1 Transformation

If cells without formidable cell wall barriers are used as host cells, transfection is carried out by the calcium phosphate precipitation method as described by Graham and Van der Eb, *Virology,* 52: 546 (1978). However, other methods for introducing DNA into cells such as by nuclear injection or by protoplast fusion may also be used.

If prokaryotic cells or cells which contain substantial cell wall constructions are used, the preferred method of transfection is calcium treatment using calcium chloride as described by Cohen, F. N. et al *Proc. Natl. Acad. Sci.* (*USA*), 69: 2110 (1972).

C.2 Vector Construction

Construction of suitable vectors containing the desired coding and control sequences employ standard ligation techniques. Isolated plasmids or DNA fragments are cleaved, tailored, and religated in the form desired to form the plasmids required. The methods employed are not dependent on the DNA source, or intended host.

Cleavage is performed by treating with restriction enzyme (or enyzmes) in suitable buffer. In general, about 1 μg plasmid or DNA fragments is used with about 1 unit of enzyme in about 20 μl of buffer solution. (Appropriate buffers and substrate amounts for particular restriction enzymes are specified by the manufacturer.) Incubation times of about 1 hour at 37° C. are workable. After incubations, protein is removed by extraction with phenol and chloroform, and the nucleic acid is recovered from the aqueous fraction by precipitation with ethanol.

If blunt ends are required, the preparation is treated for 15 minutes at 15° with 10 units of *E. coli* DNA Polymerase I (Klenow), phenol-chloroform extracted, and ethanol precipitated.

Size separation of the cleaved fragments is performed using 6 percent polyacrylamide gel described by Goeddel, D., et al, *Nucleic Acids Res.,* 8: 4057 (1980) incorporated herein by reference.

For ligation, approximately equimolar amounts of the desired components, suitably end tailored to provide correct matching are treated with about 10 units T4 DNA ligase per 0.5 µg DNA. (When cleaved vectors are used as components, it may be useful to prevent religation of the cleaved vector by pretreatment with bacterial alkaline phosphatase.)

In the examples described below correct ligations for plasmid construction are confirmed by transforming *E. coli* K12 strain 294 (ATCC 31446) with the ligation mixture. Successful transformants were selected by ampicillin or tetracycline resistance depending on the mode of plasmid construction. Plasmids from the transformants were then prepared, analyzed by restriction and/or sequenced by the method of Messing, et al, *Nucleic Acids Res.,* 9:309 (1981) or by the method of Maxam, et al, *Methods in Enzymology,* 65:499 (1980).

D. Outline of Procedures

D.1 Mammalian Antibodies

The first type of antibody which forms a part of this invention, and is prepared by the methods thereof, is "mammalian antibody"-one wherein the heavy and light chains mimic the amino acid sequences of an antibody otherwise produced by a mature mammalian B lymphocyte either in situ or when fused with an immortalized cell as part of a hybridoma culture. In outline, these antibodies are produced as follows:

Messenger RNA coding for heavy or light chain is isolated from a suitable source, either mature B cells or a hybridoma culture, employing standard techniques of RNA isolation, and the use of oligo-dT cellulose chromatography to segregate the poly-A mRNA. The poly-A mRNA may, further, be fractionated to obtain sequences of sufficient size to code for the amino acid sequences in the light or heavy chain of the desired antibody as the case may be.

A cDNA library is then prepared from the mixture of mRNA using a suitable primer, preferably a nucleic acid sequence which is characteristic of the desired cDNA. Such a primer may be hypothesized and synthesized based on the amino acid sequence of the antibody if the sequence is known. In the alternative cDNA from unfractionated poly-A mRNA from a cell line producing the desired antibody or poly-dT may also be used. The resulting cDNA is optionally size fractionated on polyacrylamide gel and then extended with, for example, dC residues for annealing with pBR322 or other suitable cloning vector which has been cleaved by a suitable restriction enzyme, such as Pst I, and extended with dG residues. Alternative means of forming cloning vectors containing the cDNA using other tails and other cloning vector remainder may, of course, also be used but the foregoing is a standard and preferable choice. A suitable host cell strain, typically *E. coli,* is transformed with the annealed cloning vectors, and the successful transformants identified by means of, for example, tetracycline resistance or other phenotypic characteristic residing on the cloning vector plasmid.

Successful transformants are picked and transferred to microtiter dishes or other support for further growth and preservation. Nitrocellulose filter imprints of these growing cultures are then probed with suitable nucleotide sequences containing bases known to be complementary to desired sequences in the cDNA. Several types of probe may be used, preferably synthetic single stranded DNA sequences labeled by kinasing with $ATP^{32}$. The cells fixed to the nitrocellulose filter are lysed, the DNA denatured, and then fixed before reaction with kinased probe. Clones which successfully hybridize are detected by contact with a photoplate, then plasmids from the growing colonies isolated and sequenced by means known in the art to verify that the desired portions of the gene are present.

The desired gene fragments are excised and tailored to assure appropriate reading frame with the control segments when inserted into suitable expression vectors. Typically, nucleotides are added to the 5' end to include a start signal and a suitably positioned restriction endonuclease site.

The tailored gene sequence is then positioned in a vector which contains a promoter in reading frame with the gene and compatible with the proposed host cell. A number of plasmids such as those described in U.S. Pat. Nos. 307,473; 291,892; and 305,657, have been described which already contain the appropriate promoters, control sequences, ribosome binding sites, and transcription termination sites, as well as convenient markers.

In the present invention, the gene coding for the light chain and that coding for the heavy chain are recovered separately by the procedures outlined above. Thus they may be inserted into separate expression plasmids, or together in the same plasmid, so long as each is under suitable promoter and translation control.

The expression vectors constructed above are then used to transform suitable cells. The light and heavy chains may be transformed into separate cell cultures, either of the same or of differing species; separate plasmids for light and heavy chain may be used to co-transform a single cell culture, or, finally, a single expression plasmid containing both genes and capable of expressing the genes for both light and heavy chain may be transformed into a single cell culture.

Regardless of which of the three foregoing options is chosen, the cells are grown under conditions appropriate to the production of the desired protein. Such conditions are primarily mandated by the type of promoter and control systems used in the expression vector, rather than by the nature of the desired protein. The protein thus produced is then recovered from the cell culture by methods known in the art, but choice of which is necessarily dependent on the form in which the protein is expressed. For example, it is common for mature heterologous proteins expressed in *E. coli* to be deposited within the cells as insoluble particles which require cell lysis and solubilization in denaturant to permit recovery. On the other hand, proteins under proper synthesis circumstances, in yeast and bacterial strains, can be secreted into the medium (yeast and gram positive bacteria) or into the periplasmic space (gram negative bacteria) allowing recovery by less drastic procedures. Tissue culture cells as hosts also appear, in general, to permit reasonably facile recovery of heterologous proteins.

When heavy and light chain are coexpressed in the same host, the isolation procedure is designed so as to recover reconstituted antibody. This can be accomplished in vitro as described below, or might be possible in vivo in a microorganism which secretes the IgG chains out of the reducing environment of the cytoplasm. A more detailed description is given in D.2, below.

D.2 Chain Recombination Techniques

The ability of the method of the invention to produce heavy and light chains or portions thereof, in isolation from each other offers the opportunity to obtain unique and unprecedented assemblies of immunoglobulins, Fab regions, and univalent antibodies. Such preparations require the use of techniques to reassemble isolated chains. Such means are known in the art, and it is, thus, appropriate to review them here.

While single chain disulfide bond containing proteins have been reduced and reoxidized to regenerate in high yield native structure and activity (Freedman, R. B., et al. In *Enzymology* of *Post Translational Modification of Proteins*, I: 157-212 (1980) Academic Press, NY.), proteins which consist of discontinuous polypeptide chains held together by disulfide bonds are more difficult to reconstruct in vitro after reductive cleavage. Insulin, a cameo case, has received much experimental attention over the years, and can now be reconstructed so efficiently that an industrial process has been built around it (Chance, R. E., et al., In *Peptides: Proceedings of the Seventh Annual American Peptide Symposium* (Rich, D. H. and Gross, E., eds.) 721-728, Pierce Chemical Co., Rockford, Ill. (1981)).

Immunoglobulin has proved a more difficult problem than insulin. The tetramer is stabilized intra and intermolecularly by, 15 or more disulfide bonds. It has been possible to recombine heavy and light chains, disrupted by cleavage of only the interchain disulfides, to regain antibody activity even without restoration of the inter-chain disulfides (Edelman, G. M., et al., *Proc. Natl. Acad. Sci.* (*USA*) 50: 753 (1963)). In addition, active fragments of IgG formed by proteolysis (Fab fragments of ~50,000 MW) can be split into their fully reduced heavy chain and light chain components and fairly efficiently reconstructed to give active antibody (Haber, E., *Proc. Natl. Acad. Sci.* (*USA*) 52: 1099 (1964); Whitney, P. L., et al., *Proc. Natl. Acad. Sci.* (*USA*) 53: 524 (1965)). Attempts to reconstitute active antibody from fully reduced native IgG have been largely unsuccessful, presumably due to insolubility of the reduced chains and of side products or intermediates in the refolding pathway (see discussion in Freedman, M. H., et al., *J. Biol. Chem.* 241: 5225 (1966)). If, however, the immunoglobulin is randomly modified by polyalanylation of its lysines before complete reduction, the separated chains have the ability to recover antigen-combining activity upon reoxidation (ibid).

A particularly suitable method for immunoglobulin reconstitution is derivable from the now classical insulin recombination studies, wherein starting material was prepared by oxidative sulfitolysis, thus generating thiol-labile S-sulfonate groups at all cysteines in the protein, non-reductively breaking disulfides (Chance et al. (supra)). Oxidative sulfitolysis is a mild disulfide cleavage reaction (Means, G. E., et al., *Chemical Modification of Proteins*, Holden-Day, San Francisco (1971)) which is sometimes more gentle than reduction (Wetzel, R., *Biochemistry*, submitted (1983)), and which generates derivatives which are stable until exposed to mild reducing agent at which time disulfide reformation can occur via thiol-disulfide interchange (Morehead, H., et al. *Biochemistry*, in press, (1983)). In the present invention the heavy and light chain S-sulfonates generated by oxidative sulfitolysis were reconstituted utilizing both air oxidation and thiol-disulfide interchange to drive disulfide bond formation. The general procedure is set forth in detail in U.S. Pat. No. 452, 187, filed Dec. 22, 1982, incorporated herein by reference.

D.3 Variants Permitted by Recombinant Technology

Using the techniques described in paragraphs D.1 and D.2, additional operations which were utilized to gain efficient production of mammalian antibody can be varied in quite straightforward and simple ways to produce a great variety of modifications of this basic antibody form. These variations are inherent in the use of recombinant technology, which permits modification at a genetic level of amino acid sequences in normally encountered mammalian immunoglobulin chains, and the great power of this approach lies in its ability to achieve these variations, as well as in its potential for economic and specific production of desired scarce, and often contaminated, molecules. The variations also inhere in the ability to isolate production of individual chains, and thus create novel assemblies.

Briefly, since genetic manipulations permit reconstruction of genomic material in the process of construction of expression vectors, such reconstruction can be manipulated to produce new coding sequences for the components of "natural" antibodies or immunoglobulins. As discussed in further detail below, the coding sequence for a mammalian heavy chain may not be derived entirely from a single source or single species, but portions of a sequence can be recovered by the techniques described in D.1 from differing pools of mRNA, such as murine-murine hybridomas, human-murine hybridomas, or B cells differentiated in response to a series of antigen challenges. The desired portions of the sequences in each case can be recovered using the probe and analysis techniques described in D.1, and recombined in an expression vector using the same ligation procedures as would be employed for portions of the same model sequence. Such chimeric chains can be constructed of any desired length; hence, for example, a complete heavy chain can be constructed, or only sequence for the Fab region thereof.

The additional area of flexibility which arises from the use of recombinant techniques results from the power to produce heavy and light chains or fragments thereof in separate cultures or of unique combinations of heavy and light chain in the same culture, and to prevent reconstitution of the antibody or immunoglobulin aggregation until the suitable components are assembled. Thus, while normal antibody production results automatically in the formation of "mammalian antibodies" because the light and heavy chain portions are constructed in response to a particular determinant in the same cell, the methods of the present invention present the opportunity to assemble entirely new mixtures. Somewhat limited quantities of "hybrid" antibodies have been produced by "quadromas" i.e., fusions of two hybridoma cell cultures which permit random assemblies of the heavy and light chains so produced.

The present invention permits a more controlled assembly of desired chains, either by mixing the desired chains in vitro, or by transforming the same culture with the coding sequences for the desired chains.

D.4 Composite Immunoglobulins

The foregoing procedure, which describes in detail the recombinant production of mammalian antibodies is employed with some modifications to construct the remaining types of antibodies or NSIs encompassed by the present invention. To prepare the particular embodiment of composite non-specific immunoglobulin wherein the homology of the chains corresponds to the sequences of immunoglobulins of different specificities, it is of course, only necessary to prepare the heavy and light chains in separate cultures and reassemble them as desired.

For example, in order to make an anti-CEA light chain/ anti-hepatitis heavy chain composite antibody, a suitable source for the mRNA used as a template for the light chain clone would comprise, for instance, the anti CEA producing cell line of paragraph E.1. The mRNA corresponding to heavy chain would be derived from B cells raised in response to hepatitis infection or from hybridoma in which the B cell was of this origin. It is clear that such composites can be assembled using the methods of the invention almost at will, and are limited only by available sources of mRNA suitable for use as templates for the respective chains. All other features of the process are similar to those described above.

D.5 Hybrid Antibodies

Hybrid antibodies are particularly useful as they are capable of simultaneous reaction with more than one antigen. Pairs of heavy and light chains corresponding to chains of antibodies for different antigens, such as those set forth in paragraph D.4 are prepared in four separate cultures, thus preventing premature assembly of the tetramer. Subsequent mixing of the four separately prepared peptides then permits assembly into the desired tetramers. While random aggregation may lead to the formation of considerable undesired product, that portion of the product in which homologous light and heavy chains are bound to each other and mismatched to another pair gives the desired hybrid antibody.

D.6 Chimeric Antibodies

For construction of chimeric antibodies (wherein, for example, the variable sequences are separately derived from the constant sequences) the procedures of paragraph D.1 and D.2 are again applicable with appropriate additions and modifications. A preferred procedure is to recover desired portions of the genes encoding for parts of the heavy and light chains from suitable, differing, sources and then to religate these fragments using restriction endonucleases to reconstruct the gene coding for each chain.

For example, in a particularly preferred chimeric construction, portions of the heavy chain gene and of the light chain gene which encode the variable sequences of antibodies produced by a murine hybridoma culture are recovered and cloned from this culture and gene fragments encoding the constant regions of the heavy and light chains for human antibodies recovered and cloned from, for example, human myeloma cells. Suitable restriction enzymes may then be used to ligate the variable portions of the mouse gene to the constant regions of the human gene for each of the two chains. The chimeric chains are produced as set forth in D.1, aggregated as set forth in D.2 and used in the same manner as the non-chimeric forms. Of course, any splice point in the chains can be chosen.

D.7 Altered Antibodies

Altered antibodies present, in essence, an extension of chimeric ones. Again, the techniques of D.1 and D.2 are applicable; however, rather than splicing portions of the chain(s), suitable amino acid alterations, deletions or additions are made using available techniques such as mutagenesis (supra). For example, genes which encode antibodies having diminished complement fixation properties, or which have enhanced metal binding capacities are prepared using such techniques. The latter type may, for example, take advantage of the known gene sequence encoding metalothionein II (Karin, M., et al., *Nature*, 299: 797 (1982)). The chelating properties of this molecular fragment are useful in carrying heavy metals to tumor sites as an aid in tumor imaging (Scheinberg, D. A., et al., *Science*, 215: 19 (1982).

D.8 Univalent Antibodies

In another preferred embodiment, antibodies are formed which comprise one heavy and light chain pair coupled with the Fc region of a third (heavy) chain. These antibodies have a particularly useful property. They can, like ordinary antibodies, be used to target antigenic surfaces of tissues, such as tumors, but, unlike ordinary antibodies, they do not cause the antigenic surfaces of the target tissue to retreat and become non-receptive. Ordinary antibody use results in aggregation and subsequent inactivation, for several hours, of such surface antigens.

The method of construction of univalent antibodies is a straightforward application of the invention. The gene for heavy chain of the desired Fc region is cleaved by restriction enzymes, and only that portion coding for the desired Fc region expressed. This portion is then bound using the technique of D.2 to separately produced heavy chain the desired pairs separated from heavy/heavy and Fc/Fc combinations, and separately produced light chain added. Pre-binding of the two heavy chain portions thus diminishes the probability of formation of ordinary antibody.

D.9 Fab Protein

Similarly, it is not necessary to include the entire gene for the heavy chain portion. All of the aforementioned variations can be superimposed on a procedure for Fab protein production and the overall procedure differs only in that that portion of the heavy chain coding for the amino terminal 220 amino acids is employed in the appropriate expression vector.

E. Specific Examples of Preferred Embodiments

The invention has been described above in general terms and there follow several specific examples of embodiments which set forth details of experimental procedure in producing the desired antibodies. Example E.1 sets forth the general procedure for preparing anti CEA antibody components, i.e. for a "mammalian antibody". Example E.3 sets forth the procedure for reconstitution and thus is applicable to preparation of mammalian, composite, hybrid and chimeric immunoglobulins, and Fab proteins and univalent antibodies. Example E.4 sets forth the procedure for tailoring the heavy or light chain so that the variable and constant regions may be derived from different sources. Example E.5 sets forth the method of obtaining a shortened heavy chain genome which permits the production of the Fab regions and, in an analogous manner, Fc region.

The examples set forth below are included for illustrative purposes and do not limit the scope of the invention.

E.1 Construction of Expression Vectors for Murine Anti-CEA Antibody Chains and Peptide Synthesis Carcinoembryonic antigen (CEA) is associated with the surface of certain tumor cells of human origin (Gold, P., et al., *J. Exp. Med.*, 122: 467 (1965)). Antibodies which bind to CEA (anti-CEA antibodies) are useful in early detection of these tumors (Van Nagell, T. R., et al., *Cancer Res.* 40: 502 (1980)), and have the potential for use in treatment of those human tumors which appear to support CEA at their surfaces. A mouse hybridoma cell line which secretes anti-CEA antibodies of the Ig$\gamma_1$ class, CEA.66-E3, has been prepared as described by Wagener, C, et al., *J. Immunol*. (in press) which is incorporated herein by reference, and was used as mRNA source. The production of anti CEA antibodies by this cell line was determined. The N-terminal sequences of the antibodies produced by these cells was compared with those of monoclonal anti CEA as follows. Purified IgG was treated with PCAse (Podell, D. N., et al., BBRC 81: 176 (1978)), and then dissociated in 6M guanidine hydrochloride, 10 mM 2-mercaptoethanol (1.0 mg of immunoglobulin, 5 min, 100° C. water bath). The dissociated chains were separated on a Waters Associates alkyl phenyl column using a linear gradient from 100 percent A (0.1 percent TFA-water) to 90 percent B (TFA/H$_2$O/MeCN 0.1/9.9/90) at a flow rate of 0.8 ml/min. Three major peaks were eluted and analyzed on SOS gels by silver staining. The first two peaks were pure light chain (MW 25,000 daltons), the third peak showed a (7:3) mixture of heavy and light chain. 1.2 nmoles of light chain were sequenced by the method of Shively, J. E., *Methods in Enzymology,* 79: 31 (1981), with an NH$_2$-terminal yield of 0.4 nmoles. A mixture of heavy and light chains (3 nmoles) was also sequenced, and sequence of light chain was deducted from the double sequence to yield the sequence of the heavy chain.

In the description which follows, isolation and expression of the genes for the heavy and light chains for anti CEA antibody produced by CEA.66-E3 are described. As the constant regions of these chains belong to the gamma and kappa families, respectively, "light chain" and "kappa chain", and "heavy chain" and "gamma chain", respectively, are used interchangeably below.

E.1.1 Isolation of Messenger RNA for Anti CEA Light and Heavy (Kappa and Gamma) Chains Total RNA from CEA.66-E3 cells was extracted essentially as reported by Lynch et al, *Virology,* 98: 251 (1979). Cells were pelleted by centrifugation and approximately 1 g portions of pellet resuspended in 10 ml of 10 mM NaCl, 10 mM Tris HCl (pH 7.4), 1.5 mM MgCl$_2$. The resuspended cells were lysed by addition of non-ionic detergent NP-40 to a final concentration of 1 percent, and nuclei removed by centrifugation. After addition of SDS (pH 7.4) to 1 percent final concentration, the supernatant was extracted twice with 3 ml portions of phenol (redistilled)/chloroform:isoamyl alcohol 25:1 at 4° C. The aqueous phase was made 0.2 M in NaCl and total RNA was precipitated by addition of two volumes of 100 percent ethanol and overnight storage at −20° C. After centrifugation, polyA mRNA was purified from total RNA by oligo-dT cellulose chromatography as described by Aviv and Leder, *Proc. Nat'l. Acad. Sci.* (*USA*), 69: 1408 (1972). 142 µg of polyA mRNA was obtained from 1 g cells.

E.1.2 Preparation of *E. coli* Colony Library Containing Plasmids with Heavy and Light DNA Sequence Inserts 5 µg of the unfractionated polyA mRNA prepared in paragraph E.1.1 was used as template for oligo-dT primed preparation of double-stranded (ds) cDNA by standard procedures as described by Goeddel et al., *Nature* 281: 544 (1979) and Wickens et al., *J. Biol. Chem.* 253: 2483 (1978) incorporated herein by reference. The cDNA was size fractionated by 6 percent polyacrylamide gel electrophoresis and 124 ng of ds cDNA greater than 600 base pairs in length was recovered by electroelution. A 20 ng portion of ds cDNA was extended with deoxy C residues using terminal deoxynucleotidyl transferase as described in Chang et al., *Nature* 275: 617 (1978) incorporated herein by reference, and annealed with 200 ng of the plasmid pBR322 (Bolivar et al., *Gene* 2: 95 (1977)) which had been cleaved with Pst I and tailed with deoxy G. Each annealed mixture was then transformed into *E. coli* K12 strain 294 (ATCC No. 31446). Approximately 8500 ampicillin sensitive, tetracycline resistant transformants were obtained.

E.1.3 Preparation of Synthetic Probes

The 14mer, 5' GGTGGGAAGATGGA 3' complementary to the coding sequence of constant region for mouse MOPC21 kappa chain which begins 25 basepairs 3' of the variable region DNA sequence was used as kappa chain probe. A 15 mer, 5' GACCAGGCATCCCAG 3', complementary to a coding sequence located 72 basepairs 3' of the variable region DNA sequence for mouse MOPC21 gamma chain was used to probe gamma chain gene.

Both probes were synthesized by the phosphotriester method described in German Offenlegungschrift 2644432, incorporated herein by reference, and made radioactive by kinasing as follows: 250 ng of deoxyoligonucleotide were combined in 25 µl of 60 mM Tris HCl (pH 8), 10 mM MgCl$_2$, 15 mM beta-mercaptoethanol, and 100 µCi ($\gamma$-$^{32}$P) ATP (Amersham, 5000 Ci/mMole). 5 units of T4 polynucleotide kinase were added and the reaction was allowed to proceed at 37° C. for 30 minutes and terminated by addition of EDTA to 20 mM.

E.1.4 Screening of Colony Library for Kappa or Gamma Chain Sequences

~2000 colonies prepared as described in paragraph E.1.2 were individually inoculated into wells of microtitre dishes containing LB (Miller, Experiments in Molecular Genetics, p. 431-3, Cold Spring Harbor Lab., Cold Spring Harbor, N.Y. (1972))+5 µg/ml tetracycline and stored at −20° C. after addition of DMSO to 7 percent. Individual colonies from this library were transferred to duplicate sets of Schleicher and Schuell BA85/20 nitrocellulose filters and grown on agar plates containing LB+5 µg/ml tetracycline. After ~10 hours growth at 37° C. the colony filters were transferred to agar plates containing LB+5 µg/ml tetracycline and 12.5 µg/ml chloramphenicol and reincubated overnight at 37° C. The DNA from each colony was then denatured and fixed to the filter by a modification of the Grunstein-Hogness procedure as described in Grunstein et al., *Proc. Natl. Acad. Sci.* (*USA*) 72: 3961 (1975), incorporated herein by reference. Each filter was floated for 3 minutes on 0.5 N NaOH, 1.5 M NaCl to lyse the colonies and denature the DNA then neutralized by floating for 15 minutes on 3 M NaCl, 0.5 M Tris HCl (pH 7.5). The filters were then floated for an additional 15 minutes on 2×SSC, and subsequently baked for 2 hours in an 80° C. vacuum oven. The filters were prehybridized for ~2 hours at room temperature in 0.9 M NaCl, 1×Denhardts, 100 mM Tris HCl (pH 7.5), 5 mM Na-EDTA, 1 mM ATP, 1 M sodium phosphate (dibasic), 1 mM sodium pyrophosphate, 0.5 percent NP-40, and 200 µg/ml *E. coli* t-RNA, and hybridized in the same solution overnight, essentially as described by Wallace et al. *Nucleic Acids Research* 9: 879 (1981) using ~40× 10$^6$ cpm of either the kinased kappa or gamma probe described above.

After extensive washing at 37° C. in 6×SSC, 0.1 percent SDS, the filters were exposed to Kodak XR-5 X-ray film with DuPont Lightning-Plus intensifying screens for 16-24 hours at −80° C. Approximately 20 colonies which hybridized with kappa chain probe and 20 which hybridized with gamma chain probe were characterized.

E.1.5 Characterization of Colonies which Hybridize to Kappa DNA Sequence Probe

Plasmid DNAs isolated from several different transformants which hybridized to kappa chain probe were cleaved with Pst I and fractionated by polyacrylamide gel electrophoresis (PAGE). This analysis demonstrated that a number of plasmid DNAs contained cDNA inserts large enough to encode full length kappa chain. The complete nucleotide sequence of the cDNA insert of one of these plasmids was determined by the dideoxynucleotide chain termination method as described by Smith, *Methods Enzymol.* 65, 560 (1980) incorporated herein by reference after subcloning restriction endonuclease cleavage fragments into M13 vectors (Messing et al., *Nucleic Acids Research* 9: 309 (1981). FIG. 2 shows the nucleotide sequence of the cDNA insert of pK17G4 and FIG. 3 shows the gene sequence with the corresponding amino acid sequence. Thus, the entire coding region of mouse anti-CEA kappa chain was isolated on this one large DNA fragment. The amino acid sequence of kappa chain, deduced from the nucleotide sequence of the pK17G4 cDNA insert, corresponds perfectly with the first 23 N-terminal amino acids of mature mouse anti-CEA kappa chain as determined by amino acid sequence analysis of purified mouse anti-CEA kappa chain. The coding region of pK17G4 contains 27 basepairs or 9 amino acids of the presequence and 642 basepairs or 214 amino acids of the mature protein. The mature unglycosylated protein (MW 24,553) has a variable region of 119 amino acids, including the J1 joining region of 12 amino acids, and a constant region of 107 amino acids. After the stop codon behind amino acid 215 begins 212 basepairs of 3' untranslated sequence up to the polyA addition. The kappa chain probe used to identify pK17G4 hybridizes to nucleotides 374-388 (FIG. 2).

E.1.6 Characterization of Colonies which Hybridize to Gamma 1 DNA Probe

Plasmid DNA isolated from several transformants positive for hybridization with the heavy chain gamma 1 probe was subjected to Pst I restriction endonuclease analysis as described in E.1.5. Plasmid DNAs demonstrating the largest cDNA insert fragments were selected for further study. Nucleotide sequence coding for mouse heavy (gamma-1) chain, shows an NcoI restriction endonuclease cleavage site near the junction between variable and constant region. Selected plasmid DNAs were digested with both PstI and NcoI and sized on polyacrylamide. This analysis allowed identification of a number of plasmid DNAs that contain NcoI restriction endonuclease sites, although none that demonstrate cDNA insert fragments large enough to encode the entire coding region of mouse anti-CEA heavy chain.

In one plasmid isolated, p γ298 the cDNA insert of about 1300 bp contains sequence information for the 5' untranslated region, the signal sequence and the N-terminal portion of heavy chain. Because pγ298 did not encode the C-terminal sequence for mouse anti-CEA gamma 1 chain, plasmid DNA was isolated from other colonies and screened with PstI and NcoI. The C-terminal region of the cDNA insert of pγ11 was sequenced and shown to contain the stop codon, 3' untranslated sequence and that portion of the coding sequence missing from p γ298.

FIG. 4 presents the entire nucleotide sequence of mouse anti-CEA heavy chain (as determined by the dideoxynucleotide chain termination method of Smith, *Methods Enzymol.*, 65: 560 (1980)) and FIG. 5 includes the translated sequence.

The amino acid sequence of gamma 1 (heavy chain) deduced from the nucleotide sequence of the pγ298 cDNA insert corresponds perfectly to the first 23 N-terminal amino acids of mature mouse anti-CEA gamma 1 chain as determined by amino acid sequence analysis of purified mouse anti-CEA gamma-1 chain. The coding region consists of 57 basepairs or 19 amino acids of presequences and 1346 basepairs or 447 amino acids of mature protein. The mature unglycosolated protein (MW 52,258) has a variable region of 135 amino acids, including a D region of 12 amino acids, and a J4 joining region of 13 amino acids. The constant region is 324 amino acids. After the stop codon behind amino acid 447 begins 96 bp of 3' untranslated sequences up to the polyA addition. The probe used to identify pγ298 and pγ11 hybridized to nucleotides 528-542 (FIG. 4).

E.1.7 Construction of a Plasmid for Direct Expression of Mouse Mature Anti-CEA Kappa Chain Gene, pKCE-Atrp207-1☆

Figure 6:
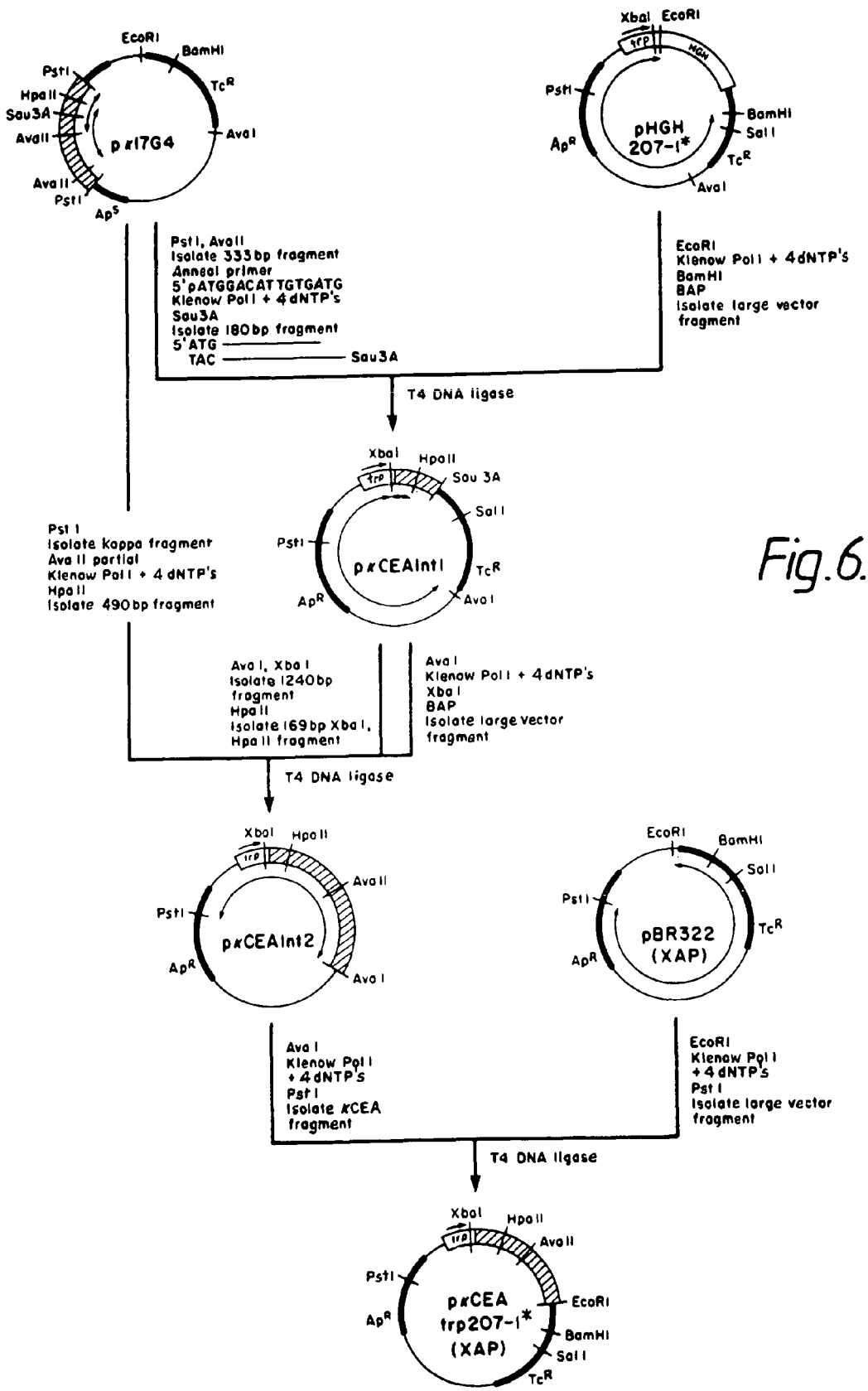
FIGS. 6 and 7 outline the construction of expression vectors for kappa and gamma anti-CEA chains respectively.

FIG. 6 illustrates the construction of pKCEAtrp207-1☆

First, an intermediate plasmid pHGH207-1☆, having a single trp promoter, was prepared as follows:

The plasmid pHGH 207 (described in U.S. Pat. No. 307, 473, filed Oct. 1, 1981) has a double lac promoter followed by the trp promoter, flanked by EcoR I sites and was used to prepare pHGH207-1. pHGH207 was digested with BamH 1, followed by partial digestion with EcoR I. The largest fragment, which contains the entire trp promoter, was isolated and ligated to the largest EcoR I-BamH I fragment from pBR322, and the ligation mixture used to transform *E. coli* 294. Tet$^R$ Amp$^R$ colonies were isolated, and most of them contained pHGH207-1. pHGH207-1☆ which lacks the EcoR1 site between the amp$^R$ gene and the trp promoter, was obtained by partial digestion of pHGH207-1 with EcoR I, filling in the ends with Klenow and dNTPs, and religation.

5 μg of pHGH207-1☆ was digested with EcoRI, and the ends extended to blunt ends using 12 units of DNA Polymerase I in a 50 μl reaction containing 60 mM NaCl, 7 mM MgCl$_2$, 7 mM Tris HCl (pH 7.4) and 1 mM in each dNTP at 37° C. for 1 hour, followed by extraction with phenol/CHCl$_3$ and precipitation with ethanol. The precipitated DNA was digested with BamH I, and the large vector fragment (fragment 1) purified using 5 percent polyacrylamide gel electrophoresis, electroelution, phenol/CHCl$_3$ extraction and ethanol precipitation.

The DNA was resuspended in 50 μl of 10 mM Tris pH 8, 1 mM EDTA and treated with 500 units Bacterial Alkaline Phosphatase (BAP) for 30' at 65° followed by phenol/CHCl$_3$ extraction and ethanol precipitation.

A DNA fragment containing part of the light chain sequence was prepared as follows: 7 μg of pK17G4 DNA was digested with Pst I and the kappa chain containing cDNA insert was isolated by 6 percent gel electrophoresis, and electroelution. After phenol/CHCl$_3$ extraction, ethanol precipitation and resuspension in water, this fragment was digested with Ava II. The 333 bp Pst I-Ava II DNA fragment was isolated and purified from a 6 percent polyacrylamide gel.

A 15 nucleotide DNA primer was synthesized by the phosphotriester method G. O. 2,644,432 (supra) and has the following sequence:

```
         Met Asp Ile Val Met
      5' ATG GAC ATT GTT ATG 3'
```

The 5' methionine serves as the initiation codon. 500 ng of this primer was phosphorylated at the 5' end with 10 units T4 DNA kinase in 20 μl reaction containing 0.5 mM ATP. ~200 ng of the Pst I-Ava II DNA fragment was mixed with the 20 μl of the phosphorylated primer, heated to 95° C. for 3 minutes and quick frozen in a dry-ice ethanol bath. The denatured DNA solution was made 60 mM NaCl, 7 mM MgCl$_2$, 7 mM Tris HCl (pH 7.4), 12 mM in each dNTP and 12 units DNA Polymerase I-Large Fragment was added. After 2 hours incubation at 37° C. this primer repair reaction was phenol/CHCl$_3$ extracted, ethanol precipitated, and digested to completion with Sau 3A. The reaction mixture was then electrophoresed on a 6 percent polyacrylamide gel and ~50 ng of the 182 basepair amino-terminal blunt-end to Sau 3A fragment (fragment 2) was obtained after electroelution.

100 ng of fragment 1 (supra) and 50 ng of fragment 2 were combined in 20 μl of 20 mM Tris HCl (pH 7.5), 10 mM MgCl$_2$, 10 mM DTT, 2.5 mM ATP and 1 unit of 14 DNA ligase. After overnight ligation at 14° C. the reaction was transformed into *E. coli* K12 strain 294. Restriction endonuclease digestion of plasmid DNA from a number of ampicillin resistant transformants indicated the proper construction and DNA sequence analysis proved the desired nucleotide sequence through the initiation codon of this new plasmid, pKCEAInt1 (FIG. 6).

The remainder of the coding sequence of the kappa light chain gene was prepared as follows:

The Pst I cDNA insert fragment from 7 μg of K17G4 DNA was partially digested with Ava II and the Ava II cohesive ends were extended to blunt ends in a DNA Polymerase I large fragment reaction. Following 6 percent polyacrylamide gel electrophoresis the 686 basepair Pst I to blunt ended Ava II DNA fragment was isolated, purified and subjected to Hpa II restriction endonuclease digestion. The 497 basepair Hpa II to blunt ended Ava II DNA fragment (fragment 3) was isolated and purified after gel electrophoresis.

10 μg of pKCEAInt1 DNA was digested with Ava I, extended with DNA polymerase I large fragment, and digested with Xba I. Both the large blunt ended Ava I to Xba I vector fragment and the small blunt ended Ava I to Xba I fragment were isolated and purified from a 6 percent polyacrylamide gel after electrophoresis. The large vector fragment (fragment 4) was treated with Bacterial Alkaline Phosphatase (BAP), and the small fragment was digested with Hpa II, electrophoresed on a 6 percent polyacrylamide and the 169 basepair Xba I-Hpa II DNA fragment (fragment 5) was purified. ~75 ng of fragment 4, ~50 ng of fragment 3 and ~50 ng of fragment 5 were combined in a T4 DNA ligase reaction and incubated overnight at 14°, and the reaction mixture transformed into E. coli K12 strain 294. Plasmid DNA from six ampicillin resistant transformants were analyzed by restriction endonuclease digestion. One plasmid DNA demonstrated the proper construction and was designated pKCEAInt2.

Final construction was effected by ligating the K-CEA fragment, including the trp promoter from pKCEAInt2 into pBR322(XAP). (pBR322(XAP) is prepared as described in U.S. Pat. No. 452,227, filed Dec. 22, 1982.)

The K-CEA fragment was prepared by treating pKCEAInt2 with Ava I, blunt ending with DNA polymerase I (Klenow fragment) in the presence of DNTPs, digestion with Pst I and isolation of the desired fragment by gel electrophoresis and electroelution.

The large vector fragment from pBR322(XAP) was prepared by successive treatment with EcoR I, blunt ending with polymerase, and redigestion with Pst I, followed by isolation of the large vector fragment by electrophoresis and electroelution.

The K-CEA and large vector fragments as prepared in the preceding paragraphs were ligated with T4 DNA ligase, and the ligation mixture transformed into E. coli as above. Plasmid DNA from several ampicillin resistant transformants were selected for analysis, and one plasmid DNA demonstrated the proper construction, and was designated pKCE-Atrp207-1☆.

E.1.8 Construction of a Plasmid Vector for Direct Expression of Mouse Mature Anti-CEA Heavy (Gamma 1) Chain Gene, pγCEAtrp207-1☆

Figure 7:
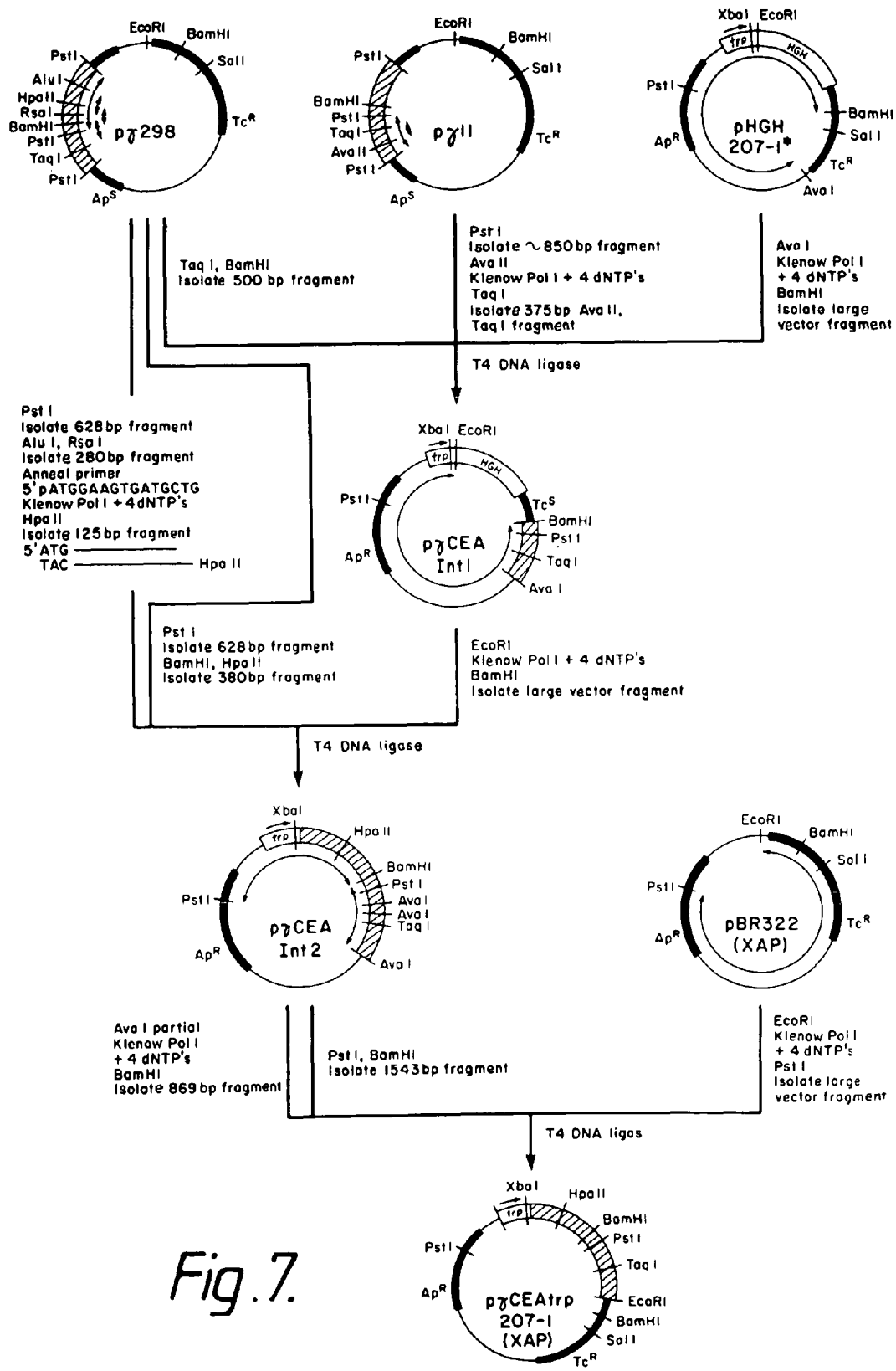

FIG. 7 illustrates the construction of pγCEAtrp207-1☆. This plasmid was constructed in two parts beginning with construction of the C-terminal region of the gamma 1 gene.

5 μg of plasmid pHGH207-1☆ was digested with Ava I, extended to blunt ends with DNA polymerase I large fragment (Klenow fragment), extracted with phenol/CHCl₃, and ethanol precipitated. The DNA was digested with BamH I treated with BAP and the large fragment (fragment A) was purified by 6 percent polyacrylamide gel electrophoresis and electroelution.

~5 μg of pγ11 was digested with Pst I and the gamma chain cDNA insert fragment containing the C-terminal portion of the gene was purified, digested with Ava II followed by extension of the Ava II cohesive ends with Klenow, followed by Taq I digestion. The 375 basepair blunt ended Ava II to Taq I fragment (fragment B) was isolated and purified by gel electrophoresis and electroelution.

9 μg of pγ298 was digested with Taq I and BamH I for isolation of the 496 basepair fragment (fragment C).

Approximately equimolar amounts of fragments A, B, and C were ligated overnight at 14° in 20 μl reaction mixture, then transformed into E. coli strain 294. The plasmid DNA from six ampicillin resistant transformants was committed to restriction endonuclease analysis and one plasmid DNA, named pγCEAInt, demonstrated the correct construction of the C-terminal portion of gamma 1 (FIG. 5).

To obtain the N-terminal sequences, 30 μg of pγ298 was digested with Pst I and the 628 basepair DNA fragment encoding the N-terminal region of mouse anti-CEA gamma chain was isolated and purified. This fragment was further digested with Alu I and Rsa I for isolation of the 280 basepair fragment. A 15 nucleotide DNA primer

```
         met glu val met leu
    5' ATG GAA GTG ATG CTG 3'
``` was synthesized by the phosphotriester method (supra).

The 5' methionine serves as the initiation codon. 500 ng of this synthetic oligomer primer was phosphorylated at the 5' end in a reaction with 10 units T4 DNA kinase containing 0.5 mM ATP in 20 μl reaction mixture. ~500 ng of the 280 basepair Alu I-Rsa I DNA fragment was mixed with the phosphorylated primer. The mixture was heat denatured for 3 minutes at 95° and quenched in dry-ice ethanol. The denatured DNA solution was made 60 mM NaCl, 7 mM MgCl₂, 7 mM Tris HCl (pH 7.4), 12 mM in each dNTP and 12 units DNA Polymerase I-Large Fragment was added. After 2 hours incubation at 37° C., this primer repair reaction was phenol/CHCl₃ extracted, ethanol precipitated, and digested to completion with HpaII. ~50 ng of the expected 125 basepair blunt-end to Hpa II DNA fragment (fragment D) was purified from the gel.

A second aliquot of pγ298 DNA was digested with Pst I, the 628 basepair DNA fragment purified by polyacrylamide gel electrophoresis, and further digested with BamH I and Hpa II. The resulting 380 basepair fragment (fragment E) was purified by gel electrophoresis.

~5 μg of pγCEAIntI was digested with EcoR I, the cohesive ends were made flush with DNA polymerase I (Klenow), further digested with BamH I, treated with BAP and electrophoresed on a 6 percent polyacrylamide gel. The large vector fragment (fragment F) was isolated and purified.

In a three fragment ligation, 50 ng fragment D, 100 ng fragment E, and 100 ng fragment F were ligated overnight at 4° in a 20 μl reaction mixture and used to transform E. coli K12 strain 294. The plasmid DNAs from 12 ampicillin resistant transformants were analyzed for the correct construction and the nucleotide sequence surrounding the initiation codon was verified to be correct for the plasmid named pγCEAInt2.

The expression plasmid, pγCEAtrp207-1☆ used for expression of the heavy chain gene is prepared by a 3-way ligation using the large vector fragment from pBR322(XAP) (supra) and two fragments prepared from pγCEAInt2.

pBR322(XAP) was treated as above by digestion with EcoR1, blunt ending with DNA polymerase (Klenow) in the presence of dNTPs, followed by digestion with Pst I, and isolation of the large vector fragment by gel electrophoresis. A 1543 base pair fragment from pγCEAInt2 containing trp promoter linked with the N-terminal coding region of the heavy chain gene was isolated by treating pγCEAInt2 with Pst I followed by BamH I, and isolation of the desired fragment using PAGE. The 869 base pair fragment containing the C-terminal coding portion of the gene was prepared by partial digestion of pγCEAInt2 with Ava I, blunt ending with Klenow, and subsequent digestion with BamH I, followed by purification of the desired fragment by gel electrophoresis.

The aforementioned three fragments were then ligated under standard conditions using T4 DNA ligase, and a ligation mixture used to transform *E. coli* strain 294. Plasmid DNAs from several tetracycline resistant transformants were analyzed; one plasmid DNA demonstrated the proper construction and was designated pγCEAtrp207-1☆.

E.1.9 Production of Immunoglobulin Chains by *E. coli*

*E. coli* strain W3110 (ATTC No. 27325) was transformed with pγCEAtrp207-1☆ or pKCEAtrp207-1☆ using standard techniques.

To obtain double transformants, *E. coli* strain W3110 cells were transformed with a modified pKCEAtrp207-1☆, pKCE-Atrp207-1☆Δ, which had been modified by cleaving a Pst I-Pvu I fragment from the $amp^R$ gene and religating. Cells transformed with pKCEAtrp207-1☆Δ are thus sensitive to ampicillin but still resistant to tetracycline. Successful transformants were retransformed using pγCEAInt2 which confers resistance to ampicillin but not tetracycline. Cells containing both pKCEAtrp207-1☆Δ and pγCEAInt2 thus identified by growth in a medium containing both ampicillin and tetracycline.

To confirm the production of heavy and/or light chains in the transformed cells, the cell samples were inoculated into M9 tryptophan free medium containing 10 μg/ml tetracycline, and induced with indoleacrylic acid (IAA) when the OD 550 reads 0.5. The induced cells were grown at 37° C. during various time periods and then spun down, and suspended in TE buffer containing 2 percent SDS and 0.1 M β-mercaptoethanol and boiled for 5 minutes. A 10× volume of acetone was added and the cells kept at 22° C. for 10 minutes, then centrifuged at 12,000 rpm. The precipitate was suspended in O'Farrell SDS sample buffer (O'Farrell, P. H., *J. Biol. Chem.*, 250: 4007 (1975)); boiled 3 minutes, recentrifuged, and fractionated using SDS PAGE (10 percent), and stained with silver stain (Goldman, D. et al., *Science* 211: 1437 (1981)); or subjected to Western blot using rabbit anti-mouse IgG (Burnett, W. N., et al., *Anal. Biochem.* 112: 195 (1981)), for identification light chain and heavy chain.

Cells transformed with pγCEAtrp207-1☆ showed bands upon SDS PAGE corresponding to heavy chain molecular weight as developed by silver stain. Cells transformed with pKCEAtrp207-1☆ showed the proper molecular weight band for light chain as identified by Western blot; double transformed cells showed bands for both heavy and light chain molecular weight proteins when developed using rabbit anti-mouse IgG by Western blot. These results are shown in FIGS. 8A, 8B, and 8C.

Figure 8A:
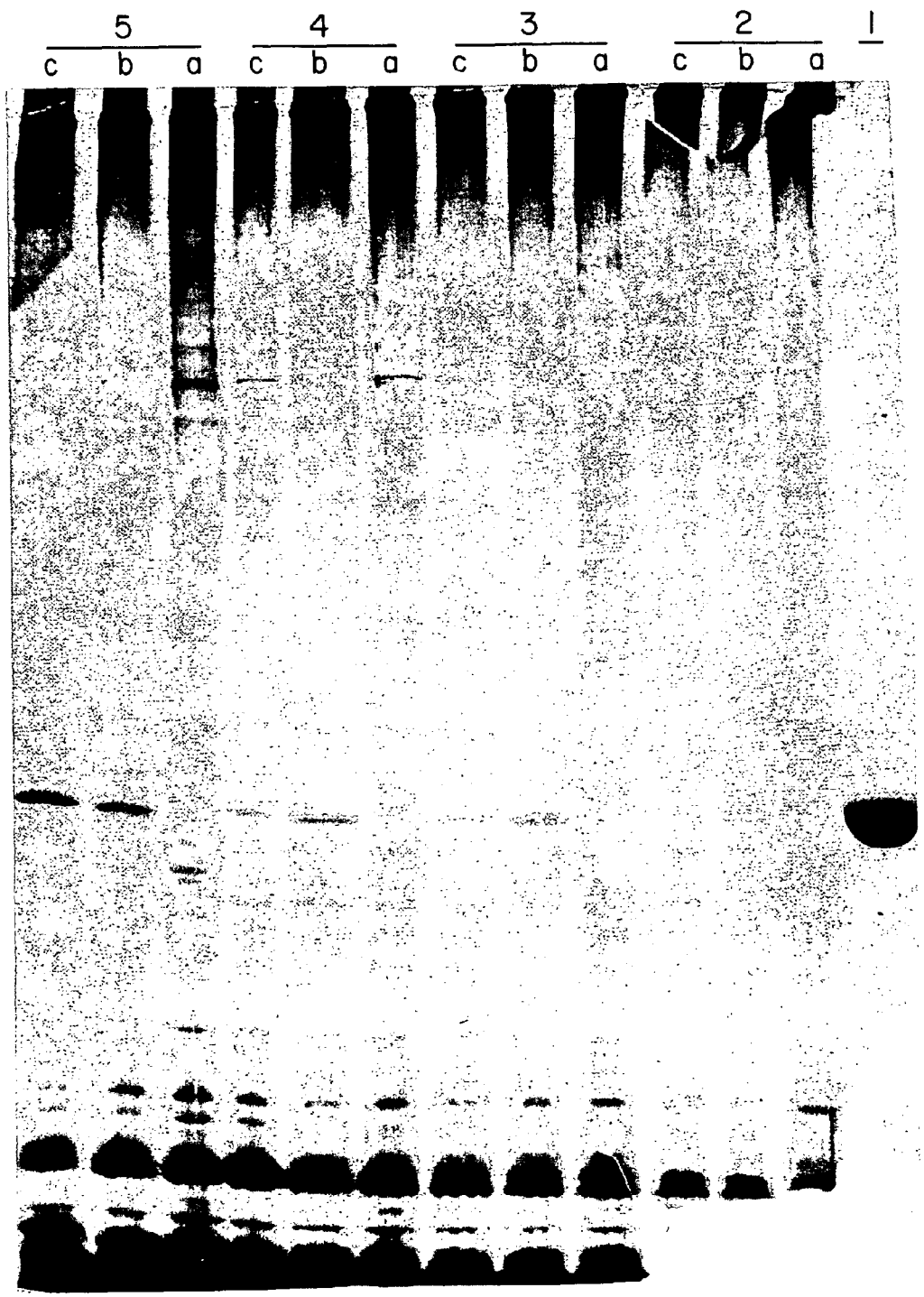
FIGS. 8A, 8B, and 8C show the results of sizing gels run on extracts of *E. coli* expressing the genes for gamma chain, kappa chain, and both kappa and gamma chains respectively.

FIG. 8A shows results developed by silver stain from cells transformed with pγCEAtrp207-1☆. Lane 1 is monoclonal anti-CEA heavy chain (standard) from CEA.66-E3. Lanes 2b-5b are timed samples 2 hrs, 4 hrs, 6 hrs, and 24 hrs after IAA addition. Lanes 2a-5a are corresponding untransformed controls; Lanes 2c-5c are corresponding uninduced transformants.

Figure 8B:
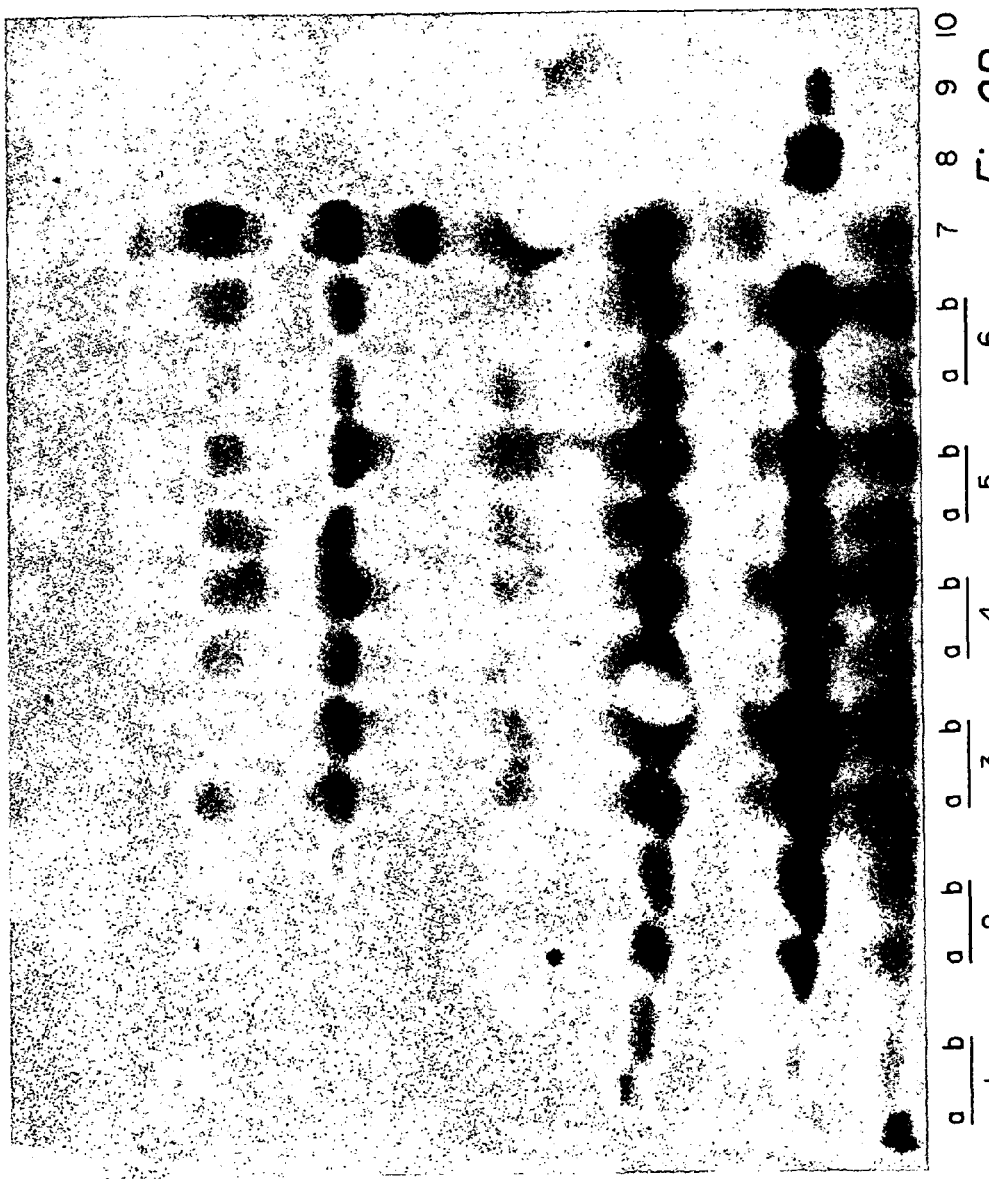

FIG. 8B shows results developed by Western blot from cells transformed with pKCEAtrp207-1☆. Lanes 1b-6b are extracts from induced cells immediately, 1 hr, 3.5 hrs, 5 hrs, 8 hrs, and 24 hrs after IAA addition, and 1a-6a corresponding uninduced controls. Lane 7 is an extract from a pγCE-Atrp207-1☆ control, lanes 8, 9, and 10 are varying amounts of anti CEA-kappa chain from CEA.66-E3 cells.

Figure 8C:
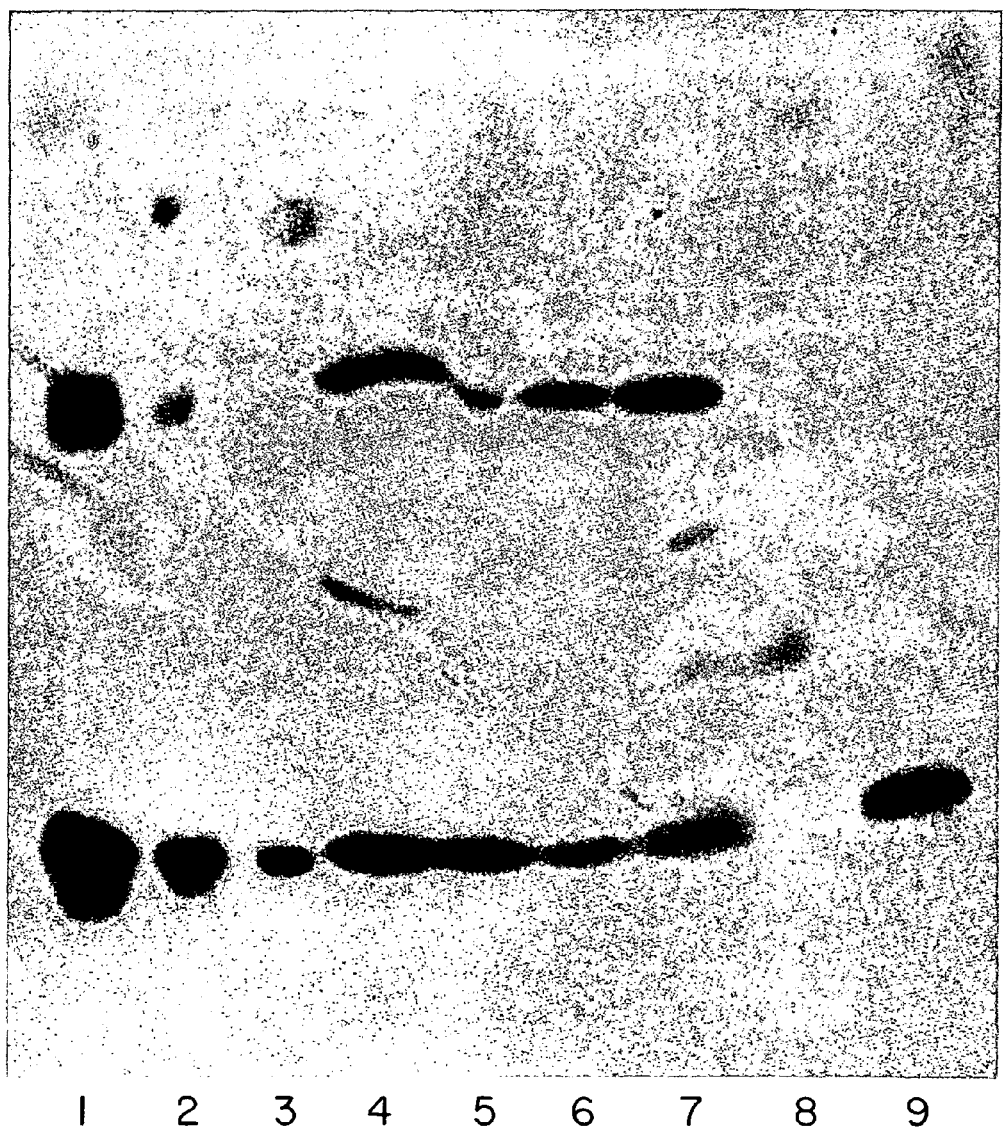

FIG. 8C shows results developed by Western blot from four colonies of double transformed cells 24 hours after IAA addition (lanes 4-7). Lanes 1-3 are varying amounts of monoclonal gamma chain controls, lanes 8 and 9 are untransformed and pγCEAtrp207-1☆ transformed cell extracts, respectively.

Figure 9:
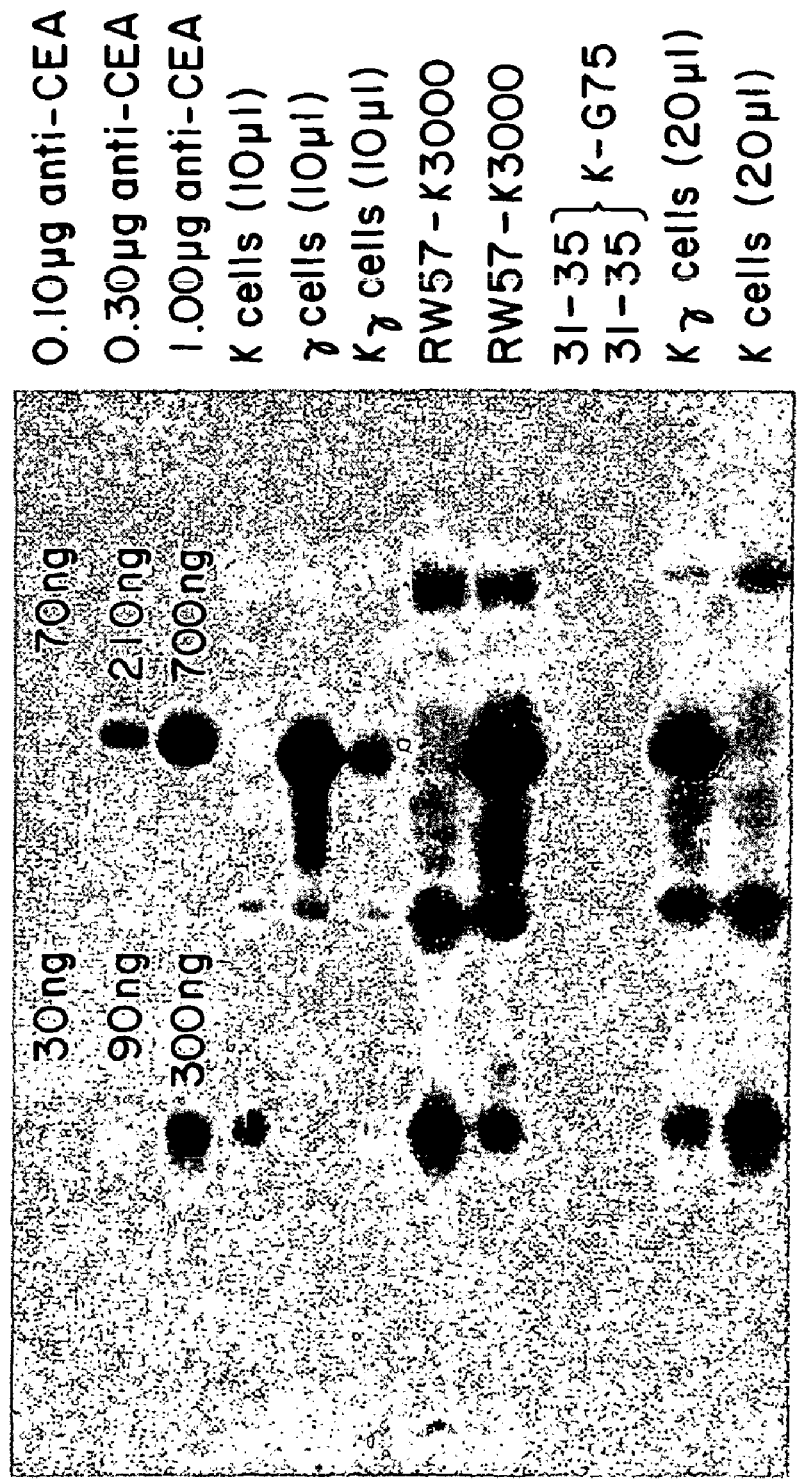
FIG. 9 shows the results of western blots of extracts of cells transformed as those in FIG. 8.

In another quantitative assay, frozen, transformed *E. coli* cells grown according to E.1.10 (below) were lysed by heating in sodium dodecyl sulfate (SDS)/γ-mercaptoethanol cell lysis buffer at 100°. Aliquots were loaded on an SDS polyacrylamide gel next to lanes loaded with various amounts of hybridoma anti-CEA. The gel was developed by the Western blot, Burnett (supra), using $^{125}$I-labeled sheep anti-mouse IgG antibody from New England Nuclear. The results are shown in FIG. 9. The figure shows that the *E. coli* products co-migrate with the authentic hybridoma chains, indicating no detectable proteolytic degradation in *E. coli*. Heavy chain from mammalian cells is expected to be slightly heavier than *E. coli* material due to glycosylation in the former. Using the hybridoma lanes as a standard, the following estimates of heavy and light chain production were made:

| | (Per gram of cells) |
|---|---|
| *E. coli* (W3110/pγCE Atrp207-1*) | 5 mg γ |
| *E. coli* (W3110/pKCE Atrp207-1*) | 1.5 mg K |
| *E. coli* (W3110/pKCE Atrp207-1*Δ, pγCEAInt2) | 0.5 mg K, 1.0 mg γ |

E.1.10 Reconstitution of Antibody from Recombinant K and Gamma Chains

In order to obtain heavy and light chain preparations for reconstitution, transformed cells were grown in larger batches, harvested and frozen. Conditions of growth of the variously transformed cells were as follows:

*E. coli* (W3110/pγCEAtrp207-1☆) were inoculated into 500 ml LB medium containing 5 μg/ml tetracycline and grown on a rotary shaker for 8 hours. The culture was then transferred to 10 liters of fermentation medium containing yeast nutrients, salts, glucose, and 2 μg/ml tetracycline. Additional glucose was added during growth and at OD 550=20, indoleacrylic (IAA), a trp derepressor, was added to a concentration of 50 μg/ml. The cells were fed additional glucose to a final OD 550=40, achieved approximately 6 hours from the IAA addition.

*E. coli* (W3110) cells transformed with pKCEA trp 207-1☆ and double transformed (with pKCEAtrp207-1☆Δ and pγCEAInt2) were grown in a manner analogous to that described above except that the OD 550 six hours after IAA addition at harvest was 25-30.

The cells were then harvested by centrifugation, and frozen.

E.2 Assay Method for Reconstituted Antibody

Figure 10:
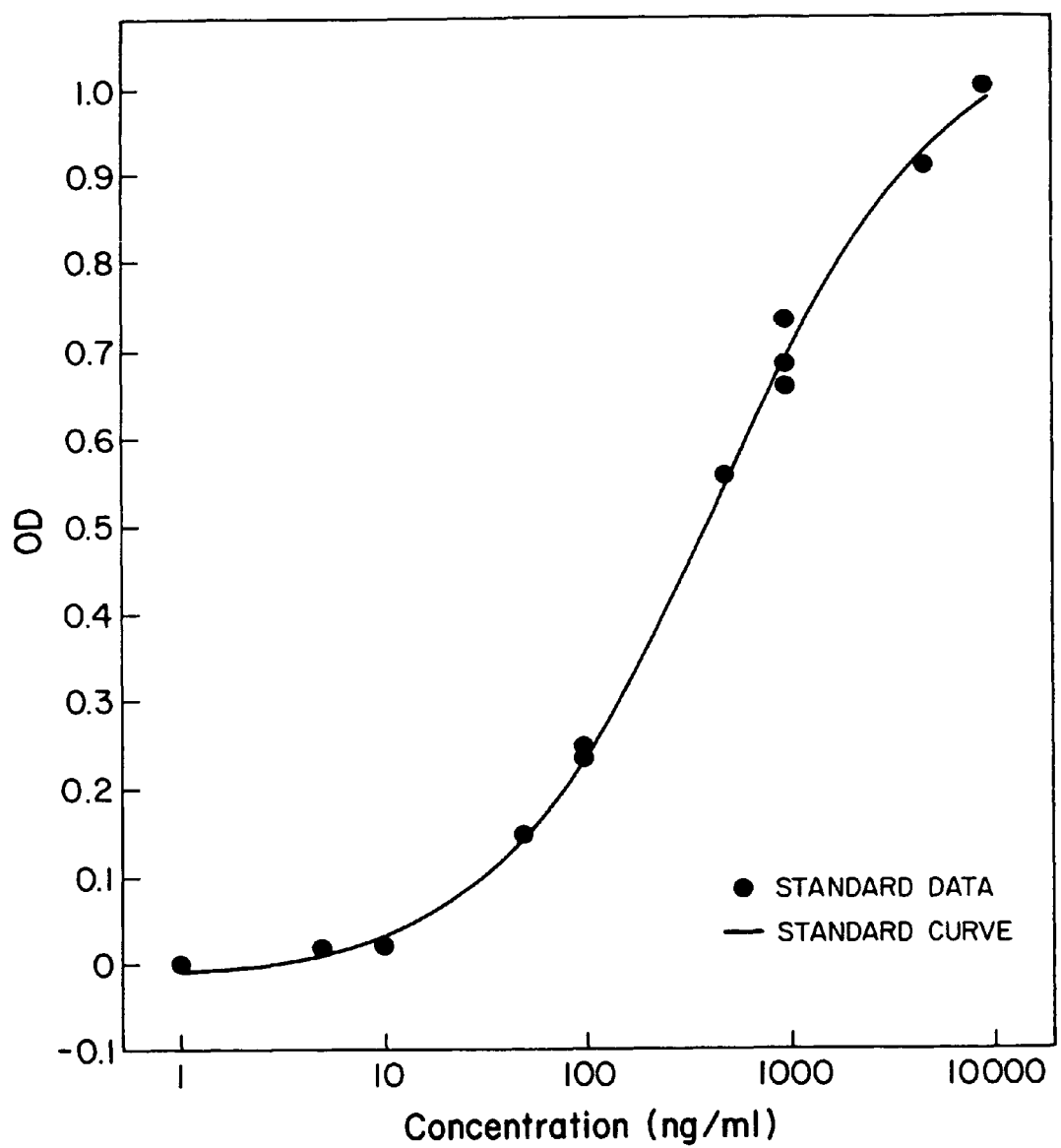
FIG. 10 shows a standard curve for ELISA assay of anti CEA activity.

Anti-CEA activity was determined by ELISA as a criterion for successful reconstitution. Wells of microtiter plates (Dynatech Immulon) were saturated with CEA by incubating 100 μl of 2-5 μg CEA/ml solution in 0.1M carbonate buffer, pH 9.3 for 12 hours at room temperature. The wells were then washed 4 times with phosphate buffered saline (PBS), and then saturated with BSA by incubating 200 μl of 0.5 percent BSA in PBS for 2 hours at 37° C., followed by washing 4 times with PBS. Fifty microliters of each sample was applied to each well. A standard curve (shown in FIG. 10), was run, which consisted of 50 μl samples of 10 μg, 5 μg, 1 μg, 500 ng, 100 ng, 50 ng, 10 ng, 5 ng and 1 ng anti-CEA/ml in 0.5 percent BSA in PBS, plus 50 μl of 0.5 percent BSA in PBS alone as a blank. All of the samples were incubated in the plate for 90 minutes at 37° C.

The plates were then washed 4 times with PBS, and sheep anti-mouse IgG-alkaline phosphate (TAGO, Inc.) was applied to each well by adding 100 µl of an enzyme concentration of 24 units/ml in 0.5 percent BSA in PBS. The solution was incubated at 37° C. for 90 minutes. The plates were washed 4 times with PBS before adding the substrate, 100 µl of a 0.4 mg/ml solution of p-nitrophenylphosphate (Sigma) in ethanolamine buffered saline, pH 9.5. The substrate was incubated 90 minutes at 37° C. for color development.

The $A_{450}$ of each well was read by the Microelisa Auto Reader (Dynatech) set to a threshold of 1.5, calibration of 1.0 and the 0.5 percent BSA in PBS (Blank) well set to 0.000. The $A_{450}$ data was tabulated in RS-1 on the VAX system, and the standard curve data fitted to a four-parameter logistic model. The unknown samples' concentrations were calculated based on the $A_{450}$ data.

E.3 Reconstitution of Recombinant Antibody and Assay

Frozen cells prepared as described in paragraph E.1.10 were thawed in cold lysis buffer [10 mM Tris HCl, pH 7.5, 1 mM EDTA, 0.1M NaCl, 1 mM phenylmethylsulfonyl fluoride (PMSF)] and lysed by sonication. The lysate was partially clarified by centrifugation for 20 mins at 3,000 rpm. The supernatant was protected from proteolytic enzymes by an additional 1 mM PMSF, and used immediately or stored frozen at −80° C.; frozen lysates were never thawed more than once.

The S-sulfonate of *E. coli* produced anti-CEA heavy chain (γ) was prepared as follows: Recombinant *E. coli* cells transformed with pγCEAtrp207-1* which contained heavy chain as insoluble bodies, were lysed and centrifuged as above; the pellet was resuspended in the same buffer, sonicated and re-centrifuged. This pellet was washed once with buffer, then suspended in 6M guanidine HCl, 0.1M Tris HCl, pH 8, 1 mM EDTA, 20 mg/ml sodium sulfite and 10 mg/ml sodium tetrathionate and allowed to react at 25° for about 16 hrs. The reaction mixture was dialyzed against 8M urea, 0.1M Tris HCl, pH 8, and stored at 4°, to give a 3 mg/ml solution of γ-SSO$_3$.

650 µl of cell lysate from cells of various *E. coli* strains producing various IgG chains, was added to 500 mg urea. To this was added β-mercaptoethanol to 20 mM, Tris-HCl, pH 8.5 to 50 mM and EDTA to 1 mM, and in some experiments, γ-SSO$_3$ was added to 0.1 mg/ml. After standing at 25° for 30-90 mins., the reaction mixtures were dialyzed at 4° against a buffer composed of 0.1M sodium glycinate, pH 10.8, 0.5M urea, 10 mM glycine ethyl ester, 5 mM reduced glutathione, 0.1 mM oxidized glutathione. This buffer was prepared from N$_2$-saturated water and the dialysis was performed in a capped Wheaton bottle. After 16-48 hours, dialysis bags were transferred to 4° phosphate buffered saline containing 1 mM PMSF and dialysis continued another 16-24 hrs. Dialysates were assayed by ELISA as described in paragraph E.2 for ability to bind CEA. The results below show the values obtained by comparison with the standard curve in×ng/ml anti-CEA. Also shown are the reconstitution efficiencies calculated from the ELISA responses, minus the background (108 ng/ml) of cells producing K chain only, and from estimates of the levels of γ and K chains in the reaction mixtures.

| | ng/ml anti-CEA | Percent recombination |
|---|---|---|
| *E. coli* W3110 producing IFN-αA (control) | 0 | — |
| *E. coli* (W3110/pKCEAtrp207-1*) | 108 | — |
| *E. coli* (W3110/pKCEAtrp207-1*), plus γ-SS0$_3$ | 848 | 0.33 |
| *E. coli* (W3110/pKCEAtrp207-1*A, pγCEAInt2) | 1580 | 0.76 |
| Hybridoma anti-CEA K-SS0$_3$ and γ-SS0$_3$ | 540 | 0.40 |

E.4 Preparation of Chimeric Antibody

Figure 11:
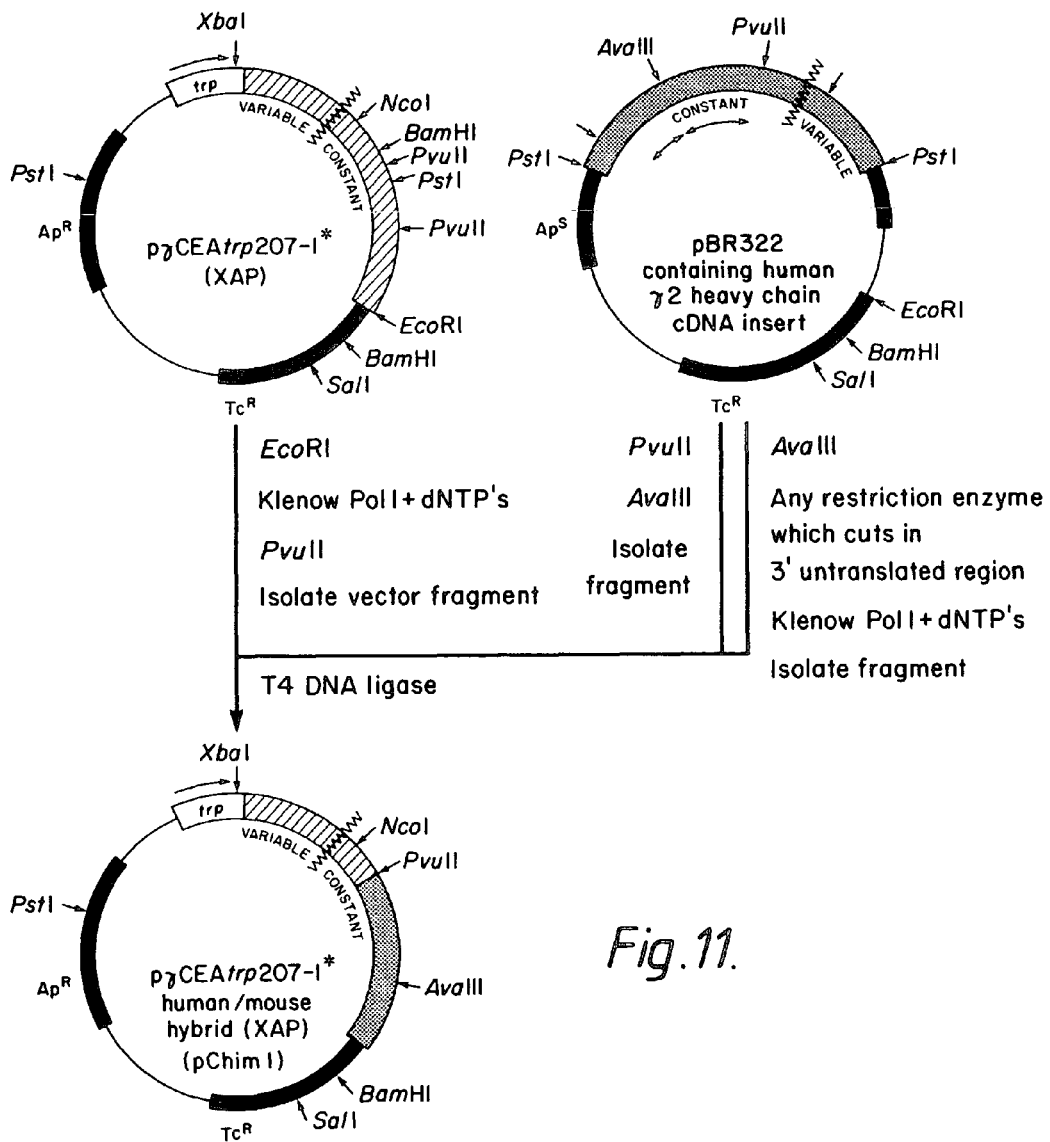
FIGS. 11 and 12 show the construction of a plasmid for expression of the gene encoding a chimeric heavy chain.
Figure 12:
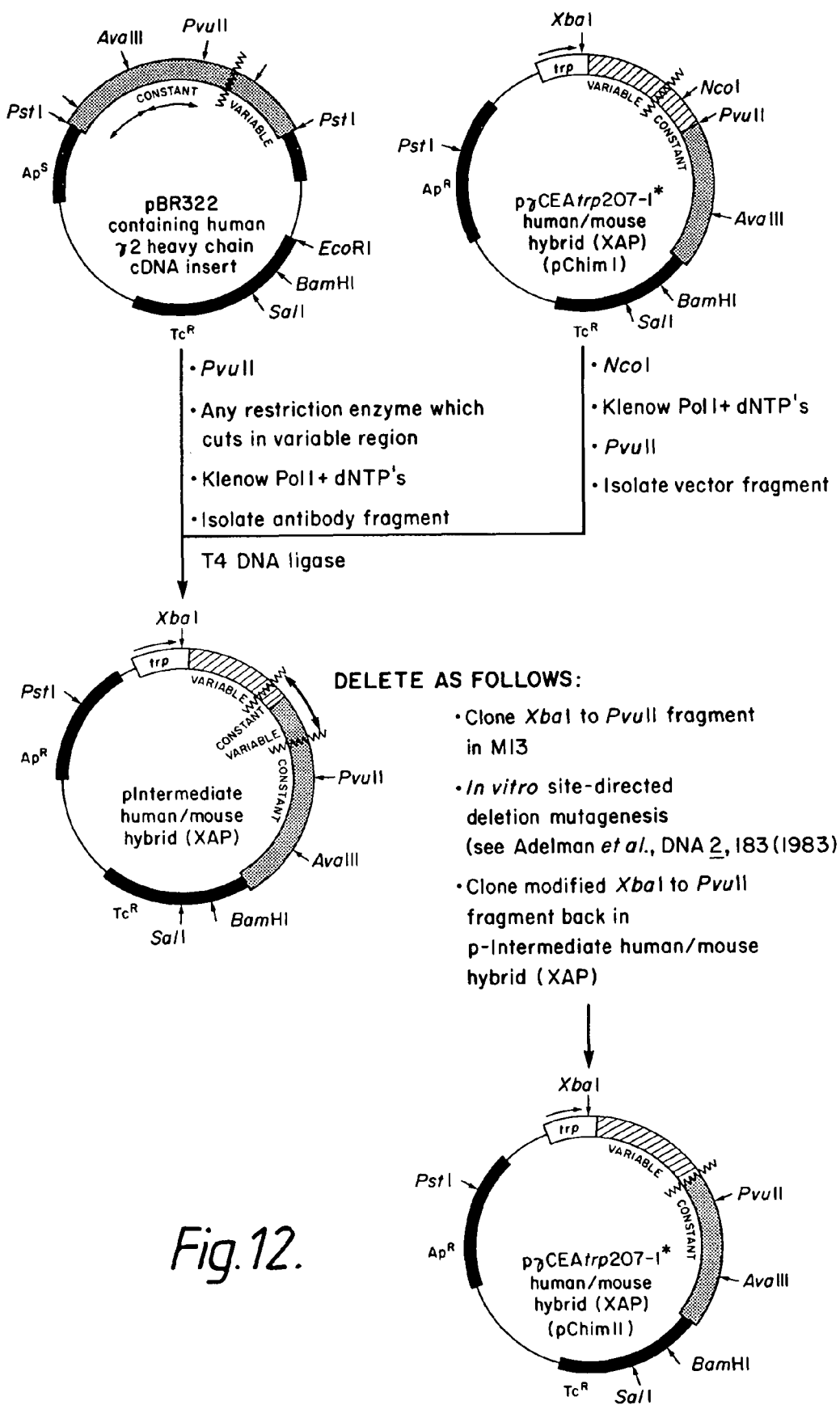

FIGS. 11 and 12 show the construction of an expression vector for a chimeric heavy (gamma) chain which comprises the murine anti CEA variable region and human γ-2 constant region.

A DNA sequence encoding the human gamma-2 heavy chain is prepared as follows: the cDNA library obtained by standard techniques from a human multiple myeloma cell line is probed with 5' GGGCACTCGACACAA 3' to obtain the plasmid containing the cDNA insert for human gamma-2 chain (Takahashi, et al., *Cell*, 29: 671 (1982), incorporated herein by reference), and analyzed to verify its identity with the known sequence in human gamma-2 (Ellison, J., et al., *Proc. Natl. Acad. Sci.* (*USA*), 79: 1984 (1982) incorporated herein by reference).

As shown in FIG. 11, two fragments are obtained from this cloned human gamma 2 plasmid (pγ2). The first fragment is formed by digestion with PvuII followed by digestion with Ava III, and purification of the smaller DNA fragment, which contains a portion of the constant region, using 6 percent PAGE. The second fragment is obtained by digesting the pγ2 with any restriction enzyme which cleaves in the 3' untranslated region of γ2, as deduced from the nucleotide sequence, filling in with Klenow and dNTPs, cleaving with Ava III, and isolating the smaller fragment using 6 percent PAGE. (The choice of a two step, two fragment composition to supply the PvuII-3' untranslated fragment provides a cleaner path to product due to the proximity of the AvaIII site to the 3 terminal end thus avoiding additional restriction sites in the gene sequence matching the 3' untranslated region site.) pγCEA207-1* is digested with EcoR 1, treated with Klenow and dNTPs to fill in the cohesive end, and digested with Pvu II, the large vector fragment containing promoter isolated by 6 percent PAGE.

The location and DNA sequence surrounding the PvuII site in the mouse gamma-1 gene are identical to the location and DNA sequence surrounding the PvuII site in the human gamma-2 gene.

The plasmid resulting from a three way ligation of the foregoing fragments, pChim1, contains, under the influence of trp promoter, the variable and part of the constant region of murine anti-CEA gamma 1 chain, and a portion of the gamma 2 human chain. pChim1 will, in fact, express a chimeric heavy chain when transformed into *E. coli*, but one wherein the change from mouse to human does not take place at the variable to constant junction.

FIG. 12 shows modification of pChim1 to construct pChim2 so that the resulting protein from expression will contain variable region from murine anti CEA antibody and constant region from the human γ-2 chain. First, a fragment is prepared from pChim1 by treating with Nco I, blunt ending with Klenow and dNTPs, cleaving with Pvu II, and isolating the large vector fragment which is almost the complete plasmid except for short segment in the constant coding region for mouse anti CEA. A second fragment is prepared from the previously described pγ2 by treating with Pvu II, followed by treating with any restriction enzyme which cleaves in the variable region, blunt ending with Klenow and dNTPs and isolating the short fragment which comprises the junction between variable and constant regions of this chain.

Ligation of the foregoing two fragments produces an intermediate plasmid which is correct except for an extraneous DNA fragment which contains a small portion of the constant region of the murine anti CEA antigen, and a small portion of the variable region of the human gamma chain. This repair can be made by excising the Xba I to Pvu II fragment and cloning into M13 phage as described by Messing et al., *Nucleic Acids Res.* 9: 309 (1981), followed by in vitro site directed deletion mutagenesis as described by Adelman, et al., *DNA,* in press (1983) which is incorporated herein by reference. The Xba I-Pvu II fragment thus modified is ligated back into the intermediate plasmid to form pChim2. This plasmid then is capable of expressing in a suitable host a cleanly constructed murine variable/human constant chimeric heavy chain.

In an analogous fashion, but using mRNA templates for cDNA construction for human kappa rather than γ chain, the expression plasmid for chimeric light chain is prepared.

The foregoing two plasmids are then double transformed into *E. coli* W3110, the cells grown and the chains reconstituted as set forth in paragraph E.1-E.3 supra;

E.5 Preparation of Altered Murine Anti-CEA Antibody
E.5.1 Construction of Plasmid Vectors for Direct Expression of Altered Murine Anti-CEA Heavy Chain Gene The cysteine residues, and the resultant disulfide bonds in the region of amino acids 216-230 in the constant region of murine anti-CEA heavy chain are suspected to be important for complement fixation (Klein, et al., *Proc. Natl. Acad. Sci., (USA),* 78: 524 (1981)) but not for the antigen binding property of the resulting antibody. To decrease the probability of incorrect disulfide bond formation during reconstitution according to the process of the invention herein, the nucleotides encoding the amino acid residues 226-232 which includes codons for three cysteines, are deleted as follows:

A "deleter" deoxyoligonucleotide, 5' CTAACACCATGT-CAGGGT is used to delete the relevant portions of the gene from pγCEAtrp207-1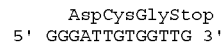 by the procedure of Wallace, et al., *Science,* 209: 1396 (1980) or of Adelman, et al., DNA (in press) 1983. Briefly, the "deleter" deoxyoligonucleotide is annealed with denatured pγCEAtrp207-1☆ DNA, and primer repair synthesis carried out in vitro, followed by screening by hybridization of presumptive deletion clones with $\rho^{32}$ labelled deleter sequence.

E.5.2 Production of Cysteine Deficient Altered Antibody

The plasmid prepared in E.5.1 is transformed into an *E. coli* strain previously transformed with pKCEAtrp207-1☆ as described above. The cells are grown, extracted for recombinant antibody chains and the altered antibody reconstituted as described in E.1.10.

E.6 Preparation of Fab
E.6.1 Construction of a Plasmid Vector for Direct Expression of Murine Anti-CEA Gamma 1 Fab Fragment Gene pγCEAFabtrp207-1☆

Figure 13:
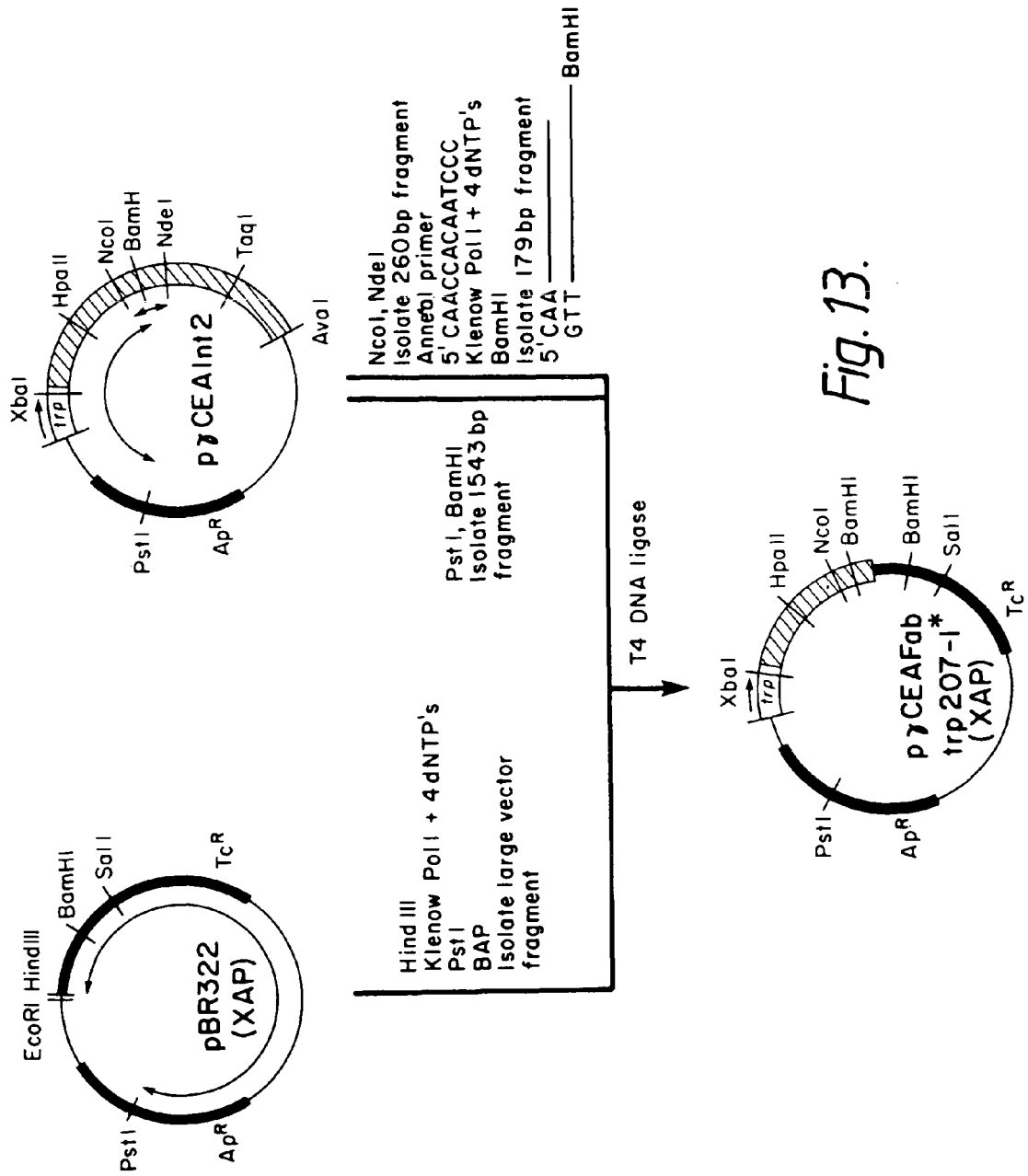
FIG. 13 shows the construction of a plasmid for expression of the gene encoding the Fab region of heavy chain.

FIG. 13 presents the construction of pγCEAFabtrp207-1☆. 5 μg of pBR322 was digested with Hind III, the cohesive ends made flush by treating with Klenow and dNTPs; digested with Pst I, and treated with BAP. The large vector fragment, fragment I, was recovered using 6 percent PAGE followed by electroelution.

5 μg of pγCEAtrp207-1☆ was digested with both BamH I and Pst I and the ~1570 bp DNA fragment (fragment II) containing the trp promoter and the gene sequence encoding the variable region continuing into constant region and further into the anti-CEA gamma 1 chain hinge region, was isolated and purified after electrophoresis.

Expression of the anti-CEA gamma 1 chain Fab fragment rather than complete heavy chain requires that a termination codon be constructed at the appropriate location in the gene. For this, the 260 bp Nco I-Nde I DNA fragment from 20 μg of the pγ298 was isolated and purified. A 13 nucleotide DNA primer, the complement of which encodes the last 3 C-terminal amino acids of the Fab gene and 2 bases of the 3 needed for the stop codon, was synthesized by the phosphotriester method (supra). The probe hybridizes to nucleotides 754 to 767 (FIG. 4) which has the following sequence:

```
         AspCysGlyStop
      5' GGGATTGTGGTTG 3'
```

The third base of the stop codon is provided by the terminal nucleotide of the filled-in Hind III site from pBR322 cleavage described above. 500 ng of this primer was used in a primer repair reaction by phosphorylation at the 5' end in a reaction with 10 units T4 DNA kinase containing 0.5 mM ATP in 20 μl, and mixing with ~200 ng of the Nco I-Nde I DNA fragment. The mixture was heat denatured for 3 minutes at 95° and quenched in dry-ice ethanol. The denatured DNA solution was made 60 mM NaCl, 7 mM MgCl$_2$, 7 mM Tris HCl (pH 7.4), 12 mM in each dNTP and 12 units DNA Polymerase I-Large Fragment was added. After 2 hours incubation at 37° C., this primer repair reaction was phenol/CHCl$_3$ extracted, ethanol precipitated, digested with BamH I and the reaction electrophoresed through a 6 percent polyacrylamide gel. ~50 ng of the 181 bp blunt end to BamH I DNA fragment, fragment III, was isolated and purified.

~100 ng of fragment I, ~100 ng each of fragments II and III were ligated overnight and transformed into *E. coli* K12 strain 294. Plasmid DNA from several tetracycline resistant transformants was analyzed for the proper construction and the nucleotide sequence through the repair blunt end filled-in Hind III junction was determined for verification of the TGA stop codon.

E.6.2 Production of Fab Protein

The plasmid prepared in E.6.1 is transformed into an *E. coli* strain previously transformed with pKCEAtrp207-1☆ as described above. The cells are grown, extracted for recombinant antibody chains and the Fab protein reconstituted as described in E.1.10.

The invention claimed is:

1. A method for making an antibody heavy chain or fragment thereof and an antibody light chain or fragment thereof each having specificity for a desired antigen, wherein the heavy chain or fragment thereof comprises a human constant region sequence and a variable region comprising non human mammalian variable region sequences, the method comprising culturing a recombinant host cell comprising DNA encoding the heavy chain or fragment thereof and the light chain or fragment thereof and recovering the heavy chain or fragment thereof and light chain or fragment thereof from the host cell culture.

2. The method of claim 1 wherein the light chain or fragment thereof comprises a human constant region sequence and a variable region comprising non human mammalian variable region sequences.

3. The method of claim 1 wherein the host cell comprises a vector comprising DNA encoding the heavy chain or fragment thereof and DNA encoding the light chain or fragment thereof.

4. The method of claim 1 wherein the host cell comprises a vector comprising DNA encoding the heavy chain or fragment thereof and a further vector comprising DNA encoding the light chain or fragment thereof.

5. The method of claim 1 wherein the non human mammalian variable region sequences are murine.

6. The method of claim 1 wherein the host cell is a prokaryotic cell.

7. The method of claim 6 wherein the prokaryotic cell is an *E. coli* cell.

8. The method of claim 1 wherein the host cell is an eukaryotic cell.

9. The method of claim 8 wherein the eukaryotic cell is a mammalian cell.

10. The method of claim 9 wherein the mammalian cell is selected from the group consisting of a VERO, HeLa, Chinese Hamster Ovary (CHO), W138, BHK, COS-7 and MDCK cell.

11. The method of claim 10 wherein the mammalian cell is a CHO cell.

12. The method of claim 10 wherein the mammalian cell is a COS-7 cell.

13. The method of claim 8 wherein the eukaryotic cell is a yeast cell.

14. The method of claim 13 wherein the yeast cell is a *Saccharomyces cerevisiae* cell.

15. A method for making an antibody or antibody fragment capable of specifically binding a desired antigen, wherein the antibody or antibody fragment comprises (a) an antibody heavy chain or fragment thereof comprising a human constant region sequence and a variable region comprising non human mammalian variable region sequences and (b) an antibody light chain or fragment thereof comprising a human constant region sequence and a variable region comprising non human mammalian variable region sequences, the method comprising coexpressing the heavy chain or fragment thereof and the light chain or fragment thereof in a recombinant host cell.

16. The method of claim 15 further comprising recovering the antibody or antibody fragment from a cell culture comprising the recombinant cell.

17. The method of claim 15 which results in the production of an antibody fragment.

18. The method of claim 17 wherein the antibody fragment is an F(ab)$_2$ fragment.

19. The method of claim 17 wherein the antibody fragment is a Fab fragment.

20. The method of claim 15 which results in the production of an antibody.

21. A method for making an antibody capable of specifically binding a desired antigen, the antibody comprising heavy and light immunoglobulin polypeptide chains each comprising a human constant region sequence and a variable region comprising non human mammalian variable region sequences, the method comprising the steps of (a) transforming a recombinant host cell with a replicable expression vector comprising DNA encoding the heavy immunoglobulin polypeptide chain and a replicable expression vector comprising DNA encoding the light immunoglobulin polypeptide chain, wherein each of the DNAs is operably linked to a promoter; and (b) culturing the host cell to produce a host cell culture that expresses said antibody.

22. A replicable expression vector comprising DNA encoding an antibody heavy chain or fragment thereof and an antibody light chain or fragment thereof each having specificity for a desired antigen, the heavy chain or fragment thereof and the light chain or fragment thereof each comprising a human constant region sequence and a variable region comprising non human mammalian variable region sequences.

23. A recombinant host cell comprising the vector of claim 22.

24. A recombinant host cell comprising (a) a vector comprising DNA encoding an antibody heavy chain or fragment thereof comprising a human constant region sequence and a variable region comprising non human mammalian variable region sequences and (b) a vector comprising DNA encoding an antibody light chain or fragment thereof comprising a human constant region sequence and a variable region comprising non human mammalian variable region sequences.

25. A method for making an antibody heavy chain or fragment thereof and an antibody light chain or fragment thereof each having specificity for a desired antigen, wherein the heavy chain or fragment thereof comprises a variable region sequence and a human constant region sequence, the method comprising culturing a recombinant host cell comprising DNA encoding the heavy chain or fragment thereof and the light chain or fragment thereof and recovering the heavy chain or fragment thereof and light chain or fragment thereof from the host cell culture.

26. The method of claim 25 wherein the light chain or fragment thereof comprises a variable region sequence and a human constant region sequence.

27. The method of claim 25 wherein the host cell comprises a vector comprising DNA encoding the heavy chain or fragment thereof and DNA encoding the light chain or fragment thereof.

28. The method of claim 25 wherein the host cell comprises a vector comprising DNA encoding the heavy chain or fragment thereof and a further vector comprising DNA encoding the light chain or fragment thereof.

29. The method of claim 25 wherein the host cell is a prokaryotic cell.

30. The method of claim 29 wherein the prokaryotic cell is an *E. coli* cell.

31. The method of claim 25 wherein the host cell is a eukaryotic cell.

32. The method of claim 31 wherein the eukaryotic cell is a mammalian cell.

33. The method of claim 32 wherein the mammalian cell is selected from the group consisting of a VERO, HeLa, Chinese Hamster Ovary (CHO), W138, BHK, COS-7 and MDCK cell.

34. The method of claim 32 wherein the mammalian cell is a CHO cell.

35. The method of claim 32 wherein the mammalian cell is a COS-7 cell.

36. The method of claim 31 wherein the eukaryotic cell is a yeast cell.

37. The method of claim 36 wherein the yeast cell is a *Saccharomyces cerevisiae* cell.

38. A method for making an antibody or antibody fragment capable of specifically binding a desired antigen, wherein the antibody or antibody fragment comprises (a) an antibody heavy chain or fragment thereof comprising a variable region sequence and a human constant region sequence and (b) an antibody light chain or fragment thereof comprising a variable region sequence and a human constant region sequence, the method comprising coexpressing the heavy chain or fragment thereof and the light chain or fragment thereof in a recombinant host cell.

39. The method of claim 38 further comprising recovering the antibody or antibody fragment from a cell culture comprising the recombinant cell.

40. The method of claim 38 which results in the production of an antibody fragment.

41. The method of claim 38 wherein the antibody fragment is an F(ab)$_2$ fragment.

42. The method of claim 40 wherein the antibody fragment is a Fab fragment.

43. The method of claim 38 which results in the production of an antibody.

44. A method for making an antibody capable of specifically binding a desired antigen, the antibody comprising heavy and light immunoglobulin polypeptide chains each comprising a variable region sequence and a human constant region sequence, the method comprising the steps of (a) transforming a recombinant host cell with a replicable expression vector comprising DNA encoding the heavy immunoglobulin polypeptide chain and a replicable expression vector comprising DNA encoding the light immunoglobulin polypeptide chain, wherein each of the DNAs is operably linked to a promoter; and (b) culturing the host cell to produce a host cell culture that expresses said antibody.

45. A replicable expression vector comprising DNA encoding an antibody heavy chain or fragment thereof and an antibody light chain or fragment thereof each having specificity for a desired antigen, the heavy chain or fragment thereof and the light chain or fragment thereof each comprising a variable region sequence and a human constant region sequence.

46. A recombinant host cell comprising the vector of claim 45.

47. A recombinant host cell comprising (a) a vector comprising DNA encoding an antibody heavy chain or fragment thereof comprising a variable region sequence and human constant region sequence and (b) a vector comprising DNA encoding an antibody light chain or fragment thereof comprising a variable region sequence and a human constant region sequence.

* * * * *